United States Patent
Congreve et al.

(10) Patent No.: US 10,112,923 B2
(45) Date of Patent: *Oct. 30, 2018

(54) 1,2,4-TRIAZINE-4-AMINE DERIVATIVES

(71) Applicant: Heptares Therapeutics Limited, Welwyn Garden, Hertfordshire (GB)

(72) Inventors: Miles Stuart Congreve, Welwyn Garden (GB); Stephen Philippe Andrews, Melbourn (GB); Jonathan Stephen Mason, Walmer (GB); Christine Mary Richardson, Saffron Walden (GB); Giles Albert Brown, Cambridge (GB)

(73) Assignee: Heptares Therapeutics Limited, Welwyn Garden (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/344,048

(22) Filed: Nov. 4, 2016

(65) Prior Publication Data

US 2017/0291888 A1 Oct. 12, 2017

Related U.S. Application Data

(63) Continuation of application No. 14/976,738, filed on Dec. 21, 2015, now abandoned, which is a (Continued)

(51) Int. Cl.
*C07D 401/04* (2006.01)
*C07D 403/04* (2006.01)
(Continued)

(52) U.S. Cl.
CPC ........ *C07D 401/04* (2013.01); *A61K 31/4427* (2013.01); *A61K 31/506* (2013.01);
(Continued)

(58) Field of Classification Search
CPC .. C07D 253/07; C07D 401/04; C07D 401/14; C07D 403/04; C07D 403/14;
(Continued)

(56) References Cited

U.S. PATENT DOCUMENTS 4,008,232 A 2/1977 Lacefield
8,809,525 B2 8/2014 Congreve et al.
(Continued)

FOREIGN PATENT DOCUMENTS

EP 0088593 A2 9/1983
EP 1400518 A1 3/2004
(Continued)

OTHER PUBLICATIONS

Zou, et al., "Study on the syntheses of new 1-o-chlorobenzoyl-3(5'-substituted phenylamino-6'-phenyl)-1', 2', 4'-triazinyl ureas", Chinese J. Chem. 1998, 16, 58-64.
Eijkelkamp et al., "Neurological perspectives on voltage-gated sodium channels" Brain J. of Neurology: 135: 2585-2612, 2012.
Imbrici et al., "Major channels involved in neuropsychiatric disorders and therapeutic perspectives" Frontiers in Genetics, vol. 4(Article 76):1-19, 2013.
"L-DOPA", Chem. Eng. News 2005, 83(25) 60.
2009 Meeting Planner, Society for Neuroscience, Chicago, IL, Program No. 714.4/B101.
Auchampach, et al., "Adenosine receptor subtypes in the heart: therapeutic opportunities and challenges", Am. J. Physiol. 1999, 276, H1113-6.
Bauer, et al., "Adenosine Receptor Ligands and PET Imaging of the CNS", Wilson and Mustafa "Adenosine Receptors in Health and Disease", Handbook of Experimental Pharmacology, 2009, Springer, Berlin, p. 617-42.

(Continued)

*Primary Examiner* — Venkataraman Balasubramanian
(74) *Attorney, Agent, or Firm* — McCarter & English, LLP; Steven G. Davis; Mei Bai

(57) ABSTRACT

According to the invention there is provided a compound of formula A1 which may be useful in the treatment of a condition or disorder ameliorated by the inhibition of the $A_1$-$A_{2b}$ or, particularly, the $A_{2a}$ receptor wherein the compound of formula A1 has the structure, wherein, A represents $Cy^1$ or $Het^A$; $Cy^1$ represents a 5- to 14-membered aromatic, fully saturated or partially unsaturated carbocyclic ring system comprising one, two or three rings, which $Cy^1$ group is optionally substituted by one or more $R^{4a}$ substituents; $Het^A$ represents a 5- to 14-membered heterocyclic group that may be aromatic, fully saturated or partially unsaturated, and which contains one or more heteroatoms selected from O, S and N, which heterocyclic group may comprise one, two or three rings and which HetA group is optionally substituted by one or more R4b substituents; B represents a $Cy^2$ or $Het^B$; $Cy^2$ represents a 3- to 10-membered aromatic, fully saturated or partially unsaturated carbocyclic ring system comprising one or two rings, which $Cy^2$ group is optionally substituted by one or more $R^{4c}$ substituents; $Het^B$ represents a 3- to 10-membered heterocyclic group that may be aromatic, fully saturated or partially unsaturated, and which contains one or more heteroatoms selected from O, S and N, which heterocyclic group may comprise one or two rings and which $Het^B$ group is optionally substituted by one or more $R^{4d}$ substituents.

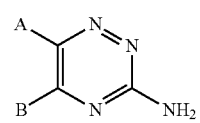

A1

3 Claims, No Drawings

Related U.S. Application Data continuation of application No. 14/322,505, filed on Jul. 2, 2014, now Pat. No. 9,249,130, which is a continuation of application No. 13/576,798, filed as application No. PCT/EP2011/051755 on Feb. 7, 2011, now Pat. No. 8,809,525.

(60) Provisional application No. 61/381,764, filed on Sep. 10, 2010, provisional application No. 61/302,060, filed on Feb. 5, 2010.

(51) Int. Cl.

| | | |
|---|---|---|
| C07D 417/04 | (2006.01) | |
| C07D 417/14 | (2006.01) | |
| C07D 253/07 | (2006.01) | |
| A61K 31/53 | (2006.01) | |
| A61K 31/4427 | (2006.01) | |
| A61P 35/00 | (2006.01) | |
| A61K 31/506 | (2006.01) | |
| A61K 31/5355 | (2006.01) | |
| C07D 401/12 | (2006.01) | |
| C07D 401/14 | (2006.01) | |
| C07D 403/12 | (2006.01) | |
| C07D 405/04 | (2006.01) | |
| C07D 405/10 | (2006.01) | |
| C07D 413/04 | (2006.01) | |
| C07D 417/12 | (2006.01) | |
| C07D 487/04 | (2006.01) | |
| C07D 413/14 | (2006.01) | |
| A61K 31/5377 | (2006.01) | |
| A61K 31/5386 | (2006.01) | |

(52) U.S. Cl.
CPC .......... *A61K 31/53* (2013.01); *A61K 31/5355* (2013.01); *A61K 31/5377* (2013.01); *A61K 31/5386* (2013.01); *C07D 253/07* (2013.01); *C07D 401/12* (2013.01); *C07D 401/14* (2013.01); *C07D 403/04* (2013.01); *C07D 403/12* (2013.01); *C07D 405/04* (2013.01); *C07D 405/10* (2013.01); *C07D 413/04* (2013.01); *C07D 413/14* (2013.01); *C07D 417/04* (2013.01); *C07D 417/12* (2013.01); *C07D 417/14* (2013.01); *C07D 487/04* (2013.01)

(58) Field of Classification Search
CPC .... C07D 417/04; C07D 417/14; A61K 31/53; A61K 31/5355; A61K 31/4427; A61K 31/506; A61K 31/4155; A61K 31/397
USPC ........................ 544/182, 112; 514/242, 231.5
See application file for complete search history.

(56) References Cited

U.S. PATENT DOCUMENTS

| 9,249,130 B2 | 2/2016 | Congreve et al. |
| 2004/0102436 A1 | 5/2004 | Asaki et al. |
| 2004/0229873 A1 | 11/2004 | Harbige et al. |
| 2007/0037033 A1 | 2/2007 | Chiba et al. |
| 2007/0135437 A1 | 6/2007 | Benjamin et al. |

FOREIGN PATENT DOCUMENTS

| FR | 2485531 A1 | 12/1981 |
| FR | 2869906 A1 | 11/2005 |
| GB | 1604085 A | 12/1981 |
| WO | 1992002513 A1 | 2/1992 |
| WO | 2000066568 A1 | 11/2000 |
| WO | 2001058241 A2 | 8/2001 |
| WO | 2002055083 A1 | 7/2002 |
| WO | 2003077921 A1 | 9/2003 |
| WO | 2004016605 A1 | 2/2004 |
| WO | 2005040151 A1 | 5/2005 |
| WO | 2005044245 A1 | 5/2005 |
| WO | 2005117883 A1 | 12/2005 |
| WO | 2006009698 A2 | 1/2006 |
| WO | 2006051311 A1 | 5/2006 |
| WO | 2006113704 A2 | 10/2006 |
| WO | 2006132275 A1 | 12/2006 |
| WO | 2009090431 A1 | 7/2009 |

OTHER PUBLICATIONS

Boovanahalli, et al., "Application of Ionic Liquid Halide Nucleophilicity for the Cleavage of Ethers: A Green Protocol for the Regeneration of Phenols form Ethers", J. Org. Chem. 2004, 69, 3340-4.
Bundgaard, "Design of prodrugs", 1985, Elsevier, New York, p. 1-92.
Byrn, et al., "Solid-State Chemistry of Drugs", 1999 2nd Ed., SSCI, Inc. of West LaFayette.
Cecil Textbook of Medicine, edited by Bennet, J.C., and Plum F., 20th edition,vol. 1, 1004-101 O, 1996.
Chan, et al., "Adenosine A2A Receptors in Diffuse Dermal Fibrosis", Arthris Rheum. 2006, 54, 2632-42.
Costello-Boerrigter, et al., "Revisiting sale and water retention: new diuretics, aquaretics, and natriuretics", Med. Clin. North Am. 2003, 87, 475-91.
Cunha, et al., "Potential therapeutic interest of adenosine A2A receptors in psychiatric disorders", Curr. Pharm. Des. 2008, 14, 1512-24.
Dall'Igna, "Caffeine and adenosine A2a receptor antagonists prevent β-amyloid (25-35)-induced cognitive deficits in nice", Exp. Neurol. 2007, 241-5.
Davidson, et al., "Synthesis of as-Triazines as Potential Antiviral Agents", J Pharm. Sci. 1978, 67, 737-9.
Dermer et al., Bio/Technology, 1994, 12:320.
Doig, et al, "Use of thermospray liquid chromatography-mass spectrometry to aid in the identification of urinary metabolites of a novel antiepileptic drug, Lamotrigine", J. Chromatogr. 1991, 554, 181-9.
Dunwiddie, et al., "The Role and Regulation of Adenosine in the Central Nervous System", Ann. Rev. Neurosci. 2001, 24, 31-55.
Eid, et al., "Reactions of 3-amino/substituted amino-6-benzyl-5-thioxo-and 5-chloro-1, 2, 4-triazines: Synthesis of 3,5-substituted diamino-1, 2, 4-triazines and 5-amino/substituted amino-8-benzyl-3-thioxo-s-triazolo [4, 3-d] [1, 2, 4] triazines", In. J. Chem. B 1990, 29B, 435-9.
Feoktistov, et al., "Adenosine A2B Receptors", Pharmacol. Rev. 1997, 49, 381-402.
Freshney et al.,Culture of Animal Cells, A Manual of Basic Technique, Alan R. Liss, Inc., 1983, New York, p. 4.
Gellai, et al., "CVT-124, a Novel Adenosine A1 Receptor Antagonist with Unique Diuretic Activity", J. Pharmacol. Exp. Ther. 1998, 286, 1191-96.
Gennaro, "Remington, The Science and Practice of Pharmacy", 1995, 19th Ed., Mack Printing Company, Easton.
Gessi, et al., "The A3 adenosine receptor an enigmatic player in cell biology", Pharmacol, Therapeut. 2008, 117, 123-40.
Givertz, et al., "The Effects of KW-3902, an Adenosine A1-Receptor Antagonist, on Diuresis and Renal Function in Patients With Acute Decompensated Heart Failure and Renal Impairment or Diuretic Resistance", J. Am. Coll. Cardiol. 2007, 50, 1551-60.
Gottlieb, "Renal Effects of Adenosine A1-Receptor Antagonists in Congestive Heart Failure", Drugs 2001, 61, 1387-93.
Greene, et al., "Protective Groups in Organic Synthesis", 1999, 3rd Ed., Wiley Interscience, New York.
Happe, et al., "Gabapentin versus Ropinirole in the Treatment of Idiopathic Restless Legs Syndrome", Neuropsychobiology 2003, 48, 82-6.
Hasko, et al., "A2B adenosine receptors in immunity and inflammation", Trends in Immunol. 2009, 30, 263-70.

(56) References Cited

OTHER PUBLICATIONS

Hodgson, et al., "Characterization of the Potent and Highly Selective A2A Receptor Antagonists Preladenant and SCH 412348 [7-[2-[4-2, 4-Difluorophenyl]-1-piperazinyl]-ethyl]-2-(2-furanyl)-7H-pyrazolo[4,3-e][1,2,4]triazolo[1,5-c]pyrimidin-5-amine] in Rodent Models of Movement Disorders and Depression", J. Pharmacol. Exp. Ther. 2009, 330, 294-303.

Jacobson, et al. "Adenosine receptors as therapeutic targets", Nature Reviews Drug Discovery 2006, 5, 247-64.

Jenner, "Pathophysiology and biochemistry of dyskinesia: clues for the development of non-dopaminergic treatments", J. Neurol, 2000, 247, 1143-50.

Langer, "New Methods of Drug Delivery", Science 1990, 249, 1527.

Lu, et als. "New Heterocycles Forming Reactions of Acyl Thioformanilides", Org. Prep. Proced. Int. 1992, 24, 358-62.

Magano, et al., "2-(Diethylamino)ethanethiol, a New Reagent for the Odorless Deprotection of Aromatic Methyl Ethers", J. Org. Chem. 2006, 71, 7103-5.

Mahajam, et al., "Synthesis of 3-amino-5-substituted phenylamino-6-phenyl-1, 2, 4-triazines", Youji Huaxue 1992, 12, 605-7.

Mallikarjuna, et al., "Synthesis and anticonvulsant activity of some potent 5,6-bis aryl 1,2,4-triazines", J. Zhejian Univ. Sci. B 2007, 8, 526-32.

March, "Advanced Organic Chemistry" 1992, 4th Ed., Wiley Interscience, New York, p. 131-133.

Mcomie, "Protective Groups in Organic Chemistry", 1973, Plenum Press, New York.

Mihara, et al., "Pharmacological Characterization of a Novel, Potent Adenosine A1 and A2A Receptor Dual Antagonist, 5-[5-Amino-3(4-fluorophenyl)pyrazin-2-yl]-1-isopropylpyridine-2(1H)-one (ASP5854), in Models of Parkinson's Disease and Cognition", J. Pharmacol. Exp. Ther. 2007, 323-708-19.

Murphy, et al., "One-Pot Synthesis of Arylboronic Acids and Aryl Trifluoroborates by Ir-Catalyzed Borylation of Arenes", Org. Lett. 2007, 9, 757-60.

Norton, et al., "Adenosine A1 receptor-mediated antiadrenergic effects are modulated by A2a receptor activation in rat heart", Am. J. Physiol. 1999, 276, H341-9.

Popoli, et al., "Blockade of Striatal Adenosine A2A Receptor Reduces, through a Presynaptic Mechanism, Quinolinic Acid-Induced Excitotoxity: Possible Relevance to Neuroprotective Interventions in Neurodegenerative Diseases of the Striatum", J. Neurosci. 2002, 22, 1967-75.

Quach, et al., "Ligand- and Base-Free Copper(II)-Catalyzed C—N Bond Formation: Cross-Coupling Reactions of Organoboron Compounds with Aliphatic Amines and Anilines", Org. Lett. 2003, 5, 4397-400.

Ryu, et al., "Phase-Vanishing Reactions that Use Fluorous Media as a Phase Screen. Facile, Controlled Bromination of Alkenes by Dibromine and Dealkylation of Aromatic Ethers by Boron Tribromide", J. Am. Chem. Soc. 2002, 124, 12946-7.

Satoh, "Activation of Adenosine A1-Receptor Pathway Induces Edema Formation in the Pancreas of Rats", Gastroenterol, 2000, 119, 829-36.

Sharma, et al., "Synthesis of Benzo [5, 6] Cyclohept [1, 2, 3, ij] Isoquinolines as Rigid Congeners of Tetrahydropapaveroline", Heterocycles 1982, 19, 1895-8.

Stone, et al., "Neuroprotection by A2A Receptor Antagonists", Drug Dev. Res. 2001, 52, 323-30.

Tuite, et al., "Recent developments in the pharmacological treatment of Parkinson's disease", J. Expert Opin. Investig. Drugs 2003, 12, 1335-52.

Wilson, "Adenosine receptors and asthma in humans", Brit. J. Pharmacol. 2008, 155, 475-86.

Wolfe, et al., "Palladium-Catalyzed Amination of Aryl Halides and Aryl Triflates: N-Hexyl-2-Methyl-4-Methoxyaniline and N-Methyl-N-(4-Chlorophenyl) Aniline", Orgn. Synth., Coll. vol. 10 2004, 10, 423.

Zhou et al., "Adenosine signaling and the regulation of chronic lung disease", Pharmacol. Therapeut. 2009, 123, 105-16.

1,2,4-TRIAZINE-4-AMINE DERIVATIVES

RELATED APPLICATIONS

This application is a continuation of U.S. patent application Ser. No. 14/976,738, filed Dec. 21, 2015, which is a continuation of U.S. patent application Ser. No. 14/322,505, filed Jul. 2, 2014, now U.S. Pat. No. 9,249,130, which is a continuation of U.S. patent application Ser. No. 13/576,798, filed Oct. 17, 2012, now U.S. Pat. No. 8,809,525, which is a 371 of International Application PCT/EP2011/051755, filed on Feb. 7, 2011, which claims benefit of priority to U.S. Provisional Application No. 61/302,060, filed on Feb. 5, 2010; and U.S. Provisional Application No. 61/381,764, filed on Sep. 10, 2010, all of which are incorporated herein by reference.

This invention relates, inter alia, to the use of certain compounds in the treatment of a condition ameliorated by the inhibition of the $A_1$ receptor or the $A_{2a}$ receptor.

The listing or discussion of an apparently prior-published document in this specification should not necessarily be taken as an acknowledgement that the document is part of the state of the art or is common general knowledge.

Parkinson's Disease (PD) is a common progressive neurodegenerative disorder with an estimated prevalence of 0.3 percent in the general population, rising to 5 percent in those over 85. The disease is characterised by tremor, rigidity and bradykinesia, which are caused by the degeneration of dopaminergic neurons in the substantia nigra pars compacta and a resulting depletion of dopamine in the striatum.

Due to an ageing population, the incidence of Parkinson's disease is rising. However, the most effective pharmacological treatment for the disease is still Levodopa (L-dopa), fifty years after its discovery as an antiparkinsonian agent (*Chemical & Engineering News* 2005, 83(25)).

L-dopa is the precursor of dopamine and achieves its pharmacological effect by increasing dopaminergic transmission (i.e. by raising the level of dopamine in the striatum). The physiological effect of L-dopa can also be achieved by the administration of directly-acting dopamine agonists such as bromocriptine or pergolide. While the above treatments are initially very effective at controlling some of the symptoms of Parkinson's Disease, particularly rigidity, continuing use results in a wide range of side effects that can be distressing to the patient (e.g. involuntary movements known as dyskinesias).

Other treatments include inhibition of the dopamine metabolizing enzymes catechol-o-methyl transferase (COMT) or monoamine oxidases (MAOIs), or the use of anticholinergics. However, these treatments only provide mild to moderate benefit and suffer from a range of adverse side effects.

Adenosine is known to be an endogenous modulator of a number of physiological functions. For example, adenosine acts on the cardiovascular system and is a strong vasodilator and a cardiac depressor and is known to have cardioprotective properties (see e.g. Norton et al. *Am J Physiol.* 1999; 276(2 Pt 2), H341-9; and Auchampach and Bolli *Am J Physiol.* 1999; 276(3 Pt 2), H1113-6). Effects of adenosine on the central nervous system include sedative, anxiolytic and antiepileptic effects. Further, adenosine acts on the respiratory system by inducing bronchoconstriction. In the kidneys, adenosine exerts a biphasic action, inducing vasoconstriction at low concentrations and vasodilation at high doses, meaning that adenosine may be involved in the pathology of certain types of acute kidney failure (Costello-Boerrigter, et al. *Med Clin North Am.* 2003 March: 87(2), 475-91; Gottlieb, *Drugs.* 2001, 61(10), 1387-93). Adenosine also acts as a lipolysis inhibitor on fat cells (Feoktistov, et al., *Pharmacol. Rev.* 1997, 49, 381-402) and as an anti-aggregant on platelets.

The action of adenosine is mediated by a family of G-protein coupled receptors. Biochemical and pharmacological studies, together with advances in molecular biology, have allowed the identification of at least four subtypes of adenosine receptors, which have been classified as adenosine $A_1$, $A_{2a}$, $A_{2b}$ and $A_3$. The $A_1$ and $A_3$ receptors inhibit the activity of the enzyme adenylate cyclase, whereas the $A_{2a}$ and $A_{2b}$ receptors stimulate the activity of the same enzyme, thereby modulating the level of cyclic AMP in cells.

In the central nervous system, adenosine is a potent endogenous neuromodulator, which controls the presynaptic release of many neurotransmitters and is thus involved in motor function, sleep, anxiety, pain and psychomotor activity. The main adenosine receptor subtypes in the brain are $A_1$ and $A_{2a}$. While the $A_1$ adenosine receptor subtype is found throughout the brain in high density, the distribution of the $A_{2a}$ receptor is more restricted and it is found in high density in the striatum (caudate-putamen, nucleus accumbens, olfactory tubercule), where it is co-localized with the dopamine D2 receptor on striatopallidal output neurons. The discrete localization of the $A_{2a}$ receptor within the striatum and its ability to functionally antagonize the actions of the D2 receptor has led to the suggestion of the potential utility of $A_{2a}$ receptor antagonists for the symptomatic treatment of Parkinson's disease (see, for example, Cunha et al., *Curr Pharm Des.* 2008, 14(15), 1512-1524).

Hence, $A_{2a}$ antagonists can improve motor impairment due to neurodegenerative diseases such as Parkinson's, Huntington's and Alzheimer's disease (Tuite P, et al., *J. Expert Opin. Investig. Drugs.* 2003; 12, 1335-52: Popoli P. et al. *J Neurosci.* 2002; 22, 1967-75; and Dalrlgna, et al., *Experimental Neurology,* 2007, 241-245). Furthermore, $A_{2a}$ antagonists may be employed for the treatment of: attention related disorders such as attention deficit disorder (ADD) and attention deficit hyperactivity disorder (ADHD); psychoses; stroke, extra pyramidal syndrome (e.g., dystonia, akathisia, pseudoparkinsonism and tardive dyskinesia (see Jenner P. *J Neurol.* 2000; 247 Suppl2: 1143-50); and disorders of abnormal movement such as restless leg syndrome (RLS) and periodic limb movement in sleep (PLMS) (see, for example WO 02/055083, WO 05/044245, WO 06/132275 and Happe S. et al., *Neuropsychobiology.* 2003, 48, 82-6). Adenosine $A_{2a}$ antagonists are disclosed in US 2007037033 as useful agents for the treatment of amyotrophic lateral sclerosis. WO 01/058241 discloses the treatment of cirrhosis, fibrosis and fatty liver by employing adenosine $A_{2a}$ antagonists. WO 06/009698 describes adenosine $A_{2a}$ antagonists as useful for the mitigation of addictive behaviour. It has been recently demonstrated that adenosine $A_{2a}$ antagonists may be employed for the treatment and prevention of dermal fibrosis in diseases such as scleroderma (Chan et al. *Arthritis & Rheumatism,* 2006, 54(8), 2632-2642).

In addition, $A_{2a}$ antagonists may have therapeutic potential as neuroprotectants (Stone T W. et al., *Drag. Dev. Res.* 2001, 52, 323-330), in the treatment of sleep disorders (Dunwiddie T V et al., *Ann. Rev. Neurosci.* 2001, 24, 31-55) and migraine (Kurokowa et al., 2009. Program No. 714.4/8101, 2009 Neuroscience Meeting Planner. Chicago, Ill.: Society for Neuroscience).

Therapeutic uses for compounds that target $A_1$ receptors are diverse (see, for example *Nature Reviews Drug Discovery* 5, 2006, 247-264: *Journal of Pharmacology and Experi-* mental Therapeutics 323(2), 2007, 708 to 719; British Journal of Pharmacology, 155, 2008, 475 to 486; Journal of the American College of Cardiology 50(16), 2007, 1551-1560; Pharmacology and Therapeutics 123, 2009, 105 to 116).

Adenosine $A_1$ receptors are expressed in the kidney and mediate adenosine's effects on both proximal tubular reabsorption and tubular glomerular feedback. Therefore blockade of the $A_1$ receptor will lead to inhibition of proximal tubular sodium reabsorption which could be beneficial in diseases such as congestive heart failure, chronic renal disease and cirrhosis (Gellai et al., 1998, J Pharmacol Exp Ther 286, 1191-1196; J Am Coil Cardiol, 2007; 50:1551-1560). Compounds being developed as adenosine $A_1$ receptor antagonists for acute renal failure include rolofylline by Merck and derenofylline by Astellas. Adenosine $A_1$ receptor antagonists may be employed to treat oedema (Satoh et al., 2000. Gastroenterol, 119(3):829-36), macular degeneration and cirrhosis.

While compounds with significant biological activity at multiple adenosine receptor subtypes may be therapeutically useful, they may cause unwanted side-effects. For example (as described in Gessi S et al. Pharmacol. Ther. 117(1), 2008, 123-140), adenosine $A_3$ receptor antagonism has various effects, such as an increased propensity for tissue damage following ischaemia (e.g. in the CNS, heart, kidney, lung and eye), increased reperfusion injury, increased neurodegeneration in response to hypoxia, potentially deleterious effects on motor function or pain thresholds, immunosuppression or immunostimulation.

A number of compounds are currently being developed as $A_{2a}$ receptor antagonists for the treatment of Parkinson's Disease. These compounds include KW6002 (istradefylline, 8-[(E)-2-(3,4-dimethoxyphenyl)vinyl]-1,3-diethyl-7-methyl-3,7-dihydro-1H-purine-2,6-dione) by Kyowa Hakko Kogyo, SCH-420814 (preladenant, 2-(furan-2-yl)-7-[2-[4-[4-(2-methoxyethoxy)phenyl]piperazin-1-yl]ethyl]-7H-pyrazolo[4,3-e][1,2,4]-triazolo[1,5-c]pyrimidin-5-amine) by Schering-Plough/Merck, BIIB014 by Biogen Idec, Lu AA47070 by Lundbeck, ST-1535 by Sigma-Tau Farm Riunite SpA. SYN 115 by Synosia, and ASP 5854 by Astellas.

However, the compounds mentioned above suffer from a number of drawbacks, such as low solubility (KW6002, SCH-420814, BIIB014 and Lu AA47070), light sensitivity (KW6002), low selectivity (Lu AA47070 and ASP 5854), potential toxicity due to the inclusion of known potential toxicophores (SCH-420814 and BIIB014) and limited efficacy in vivo (KW6002).

International patent applications WO 92/02513, WO 00/66568, WO 03/077921, WO 2005/117883, WO 2006/051311, WO 2006/113704 and WO 2009/090431, US patent application publications US 2004/0102436, US 2004/0229873, US 2007/0135437, European patent publication No. 1 400 518 and GB patent No. 1,604,085 disclose 1,2,4-triazine compounds with varying biological activities. There is no suggestion or disclosure in the documents above of 1,2,4-triazine compounds bearing the required substitution pattern required herein, or that any of the compounds disclosed in the documents above might be useful as $A_1$ or, particularly, $A_{2a}$ receptor antagonists.

U.S. Pat. No. 4,008,232 and French patent No. 2,869,906 disclose a number of 1,2,4-triazine compounds for use in the treatment of inflammation and as sun-block agents, respectively. Doig et al., Journal of Chromatography 1991 554(1-2), 181-189 discloses a metabolite of the anticonvulsant agent Lamotrigine. A number of 1,2,4-triazine compounds with anticonvulsant activity are disclosed in Mallikarjuna et al. J Zhejian Univ Sci B 2007 8(7), 526-532. A number of 1,2,4-triazine compounds with antiviral activity are disclosed in Davidson et al. Journal of Pharmaceutical Sciences 67(5), 1978, 737-739. A number of 1,2,4-triazine compounds are disclosed in Eid at al., Indian Journal of Chemistry, Section B 1990 29B(5) 435-439, Zou et al., Chinese Journal of Chemistry 1998 16(1), 58-64, Lu et al., Youji Huaxue 1992 12(6), 605-607, Lu et al., Organic Preparations and Procedures International 1992 24(3), 358-362 and Konno et al. Heterocycles 19(10), 1982, 1865-8. There is no suggestion or disclosure that any of the above compounds might be useful as $A_1$ or, particularly, $A_{2a}$ receptor antagonists.

We have now discovered, surprisingly, that certain 1,2,4-triazine compounds bearing certain substituents are useful as $A_1$ and, particularly, $A_{2a}$ receptor antagonists.

Thus, according to the first aspect of the invention, there is provided a compound of formula I for use in the treatment of a condition or disorder ameliorated by the inhibition of the $A_1$ or, particularly, the $A_{2a}$ receptor, wherein the compound of formula I has the structure

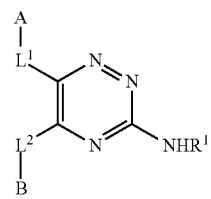

wherein:

$R^1$ represents H or $C_{1-6}$ alkyl, which latter group may be optionally substituted by one or more of halo. $OR^{2a}$ or $NR^{2b}R^{2c}$;

$L^1$ and $L^2$ independently represent CH=CH, a direct bond, O, $NR^{2a}$, $S(O)_p$, $CH_2$ or C(O);

$R^{2a}$, $R^{2b}$, $R^{2c}$ and $R^{3a}$ independently represent H or $C_{1-6}$ alkyl, which latter group is optionally substituted by one or more halo atoms;

A represents $Cy^1$ or $Het^A$;

$Cy^1$ represents a 5- to 14-membered aromatic, fully saturated or partially unsaturated carbocyclic ring system comprising one, two or three rings, which $Cy^1$ group is optionally substituted by one or more $R^{4a}$ substituents:

$Het^A$ represents a 5- to 14-membered heterocyclic group that may be aromatic, fully saturated or partially unsaturated, and which contains one or more heteroatoms selected from O, S and N, which heterocyclic group may comprise one, two or three rings and which $Het^A$ group is optionally substituted by one or more $R^{4b}$ substituents;

B represents a $Cy^2$ or $Het^B$;

$Cy^2$ represents a 3- to 10-membered aromatic, fully saturated or partially unsaturated carbocyclic ring system comprising one or two rings, which $Cy^2$ group is optionally substituted by one or more $R^{4c}$ substituents;

$Het^B$ represents a 3- to 10-membered heterocyclic group that may be aromatic, fully saturated or partially unsaturated, and which contains one or more heteroatoms selected from O, S and N, which heterocyclic group may comprise one or two rings and which Het$^B$ group is optionally substituted by one or more R$^{4d}$ substituents;

R$^{4a}$ to R$^{4d}$ represent, independently at each occurrence,
(a) halo,
(b) CN,
(c) C$_{1-12}$ alkyl, C$_{2-12}$ alkenyl, C$_{2-12}$ alkynyl, which latter three groups are optionally substituted by one or more substituents selected from halo, nitro, CN, C$_{1-6}$ alkyl, C$_{2-6}$ alkenyl, C$_{2-8}$ alkynyl (which latter three groups are optionally substituted by one or more substituents selected from OH, =O, halo, C$_{1-4}$ alkyl and C$_{1-4}$ alkoxy), OR$^{5a}$, S(O)$_q$R$^{5b}$, S(O)$_2$N(R$^{5c}$)(R$^{5d}$), N(R$^{5e}$)S(O)$_2$R$^{5f}$, N(R$^{5g}$)(R$^{5h}$), B$^1$—C(G$^1$)-B$^2$—R$^{5i}$, aryl and Het$^1$,
(d) Cy$^3$, which Cy$^5$ group is optionally substituted by one or more substituents selected from halo, nitro, CN, C$_{1-6}$ alkyl, C$_{2-6}$ alkenyl, C$_{2-6}$ alkynyl (which latter three groups are optionally substituted by one or more substituents selected from OH, =O, halo, C$_{1-4}$ alkyl and C$_{1-4}$ alkoxy), OR$^{6a}$, S(O)R$^{6b}$, S(O)$_2$N(R$^{6c}$)(R$^{6d}$), N(R$^{6e}$)S(O)$_2$R$^{6f}$, N(R$^{6g}$)(R$^{6h}$), B$^3$—C(G$^1$)-B$^4$—R$^{6i}$, aryl and Het$^2$,
(e) Het$^a$, which Het$^a$ group is optionally substituted by one or more substituents selected from halo, nitro, CN, C$_{1-6}$ alkyl, C$_{2-6}$ alkenyl, C$_{2-4}$ alkynyl (which latter three groups are optionally substituted by one or more substituents selected from OH, =O, halo, C$_{1-4}$ alkyl and C$_{1-4}$ alkoxy), OR$^{7a}$, S(O)$_q$R$^{7b}$, S(O)$_2$N(R$^{7c}$)(R$^{7d}$), N(R$^{7e}$)S(O)$_2$R$^{7f}$, N(R$^{7g}$)(R$^{7h}$), B$^5$—C(G$^1$)-B$^6$—R$^{7i}$, aryl and Het$^3$,
(f) OR$^8$,
(g) S(O)$_r$R$^{9a}$,
(h) S(O)$_2$N(R$^{9b}$)(R$^{9c}$),
(i) N(R$^{9d}$)S(O)$_2$R$^{9e}$,
(j) N(R$^{9f}$)(R$^{9g}$),
(k) B$^7$—C(G$^1$)-B—R$^{9h}$.
(l) =O,
(m) =S,
or when two R$^{4a}$, R$^{4b}$, R$^{4c}$ or R$^{4d}$ groups are attached to the same carbon atom in a non-aromatic portion of a Cy$^1$, Het$^A$, Cy$^2$ or Het$^B$ group, they may form, together with the carbon atom to which they are attached, a saturated or unsaturated 3 to 6-membered ring, which ring optionally contains one to three heteroatoms selected from O, S and N, and which ring is optionally substituted by one or more R$^{9i}$ substituents;

G$^1$ represents, independently at each occurrence, O, S or NR$^{5i}$;

R$^8$ represents, independently at each occurrence,
H,
Cy$^3$, Het$^a$, aryl$^a$, C$_{1-8}$ alkyl, C$_{2-8}$ alkenyl, C$_{2-8}$ alkynyl, C$_{3-5}$ cycloalkyl, which latter seven groups are optionally substituted by one or more substituents selected from halo, —CN, C$_{3-6}$ cycloalkyl, aryl, Het$^4$, —C(O)OR$^{10}$, —C(O)R$^{11}$, —C(O)N(R$^{N1}$)(R$^{N2}$), S(O)$_r$R$^{9aa}$, S(O)$_2$N(R$^{9ba}$)(R$^{9ca}$), N(R$^{da}$)S(O)$_2$R$^{9ea}$ and N(R$^{9fa}$)(R$^{9ga}$);

Cy$^3$ represents, independently at each occurrence, a 3- to 6-membered aromatic, fully saturated or partially unsaturated carbocyclic ring;

Het$^a$ represents, independently at each occurrence, a 3- to 6-membered heterocyclic ring that may be aromatic, fully saturated or partially unsaturated and which contains one or more heteroatoms selected from O, S and N;

R$^{10}$ and R$^{11}$ independently represent
(a) H,
(b) C$_{1-6}$ alkyl optionally substituted by one or more substituents selected from halo, aryl, —N(R$^{N3}$)(R$^{N4}$) and —OR$^a$,
(c) aryl or (d) C$_{3-7}$ cycloalkyl (which group is optionally substituted by one or more substituents selected from OH, =O, halo, C$_{1-4}$ alkyl and C$_{1-4}$ alkoxy);

B$^1$ to B$^8$ independently represent, at each occurrence, a direct bond, O, S or N(R$^{N3}$);

each aryl$^a$ independently represents a C$_{6-14}$ carbocyclic aromatic group, which group may comprise one, two or three rings;

each aryl independently represents a C$_{6-14}$ carbocyclic aromatic group, which group may comprise one, two or three rings and may be substituted by one or more substituents selected from
halo,
C$_{1-6}$ alkyl, which latter group is optionally substituted by one or more substituents selected from halo, —N(R$^{N4}$)(R$^{N5}$) and —OR$^a$, and —OR$^a$;

Het$^1$ to Het$^4$ independently represent 4- to 14-membered heterocyclic groups containing one or more heteroatoms selected from O, S and N, which heterocyclic groups may comprise one, two or three rings and may be substituted by one or more substituents selected from
halo,
C$_{1-6}$ alkyl, which latter group is optionally substituted by one or more substituents selected from halo, —N(R$^{N6}$)(R$^{N7}$) and —OR$^a$, and —OR$^a$;

R$^{N1}$ to R$^{N7}$ independently represent
H,
C$_{1-6}$ alkyl or C$_{3-6}$ cycloalkyl, which latter two groups are optionally substituted by one or more substituents selected from halo and —OR$^a$;

R$^a$ represents, independently at each occurrence,
(a) H;
(b) C$_{1-12}$ alkyl, C$_{2-12}$ alkenyl, C$_{2-12}$ alkynyl, C$_{3-12}$ cycloalkyl, C$_{4-12}$ cycloalkenyl, which latter five groups are optionally substituted by one or more substituents selected from halo, nitro, CN, C$_{1-6}$ alkyl, C$_{2-6}$ alkenyl, C$_{2-6}$ alkynyl, C$_{3-8}$ cycloalkyl (which latter four groups are optionally substituted by one or more substituents selected from OH, =O, halo, C$_{1-4}$ alkyl and C$_{1-4}$ alkoxy), OR$^{12a}$, S(O)$_q$R$^{12b}$, S(O)$_2$N(R$^{12c}$)(R$^{12d}$), N(R$^{12e}$)S(O)$_2$R$^{12f}$, N(R$^{12g}$)(R$^{12h}$), B$^9$—C(G$^2$)-B$^{10}$—R$^{12i}$, aryl$^1$ and Het$^b$, and which C$_{3-12}$ cycloalkyl or C$_{4-12}$ cycloalkenyl groups may additionally be substituted by =O.
(c) S(O)$_r$R$^{13a}$,
(d) S(O)$_2$N(R$^{13b}$)(R$^{13c}$) or
(e) C(O)—B$^{11}$—R$^{13d}$;

R$^{5a}$ to R$^{5j}$, R$^{6a}$ to R$^{6i}$, R$^{7a}$ to R$^{7i}$, R$^{9a}$ to R$^{9i}$, R$^{9aa}$ to R$^{9ga}$, R$^{12a}$ to R$^{12i}$ and R$^{13a}$ to R$^{13d}$ independently represent, at each occurrence,
(a) H,
(b) C$_{1-10}$ alkyl, C$_{2-10}$ alkenyl, C$_{2-10}$ alkynyl which latter three groups are optionally substituted by one or more substituents selected from halo, nitro, CN, C$_{1-6}$ alkyl, C$_{2-6}$ alkenyl, C$_{2-6}$ alkynyl, C$_{3-6}$ cycloalkyl (which latter three groups are optionally substituted by one or more substituents selected from OH, =O, halo, C$_{1-4}$ alkyl and C$_{1-4}$ alkoxy), OR$^{5aa}$, S(O)$_q$R$^{5ab}$, S(O)$_2$N(R$^{5ac}$)(R$^{5ad}$), N(R$^{5ae}$)S(O)$_2$R$^{5af}$, N(R$^{5ag}$)(R$^{5ah}$), B$^{12}$—C(G$^2$)-B$^{13}$—R$^{5ai}$, aryl$^1$ and Het$^c$;
(c) C$_{3-10}$ cycloalkyl, or C$_{4-10}$ cycloalkenyl (which latter two groups are optionally substituted by one or more substituents selected from halo, OH, =O, C$_{1-6}$ alkyl and C$_{1-6}$ alkoxy),
(d) Het$^d$;

$G^2$ represents, independently at each occurrence, O, S, or $NR^{5aj}$;

$R^{5aa}$ to $R^{5aj}$ independently represent at each occurrence,
(a) H,
(b) $C_{1-4}$ alkyl, $C_{2-4}$ alkenyl, $C_{2-4}$ alkynyl which latter three groups are optionally substituted by one or more substituents selected from halo, nitro, CN, $C_{1-4}$ alkyl, $C_{2-4}$ alkenyl, $C_{2-4}$ alkynyl (which latter three groups are optionally substituted by one or more substituents selected from OH, =O, halo, $C_{1-4}$ alkyl and $C_{1-4}$ alkoxy),
(c) $C_{3-6}$ cycloalkyl, or $C_{4-6}$ cycloalkenyl (which latter two groups are optionally substituted by one or more substituents selected from halo, OH, =O, $C_{1-4}$ alkyl and $C_{1-4}$ alkoxy),
(d) $Het^e$, or $R^{5ag}$ and $R^{5ah}$ may represent, together with the nitrogen atom to which they are attached, a 3- to 10-membered heterocyclic ring that may be aromatic, fully saturated or partially unsaturated and which may additionally contain one or more heteroatoms selected from O, S and N, which heterocyclic ring is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy);

$B^9$ to $B^{13}$ independently represent a direct bond, O, S or $N(R^{N8})$;

$aryl^1$ represents, independently at each occurrence, a $C_{6-10}$ carbocyclic aromatic group, which group may comprise one or two rings and may be substituted by one or more substituents selected from
halo,
$C_{1-6}$ alkyl, which latter group is optionally substituted by one or more substituents selected from halo, —$N(R^{N10})(R^{N11})$ and $C_{1-6}$ alkoxy (which latter substituent is optionally substituted by one or more halo atoms), and
$C_{1-6}$ alkoxy (which latter substituent is optionally substituted by one or more halo atoms);

$R^{N8}$, $R^{N10}$ and $R^{N11}$ independently represent
H,
$C_{1-6}$ alkyl or $C_{3-6}$ cycloalkyl, which latter two groups are optionally substituted by one or more halo atoms;

$Het^b$ represents a 5- or 6-membered that may be aromatic, fully saturated or partially unsaturated and which contains one or more heteroatoms selected from O, S and N, which heterocyclic group may be substituted by one or more substituents selected from halo, =O and $C_{1-6}$ alkyl;

$Het^c$ to $Het^e$ independently represent, a 3- to 6-membered heterocyclic ring that may be aromatic, fully saturated or partially unsaturated and which contains one or more heteroatoms selected from O, S and N, which $Het^c$ to $Het^e$ groups are optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy);

p, q and r independently represent at each occurrence 0, 1 or 2; and unless otherwise specified alkyl, alkenyl, alkynyl, cycloalkyl and the alkyl part of alkoxy groups may be substituted by one or more halo atoms.

References herein (in any aspect or embodiment of the invention) to compounds of formula I includes references to such compounds per se, to tautomers of such compounds, as well as to pharmaceutically acceptable salts or solvates, or pharmaceutically functional derivatives of such compounds.

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic. (+)-(1S)-camphor-10-sulfonic, capric, caproic, caprylic, cinnamic, citric, cyclamic, dodecylsulfuric, ethane-1,2-disulfonic, ethanesufonic, 2-hydroxyethanesufonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic acids; and from metals such as sodium, magnesium, or preferably, potassium and calcium.

As mentioned above, also encompassed by formula I are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al.,

*Solid-State Chemistry of Drugs*, Second Edition, published by SSCI, Inc of West Lafayette, Ind., USA, 1999. ISBN 0-967-06710-3.

"Pharmaceutically functional derivatives" of compounds of formula I as defined herein includes ester derivatives and/or derivatives that have, or provide for, the same biological function and/or activity as any relevant compound of the invention. Thus, for the purposes of this invention, the term also includes prodrugs of compounds of formula I.

The term "prodrug" of a relevant compound of formula I includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds of formula I may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of formula I wherein a hydroxyl, amino, sulfhydryl, carboxyl or carbonyl group in a compound of formula I is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of formula I, as well as pharmaceutically acceptable salts, solvates and pharmaceutically functional derivatives of such compounds are, for the sake of brevity, hereinafter referred to together as the "compounds of formula I".

Compounds of formula I may contain double bonds and may thus exist as E (entgegen) and Z (zusammen) geometric isomers about each individual double bond. All such isomers and mixtures thereof are included within the scope of the invention.

Compounds of formula I may exist as regioisomers and may also exhibit tautomerism. All tautomeric forms and mixtures thereof are included within the scope of the invention. For example, the following tautomers are included within the scope of the invention:

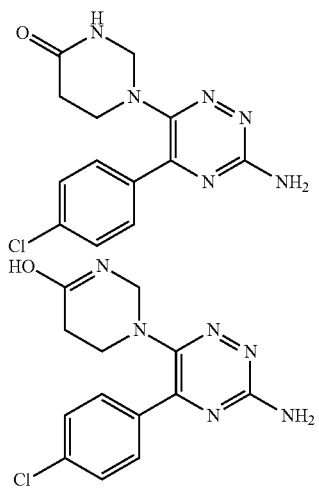

Compounds of formula I may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

For the avoidance of doubt, compounds of formula I may contain the stated atoms in any of their isotopic forms. In this respect, embodiments of the invention that may be mentioned include those in which:
(a) the compound of formula I is not isotopically enriched or labelled with respect to any atoms of the compound; and
(b) the compound of formula I is isotopically enriched or labelled with respect to one or more atoms of the compound.

The compound for use mentioned in the above-mentioned aspect of the invention may be utilised in a method of medical treatment. Thus, according to further aspects of the invention, there is provided:
(i) the use of a compound formula I for the manufacture of a medicament for the treatment of a condition or disorder ameliorated by inhibition of the $A_1$ or, particularly, the $A_{2a}$ receptor; and
(ii) a method of treatment of a disorder or condition ameliorated by antagonising the $A_1$ or, particularly, the $A_{2a}$ receptor, which method comprises the administration of an effective amount of a compound of formula I to a patient in need of such treatment.

The term "disorder or condition ameliorated by the inhibition of the $A_1$ or, particularly, the $A_{2a}$ receptor" will be understood by those skilled in the art to include: heart failure (such as acute decompensated heart failure and congestive heart failure); kidney failure (e.g. caused by heart failure); oedema; cancer (such as prostate, rectal, renal, ovarian, endometrial, thyroid, pancreatic, particularly breast, colon, bladder, brain, glia, melanoma, pineal gland and, more particularly, lung cancer (e.g. Lewis lung carcinoma)); diabetes; diarrhea; macular degeneration (such as macular degeneration caused by angiogenesis (e.g. retinal angiogenesis)); or, particularly (e.g. for disorders or conditions ameliorated by the inhibition of the $A_{2a}$ receptor), a disease of the central nervous system such as depression, a cognitive function disease, a neurodegenerative disease (such as Parkinson's disease, Huntington's disease, Alzheimer's disease, amyotrophic lateral sclerosis) and psychoses; an attention related disorder (such as attention deficit disorder (ADD) and attention deficit hyperactivity disorder (ADHD)); extra pyramidal syndrome (e.g. dystonia, akathisia, pseudoparkinsonism and tardive dyskinesia); a disorder of abnormal movement (such as restless leg syndrome (RLS) and periodic limb movement in sleep (PLMS)); cirrhosis; liver fibrosis; fatty liver; dermal fibrosis (e.g. in diseases such as scleroderma); a sleep disorder; stroke; brain injury and neuroinflammation (e.g. migraine or any disorder or condition caused by ischemia, stroke, head injury or CNS inflammation); addictive behaviour.

Thus, further aspects of the invention relate to the following.

(a) A compound of formula I, as hereinbefore defined, for use in the treatment of a condition or disorder selected from heart failure (such as acute decompensated heart failure and congestive heart failure); kidney failure (e.g. caused by heart failure); oedema; cancer (such as prostate, rectal, renal, ovarian, endometrial, thyroid, pancreatic, particularly breast, colon, bladder, brain, glia, melanoma, pineal gland and, more particularly, lung cancer (e.g. Lewis lung carcinoma)); diabetes; diarrhea; macular degeneration (such as macular degeneration caused by angiogenesis (e.g. retinal angiogenesis)); or, particularly (e.g. for disorders or conditions ameliorated by the inhibition of the $A_{2a}$ receptor), a disease of the central nervous system such as depression, a cognitive function disease, a neurodegenerative disease (such as Parkinson's disease, Huntington's disease, Alzheimer's disease, amyotrophic lateral sclerosis) and psychoses; an attention related disorder (such as attention deficit disorder (ADD) and attention deficit hyperactivity disorder (ADHD)); extra pyramidal syndrome (e.g. dystonia, akathisia, pseudoparkinsonism and tardive dyskinesia): a disorder of abnormal movement (such as restless leg syndrome (RLS) and periodic limb movement in sleep (PLMS)); cirrhosis; liver fibrosis; fatty liver; dermal fibrosis (e.g. in diseases such as scleroderma); a sleep disorder; stroke; brain injury and neuroinflammation (e.g. migraine or any disorder or condition caused by ischemia, stroke, head injury or CNS inflammation): addictive behaviour.

(b) Use of a compound of formula I, as hereinbefore defined, for the preparation of a medicament for the treatment of a condition or disorder selected from heart failure (such as acute decompensated heart failure and congestive heart failure); kidney failure (e.g. caused by heart failure); oedema; cancer (such as prostate, rectal, renal, ovarian, endometrial, thyroid, pancreatic, particularly breast, colon, bladder, brain, glia, melanoma, pineal gland and, more particularly, lung cancer (e.g. Lewis lung carcinoma)); diabetes; diarrhea; macular degeneration caused by angiogenesis (e.g. retinal angiogenesis)); or, particularly (e.g. for disorders or conditions ameliorated by the inhibition of the $A_{2a}$ receptor), a disease of the central nervous system such as depression, a cognitive function disease, a neurodegenerative disease (such as Parkinson's disease, Huntington's disease, Alzheimer's disease, amyotrophic lateral sclerosis) and psychoses; an attention related disorder (such as attention deficit disorder (ADD) and attention deficit hyperactivity disorder (ADHD)); extra pyramidal syndrome (e.g. dystonia, akathisia, pseudoparkinsonism and tardive dyskinesia); a disorder of abnormal movement (such as restless leg syndrome (RLS) and periodic limb movement in sleep (PLMS)); cirrhosis; liver fibrosis; fatty liver; dermal fibrosis (e.g. in diseases such as scleroderma); a sleep disorder; stroke; brain injury and neuroinflammation (e.g. migraine or any disorder or condition caused by ischemia, stroke, head injury or CNS inflammation); addictive behaviour.

(c) A method of treatment of a disorder or condition selected from heart failure (such as acute decompensated heart failure and congestive heart failure); kidney failure (e.g. caused by heart failure); oedema; cancer (such as prostate, rectal, renal, ovarian, endometrial, thyroid, pancreatic, particularly breast, colon, bladder, brain, glia, melanoma, pineal gland and, more particularly, lung cancer (e.g. Lewis lung carcinoma)); diabetes; diarrhea; macular degeneration (such as macular degeneration caused by angiogenesis (e.g. retinal angiogenesis)); or, particularly (e.g. for disorders or conditions ameliorated by the inhibition of the $A_{2a}$ receptor), a disease of the central nervous system such as depression, a cognitive function disease, a neurodegenerative disease (such as Parkinson's disease, Huntington's disease, Alzheimer's disease, amyotrophic lateral sclerosis) and psychoses; an attention related disorder (such as attention deficit disorder (ADD) and attention deficit hyperactivity disorder (ADHD)); extra pyramidal syndrome (e.g. dystonia, akathisia, pseudoparkinsonism and tardive dyskinesia); a disorder of abnormal movement (such as restless leg syndrome (RLS) and periodic limb movement in sleep (PLMS)); cirrhosis; liver fibrosis; fatty liver; dermal fibrosis (e.g. in diseases such as scleroderma); a sleep disorder: stroke; brain injury and neuroinflammation (e.g. migraine or any disorder or condition caused by ischemia, stroke, head injury or CNS inflammation); addictive behaviour, which method comprises the administration of an effective amount of a compound of formula I, as hereinbefore defined.

Particular disorders or conditions that may be mentioned in relation to the aspects of the invention described hereinbefore include addictive behaviour, ADHD and, particularly, neurodegenerative disease (e.g. Alzheimer's, Huntington's, and, particularly, Parkinson's Disease).

Embodiments of the invention that may be mentioned include those in which the compounds of formula I selectively inhibit the $A_1$ and $A_{2a}$ receptor subtypes.

When used herein in relation to inhibition of the $A_1$ or $A_{2a}$ receptor, the terms "selective" and "selectivity" includes references to the binding of a compound to the $A_1$ or, more particularly, $A_{2a}$ receptor with an $IC_{50}$ value that is at least 10-fold lower (e.g. at least 20-, 50-, 100-, 500- or 1000-fold lower) than the $IC_{50}$ value determined for the binding of the same compound to the $A_3$, receptor sub-type at the same temperature (e.g. room temperature, such as 298 K).

Embodiments of the invention that may also be mentioned include those in which the compounds of formula I are selective inhibitors of the $A_{2a}$ receptor.

When used herein in relation to inhibition of the $A_{2a}$ receptor, the terms "selective" and "selectivity" includes references to the binding of a compound to the $A_{2a}$ receptor with an $IC_{50}$ value that is at least 10-fold lower (e.g. at least 20-, 50-, 100-, 500- or 1000-fold lower) than the $IC_{50}$ value determined for the binding of the same compound to another adenosine receptor subtype (e.g. the $A_{2b}$, particularly $A_1$, or, more particularly, $A_3$, receptor sub-type) at the same temperature (e.g. room temperature, such as 298 K). Selectivity for the $A_{2a}$ receptor can be over one other adenosine receptor subtype but, in certain embodiments of the invention, is over two or more (e.g. all other) adenosine receptor subtypes.

Antagonising the $A_{2a}$ receptor may have neuroprotective effects. Thus, according to further aspects of the invention there are provided:

(i) a compound of formula I for use as a neuroprotectant;
(ii) the use of a compound of formula I for the manufacture of a medicament for use as a neuroprotectant; and
(iii) a method of mitigating damage to brain neurons caused by a neurodegenerative disease (such as Parkinson's disease, Huntington's disease, Alzheimer's disease or amyotrophic lateral sclerosis), stroke or other cerebral trauma, neurotoxins (e.g. mercury and compounds thereof, lead and compounds thereof, organic phosphates and nitrogen mustards), CNS infections (e.g. meningitis, encephalitis, poliomyelitis, tuberculosis, toxoplasmosis, neurosyphilis) or drug use (e.g. cocaine), which method comprises the administration of an effective amount of a compound of formula I to a patient at risk of damage to brain neurons from neurodegenerative disease, stroke or other cerebral trauma, neurotoxins, CNS infections or drug use.

References herein to patients at risk of damage to brain neurons from neurodegenerative disease, stroke or other cerebral trauma include references to patients who have been determined by clinical assessment to have a higher than average risk (as determined, for example, by comparison to normal individuals of the same age) of developing a neurodegenerative disease (e.g. Parkinson's disease, Huntington's disease. Alzheimer's disease or amyotrophic lateral sclerosis) or of having a stroke.

Antagonising the $A_1$ receptor may have effects on kidney function. Thus, according to further aspects of the invention there are provided:
(i) a compound of formula I for use in mitigating kidney damage caused by acute renal failure, oedema, heart failure, chronic renal disease and/or cirrhosis;
(ii) the use of a compound of formula I for the manufacture of a medicament for mitigating kidney damage caused by acute renal failure, oedema, heart failure, chronic renal disease and/or cirrhosis; and
(iii) a method of mitigating kidney damage caused by acute renal failure, oedema, heart failure, chronic renal disease and/or cirrhosis, which method comprises the administration of an effective amount of a compound of formula I to a patient at risk of damage to kidney function by acute renal failure, congestive heart failure, chronic renal disease or cirrhosis.

References herein to kidney damage include, in particular, kidney damage caused by acute renal failure.

References herein to patients at risk of damage to kidney function by acute renal failure, heart failure, chronic renal disease or cirrhosis include references to patients who have been determined by clinical assessment to have a higher than average risk (as determined, for example, by comparison to normal individuals of the same age) of developing acute renal failure, heart failure, chronic renal disease or cirrhosis.

For the avoidance of doubt, in the context of the present invention, the term "treatment" includes references to therapeutic or palliative treatment of patients in need of such treatment, as well as to the prophylactic treatment and/or diagnosis of patients which are susceptible to the relevant disease states.

The terms "patient" and "patients" include references to mammalian (e.g. human) patients.

The term "effective amount" refers to an amount of a compound, which confers a therapeutic effect on the treated patient (e.g. sufficient to treat or prevent the disease). The effect may be objective (i.e. measurable by some test or marker) or subjective (i.e. the subject gives an indication of or feels an effect).

The term "halo", when used herein, includes references to fluoro, chloro, bromo and iodo.

Unless otherwise stated, the term "carbocyclic" when used herein in connection with groups $Cy^1$ and $Cy^2$ includes references to carbocyclic groups (e.g. $C_{5-6}$ carbocyclic groups) that are mono-, bi- or tricyclic and which may be may be fully saturated, partly unsaturated or wholly aromatic in character. For example, $Cy^1$ and $Cy^2$ groups may be selected from the group comprising of cyclobutyl, cyclobutenyl, cyclopropyl, cydopropenyl, particularly cyclopentyl, cyclopentenyl, (1Z,2Z,4Z,6Z,8Z)-cyclodecapentaenyl, more particularly, cyclohexyl, cyclohexenyl, indanyl, indenyl, napthalenyl (e.g. 1,2,3,4-tetrahydronapthyl), and, yet more particularly, phenyl). The point of attachment of carbocyclic groups may be via any atom of the ring system.

Unless otherwise stated herein, the term "heterocyclic", when used herein in connection with groups $Het^A$ and $Het^B$ includes references to heterocyclic groups which may be fully saturated, partly unsaturated or wholly aromatic in character.

Thus $Het^A$ and $Het^B$ represent a 5- to 14- or a 3- to 10-membered heterocyclic group, respectively, that may be aromatic, fully saturated or partially unsaturated, and which contains one or more heteroatoms selected from O, S and N, which heterocyclic groups may comprise one, two or three rings and which $Het^A$ or $Het^B$ group is optionally substituted by one or more $R^{4b}$ or $R^{4d}$ substituents, respectively.

The heterocyclic group (e.g. $Het^A$ or $Het^B$) may contain up to 5 heteroatom ring members selected from O, N and S, and more particularly up to 4 heteroatom ring members. For example, the heterocyclic group may contain 1, 2 or 3 heteroatom ring members.

In one embodiment, $Het^A$ and $Het^B$ may each represent a monocyclic, bicyclic or tricyclic 5- to 14- or 3- to 10-membered heterocyclic group, respectively, containing 1, 2, 3 or 4 heteroatom ring members selected from O, N and S. Within this subset, $Het^A$ or $Het^B$ (where appropriate) may be selected, for example, from (i) monocyclic heterocyclic groups of 5 to 7 ring members containing 1, 2, 3 or 4 heteroatom ring members selected from O, N and S; (ii) 6.5 fused bicyclic heterocyclic groups of 9 ring members containing 1, 2, 3 or 4 heteroatom ring members selected from O, N and S; (iii) 6.6 fused bicyclic heterocyclic groups of 9 ring members containing 1, 2, 3 or 4 heteroatom ring members selected from O, N and S; (iv) 6.5.6 fused tricyclic heterocyclic groups of 13 ring members containing 1, 2, 3 or 4 heteroatom ring members selected from O, N and S; (v) 6.6.6 fused tricyclic heterocyclic groups of 14 ring members containing 1, 2, 3 or 4 heteroatom ring members selected from O, N and S; and (vi) bridged bicyclic heterocyclic groups of 7 or 8 ring members containing 1 or 2 heteroatom ring members selected from O, N and S.

By "bridged ring systems" is meant ring systems in which two rings share more than two atoms, see for example *Advanced Organic Chemistry*, by Jerry March, 4$^{th}$ Edition, Wiley Interscience, pages 131-133, 1992.

In another embodiment, $Het^A$ and $Het^B$ may be the same or different and each represents a monocyclic or bicyclic 5 to 10 membered heterocyclic group containing 1, 2, 3 or 4 heteroatom ring members selected from O, N and S. Within this subset, $Het^A$ or $Het^B$ may be selected, for example, from (i) monocyclic heterocyclic groups of 5 to 7 ring members containing 1, 2, 3 or 4 heteroatom ring members selected from O, N and S; (ii) 6.5 fused bicyclic heterocyclic groups of 9 ring members containing 1, 2, 3 or 4 heteroatom ring members selected from O, N and S; (iii) 6.6 fused bicyclic heterocyclic groups of 9 ring members containing 1, 2, 3 or 4 heteroatom ring members selected from O, N and S; and (vi) bridged bicyclic heterocyclic groups of 7 or 8 ring members containing 1 or 2 heteroatom ring members selected from O, N and S.

In each of the foregoing subsets of compounds, when $Het^A$ is a pyridonyl group, it may be other than a pyridin-2-one group (for example it may be a pyridin-4-one group).

For example, Het$^A$ and Het$^B$ may be selected from the group comprising of azepinyl, diazepinyl, dihydrofuranyl (e.g. 2,3-dihydrofuranyl, 2,5-dyhdrofuranyl), 4,5-dihydro-1H-maleimido, dioxolanyl, furanyl, furazanyl, hydantoinyl, imidazolyl, isothiazolyl, isoxazolidinyl, isoxazolyl, morpholinyl, oxadiazolyl, 1,2- or 1,3-oxazinanyl, oxazolidinyl, oxazolyl, piperazinyl, piperidinyl, pyrazolyl, pyridinyl, pyrimidinyl, pyrrolidinyl, pyrrolidinonyl, pyrrolinyl, pyrrolyl, sulfolanyl, 3-suffolenyl, tetrahydrofuranyl, tetrazolyl, thiadiazolyl, thiazolyl, thienyl, thiomorpholinyl, thiophenetyl, triazolyl, more particularly, dihydropyranyl (e.g. 3,4-dihydropyranyl, 3,6-dihydropyranyl), dioxanyl, hexahydropyrimidinyl, isobenzofuranyl, pyranyl, pyrazinyl, pyrazolyl, pyridazinyl, tetrahydropyranyl, 3,4,5,6-tetrahydropyridinyl, 1,2,3,4-tetrahydropyrimidinyl, 3,4,5,6-tetrahydropyrimidinyl, tetrahydrothiophenyl, tetramethylenesufoxide, thiazolidinyl, triazinanyl and the like. The point of attachment of carbocyclic groups may be via any atom of the ring system.

Definitions of A that may be mentioned therefore include indolinonyl, pyridazinonyl, octahydroisoquinolin-(1H)-yl, 2,2,6,6,-tetramethyl-3,6-dihydro-2H-pyran-4-yl, indolinonyl, 6-oxa-9-azaspiro[4.5]decanyl, octahydroisoquinolin-(1H)-yl, hexahydropyrrolo[1,2-a]pyrazin-(1H)-yl, pyridazinonyl or, particularly, cyclopentyl, cyclopentenyl, dihydrofuranyl (e.g 2,3-dihydrofuranyl, 2,5-dyhdrofuranyl), 4,5-dihydro-1H-maleimido, dioxolanyl, furanyl, furazanyl, hydantoinyl, imidazolyl, isoxazolyl, isoxazolidinyl, isothiaziolyl, oxadiazolyl, oxazolyl, pyrrolidinyl, pyrrolidinonyl, pyrazolyl, pyrrolinyl (e.g. 3-pyrrolinyl), pyrrolyl, sulfolanyl, 3-sulfolenyl, tetrahydrofuranyl, tetramethylenesulfoxide, tetrazolyl, thiadiazolyl, thiazolyl, thiazolidinyl, thienyl, triazolyl, or more particularly, acridinyl, 2-azabicyclo[4.1.0]heptanyl, 1-azabicyclo-[2.2.2]octanyl, azepinyl, benzimidazolyl, benzisothiazolyl, benzisoxazolyl, benzodioxanyl, benzodioxepanyl, benzodioxepinyl, benzodioxolyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzoxazolyl, benzopyrazolyl, benzo[e]pyrimidine, 2,1,3-benzothiadiazolyl, benzothiazolyl, benzothienyl, benzotriazolyl, carbazolyl, chromanyl, chromenyl, cinnolinyl, (1Z,2Z,4Z,6Z,8Z)-cyclodecapentaenyl, cyclohexyl, cyclohexenyl, decahydroisoquinolenyl, diazepinyl, 2,3-dihydrobenzimidazolyl, 2,3-dihydrobenzo[b]furanyl, 1,3-dihydrobenzo-[c]furanyl, 1,3-dihydro-2,1-benzisoxazolyl, dihydropyranyl (e.g. 3,4-dihydropyranyl, 3,6-dihydropyranyl), 2,3-dihydropyrrolo[2,3-b]pyridinyl, dioxolanyl, dioxanyl, hexahydropyrimidinyl, imidazo[1,2-a]pyridinyl, imidazo[1,5-a]pyridinyl, imidazo[2,3-b]thiazolyl, indanyl, indazolyl, indenyl, indolinyl, indolyl, isobenzofuranyl, isochromanyl, isoindolinyl, isoindolyl, isoquinolinyl, isothiochromanyl, ketopiperidinyl (e.g. 2-ketopiperidinyl, 3-ketopiperidinyl or 4-ketopiperidinyl), morpholinyl, napthalenyl (e.g. 1,2,3,4-tetrahydronaphthyl), naphtho[1,2-b]furanyl, naphthyridinyl (including 1,6-naphthyridinyl or, particularly, 1,5-naphthyridinyl and 1,8-naphthyridinyl), 1,2- or 1,3-oxazinanyl, oxazolidinyl, phenazinyl, phenothiazinyl, phenyl, phthalazinyl, piperidinyl, piperazinyl, pteridinyl, purinyl, pyranyl, pyrazinyl, pyridazinyl, pyridinyl (e.g. 2-pyridinyl, 3-pyridinyl, 4-pyridinyl), pyridinonyl (such as 5-1H-pyridin-2-onyl, particularly, 1-1H-pyridin-2-onyl, 3-1H-pyridin-2-onyl, 4-1H-pyridin-2-onyl, 6-1H-pyridin-2-onyl (wherein 1-, 3-, 4- and 6-refer to the point of attachment of the 1H-pyridin-2-onyl group to the rest of the molecule), or, particularly, 1H-pyridin-4-onyl), pyrimidinyl, pyrrolo[2,3-b]pyridinyl, pyrrolo[5,1-b]pyridinyl, pyrrolo[2,3-c]pyridinyl, quinazolinyl, quinolinyl, quinolizinyl, quinoxalinyl, 4,5,6,7-tetrahydrobenzimidazolyl, 4,5,6,7-tetrahydrobenzopyrazolyl, 5,6,7,8-tetrahydrobenzo-[e]pyrimidine, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrahydropyranyl, tetrahydropyridinyl (e.g 3,4,5,6-tetrahydropyridinyl), 1,2,3,4-tetrahydropyrimidinyl, 3,4,5,6-tetrahydropyrimidinyl, tetrahydrothiophenyl, thieno[5,1-c]pyridinyl, thiochromanyl, thiophenetyl, thiomorpholinyl, triazinanyl, 1,3,4-triazolo[2,3-b]pyrimidinyl, or xanthenyl and the like.

Further, definitions of B that may be mentioned include 2-azabicyclo[4.1.0]heptanyl, 1-azabicyclo-[2.2.2]octanyl, azepinyl, azetidinyl, aziridinyl, benzimidazolyl, benzisothiazolyl, benzisoxazolyl, benzodioxanyl, benzodioxolyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzoxazolyl, benzopyrazolyl, benzo[e]pyrimidine, 2,1,3-benzothiadiazolyl, benzothiazolyl, benzothienyl, benzotriazolyl, chromanyl, chromenyl, cinnolinyl, cyclohexyl, cyclohexenyl, cyclopentyl, cyclopentenyl, cyclopropyl, cyclopropenyl, decahydroisoquinolenyl, 2,3-dihydrobenzimidazolyl, diazepinyl, dihydrofuranyl (e.g. 2,3-dihydrofuranyl, 2,5-dyhdrofuranyl), 2,3-dihydrobenzo[b]furanyl, 1,3-dihydrobenzo-[c]furanyl, dihydropyranyl (e.g. 3,4-dihydropyranyl, 3,6-dihydropyranyl), 4,5-dihydro-1H-maleimido, 1,3-dihydro-2,1-benzisoxazolyl 2,3-dihydropyrrolo[2,3-b]pyridinyl, dioxanyl, dioxolanyl, furazanyl, hexahydropyrimidinyl, hydantoinyl, imidazolyl, imidazo[1,2-a]pyridinyl, imidazo[2,3-b]thiazolyl, indanyl, indenyl, indolinyl, isobenzofuranyl, isochromanyl, isoindolinyl, isoindolyl, isoquinolinyl, isothiazolyl, isothiochromanyl, isoxazolyl, isoxazolidinyl, ketopiperidinyl (e.g. 2-ketopiperidinyl, 3-ketopiperidinyl or 4-ketopiperidinyl), morpholinyl, napthalenyl (e.g. 1,2,3,4-tetrahydronaphthyl), naphthyridinyl (including 1,6-naphthyridinyl or, particularly, 1,5-naphthyridinyl and 1,8-naphthyridinyl), oxadiazolyl, 1,2- or 1,3-oxazinanyl, oxazolidinyl, oxazolyl, piperidinyl, piperazinyl, phthalazinyl, pteridinyl, purinyl, pyranyl, pyridazinyl, pyrrolidinonyl, pyrrolinyl (e.g. 3-pyrrolinyl), pyrrolyl, pyrrolo[2,3-b]pyridinyl, pyrrolo[5,1-b]pyridinyl, pyrrolo[2,3-c]pyridinyl, quinazolinyl, quinolinyl, quinolizinyl, quinoxalinyl, sulfolanyl, 3-sulfolenyl, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, tetrahydrothiophenyl, 4,5,6,7-tetrahydrobenzimidazolyl, 4,5,6,7-tetrahydrobenzopyrazolyl, 5,6,7,8-tetrahydrobenzo-[e]pyrimidine, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetramethylenesulfoxide, tetrazolyl, thiazolidinyl, thiazolyl, thienyl, thieno[5,1-c]pyridinyl, thiochromanyl, thiophenetyl, thiomorpholinyl, triazinanyl, triazoly, 1,3,4-triazolo[2,3-b]pyrimidinyl or more particularly, benzofuranyl, furanyl, indazolyl, indolyl, pyrazinyl, pyrazolyl, pyridinyl (e.g. 2-pyridinyl, 3-pyridinyl, 4-pyridinyl), pyridinonyl, pyrimidinyl, pyrrolo[1,5-a]pyridinyl, or phenyl and the like.

Unless otherwise stated, the term "aryl" when used herein includes $C_{6-14}$ (such as $C_{6-10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

$Het^1$ to $Het^4$ groups may be fully saturated, partly unsaturated, wholly aromatic or partly aromatic in character. Values of $Het^1$ to $Het^4$ groups that may be mentioned include acridinyl, 1-azabicyclo-[2.2.2]octanyl, azetidinyl, benzimidazolyl, benzisothiazolyl, benzisoxazolyl, benzodioxanyl, benzodioxepanyl, benzodioxepinyl, benzodioxolyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzoxazolyl, benzopyrazolyl, benzo[e]pyrimidine, 2,1,3-benzothiadiazolyl, benzothiazolyl, benzothienyl, benzotriazolyl, carbazolyl, chromanyl, chromenyl, cinnolinyl, 2,3-dihydrobenzimidazolyl, 2,3-dihydrobenzo[b]furanyl, 1,3-dihydrobenzo-[c]furanyl, 1,3-dihydro-2,1-benzisoxazolyl 2,3-dihydropyrrolo[2,3-b]pyridinyl, dioxanyl, furanyl, furazanyl, hexahydropyrimidinyl, hydantoinyl, imidazolyl, imidazo[1,2-a]pyridinyl, imidazo[2,3-b]thiazolyl, indazolyl, indolinyl, indolyl, isobenzofuranyl, isochromanyl, isoindolinyl, isoindolyl, isoquinolinyl, isothiazolyl, isothiochromanyl, isoxazolidinyl, isoxazolyl, maleimido, morpholinyl, naphtho[1,2-b]furanyl, naphthyridinyl (including 1,6-naphthyridinyl or, particularly, 1,5-naphthyridinyl and 1,8-naphthyridinyl), oxadiazolyl, 1,2- or 1,3-oxazinanyl, oxazolyl, phenazinyl, phenothiazinyl, phthalazinyl, piperazinyl, piperidinyl, pteridinyl, purinyl, pyranyl, pyrazinyl, pyrazolyl, pyridazinyl, pyridinyl, pyrimidinyl, pyrrolidinonyl, pyrrolidinyl, pyrrolinyl, pyrrolo[2,3-b]pyridinyl, pyrrolo[5,1-b] pyridinyl, pyrrolo[2,3-c]pyridinyl, pyrrolyl, quinazolinyl, quinolinyl, quinolizinyl, quinoxalinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo-[e]pyrimidine, tetrahydrofuranyl, tetrahydroisoquinolinyl (including 1,2,3,4-tetrahydroisoquinolinyl and 5,6,7,8-tetrahydroisoquinolinyl), tetrahydropyranyl, 3,4,5,6-tetrahydropyridinyl, 1,2,3,4-tetrahydropyrimidinyl, 3,4,5,6-tetrahydropyrimidinyl, tetrahydroquinolinyl (including 1,2,3,4-tetrahydroquinolinyl and 5,6,7,8-tetrahydroquinolinyl), thiadiazolyl, thiazolidinyl, thiazolyl, thienyl, thieno[5,1-c]pyridinyl, thiochromanyl, thiophenetyl, triazolyl, 1,3,4-triazolo[2,3-b]pyrimidinyl, xanthenyl and the like.

$Het^a$ and $Het^c$ to $Het^e$ groups may be fully saturated, partly unsaturated, wholly aromatic or partly aromatic in character. $Het^a$ groups that may be mentioned include azetidinyl, aziridinyl, dioxanyl, furanyl, furazanyl, hexahydropyrimidinyl, hydantoinyl, imidazolyl, maleimido, morpholinyl, oxadiazolyl, 1,2- or 1,3-oxazinanyl, oxazolyl, piperazinyl, piperidinyl, pyranyl, pyrazinyl, pyrazolyl, pyridazinyl, pyridinyl, pyrimidinyl, pyrrolidinonyl, pyrrolidinyl, pyrrolinyl, pyrrolyl, sulfolanyl, 3-sulfolenyl, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, thiadiazolyl, thiazolidinyl, thiazolyl, thienyl, thiophenetyl, triazolyl and the like.

$Het^b$ groups may be fully saturated, partly unsaturated, wholly aromatic or partly aromatic in character. $Het^b$ groups that may be mentioned include dioxanyl, furanyl, furazanyl, hexahydropyrimidinyl, hydantoinyl, imidazolyl, maleimido, morpholinyl, oxadiazolyl, 1,2- or 1,3-oxazinanyl, oxazolyl, piperazinyl, piperidinyl, pyranyl, pyrazinyl, pyrazolyl, pyridazinyl, pyridinyl, pyrrolyl, pyrrolidinonyl, pyrrolidinyl, pyrrolinyl, pyrrolyl, sulfolanyl, 3-suffolenyl, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, thiadiazolyl, thiazolidinyl, thiazolyl, thienyl, thiophenetyl, triazolyl and the like.

Substituents on heterocyclic ($Het^4$, $Het^B$, $Het^1$ to $Het^4$, $Het^a$ to $Het^e$) groups may, where appropriate, be located on any atom in the ring system including a heteroatom. The point of attachment of heterocyclic ($Het^4$, $Het^B$, $Het^1$ to $Het^4$, $Het^a$ to $Het^e$) groups may be via any atom in the ring system including (where appropriate) a heteroatom (such as a nitrogen atom), or an atom on any fused carbocyclic ring that may be present as part of the ring system. Heterocyclic ($Het^4$, $Het^B$, $Het^1$ to $Het^4$, $Het^a$ to $Het^e$) groups may also be in the N- or S-oxidised form.

Embodiments of the invention that may be mentioned include those in which $L^1$ and $L^2$ independently represent a direct bond, O, $NR^{3a}$, $S(O)_p$, $CH_2$ or $C(O)$.

In certain embodiments of the invention, $L^1$ and $L^2$ represent single bonds, $R^1$ represents H, and the compound of formula I may be represented as a compound of formula A1.

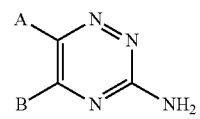

A1 wherein A represents $Cy^{AA}$ or $Het^{AA}$;

$Cy^{AA}$ represents a 6-membered aromatic, fully saturated or partially unsaturated carbocyclic ring system, which $Cy^{AA}$ group is substituted, in the 3-position relative to the point of attachment to the triazine ring, with a $R^{4a}$ substituent and is optionally substituted by one or more additional $R^{4a}$ substituents;

$Het^{AA}$ represents a 6-membered heterocyclic group that may be aromatic, fully saturated or partially unsaturated, and which contains one or more heteroatoms selected from O, S and N, and which $Het^{AA}$ group is substituted, in the 3-position relative to the point of attachment to the triazine ring, with a R substituent and is optionally substituted by one or more additional $R^{4b}$ substituents;

B represents a $Cy^{BB}$ or $Het^{BB}$;

$Cy^{BB}$ represents phenyl optionally substituted by one or more $R^{4c}$ substituents;

$Het^{BB}$ represents a 6-membered aromatic heterocyclic group which contains one or more N atoms, and which $Het^{BB}$ group is optionally substituted by one or more $R^{4d}$ substituents;

$R^{4a}$, $R^{4b}$, $R^{4c}$ and $R^{4d}$ are as defined above in relation to compounds of formula I.

Embodiments of the invention that may be mentioned include those that relate to compounds of formula I (or, particularly, formula A1) in which A represents $Cy^{AA'}$, $Het^{AA'}$, $Het^{AA''}$ or $Het^{AA'''}$, wherein:

$Cy^{AA'}$ represents a 6-membered aromatic, fully saturated or partially unsaturated carbocyclic ring system, which $Cy^{AA'}$ group is substituted, in the 3-position relative to the point of attachment to the triazine ring, with a $R^{4a}$ substituent and is substituted in the 4-position relative to the point of attachment to the triazine ring, with a $OR^8$ substituent and is optionally further substituted by one or more additional $R^{4a}$ substituents;

$Het^{AA'}$ represents a 6-membered heterocyclic group that may be aromatic, fully saturated or partially unsaturated, and which contains one or more heteroatoms selected from O, S and N, and which $Het^{AA'}$ group is substituted, in the 3-position relative to the point of attachment to the triazine ring, with a $R^{4b}$ substituent and is substituted, in the 4-position relative to the point of attachment to the triazine ring, with a $OR^8$ substituent, and is optionally further substituted by one or more additional $R^{4b}$ substituents;

$Het^{AA''}$ represents a 6-membered heterocyclic group that may be aromatic, fully saturated or partially unsaturated, and which contains, in the 4-position relative to the point of attachment to the triazine ring, a N-atom, and which group optionally contains one or more further heteroatoms selected from O, S and N, which $Het^{AA''}$ group is substituted, in the 3-position relative to the point of attachment to the triazine ring, with a $R^{4b}$ substituent and is optionally substituted by one or more additional $R^{4b}$ substituents; and $Het^{AA'''}$ represents a 6-membered heterocyclic group that may be aromatic, fully saturated or partially unsaturated, and which contains one or more heteroatoms selected from O, S and N, which $Het^{AA'''}$ group is substituted, in the 3-position relative to the point of attachment to the triazine ring, with a $R^{4b}$ substituent and is substituted, in the 4-position relative to the point of attachment to the triazine ring, with an oxo (=O) group, and is optionally further substituted by one or more additional $R^{4b}$ substituents (e.g. $Het^{AA'''}$ represents a 4-pyridon-1-yl optionally substituted by one or more $R^{4b}$ substituents).

Further embodiments of the invention that may be mentioned include those that relate to compounds of formula I (or, particularly, formula A1) in which:
when A represents $Cy^{AA}$ or $Cy^{AA'}$, that 6-membered carbocyclic ring is further substituted, in the 5-position relative to the point of attachment to the triazine ring, with a $R^{4a}$ substituent; or
when A represents $Het^{AA}$, $Het^{AA'}$, $Het^{AA''}$ or $Het^{AA'''}$, that 6-membered heterocyclic ring is further substituted, in the 5-position relative to the point of attachment to the triazine ring, with a $R^{4b}$ substituent.

Still further embodiments of the invention that may be mentioned include those that relate to compounds of formula I (or, particularly, formula A1) in which:
(1) $Het^{BB}$ represents a 6-membered aromatic heterocyclic group which contains 3, 2 or, particularly, 1 N atoms, and which $Het^{BB}$ group is optionally substituted by one or more $R^{4d}$ substituents;
(2) B represents $Cy^{BB}$;
(3) $Cy^{BB}$ represents phenyl optionally substituted by one or two $R^{4c}$ substituents;
(4) $Cy^{AA}$ represents phenyl substituted, in the 3-position relative to the point of attachment to the triazine ring, with a $R^{4a}$ substituent, and optionally substituted by one or more additional $R^{4a}$ substituents;
(5) $Het^{AA}$ represents a 6-membered aromatic heterocyclic group which contains one or more (e.g. 3, 2 or particularly 1) N atoms, and which $Het^{AA}$ group is substituted, in the 3-position relative to the point of attachment to the triazine ring, with a $R^{4b}$ substituent and is optionally substituted by one or more additional $R^{4b}$ substituents;
(6) B represents a pyrimidinyl ring or, particularly, a phenyl or pyridinyl (e.g. a pyridin-4-yl) ring, which ring is optionally substituted by one or more $R^{4c}$ or $R^{4d}$ substituents;
(7) $R^{4c}$ and $R^{4d}$ represent, independently at each occurrence,
(a) halo (e.g. chloro or, particularly, fluoro),
(b) CN,
(c) $C_{1-6}$ alkyl optionally substituted by one or more substituents selected from halo and $OR^{5a}$, or
(d) $OR^8$;
(8) A represents a $Cy^{AA}$ or $Het^{AA}$ group that is unsubstituted in the ortho-positions relative to the point of attachment to the triazine ring;
(9) $R^{4a}$ and $R^{4b}$ represent, independently at each occurrence,
(a) halo,
(b) CN,
(c) $C_{1-6}$ alkyl, $C_{2-6}$ alkenyl, $C_{2-6}$ alkynyl, which latter three groups are optionally substituted by one or more substituents selected from halo, nitro, CN, $C_{1-4}$ alkyl, (which latter group is optionally substituted by one or more substituents selected from OH, =O, halo), $OR^{5a}$, $N(R^{5g})(R^{5h})$, $B^1$—$C(G^1)$-$B^2$—$R^{5i}$, aryl and $Het^1$,
(d) $Cy^3$, which $Cy^3$ group is optionally substituted by one or more substituents selected from halo, nitro, CN, $C_{1-4}$ alkyl, (which latter group is optionally substituted by one or more substituents selected from OH, =O, halo), $OR^{6a}$, $N(R^{6g})(R^{6h})$, $B^3$—$C(G^1)$-$B^4$—$R^{6i}$, aryl and $Het^2$,
(e) $Het^a$, which $Het^a$ group is optionally substituted by one or more substituents selected from halo, nitro, CN, $C_{1-4}$ alkyl, (which latter group is optionally substituted by one or more substituents selected from OH, =O, halo), $OR^{7a}$, $N(R^{7g})(R^{7h})$, $B^5$—$C(G^1)$-$B^6$—$R^{7i}$, aryl and $Het^3$,
(f) $OR^8$,
(g) $S(O)_tR^{9a}$,
(j) $N(R^{9f})(R^{9g})$,
(k) $B^7$—$C(G^1)$-$B^8$—$R^{9h}$,
(l) =O,
or when two $R^{4a}$ or $R^{4b}$ groups are attached to the same carbon atom in a non-aromatic portion of a $Cy^1$, $Cy^{AA}$, $Het^A$ or $Het^{AA}$ group, they may form, together with the carbon atom to which they are attached, a saturated or unsaturated 3 to 6-membered ring, which ring optionally contains one to three heteroatoms selected from O, S and N, and which ring is optionally substituted by one or more $R^{9i}$ substituents;

Still further embodiments of the invention that may be mentioned include those that relate to compounds of formula I (or, particularly, formula A1) in which $R^{4a}$ to $R^{4b}$ represent, independently at each occurrence,
(a) halo,
(b) CN,
(c) $C_{1-4}$ alkyl, $C_{2-4}$ alkenyl, $C_{2-4}$ alkynyl, which latter three groups are optionally substituted by one or more substituents selected from halo, $C_{1-4}$ alkyl and $OR^{5a}$,
(d) $Cy^3$,
(e) $Het^a$,
(f) $OR^8$, wherein $R^8$ represents H or $C_{1-4}$ alkyl optionally substituted by one or more halo atoms;
(g) $S(O)_fR^{9a}$, wherein $R^{9a}$ represents $C_{1-3}$ alkyl optionally substituted by one or more halo atoms;
(h) $N(R^{9f})(R^{9g})$, wherein $R^{9f}$ and $R^{9g}$ independently represent $C_{1-3}$ alkyl optionally substituted by one or more halo atoms;
(i) $B^7$—$C(G^1)$-$B^6$—$R^{9h}$, wherein $R^{9h}$ represents $C_{1-3}$ alkyl optionally substituted by one or more halo atoms;
(j) =O,
or when two $R^{4a}$ or $R^{4b}$ groups are attached to the same carbon atom in a non-aromatic portion of a $Cy^1$, $Cy^{AA}$, $Het^A$ or $Het^{AA}$ group, they may form, together with the carbon atom to which they are attached, a saturated 3 to 6-membered ring.

Still further embodiments of the invention that may be mentioned include those that relate to compounds of formula I (or, particularly, formula A1) in which B represents a $Cy^{BB}$ or $Het^{BB}$ group (e.g. phenyl), which group is either unsubstituted or is substituted by one or more substituents selected from fluoro, CN, $OR^8$ or $C_{1-6}$ alkyl optionally substituted by one or more substituents selected from halo and $OR^{5a}$, wherein $R^{5a}$ and $R^6$ are as hereinbefore defined.

In particular embodiments, B represents a $Cy^{BB}$ or $Het^{BB}$ group (e.g. phenyl), which group is either unsubstituted or is substituted by one or more fluoro atoms (e.g. at the 4-position relative to the point of attachment to the triazine ring) only.

In other embodiments of the invention, $R^{4a}$ is (or $R^{4a}$ and $R^{4b}$ are) as defined above except that it does (they do) not represent $OR^8$ in which $R^8$ represents $CH_3$. In such circumstances, $R^{4a}$ (or $R^{4a}$ and $R^{4b}$) may, for example, (independently) represent, at each occurrence, halo, OH, N(H)—C(O)—$C_{1-3}$ alkyl or $C_{1-3}$ alkyl optionally substituted by one or more fluoro atoms.

In certain embodiments of the invention, the compound of formula I may be represented as a compound of formula Ix, Iy or Iz,

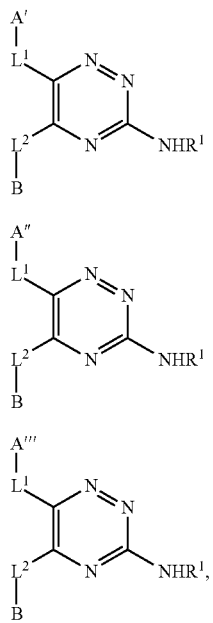

respectively, wherein:

A' represents $Cy^{1'}$ or $Het^{4'}$.

$Cy^{1'}$ represents a 6-membered aromatic, fully saturated or partially unsaturated carbocyclic ring system comprising one, two or three rings, which $Cy^{1'}$ group is substituted, in the 4-position relative to the point of attachment to $L^1$, with a $OR^8$ substituent and is optionally further substituted by one or more $R^{4a}$ substituents;

$Het^{4'}$ represents a 6-membered heterocyclic group that may be aromatic, fully saturated or partially unsaturated, and which contains one or more heteroatoms selected from O, S and N, which heterocyclic group may comprise one, two or three rings and which $Het^{4'}$ group is substituted, in the 4-position relative to the point of attachment to $L^1$, with a $OR^8$ substituent and is optionally further substituted by one or more $R^{4b}$ substituents;

(e.g. A' represents phenyl which group is substituted, in the 4-position relative to the point of attachment to $L^1$, with a $OR^8$ substituent and is optionally further substituted by one or more $R^{4a}$ substituents);

A" represents $Het^{4''}$;

$Het^{4''}$ represents a 6-membered heterocyclic group that may be aromatic, fully saturated or partially unsaturated, and which contains, in the 4-position relative to the point of attachment to $L^1$, a N-atom, and which group optionally contains one or more further heteroatoms selected from O, S and N, which $Het^{4''}$ group is optionally substituted by one or more $R^{4b}$ substituents;

(e.g. A" represents 6-membered aromatic heterocyclic group (e.g. pyridyl) that contains, in the 4-position relative to the point of attachment to $L^1$, a N atom, which heterocyclic group is optionally substituted by one or more $R^{4b}$ substituents);

A''' represents $Het^{4'''}$;

$Het^{4'''}$ represents a 6-membered heterocyclic group that may be aromatic, fully saturated or partially unsaturated, and which contains one or more heteroatoms selected from O, S and N, which $Het^{4'''}$ group is substituted, in the 4-position relative to the point of attachment to $L^1$, an oxo (=O) group, and is optionally further substituted by one or more $R^{4b}$ substituents;

(e.g. A''' represents 4-pyridon-1-yl optionally substituted by one or more $R^{4b}$ substituents); and B, $L^1$, $L^2$, $R^1$, $R^{4a}$, $R^{4b}$ and $R^6$ are as defined above in relation to compounds of formula I (or A1).

Embodiments of the invention that may be mentioned include those that relate to compounds of formula I in which at least one of $L^1$ and $L^2$ represents a direct bond, while the other may represent CH=CH or, particularly, a direct bond, O, $NR^{3a}$, $S(O)_p$, $CH_2$ or C(O) (e.g. at least one of $L^1$ and $L^2$ represents a direct bond, and the other represents CH=CH or, particularly, C(O) or, more particularly, a direct bond, O, $NR^{3a}$ or $S(O)_p$).

Thus, in an embodiment of the invention, $L^1$ and $L^2$ are both direct bonds.

Embodiments of the invention that may be mentioned include those that relate to compounds of formula I wherein $L^1$ represents a direct bond and $L^2$ is selected from CH=CH or, particularly, a O, $NR^{3a}$, $S(O)_p$, $CH_2$ and C(O) (e.g. $L^1$ represents a direct bond and $L^2$ is selected from O, $CH_2$ or C(O)).

Further embodiments of the invention that may be mentioned include those that relate to compounds of formula I wherein $L^2$ represents a direct bond and $L^1$ is selected from CH=CH or, particularly, O, $NR^{3a}$, $S(O)_p$, $CH_2$ and C(O) (e.g. $L^2$ represents a direct bond and $L^1$ is selected from O, $CH_2$ or C(O)).

Embodiments of the invention that may be mentioned include those that relate to compounds of formula I in which:

(1) $R^1$ represents H or $C_{1-3}$ alkyl, which latter group is optionally substituted by one or more of halo, $OR^{2a}$ or $NR^{2b}R^{2c}$ (e.g. $R^1$ represents H or $C_{1-3}$ alkyl, which latter group is optionally substituted by one or more of halo or $NR^{2b}R^{2c}$ or, particularly, $R^1$ represents H or $C_{1-2}$ alkyl, which latter group is optionally substituted by one or more of halo or $NR^{2b}R^{2c}$);

(2) $L^1$ and $L^2$ independently represent CH=CH or, particularly, $NR^{3a}$, $S(O)_p$, or, more particularly, $CH_2$, or, still more particularly, a direct bond, O, or C(O);

(3) $R^{2a}$, $R^{2b}$ and $R^{2c}$ and $R^{3a}$ represents H or $C_{1-3}$ alkyl, which latter group is optionally substituted by one or more halo atoms (e.g. $R^{2a}$ represents $C_{1-3}$ alkyl, which group is optionally substituted by one or more halo atoms; $R^{2b}$ and $R^{2c}$ independently represent H or methyl, which latter group is optionally substituted by one or more halo atoms; and $R^{3a}$ represents H or $C_{1-3}$ alkyl, which latter group is optionally substituted by one or more halo atoms);

(4) $Cy^1$ represents a 5- to 13-membered (e.g. 5- to 10- or more particularly 6- to 10-membered) aromatic, fully saturated or partially unsaturated carbocyclic ring system comprising one to three (e.g. one or two) rings, which $Cy^1$ group is optionally substituted by one or more $R^{4a}$ substituents;

(5) $Het^4$ represents a 5- to 13-membered (e.g. 5- to 10- or more particularly 6- to 10-membered) heterocyclic group that may be aromatic, fully saturated or partially unsaturated, and which contains one or more heteroatoms selected from O, S and N, which heterocyclic group may comprise one to three (e.g. one or two) rings and which $Het^4$ group is optionally substituted by one or more $R^{4b}$ substituents;

(6) $Cy^2$ represents a 5- to 10-membered (e.g. 5- to 9-membered or, particularly, 6- to 9-membered) aromatic, fully saturated or partially unsaturated carbocyclic ring system comprising one or two rings, which $Cy^2$ group is optionally substituted by one or more $R^{4c}$ substituents;

(7) $Het^B$ represents a 5- to 10-membered (e.g. 5- to 9-membered or, particularly, 6- to 9-membered) heterocyclic group that may be aromatic, fully saturated or partially unsaturated, and which contains one or more heteroatoms selected from O, S and N, which heterocyclic group may comprise one to three (e.g. one or two) rings and which $Het^B$ group is optionally substituted by one or more $R^{4d}$ substituents;

(8) $R^{4a}$ to $R^{4d}$ represent, independently at each occurrence,
halo,
CN,
$C_{1-6}$ alkyl (e.g. $C_{2-6}$ alkyl), $C_{2-6}$ alkenyl, $C_{2-6}$ alkynyl (which latter three groups are optionally substituted by one or more substituents selected from halo, nitro, CN, $C_{1-3}$ alkyl, $C_{2-3}$ alkenyl, $C_{2-3}$ alkynyl (which latter three groups are optionally substituted by one or more substituents selected from OH, =O, halo, $C_{1-3}$ alkyl and $C_{1-3}$ alkoxy). $OR^{5a}$, $S(O)_qR^{5b}$, $S(O)_2N(R^{5c})(R^{5d})$, $N(R^{5e})S(O)_2R^{5f}$, $N(R^{5g})(R^{5h})$, $B^1$—$C(G^1)$-$B^2$—$R^{5i}$, aryl and $Het^1$,
$Cy^3$, which $Cy^3$ group is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{6a}$, $S(O)_qR^{6b}$, $S(O)_2N(R^{6c})(R^{6d})$, $N(R^{6e})S(O)_2R^{6f}$, $N(R^{6g})(R^{6h})$, $B^3$—$C(G^1)$-$B^4$—$R^{6i}$, aryl and $Het^2$,
$Het^a$, which $Het^a$ group is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{7a}$, $S(O)_qR^{7b}$, $S(O)_2N(R^{7c})(R^{7d})$, $N(R^{7e})S(O)_2R^{7f}$, $N(R^{7g})(R^{7h})$, $B^5$—$C(G^1)$-$B^6$—$R^{7i}$, aryl and $Het^3$,
$OR^8$,
$S(O)_rR^{9a}$,
$S(O)_2N(R^{9b})(R^{9c})$,
$N(R^{9c})S(O)_2R^{9e}$,
$N(R^{9f})(R^{9g})$
$B^7$—$C(G^1)$-$B^8$—$R^{9h}$,
=O,
=S,
or when two $R^{4a}$, $R^{4b}$, $R^{4c}$ or $R^{4d}$ groups are attached to the same carbon atom in a non-aromatic portion of a $Cy^1$, $Het^4$, $Cy^2$ or $Het^B$ group, they may form, together with the carbon atom to which they are attached, a saturated or unsaturated 3 to 6-membered ring, which ring optionally contains one to three heteroatoms selected from O, S and N, and which ring is optionally substituted by one or more $R^{9i}$ substituents;

(9) $G^1$ represents, independently at each occurrence, O or S;

(10) $R^8$ represents, independently at each occurrence,
H,
$Cy^3$, $Het^a$, $aryl^a$, $C_{1-6}$ alkyl, $C_{2-6}$ alkenyl, $C_{2-6}$ alkynyl, $C_{3-6}$ cycloalkyl, which latter seven groups are optionally substituted by one or more substituents selected from halo, —CN, $C_{3-6}$ cycloalkyl, aryl, $Het^4$, —C(O)$OR^{10}$, —C(O)$R^{11}$ and —C(O)N($R^{N1}$)($R^{N2}$), $S(O)_rR^{9aa}$, $S(O)_2N(R^{9ba})(R^{9ca})$, $N(R^{9da})S(O)_2R^{9ea}$ and $N(R^{9fa})(R^{9ga})$;

(11) $Cy^3$ represents, independently at each occurrence, $C_{3-6}$ cycloalkyl, $C_{3-6}$ cycloalkenyl or phenyl;

(12) $Het^a$ represents, independently at each occurrence, a 4- to 6-membered heterocyclic ring that may be aromatic, fully saturated or partially unsaturated and which contains one or more heteroatoms selected from O, S and N;

(13) $R^{10}$ and $R^{11}$ independently represent
H,
$C_{1-3}$ alkyl optionally substituted by one or more substituents selected from halo, aryl, —N($R^{N3}$)($R^{N4}$) and —$OR^a$,
phenyl (which latter group is optionally substituted by one or more substituents selected from OH, halo, $C_{1-4}$ alkyl and $C_{1-4}$ alkoxy) or
$C_{3-6}$ cycloalkyl (which latter group is optionally substituted by one or more substituents selected from OH, =O, halo, $C_{1-4}$ alkyl and $C_{1-4}$ alkoxy);

(14) $B^1$ to $B^8$ independently represent, at each occurrence, O or, particularly, a direct bond or N($R^{N3}$);

(15) each $aryl^a$ independently represents a $C_{6-10}$ carbocyclic aromatic group (e.g. phenyl), which group may comprise one or two rings:

(16) each aryl independently represents a $C_{6-10}$ carbocyclic aromatic group (e.g. phenyl), which group may comprise one or two rings and may be substituted by one or more substituents selected from
halo,
$C_{1-6}$ alkyl, which latter group is optionally substituted by one or more substituents selected from halo, —N($R^{N4}$)($R^{N5}$) and —$OR^a$, and
—$OR^a$;

(17) $Het^1$ to $Het^4$ independently represent 5- to 13-membered heterocyclic groups containing one or more heteroatoms selected from O, S and N, which heterocyclic groups may comprise one, two or three rings and may be substituted by one or more substituents selected from
halo,
$C_{1-6}$ alkyl, which latter group is optionally substituted by one or more substituents selected from halo, —N($R^{N6}$)($R^{N7}$) and —$OR^a$, and —$OR^a$;

(18) $R^{N1}$ to $R^{N7}$ independently represent
H,
$C_{1-3}$ alkyl or $C_{3-5}$ cycloalkyl, which latter two groups are optionally substituted by one or more substituents selected from halo and —$OR^a$;

(19) $R^a$ represents, independently at each occurrence,
H,
C$_{1-6}$ alkyl, C$_{2-6}$ alkenyl, C$_{2-6}$ alkynyl, C$_{3-6}$ cycloalkyl, C$_{4-6}$ cycloalkenyl (which latter five groups are optionally substituted by one or more substituents selected from halo, nitro, CN, C$_{1-6}$ alkyl, C$_{2-6}$ alkenyl, C$_{2-6}$ alkynyl, C$_{3-8}$ cycloalkyl (which latter three groups are optionally substituted by one or more substituents selected from OH, =O, halo, C$_{1-4}$ alkyl and C$_{1-4}$ alkoxy), OR$^{12a}$, S(O)$_q$R$^{12b}$, S(O)$_2$N(R$^{12c}$)(R$^{12d}$), N(R$^{12e}$)S(O)$_2$R$^{12f}$, N(R$^{12g}$)(R$^{12h}$), B$^9$—C(G$^2$)-B$^{10}$—R$^{12i}$, aryl$^1$ and Het$^b$, and which C$_{3-6}$ cycloalkyl or C$_{4-6}$ cycloalkenyl groups may additionally be substituted by =O),
S(O)$_r$R$^{13a}$,
S(O)$_2$N(R$^{13b}$)(R$^{13c}$) or
C(O)—B$^{13}$—R$^{13d}$;
(20) R$^{5a}$ to R$^{5i}$, R$^{6a}$ to R$^{6i}$, R$^{7a}$ to R$^{7i}$, R$^{9a}$ to R$^{9i}$, R$^{9aa}$ to R$^{9ga}$, R$^{12a}$ to R$^{12i}$ and R$^{13a}$ to R$^{13d}$ independently represent, at each occurrence,
H,
C$_{1-6}$ alkyl, C$_{2-6}$ alkenyl, C$_{2-6}$ alkynyl (which latter three groups are optionally substituted by one or more substituents selected from halo, OH and C$_{1-4}$ alkoxy),
C$_{3-6}$ cycloalkyl or C$_{4-8}$ cycloalkenyl (which latter two groups are optionally substituted by one or more substituents selected from halo, OH, =O, C$_{1-6}$ alkyl and C$_{1-6}$ alkoxy),
Het$^d$;
(21) G$^2$ represents, independently at each occurrence, O or S;
(22) R$^{5aa}$ to R$^{5aj}$ independently represent at each occurrence,
H,
C$_{1-3}$ alkyl, C$_{2-3}$ alkenyl, C$_{2-3}$ alkynyl which latter three groups are optionally substituted by one or more substituents selected from halo, nitro, CN, C$_{1-4}$ alkyl, C$_{2-4}$ alkenyl, C$_{2-4}$ alkynyl (which latter three groups are optionally substituted by one or more substituents selected from OH, =O, halo, C$_{1-4}$ alkyl and C$_{1-4}$ alkoxy),
C$_{3-5}$ cycloalkyl, or C$_{4-5}$ cycloalkenyl (which latter two groups are optionally substituted by one or more substituents selected from halo, OH, =O, C$_{1-4}$ alkyl and C$_{1-4}$ alkoxy),
Het$^a$;
(23) B$^9$ to B$^{13}$ independently represent a direct bond or N(R$^{N8}$);
(24) aryl$^1$ represents, independently at each occurrence, phenyl or naphthyl, which may be substituted by one or more substituents selected from
halo,
C$_{1-3}$ alkyl, which letter group is optionally substituted by one or more substituents selected from halo, —N(R$^{N10}$)(R$^{N11}$) and C$_{1-4}$ alkoxy (which latter substituent is optionally substituted by one or more halo atoms), and
C$_{1-4}$ alkoxy (which latter substituent is optionally substituted by one or more halo atoms);
(25) R$^{N8}$, R$^{N10}$ and R$^{N11}$ independently represent
H,
C$_{1-3}$ alkyl or C$_{3-3}$ cycloalkyl, which latter two groups are optionally substituted by one or more halo atoms;
(26) Het$^b$ represents a heterocyclic group selected from dioxanyl, furanyl, furazanyl, hexahydropyrimidinyl, hydantoinyl, imidazolyl, maleimido, morpholinyl, oxadiazolyl, 1,2- or 1,3-oxazinanyl, oxazolyl, piperazinyl, piperidinyl, pyranyl, pyrazinyl, pyrazolyl, pyridazinyl, pyridinyl, pyrimidinyl, pyrrolidinonyl, pyrrolidinyl, pyrrolinyl, pyrrolyl, sulfolanyl, 3-sulfolenyl, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, thiadiazolyl, thiazolidinyl, thiazolyl, thienyl, thiophenetyl, triazolyl, which heterocyclic group may be substituted by one or more substituents selected from halo, =O and C$_{1-6}$ alkyl;
(27) Het$^c$ to Het$^e$ independently represent, a 4- to 6-membered heterocyclic ring that may be aromatic, fully saturated or partially unsaturated and which contains one or more heteroatoms selected from O, S and N, which Het$^c$ to Het$^e$ groups are optionally substituted by one or more substituents selected from halo, nitro, CN, C$_{1-4}$ alkyl, C$_{2-4}$ alkenyl, C$_{2-4}$ alkynyl (which latter three groups are optionally substituted by one or more substituents selected from OH, =O, halo, C$_{1-4}$ alkyl and C$_{1-4}$ alkoxy).

Embodiments of the invention that may be mentioned include those that relate to compounds of formula I in which:
(1) Cy$^1$ represents a 5- to 10-membered (e.g. 6- to 10-membered) aromatic, fully saturated or partially unsaturated carbocyclic ring system comprising one or two rings, which Cy$^1$ group is optionally substituted by one or more R$^{4a}$ substituents;
(2) Het$^A$ represents a 5- to 10-membered (e.g. 6- to 10-membered) heterocyclic group that may be aromatic, fully saturated or partially unsaturated, and which contains one or more heteroatoms selected from O, S and N, which heterocyclic group may comprise one or two rings and which Het$^A$ group is optionally substituted by one or more R$^{4b}$ substituents;
(3) B represents a group, selected from 2-azabicyclo[4.1.0]heptanyl, 1-azabicyclo[2.2.2]octanyl, benzimidazolyl, benzisothiazolyl, benzisoxazolyl, benzodioxanyl, benzodioxolyl, benzofurazanyl, benzo[c]isoxazolidinyl, 2,1,3-benzoxadiazolyl, benzoxazolidinyl, benzoxazolyl, benzopyrazolyl, 2,1,3-benzothiadiazolyl, benzothiazolyl, benzothienyl, benzotriazolyl, cyclopentyl, cyclohexyl, cyclopentenyl, cyclohexenyl, 2,3-dihydrobenzimidazolyl, dihydrofuranyl (e.g. 2,3-dihydrofuranyl, 2,5-dyhdrofuranyl), 2,3-dihydrobenzo[b]furanyl, 1,3-dihydrobenzo-[c]furanyl, dihydropyranyl (e.g. 3,4-dihydropyranyl, 3,6-dihydropyranyl), 4,5-dihydro-1H-maleimido, 1,3-dihydro-2,1-benzisoxazolyl 2,3-dihydropyrrolo[2,3-b]pyridinyl, dioxanyl, dioxolanyl, furazanyl, hexahydropyrimidinyl, hydantoinyl, imidazolyl, imidazo[1,2-a]pyridinyl, imidazo[2,3-b]thiazolyl, indanyl, indenyl, indolinyl, isobenzofuranyl, isoindolinyl, isoindolyl, isothiaziolyl, isoxazolyl, isoxazolidinyl, ketopiperidinyl (e.g. 2-ketopiperidinyl, 3-ketopiperidinyl or 4-ketopiperidinyl), morpholinyl, oxadiazolyl, 1,2- or 1,3-oxazinanyl, oxazolidinyl, oxazolyl, piperidinyl (e.g. piperidin-1-yl or, particularly, piperidin-2-yl, piperidin-3-yl, piperidin-4-yl, piperidin-5-yl or piperidin-6-yl), piperazinyl, phthalazinyl, pteridinyl, purinyl, pyranyl, pyridazinyl, pyrrolidinonyl, pyrrolinyl (e.g. 3-pyrrolinyl), pyrrolyl, pyrrolo[2,3-b]pyridinyl, pyrrolo[5,1-b]pyridinyl, pyrrolo[2,3-c]pyridinyl, sulfolanyl, 3-sulfolenyl, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, tetrahydrothiophenyl, 4,5,6,7-tetrahydrobenzimidazolyl, 4,5,6,7-tetrahydrobenzopyrazolyl, tetramethylenesulfoxide, tetrazolyl, thiazolidinyl, thiazolyl, thienyl, thieno[5,1-c]pyridinyl, thiophenetyl, triazinanyl, triazoly, 1,3,4-triazolo[2,3-b]pyrimidinyl, more particularly, benzofuranyl, indazolyl, indolyl, pyrazinyl, pyrazolyl, pyridinyl (e.g. 2-pyridinyl, 3-pyridinyl, 4-pyridinyl), pyridinonyl, pyrimidinyl, pyrrolo[1,5-a]pyridinyl, and, yet more particularly, phenyl, wherein B is optionally substituted by one or more $R^{4c}$ or $R^{4d}$ substituents, as appropriate (e.g. B represents a group selected from benzofuranyl, furanyl, indazolyl, indolyl, pyrazinyl, pyrazolyl, pyridinyl (e.g. 2-pyridinyl, 3-pyridinyl, 4-pyridinyl), pyridinonyl, pyrimidinyl, pyrrolo[1,5-a]pyridinyl, and phenyl, wherein B is optionally substituted by one or more $R^{4c}$ or $R^{4d}$ substituents, as appropriate).

In certain embodiments of the invention, B represents phenyl and the compound of formula I may be represented as a compound of formula Ia,

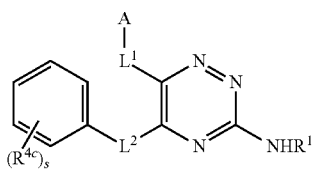

Ia wherein s represents 0 to 5 (e.g. 0 to 3 or, particularly, 0 to 2), and $R^{4c}$, A, $L^1$, $L^2$ and $R^1$ are as defined above in relation to compounds of formula I.

In certain embodiments of the invention, the compound of formula I may be represented as a compound of formula Ixa, Iya or Iza,

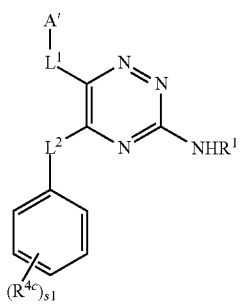

Ixa

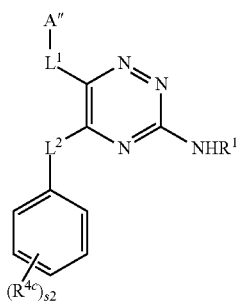

Iya

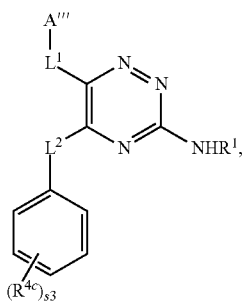

Iza respectively, wherein s1, s2 and s3 independently represent 0 to 5 (e.g. 0 to 3 or, particularly, 0 to 2), and A', A", A''', $L^1$, $L^2$, $R^{4c}$ and $R^1$ are as defined above in relation to compounds of formula I (or A1, or particularly, Ix, Iy or Iz).

Embodiments of the invention that may be mentioned include those that relate to compounds of formula I (or A1 or, particularly, Ix, Iy Iz, Ixa, Iya and Iza or, more particularly, Ia) in which:

(1) $R^1$ represents H, $CH_3$, $CF_3$, $CH_2F$, $CHF_2$, $CH_2CH_3$, $CH_2CF_3$, $(CH_2)_2OCH_3$, $(CH_2)_2OCF_3$, $(CH_2)_3OCH_3$, $(CH_2)_3OCF_3$, $(CH_2)_2NH_2$, $(CH_2)_2NH(CH_3)$, $(CH_2)_2N(CH_3)_2$, $(CH_2)_3NH_2$, $(CH_2)_3NH(CH_3)$ or $(CH_2)_3N(CH_3)_2$;

(2) $L^1$ represents S, NH, CH=CH or, particularly, $CH_2$, a direct bond, O, or C(O) (e.g. $L^1$ represents S, NH, CH=CH, a direct bond, O or C(O) or, particularly, a direct bond, O or C(O) or, more particularly, $L^1$ represents a direct bond);

(3) $L^2$ represents $CH_2$, a direct bond, O, or C(O) (e.g. $L^2$ represents a direct bond or O or, particularly, $L^2$ represents a direct bond);

(4) $R^{2a}$, $R^{2b}$, $R^{2c}$ and $R^{3a}$ independently represent H, $CH_3$, $CF_3$, $CH_2F$, $CHF_2$, $CH_2CH_3$ or $CH_2CF_3$
(e.g. $R^{2a}$ represents $CH_3$, $CF_3$, $CH_2F$, $CHF_2$, $CH_2CH_3$ or $CH_2CF_3$ and $R^{2b}$, $R^{2c}$ and $R^{3a}$ independently represent H, $CH_3$, $CF_3$, $CH_2F$, $CHF_2$, $CH_2CH_3$ or $CH_2CF_3$);

(5) A represents a group selected from 2,2,6,6-tetramethyl-3,6-dihydro-2H-pyran-4-yl, 6-oxa-9-azaspiro[4.5]decanyl, octahydroisoquinolin-(1H)-yl, hexahydropyrrolo[1,2-a]pyrazin-(1H)-yl, pyridazinonyl or, particularly, cyclopentyl, dihydrofuranyl (e.g 2,3-dihydrofuranyl, 2,5-dihydrofuranyl), 4,5-dihydro-1H-maleimido, dioxanyl, furazanyl, hydantoinyl, imidazolyl, isoxazolyl, isoxazolidinyl, isothiaziolyl, oxadiazolyl, oxazolyl, pyrazolyl, pyrrolinyl (e.g. 3-pyrrolinyl), pyrrolyl, pyrrolidinonyl, sulfolanyl, 3-sulfolenyl, tetrahydrofuranyl, tetramethylenesulfoxide, tetrazolyl, thiadiazolyl, thiazolyl, thiazolidinyl, thienyl, triazolyl, particularly 2-azabicyclo[4.1.0]heptanyl, 1-azabicyclo-[2.2.2]octanyl, benzimidazolyl, benzisothiazolyl, benzisoxazolyl, benzodioxanyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzopyrazolyl, benzo[e]pyrimidine, 2,1,3-benzothiadiazolyl, benzothiazolyl, benzothienyl, benzotriazolyl, carbazolyl, chromanyl, chromenyl, cinnolinyl, (1Z,2Z,4Z,6Z,8Z)-cyclodecapentaenyl, cyclohexyl, cyclopentenyl, decahydroisoquinolenyl, 2,3-dihydrobenzimidazolyl, 1,3-dihydrobenzo-[c]furanyl, 1,3-dihydro-2,1-benzisoxazolyl, dihydropyranyl (e.g. 3,4-dihydropyranyl, 3,6-dihydropyranyl), 2,3-dihydropyrrolo[2,3-b]pyridinyl, dioxolanyl, hexahydropyrimidinyl, imidazo[2,3-b]thiazolyl, indanyl, indazolyl, indenyl, indolinyl, isobenzofuranyl, isochromanyl, isoindolinyl, isoindolyl, isothiochromanyl, ketopiperidinyl (e.g. 2-ketopiperidinyl, 3-ketopiperidinyl or 4-ketopiperidinyl), naphtho[1,2-b]furanyl, naphthyridinyl (including 1,6-naphthyridinyl or, particularly, 1,5-naphthyridinyl and 1,8-naphthyridinyl), 1,2- or 1,3-oxazinanyl, oxazolidinyl, phenazinyl, phenothiazinyl, phthalazinyl, piperazinyl, pteridinyl, purinyl, pyranyl, pyridazinyl, pyrrolo[2,3-b]pyridinyl, pyrrolo[5,1-b]pyridinyl, pyrrolo[2,3-c]pyridinyl, quinazolinyl, quinolizinyl, quinoxalinyl, 4,5,6,7-tetrahydrobenzimidazolyl, 4,5,6,7-tetrahydrobenzopyrazolyl, 5,6,7,8-tetrahydrobenzo-[e]pyrimidine, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrahydropyranyl, tetrahydropyridinyl (e.g. 3,4,5,6-tetrahydropyridinyl), 1,2,3,4-tetrahydropyrimidinyl, 3,4,5,6-tetrahydropyrimidinyl, tetrahydrothiophenyl, thieno[5,1-c]pyridinyl, thiochromanyl, thiophenetyl, triazinanyl, 1,3,4-triazolo[2,3-b]pyrimidinyl, particularly, benzoxazolyl, benzodioxolyl, 2,3-dihydrobenzo[b]furanyl, cyclohexyl, furanyl, imidazo[1,2-a]pyridinyl, imidazo[1,5-e]pyridinyl, indolyl, isoquinolinyl, morpholinyl, napthalenyl (e.g. 1-napthalenyl, 2-napthalenyl, 1,2,3,4-tetrahydronaphthyl), piperidinyl, pyrimidinyl, pyrrolidinyl pyrrolo[1,5-a]pyridinyl, pyrazinyl, pyridinonyl (such as 1-1H-pyridin-2-onyl, 3-1H-pyridin-2-onyl, 4-1H-pyridin-2-onyl, 6-1H-pyridin-2-onyl, or, particularly, 4-pyridinonyl), quinolinyl, more particularly, phenyl and pyridinyl (e.g. 2-pyridinyl, 3-pyridinyl, 4-pyridinyl), which cyclic system is optionally substituted by one or more $R^{4a}$ or $R^{4b}$ substituents, as appropriate:

(6) $R^{4a}$ to $R^{4d}$ represent, independently at each occurrence,
halo,
CN,
$C_{1-6}$ alkyl (which latter group is optionally substituted by one or more substituents selected from halo, nitro, CN, $C_{1-3}$ alkyl (which latter group is optionally substituted by one or more substituents selected from OH, =O, halo, $C_{1-3}$ alkyl and $C_{1-3}$ alkoxy), $OR^5$, $S(O)_q R^{5b}$, $S(O)_2 N(R^{5c})(R^{5d})$, $N(R^{5e})S(O)_2 R^{5f}$, $N(R^{5g})(R^{5h})$ and $B^1$—$C(G^1)$-$B^2$—$R^{5i}$), $Cy^3$, wherein $Cy^3$ is a group selected from cyclobutyl, cyclopentyl, cyclohexyl, cyclopropenyl, cyclobutenyl, cyclopentenyl, cyclohexenyl, phenyl and, particularly, cyclopropyl, which $Cy^3$ group is optionally substituted by one or more substituents selected from halo, nitro, CN, $C_{1-3}$ alkyl (which group is optionally substituted by one or more substituents selected from OH, =O, halo, $C_{1-3}$ alkyl and $C_{1-3}$ alkoxy), $OR^{6a}$, $S(O)_q R^{6b}$, $S(O)_2 N(R^{6c})(Re)$, $N(R^{6d})S(O)_2 R^{6f}$, $N(R^{6g})(R^{6h})$, $B^3$—$C(G^1)$-$B^4$—$R^{6i}$ and aryl, $Het^a$, wherein $Het^a$ is a group selected from azetidinyl, dihydrofuranyl (e.g. 2,3-dihydrofuranyl, 2,5-dihydrofuranyl), dihydropyranyl (e.g. 3,4-dihydropyranyl, 3,6-dihydropyranyl), 4,5-dihydro-1H-maleimido, dioxanyl, dioxolanyl, furanyl, furazanyl, hexahydropyrimidinyl, hydantoinyl, imidazolyl, isothiaziolyl, isoxazolidinyl, isoxazolyl, morpholinyl, 1,2- or 1,3-oxazinanyl, oxazolidinyl, oxazolyl, piperidinyl, piperazinyl, pyranyl, pyrazinyl, pyridazinyl, pyrazolyl, pyridinyl, pyrimidinyl, pyrrolinyl (e.g. 3-pyrrolinyl), pyrrolyl, pyrrolidinyl, pyrrolidinonyl, 3-sulfolenyl, sulfolanyl, tetrahydrofuranyl, tetrahydropyranyl, tetrahydropyridinyl (e.g. 3,4,5,6-tetrahydropyridinyl), 1,2,3,4-tetrahydropyrimidinyl, 3,4,5,6-tetrahydropyrimidinyl, tetrahydrothiophenyl, tetramethylenesulfoxide, tetrazolyl, thiadiazolyl, thiazolyl, thiazolidinyl, thienyl, thiophenethyl, triazolyl and triazinanyl, which $Het^a$ group is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-3}$ alkyl and $C_{1-3}$ alkoxy), $OR^{7a}$, $S(O)_q R^{7b}$, $S(O)_2 N(R^{7c})(R^{7d})$, $N(R^{7e})S(O)_2 R^{7f}$, $N(R^{7g})(R^{7h})$, $B^5$—$C(G)$-$B^6$—$R^{7i}$ and aryl,
$OR^8$,
$S(O)_r R^{9a}$,
$S(O)_2 N(R^{9b})(R^{9c})$,
$N(R^{9d})S(O)_2 R^{9e}$,
$N(R^{9f})(R^{9g})$ $B^7$—C(O)—$B^8$—$R^{9h}$,
$B^7$—$C(G^1)$-$B^8$—$R^{9h}$,
=O, or when two $R^{4a}$, $R^{4b}$, $R^{4c}$ or $R^{4d}$ groups are attached to the same carbon atom in a non-aromatic portion of a $Cy^1$, $Het^A$, $Cy^2$ or $Het^B$ group, they may form, together with the carbon atom to which they are attached, a saturated or unsaturated 3 to 6-membered ring (e.g. dioxolanyl or 1,4-dioxanyl), which ring optionally contains one to three heteroatoms selected from O, S and N, and which ring is optionally substituted by one or more $R^{9i}$ substituents;

(7) $G^1$ represents, independently at each occurrence, O;

(8) $R^8$ represents, independently at each occurrence,
H,
$C_{1-6}$ alkyl, which latter group is optionally substituted by one or more substituents selected from halo, —CN, $C_{3-6}$ cycloalkyl, aryl, $Het^4$, —$C(O)OR^{10}$, —$C(O)R^{11}$ and —$C(O)N(R^{N1})(R^{N2})$
(e.g. $R^8$ represents, independently at each occurrence, H or $C_{1-3}$ alkyl optionally substituted by fluoro (e.g. $CH_2F$, $CHF_2$, $CH_2CH_3CH_2CF_3$, or particularly $CH_3$ or $CF_3$);

(9) each aryl independently represents a phenyl group and is optionally substituted by one or more substituents selected from
halo,
$C_{1-3}$ alkyl, which latter group is optionally substituted by one or more substituents selected from halo, —$N(R^{N4})(R^{N5})$ and —$OR^a$, and
—$OR^a$;

(10) $R^a$ represents independently at each occurrence,
H,
$C_{1-3}$ alkyl, (which latter group is optionally substituted by one or more substituents selected from halo, OH and $C_{1-4}$ alkoxy) or
$C_{3-6}$ cycloalkyl (which latter group is optionally substituted by one or more substituents selected from halo, OH, =O, $C_{1-6}$ alkyl and $C_{1-4}$ alkoxy).

In certain other embodiments of the invention, B represents phenyl and $L^2$ represents a direct bond and the compound of formula I may be represented as a compound of formula Ib,

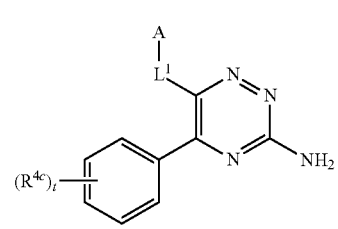

Ib wherein $R^{4c}$, A and $L^1$ are as defined above in relation to compounds of formula I (or A1 or, particularly, Ia) and t represents 0 to 5 (e.g. from 0 to 3, or particularly from 0 to 2).

In certain embodiments of the invention, the compound of formula I may be represented as a compound of formula Ixb, Iyb or Izb,

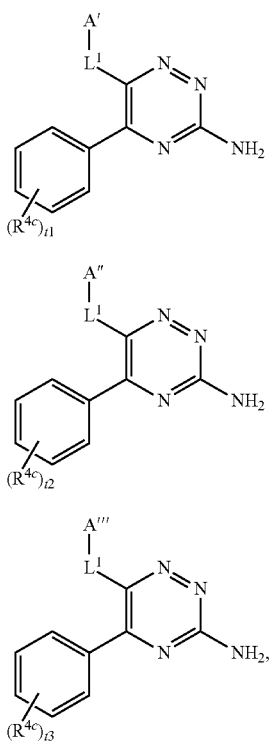

respectively, wherein t1, t2 and t3 independently represent 0 to 5 (e.g. 0 to 3 or, particularly, 0 to 2), and A', A'', A''', $R^{4c}$ and $L^1$ are as defined above in relation to compounds of formula I (or A1 or, particularly, Ix, Iy, Iz, Ia, Ixa, Iya or Iza).

In certain embodiments of the invention, the compounds of formula I (or A1 or, particularly, Ix, Iy Iz, Ixa, Iya, Iza, Ixb, Iyb, Izb or, more particularly, Ia or Ib) are those in which:

(1) $L^1$ represents S, NH, CH=CH or, particularly, a direct bond or O (e.g. $L^1$ represents a direct bond);

(2) A represents a group selected from furanyl, pyrrolidinyl, pyrazolyl, oxazolyl, particularly benzoxazolyl, benzodioxolyl, 2,3-dihydrobenzo[b]furanyl, cyclohexenyl, decahydroisoquinolenyl, imidazo[1,2-a]pyridinyl, imidazo[1,5-a]pyridinyl, indolyl, isoquinolinyl, morpholinyl, napthalenyl (e.g. 1-napthalenyl, 2-napthalenyl, 1,2,3,4-tetrahydronaphthyl), piperidinyl, pyrimidinyl, pyrrolo[1,5-a]pyridinyl, pyrazinyl, pyridinonyl (such as 1-1H-pyridin-2-onyl, 3-1H-pyridin-2-onyl, 4-1H-pyridin-2-onyl, 6-1H-pyridin-2-onyl, or, particularly, 4-pyridinonyl), quinolinyl, particularly, phenyl and pyridinyl (e.g. 2-pyridinyl, 3-pyridinyl, 4-pyridinyl), which A group is optionally substituted by one or more $R^{4a}$ or $R^{4b}$ substituents, as appropriate;

(3) $R^{4a}$ and $R^{4b}$ represent, independently at each occurrence, halo (e.g. iodo or, particularly, chloro, bromo or fluoro), CN,
$C_{1-6}$ alkyl, (which latter group is optionally substituted by one or more substituents selected from aryl or, particularly, halo and $OR^{5a}$),
$Cy^3$ wherein $Cy^3$ is a group selected from cyclobutyl, cyclopentyl, cyclohexyl phenyl and, particularly, cyclopropyl, which $Cy^3$ group is optionally substituted by one or more substituents halo, nitro, CN, $C_{1-3}$ alkyl (which group is optionally substituted by one or more substituents selected from OH, =O, halo, $C_{1-3}$ alkyl and $C_{1-3}$ alkoxy), $OR^{6a}$, $S(O)_qR^{6b}$, $S(O)_2N(R^{6c})(R^{6d})$, $N(R^{6e})S(O)_2R^{6f}$, $N(R^{6g})(R^{6h})$, $B^3$—$C(G^1)$-$B^4$—$R^{6i}$ and aryl, $Het^B$ wherein $Het^a$ is a group selected from azetidine and, particularly, dioxanyl and dioxolanyl which $Het^a$ group is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-3}$ alkyl and $C_{1-3}$ alkoxy), $OR^{7a}$, $S(O)_qR^{7b}$, $S(O)_2N(R^{7c})(R^{7d})$, $N(R^{7e})S(O)_2R^{7f}$, $N(R^{7g})(R^{7h})$, $B^5$—$C(G^1)$-$B^6$—$R^{7i}$ and aryl, $OR^8$, $S(O)_rR^{9a}$, $N(R^{9f})(R^{9g})$ $B^7$—$C(G^1)$-$B^8$—$R^{9h}$,

=O, or when two $R^{4a}$ or $R^{4b}$ groups are attached to the same carbon atom in a non-aromatic portion of a $Cy^1$ or $Het^A$ group, they may form, together with the carbon atom to which they are attached, a saturated or unsaturated 5-membered ring (e.g. dioxolanyl), which ring optionally contains one to two heteroatoms selected from O and N, and which ring is optionally substituted by one or more $R^{9i}$ substituents, (e.g. $R^{4a}$ or $R^{4b}$ represents, independently at each occurrence, $CH_2F$ or, particularly, iodo, butyl, $CH(CH_3)OH$, $OCH_2CH_2CH_3$, $NH(CH_3)$, NHC(O)O-tert-butyl, morpholino, phenyl or, more particularly, bromo, pyrazolyl, imidazolyl, benzyl, or, particularly, chloro, fluoro, CN, ethyl, methyl, isopropyl, $CF_3$, $CHF_2$, $CH_2CF_3$. $CF_2CF_3$, OH, $OCH(CH_3)_2$, $OCH_3$, $OCH_2CH_3$, $OCH_2F$, $OCHF_2$, $OCH_2CH_3$, $OCH_2CF_3$, $OCH_3$, $OCF_3$, $(CH_2)_3OH$, $CH_2OH$, $CH_2OCH_3$, $N(CH_3)_2$, cyclopropyl, dioxolanyl, $SCH_3$, $SCH_3$. $C(O)CH_3$, $C(O)CH_2CH_3$, $C(O)NH_2$, $C(O)NHCH_3$, $C(O)N(CH_3)_2$, $C(O)NHCH_2CH_3$, $S(O)CH_3$, $S(O)_2CH_3$, $S(O)_2CH_2CH_3$, $NHC(O)CH_3$, $NHS(O)_2CH_3$, =O, or when two $R^{4a}$ or $R^{4b}$ groups are attached to the same carbon atom in a non-aromatic portion of a $Cy^1$ or $Het^A$ group, they may form dioxolanyl, which ring optionally contains one to two heteroatoms selected from O and N, and which ring is optionally substituted by one or more $R^a$ substituents;

(4) $R^{4c}$ or $R^{4d}$ represent, independently at each occurrence, halo

CN, $C_{1-3}$ alkyl, (which latter group is optionally substituted by one or more substituents selected from halo and $OR^{5a}$), $OR^8$, $N(R^{9f})(R^{9g})$ or $B^7$—$C(G^1)$-$B^8$—$R^{9h}$ (e.g. $R^{4c}$ or $R^{4d}$ represents, independently at each occurrence, $CH_2OCH_3$, or particularly, bromo imidazolyl, $S(O)_2CH_3$, =O or more particularly, chloro, fluoro, CN, methyl, ethyl, n-propyl, isopropyl, $CF_3$, $CHF_2$, $CH_2CF_3$, OH, OCH, $OCH_2F$, $OCHF_2$, $OCH_2CH_3$, $OCH_2CF_3$, $OCH_3$, $OCF_3$, $N(CH_3)_2$, $CH_2OH$, $CH_2OCH_3$, $CH_2CN$, $C(O)CH_3$, $C(O)CH_2CH_3$, NHC(O)CH_3$).

In certain embodiments of the invention, the compound of formula Ixb, Iyb or Izb may be represented as a compound of formula Ixb1, Iyb1 or Izb1,

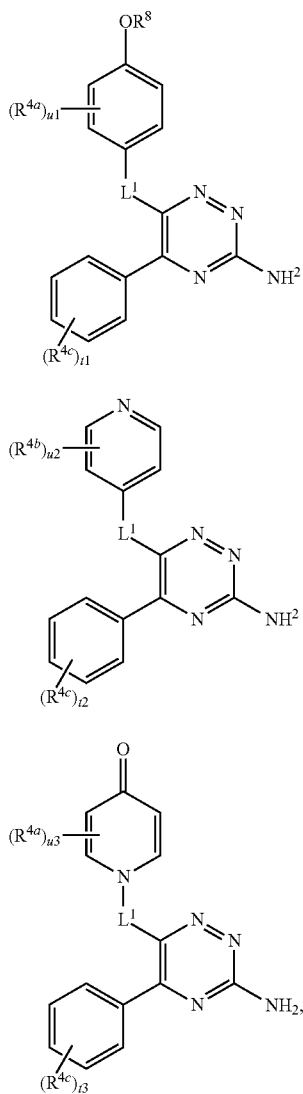

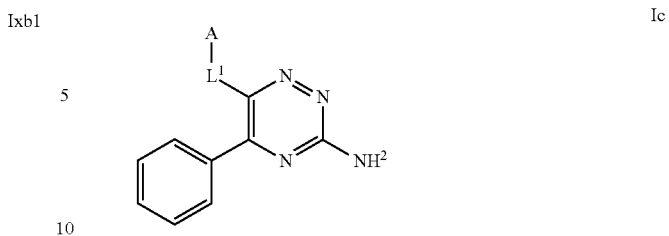

respectively, wherein u1, u2 and u3 independently represent 0 to 4 (e.g. 0 to 3 or, particularly 1 or 2) and $L^1$, $R^{4a}$, $R^{4b}$, $R^{4c}$, $R^3$ t1, t2 and t3 are as defined above in relation to compounds of formula I (or A1 or, particularly, Ix, Iy, Iz, Ia, Ixa, Iya, Iza, Ib, Ixb, Iyb or Izb) (e.g. $L^1$ represents a bond and $R^{4a}$, $R^{4b}$, $R^{4c}$ and $R^6$ are as defined above in relation to compounds of formula I (or A1 or, particularly, Ix, Iy, Iz, Ia, Ixa, Iya, Iza, Ib, Ixb, Iyb or Izb)).

In certain further embodiments of the invention, the compound of formula Ib, Ixb, Iyb, Izb, Ixb1, Iyb1 or Izb1 (e.g. the compound of Iyb1) is a compound in which:

(1) t, t1, t2 or t3 represents 3 or, particularly, 2, 1 or 0; and (2) the phenyl group that is substituted by $(R^{4c})_t$, $(R^{4c})_{t1}$, $(R^{4c})_{t2}$ or $(R^{4c})_{t3}$ is unsubstituted in the ortho-positions relative to the point of attachment to the 1,2,4-triazine group.

In certain other embodiments of the invention, B represents unsubstituted phenyl and $L^2$ represents a direct bond and the compound of formula I may be represented as a compound of formula Ic, wherein A and $L^1$ are as defined above in relation to compounds of formula I (or A1 or, particularly, Ia or Ib).

Embodiments of the invention that may be mentioned include those in which the compounds of formula I (or A1 or, particularly, Ix, Iy Iz, Ixa, Iya, Iza, Ixb, Iyb, Izb, Ixb1, Iyb1, Izb1, or, more particularly, Ia, Ib or Ic) are those in which:

(1) $L^1$ represents a bond or O (e.g. $L^1$ represents a direct bond):

(2) A represents furanyl, imidazolyl, ketopiperidinyl (e.g. 2-ketopiperidinyl, 3-ketopiperidinyl or 4-ketopiperidinyl), pyrazinyl, pyrrolidinyl, pyrrolidinonyl, particularly, cyclohexenyl, pyridinonyl (such as 1-1H-pyridin-2-onyl, 3-1H-pyridin-2-onyl, 4-1H-pyridin-2-onyl, 6-1H-pyridin-2-onyl, or, particularly, 4-pyridinonyl), or more particularly morpholinyl, piperidinyl, phenyl or pyridinyl (e.g. 2-pyridinyl, 3-pyridinyl, 4-pyridinyl), which A group is optionally substituted by one or more $R^{4a}$ or $R^{4b}$ substituents, as appropriate;

(3) $R^{4a}$ or $R^{4b}$ represents, independently at each occurrence, $CH_2F$, cyclopropyl, $N(Me)_2$, Br, =O, azetidine, or, particularly, chloro, fluoro, ethyl, methyl, $CF_3$, $CHF_2$, $CH_2CF_3$, $CF_2CF_3$, OH, $OCH(CH_3)_2$, $OCH_3$, $OCH_2CH_3$, $OCH_2F$, $OCHF_2$, $OCH_2CH_3$, $OCH_2CF_3$, $OCH_3$, $OCF_3$, $(CH_2)_3OH$, $CH_2OH$ or $CH_2OCH_3$ (e.g. $R^{4a}$ or $R^{4b}$ represents, independently at each occurrence, chloro, fluoro, ethyl, methyl, $CF_3$, $CHF_2$, $CH_2CF_3$, $CF_2CF_3$).

Further embodiments of the invention that may be mentioned relate to compounds of formula I (or A1 or, particularly, Ia, Ib or, more particularly, Ic) in which:

(1) $L^1$ represents a direct bond;

(2) A represents a non-aromatic, 6-membered $Het^4$ ring containing at least one N atom, which $Het^4$ group is optionally substituted by one or more $R^{4b}$ substituents, wherein the $Het^4$ ring is attached to the remainder of the molecule by the essential N atom.

These embodiments include those in which $L^1$ represents a direct bond, A represents piperidinyl or morpholinyl optionally substituted by one or more $R^{4b}$ substituents, $R^1$ represents H, $L^2$ represents a direct bond and B represents phenyl optionally substituted by one or more $R^{4c}$ substituents).

Still further embodiments of the invention that may be mentioned relate to compounds of formula I (or A1 or, particularly, Ia, Ib or, more particularly, Ic) in which:

(1) $L^1$ represents O;

(2) A represents a 6-membered $Cy^1$ group which is optionally substituted by one or more $R^{4a}$ substituents.

These embodiments include those in which $L^1$ represents O, A represents pyrazinyl, pyridazinyl, pyridinyl, pyrimidinyl or, particularly, phenyl optionally substituted by one or more $R^{4a}$ substituents, $R^1$ represents H, $L^2$ represents a direct bond and B represents phenyl optionally substituted by one or more $R^{4c}$ substituents.

In certain other embodiments of the invention, B represents phenyl and $L^1$ and $L^2$ represent a direct bond and the compound of formula I may be represented as a compound of formula Iyc,

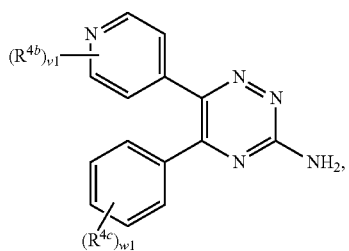

Iyc wherein v1 represents 0 to 4 (e.g. 0 to 3 or, particularly 1 or 2), w1 independently represents 0 to 5 (e.g. 0 to 3 or, particularly, 0 to 2), and $R^{4b}$ and $R^{4c}$ are as defined above in relation to compounds of formula I (or A1 or, particularly, Iy, Ia, Iya, Ib, Iyb, Iyb1 or Ic).

Embodiments of the invention that may be mentioned relate to compounds of formula Iyc in which:
(1) $R^{4b}$ represents, independently at each occurrence, $NMe_2$, Br, azetidin-1-yl, $CH_2F$ or, particularly, chloro, fluoro, ethyl, methyl, cyclopropyl, $CF_3$, $CHF_2$, $CH_2CF_3$, $CF_2CF$; or $OCH_3$;
(2) $R^{4c}$ represents, independently at each occurrence, CN, chloro, fluoro, ethyl, methyl, $CH_2OCH_3$, $CF_3$, $CHF_2$, $CH_2CF_3$, $CF_2CF_3$, OH, $OCH(CH_3)_2$, $OCH_3$, $OCH_2CH_3$. $OCH_2F$, $OCHF_2$, $OCH_2CH_3$. $OCH_2CF_3$, $OCH_3$, $OCF_3$, $(CH_2)_3OH$, $CH_2OH$ or $CH_2OCH_3$;
(3) v1 represents 0 to 4;
(4) w1 represents 0 to 3.

Further embodiments of the invention that may be mentioned relate to compounds of formula Iyc in which:
(1) $R^{4b}$ represents, independently at each occurrence, $NMe_2$, Br, azetidin-1-yl, $CH_2F$, $CHF_2$ or, particularly, cyclopropyl, $OCH_3$ or, more particularly, chloro, methyl or $CF_3$;
(2) $R^{4c}$ represents, independently at each occurrence, CN, chloro, fluoro, $CH_2OCH_3$, $OCH_3$, $OCH_2CH_3$. $OCH_2F$ or $OCHF_2$;
(3) v1 represents 1 or 2;
(4) w1 represents 0 to 3 (e.g. 3 or, particularly, 2, 1 or 0);
(5) the $R^{4b}$ substituent(s) is (are) attached to the 3- and/or 5-position(s) of the pyridyl group, relative to the point of attachment to the 1,2,4-triazine group;
(6) the phenyl ring is either unsubstituted or is substituted by one to three $R^{4c}$ substituents attached in the meta- and/or para-positions relative to the point of attachment to the 1,2,4-triazine group.

Still further embodiments of the invention that may be mentioned relate to compounds of formula Iyc in which:
(1) $R^{4b}$ represents, independently at each occurrence, $NMe_2$, Br, azetidin-1-yl, $CH_2F$, $CHF_2$ or, particularly, cyclopropyl, $OCH_3$ or, more particularly, chloro, methyl or $CF_3$;
(2) $R^{4c}$ represents, independently at each occurrence, CN, chloro, fluoro, $CH_2OCH_3$, $OCH_3$, $OCH_2CH_3$. $OCH_2F$ or $OCHF_2$;
(3) vi represents 1 or 2;
(4) w1 represents 0 to 3 (e.g. 3 or, particularly, 2, 1 or 0);
(5) the $R^{4b}$ substituent(s) is (are) attached to the 3- and/or 5-position(s) of the pyridyl group, relative to the point of attachment to the 1,2,4-triazine group; and
(6) the phenyl ring is either unsubstituted or is substituted by one to three $R^{4c}$ substituents attached in the meta- and/or para-positions relative to the point of attachment to the 1,2,4-triazine group.

Yet further embodiments of the invention that may be mentioned relate to compounds of formula Iyc in which:
(1) v1 represents 1 and the $R^{4b}$ substituent is attached to the 3-position of the pyridyl group, relative to the point of attachment to the 1,2,4-triazine group;
(2) v1 represents 2 and the $R^{4b}$ substituents are attached to the 3- and 5-positions of the pyridyl group, relative to the point of attachment to the 1,2,4-triazine group.

Compounds of formula I (or Ix, Iy Iz, Ixa, Iya, Iza, Ixb, Iyb, Izb, Ixb1, Iyb1, Izb1 and Iyc or, more particularly, Ia, Ib or Ic) that may be mentioned include those wherein, when A', A'', A''' or, particularly, A is a substituted 6-membered $Cy^1$ or $Het^4$ group (or $Cy^{1'}$, $Het^{4'}$, $Het^{4''}$ or $Het^{4'''}$ group), the substituent(s) is (are) in the ortho- or, particularly, meta- or para-position(s), relative to the point of attachment to the rest of the molecule (e.g. when A represents a substituted 6-membered $Cy^1$ or $Het^4$ group then there is at least one substituent in the meta- or para-positions and, optionally, a substituent in the ortho-position of A or, more particularly, there is at least one substituent in the meta- or para-position and no substituents in the ortho-position of A relative to the point of attachment to the rest of the molecule). In particular embodiments, the 6-membered $Cy^1$, $Cy^{1'}$, $Het^4$, $Het^{4'}$, $Het^{4''}$ or $Het^{4'''}$ group has:

no substituents in the ortho-positions;

a substituent in one or both of the meta-positions; and, optionally, for $Cy^1$, $Cy^{1'}$ or $Het^4$ a substituent in the para-position.

For example, in a particular embodiment of the invention, the compound of formula I (or A1 or, particularly, Ix, Iy Iz, Ia, Ixa, Iya, Iza, Ib, Ixb, Iyb, Izb, Ixb1, Iyb1, Izb1, Ic or Iyc) may be represented as a compound of formula Ixd, Iyd or Izd,

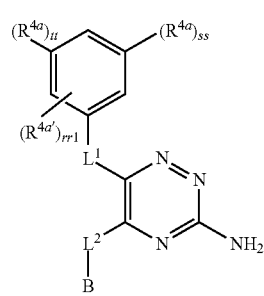

Ixd

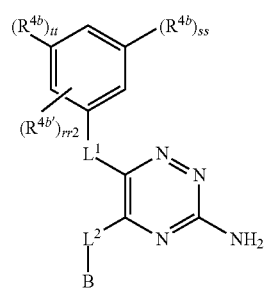

Iyd

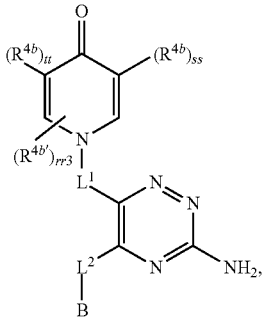

respectively, wherein:

rr1 represents 0 to 3 (e.g. 1 or, particularly 0);

rr2 and rr3 independently represent 0 to 2 (e.g. 1 or, particularly 0);

ss and tt independently represent, at each occurrence 0 or 1, provided that ss and tt do not both represent 0;

$R^{4a'}$ takes the same definition as $R^{4a}$;

$R^{4b'}$ takes the same definition as $R^{4b}$; and

B, $L^1$, $L^2$, $R^{4a}$ and $R^{4b}$ are as defined above in relation to compounds of formula I (or A1 or, particularly, Ix, Iy Iz, Ia, Ixa, Iya, Iza, Ib, Ixb, Iyb, Izb, Ixb1, Iyb1, Izb1, Ic or Iyc).

Embodiments of the invention that may be mentioned relate to compounds of formulae Ixd, Iyd and Izd in which $R^{4a}$, $R^{4a'}$, $R^{4b}$ and $R^{4b'}$ independently represent cyclopropyl, iodo, bromo, chloro, fluoro, ethyl, methyl, $d_3$-methyl, iso-propyl, —C≡CH, phenyl, $CF_3$, $CHF_2$, $CH_2F$, $CH_2CF_3$, $CF_2CF_3$, CN, =O, OH, $OCH(CH_3)_2$, $OCH_3$, $OCH_2CH_3$, $OCH_2F$, $OCHF_2$, $OCH_2CF_3$, $OCF_3$, $(CH_2)_3OH$, $CH_2OH$ or $CH_2OCH_3$, $CH(CH_3)OH$, $C(CH_3)_3OH$, $CH_2CH_2OH$, $NH_2$, $N(CH_3)_2$, $N(H)CH_2CH_3$, $N(H)C(O)CH_3$, $C(O)CH_3$, $C(O)N(CH_3)_2$, $S(O)_2CH_3$, $S(O)CH_3$, $SCH_3$, $S(O)_2CF_3$, azetidine, morpholine or dioxolane (e.g. OH, chloro, fluoro, bromo, ethyl, methyl, $d_3$-methyl, $CF_3$, $CHF_2$, $CH_2F$, $CH_2CF_3$, $CF_2CF_3$, or $N(H)C(O)CH_3$).

Embodiments of the invention that may be mentioned relate to compounds of formulae Ixd, Iyd and Izd in which $R^{4a}$, $R^{4a'}$, $R^{4b}$ and $R^{4b'}$ represent, independently at each occurrence (a) halo, (b) CN, (c) $C_{1-4}$ alkyl, $C_{2-4}$ alkenyl, $C_{2-4}$ alkynyl, which latter three groups are optionally substituted by one or more substituents selected from halo, nitro, CN, $OR^{5a}$, $S(O)_qR^{5b}$, $S(O)_2N(R^{5c})(R^{5d})$, $N(R^{5e})S(O)_2R^{5f}$, $N(R^{5g})(R^{5h})$, $B^1$—C($G^1$)-$B^2$—$R^{5i}$ and $Het^1$ (e.g. one or more substituents selected from nitro, CN, $OR^{5a}$, $S(O)_qR^{5b}$, $S(O)_2N(R^{5c})(R^{5d})$, $N(R^{5e})S(O)_2R^{5f}$, $N(R^{5g})(R^{5h})$, $B^1$—C($G^1$)-$B^2$—$R^{5i}$ and $Het^1$), (d) $Cy^3$, which $Cy^3$ group is optionally substituted by one or more substituents selected from nitro, CN, $OR^{6a}$, $S(O)_qR^{6b}$, $S(O)_2N(R^{6c})(R^{6d})$, $N(R^{6e})S(O)_2R^{6f}$, $N(R^{6g})(R^{6h})$, $B^3$—C($G^1$)-$B^4$—$R^{6i}$ and $Het^2$, (e) $Het^a$, which $Het^a$ group is optionally substituted by one or more substituents selected from halo, nitro, CN, $OR^{7a}$, $S(O)_qR^{7b}$, $S(O)_2N(R^{7c})(R^{7d})$, $N(R^{7e})S(O)_2R^{7f}$, $N(R^{7g})(R^{7h})$, $B^5$—C($G^1$)-$B^6$—$R^{7i}$ and $Het^3$, (f) $OR^8$, (g) $S(O)_rR^{9a}$, (h) $S(O)_2N(R^{9b})(R^{9c})$, (i) $N(R^{9d})S(O)_2R^{9e}$, (j) $N(R^{9f})(R^{9g})$ or (k) $B^7$—C($G^1$)-$B^8$—$R^{9h}$, wherein $R^{5a}$ to $R^{5i}$, $R^{6a}$ to $R^{6i}$, $R^{7a}$ to $R^{7i}$, $R^8$, $R^{9a}$ to $R^{9h}$, $Cy^3$, $Het^1$ to $Het^3$, $Het^a$, $B^1$ to $B^8$, $G^1$, q and r are as defined above.

Embodiments of the invention that may be mentioned relate to compounds of formulae Ixd, Iyd and Izd in which:

(1) $R^{4a}$ and $R^{4b}$ represent, independently at each occurrence, OH, $OCH(CH_3)_2$, $OCH_3$, $OCH_2CH_3$, $OCH_2F$, $OCHF_2$, $OCH_2CH_3$, $OCH_2CF_3$, $OCH_3$, $OCF_3$, $(CH_2)_3OH$, $CH_2OH$ or $CH_2OCH_3$, $NH_2$, $NHCH(CH_3)$, $NHCH_3$, $NHCH_2CH_3$, $NHCH_2CH_3$, $NH(CH(CH_3)_2)_2$, $NH(CH_3)_2$, $NH(CH_2CH_3)_2$ or $NH(CH_2CH_3)_2$);

(2) the sum of ss and tt is 1;

(3) rr1, rr2 and rr3 are 0;

(4) $L^1$ and $L^2$ both represent direct bonds.

Further embodiments of the invention that may be mentioned relate to compounds of formulae Ixd, Iyd and Izd in which:

(1) $R^{4a}$ and $R^{4b}$ represent, independently at each occurrence, $CH_2F$ or, particularly, cyclopropyl, chloro, fluoro, ethyl, methyl, $CF_3$, $CHF_2$, $CH_2CF_3$, $CF_2CF_3$, OH, $OCH(CH_3)_2$, $OCH_3$, $OCH_2CH_3$, $OCH_2F$, $OCHF_2$, $OCH_2CH_3$, $OCH_2CF_3$, $OCH_3$, $OCF_3$, $(CH_2)_3OH$, $CH_2OH$ or $CH_2OCH_3$;

(2) ss and tt are both 1;

(3) rr1 is 1 or, particularly, 0;

(4) rr2 and rr3 are 0;

(5) if present, $R^{4a'}$ is attached at the 4-position relative to $L^1$ and represents cyclopropyl, chloro, fluoro, ethyl, methyl, $CF_3$, $CHF_2$, $CH_2CF_3$, $CF_2CF_3$, OH, $OCH(CH_3)_2$, $OCH_3$, $OCH_2CH_3$, $OCH_2F$, $OCHF_2$, $OCH_2CH_3$, $OCH_2CF_3$, $OCH_3$, $OCF_3$, $(CH_2)_3OH$, $CH_2OH$ or $CH_2OCH_3$;

(6) $L^1$ and $L^2$ both represent direct bonds.

Still further embodiments of the invention that may be mentioned relate to compounds of formulae Ixd, Iyd and Izd in which:

(1) $R^{4a}$ and $R^{4b}$ represent, independently at each occurrence, $CH_2F$ or, particularly, cyclopropyl, chloro, fluoro, ethyl, methyl, $CF_3$, $CHF_2$, $CH_2CF_3$, $CF_2CF_3$, OH, $OCH(CH_3)_2$, $OCH_3$, $OCH_2CH_3$, $OCH_2F$, $OCHF_2$, $OCH_2CH_3$, $OCH_2CF_3$, $OCH_3$, $OCF_3$, $(CH_2)_3OH$, $CH_2OH$ or $CH_2OCH_3$ (e.g. chloro, fluoro, ethyl, methyl, $CF_3$, $CHF_2$, $CH_2CF_3$, $CF_2CF_3$);

(2) ss and tt are both 1;

(3) rr1, rr2 and rr3 are 0; and (4) $L^1$ and $L^2$ both represent direct bonds.

Embodiments of the invention that may be mentioned relate to compounds of formulae Ixd, Iyd and Izd in which $R^{4a}$, $R^{4a'}$, $R^{4b}$ and $R^{4b'}$ are as hereinbefore defined and the compounds are compounds of formula A1 (i.e. wherein $L^1$ and $L^2$ both represent direct bonds; and B represents $Cy^{BB}$ or $Het^{BB}$ as hereinbefore defined. In such embodiments of the invention, $R^{4a}$, $R^{4a'}$, $R^{4b}$ and $R^{4b'}$ independently represent cyclopropyl, iodo, bromo, chloro, fluoro, ethyl, methyl, $d_3$-methyl, iso-propyl, —C≡CH, phenyl, $CF_3$, $CHF_2$, $CH_2F$, $CH_2CF_3$, $CF_2CF_3$, CN, =O, OH, $OCH(CH_3)_2$, $OCH_3$, $OCH_2CH_3$, $OCH_2F$, $OCHF_2$, $OCH_2CF_3$, $OCF_3$, $(CH_2)_3OH$, $CH_2OH$ or $CH_2OCH_3$, $CH(CH_3)OH$, $C(CH_3)_2OH$, $CH_2CH_2OH$, $NH_2$, $N(CH_3)_2$, $N(H)CH_2CH_3$, $N(H)C(O)CH_3$, $C(O)CH_3$, $C(O)N(CH_3)_2$, $S(O)_2CH_3$, $S(O)CH_3$, $SCH_3$, $S(O)_2CF_3$, azetidine, morpholine or dioxolane (e.g. OH, chloro, fluoro, bromo, ethyl, methyl, $d_3$-methyl, $CF_3$, $CHF_2$, $CH_2F$, $CH_2CF_3$, $CF_2CF_3$ or $N(H)C(O)CH_3$).

Other compounds of formula I that may be mentioned include the compounds of the examples described hereinafter. Thus, embodiments of the invention that may be mentioned include those in which the compound of formula I is a compound selected from the list:
(i) 5,6-diphenyl-1,2,4-triazin-3-amine; or, particularly,
(ii) 6-(2-methoxyphenyl)-5-phenyl-1,2,4-triazin-3-amine;
(iii) 6-(3-methoxyphenyl)-5-phenyl-1,2,4-triazin-3-amine;
(iv) 6-(4-fluorophenyl)-5-phenyl-1,2,4-triazin-3-amine;
(v) 6-(5-chloro-2-methoxyphenyl)-5-phenyl-1,2,4-triazin-3-amine;
(vi) 6-(3-chlorophenyl)-5-phenyl-1,2,4-triazin-3-amine;
(vii) 6-(4-chlorophenyl)-5-phenyl-1,2,4-triazin-3-amine;
(viii) 5-phenyl-6-(piperidin-1-yl)-1,2,4-triazin-3-amine;
(ix) 6-(2-chlorophenyl)-5-phenyl-1,2,4-triazin-3-amine;
(x) 6-(furan-2-yl)-5-phenyl-1,2,4-triazin-3-amine;
(xi) 6-phenoxy-5-phenyl-1,2,4-triazin-3-amine;
(xii) 6-(morpholin-4-yl)-5-phenyl-1,2,4-triazin-3-amine;
(xiii) 6-(3-methylpiperidin-1-yl)-5-phenyl-1,2,4-triazin-3-amine;
(xiv) 6-(4,4-difluoropiperidin-1-yl)-5-phenyl-1,2,4-triazin-3-amine;
(xv) 6-(3-fluorophenoxy)-5-phenyl-1,2,4-triazin-3-amine;
(xvi) 6-(4-fluorophenoxy)-5-phenyl-1,2,4-triazin-3-amine;
(xvii) 6-(2-fluorophenoxy)-5-phenyl-1,2,4-triazin-3-amine;
(xviii) 6-(4-methoxyphenoxy)-5-phenyl-1,2,4-triazin-3-amine;
(xix) 6-(3-chlorophenyl)-5-(2,4-difluorophenyl)-1,2,4-triazin-3-amine;
(xx) 5-phenyl-6-(3,4,5-trifluorophenyl)-1,2,4-triazin-3-amine;
(xxi) 6-2,6-dimethylmorpholin-4-yl)-5-phenyl-1,2,4-triazin-3-amine;
(xxii) 5-phenyl-6-[3-(trifluoromnethyl)phenoxy]-1,2,4-triazin-3-amine;
(xxiii) 6-(3-chlorophenyl)-5-(3-methoxyphenyl-1,2,4-tiazin-3-amine;
(xxiv) 5-phenyl-6-[3-(trifluoromethyl)phen]-1,2,4-triazin-3-amine;
(xxv) 6-(3,5-difluorophenyl)-5-phenyl-1,2,4-triazin-3-amine;
(xxvi) 5-phenyl-6-[2-(propan-2-yl)phenoxy-1,2,4-triazin-3-amine;
(xxvii) 6-(3-fluoro-5-(trifluoromiethyl)phenyl]-5-phenyl-1,2,4-triazin-3-amine;
(xxviii) 6-(3,5-dichlorophenyl)-5-phenyl-1,2,4-triazin-3-amine;
(xxix) 6-(5-chloropyridin-3-yl)-5-phenyl-1,2,4-triazin-3-amine;
(xxx) 6-(3-chloro-4-fluorophenyl)-5-phenyl-1,2,4-triazin-3-amine;
(xxxi) 6-(3-fluoro-5-methoxyphenyl)-5-phenyl-1,2,4-triazin-3-amine;
(xxxii) 6-[4-fluoro-3-(trifluoromethyl)phenoxy]-5-phenyl-1,2,4-triazin-3-amine;
(xxxiii) 5-phenyl-6-[3-(trifluoromethoxy)phenoxy]-1,2,4-triazin-3-amine;
(xxxiv) 6-(3-chlorophenyl)-5-(4-fluorophenyl)-1,2,4-triazin-3-amine;
(xxxv) 6-(3-chloro-5-methoxyphenyl)-5-phenyl-1,2,4-triazin-3-amine;
(xxxvi) 6-(3-aminophenoxy)-5-phenyl-1,2,4-triazin-3-amine:
(xxxvii) 6-(3-chlorophenoxy)-5-phenyl-1,2,4-triazin-3-amine;
(xxxviii) 6-(3,3-dimethylpiperidin-1-yl)-5-phenyl-1,2,4-triazin-3-amine;
(xxxix) 6-(3-bromophenyl)-5-phenyl-1,2,4-triazin-3-amine;
(xl) 6-(3,5-dichlorophenoxy)-5-phenyl-1,2,4-triazin-3-amine;
(xli) 5-phenyl-6-[3-(trifluoromethyl)piperidin-1-yl]-1,2,4-triazin-3-amine;
(xlii) 6-(1H-indol-6-yl)-5-phenyl-1,2,4-triazin-3-amine;
(xliii) 6-(3,5-difluorophenoxy)-5-phenyl-1,2,4-triazin-3-amine;
(xliv) 6-(octahydroquinolin-1 (2H)-yl)-5-phenyl-1,2,4-triazin-3-amine;
(xlv) 6-(3,4-dichlorophenyl)-5-phenyl-1,2,4-triazin-3-amine:
(xlvi) 6-(3-fluorophenyl)-5-phenyl-1,2,4-triazin-3-amine;
(xlvii) 6-(1,3-benzodioxol-5-yl)-5-phenyl-1,2,4-triazin-3-amine;
(xlviii) 3-(3-amino-5-phenyl-1,2,4-triazin-6-yl)benzonitrile;
(xlix) 6-(3,5-dimethoxyphenyl)-5-phenyl-1,2,4-triazin-3-amine;
(l) 6-(3,5-dimethylphenyl)-5-phenyl-1,2,4-triazin-3-amine;
(li) 6-(3,4-dimethylphenyl)-5-phenyl-1,2,4-triazin-3-amine;
(lii) 6-[3-(dimethylamino)phenyl]-5-phenyl-1,2,4-triazin-3-amine;
(liii) N-[3-(3-amino-5-phenyl-1,2,4-triazin-6-yl)phenyl]acetamide;
(liv) N-[3-(3-amino-5-phenyl-1,2,4-triazin-6-yl)phenyl]methanesulfonamide;
(lv) 6-(3-trifluoromethoxyphenyl)-5-phenyl-1,2,4-triazin-3-amine;
(lvi) 6-(1-benzofuran-5-yl)-5-phenyl-1,2,4-triazin-3-amine;
(lvii) 5-phenyl-6-[3-(propan-2-yl)phenyl]-1,2,4-triazin-3-amine;
(lviii) 6-(3,5-dichlorophenyl)-5-(4-fluorophenyl)-1,2,4-triazin-3-amine;
(lix) 6-(3,5-bis(trifluormethyl)phenyl)-5-phenyl-1,2,4-triazin-3-amine;
(lx) 4-(3-amino-5-phenyl-1,2,4-triazin-6-yl)-2-methoxyphenol;
(lxi) 4-(3-amino-5-phenyl-1,2,4-triazin-6-yl)-2,6-dimethylphenol
(lxii) 4-(3-amino-5-phenyl-1,2,4-triazin-6-yl)-2-chlorophenol;
(lxiii) 6-(2-chloropyridin-4-yl)-5-phenyl-1,2,4-triazin-3-amine;
(lxiv) 6-(3-(methylsulfonyl)phenyl)-5-phenyl-1,2,4-triazin-3-amine;
(lxv) 6-(3,5-dichloro-4-methoxyphenyl)-5-phenyl-1,2,4-triazin-3-amine;
(lxvi) 6-(4-methoxy-(trifluoromethyl)phenyl)-5-phenyl-1,2,4-triazin-3-amine;
(lxvii) 6-(3-chloro-5-(dimethylamino)phenyl)-5-phenyl-1,2,4-triazin-3-amine;
(lxviii) 3-(3-amino-5-phenyl-1,2,4-triazin-6-yl)-5-(trifluoromethyl)benzonitrile;
(lxix) 4-(3-amino-5-phenyl-1,2,4-triazin-6-yl)-2,6-dimethylbenzonitrile;
(lxx) 6-(3-chloro-5-(trifluoromethyl)phenyl)-5-phenyl-1,2,4-triazin-3-amine;
(lxxi) 6-(3-chloro-5-methylphenyl)-5-phenyl-1,2,4-triazin-3-amine;
(lxxii) 6-(3-(methylthio)-5-(trifluoromethyl)phenyl)-5-phenyl-1,2,4-triazin-3-amine;
(lxxiii) 6-(3-methoxy-5-(trifluoromethyl)phenyl)-5-phenyl-1,2,4-triazin-3-amine;
(lxxiv) 6-(3-ethoxy-5-(trifluoromethyl)phenyl)-5-phenyl-1,2,4-triazin-3-amine;
(lxxv) 6-(3-tert-butyl-5-methylphenyl)-5-phenyl-1,2,4-triazin-3-amine;
(lxxvi) 6-(2-chloro-6-methylpyridin-4-yl)-5-phenyl-1,2,4-triazin-3-amine;

(lxxvii) 4-(3-amino-5-phenyl-1,2,4-triazin-6-yl)-2-chlorobenzonitrile;
(lxxviii) 6-(3-ethylphenyl)-5-phenyl-1,2,4-triazin-3-amine;
(lxxix) 6-(2-methoxy-6-(trifluoromethyl)pyridin-4-yl)-5-phenyl-1,2,4-triazin-3-amine;
(lxxx) 6-(3-methyl-5-(trifluoromethoxy)phenyl)-5-phenyl-1,2,4-triazin-3-amine;
(lxxxi) 6-(3-(1,3-dioxolan-2-yl)-5-(trifluoromethyl)phenyl)-5-phenyl-1,2,4-triazin-3-amine;
(lxxxii) 5-phenyl-6-(3-(2,2,2-trifluoroethoxy)phenyl)-1,2,4-triazin-3-amine;
(lxxxiii) 6-(3-(methoxymethyl)phenyl)-5-phenyl-1,2,4-triazin-3-amine;
(lxxxiv) 5-(3-amino-5-phenyl-1,2,4-triazin-1-yl)-1-methylpyridin-2(1H)-one;
(lxxxv) 6-3-methyl-5-(trifluoromethyl)phenyl)-5-phenyl-1,2,4-triazin-3-amine;
(lxxxvi) 6-(2-methoxypyridin-4-yl)-5-phenyl-1,2,4-triazin-3-amine;
(lxxxvii) 1-(3-(3-amino-5-phenyl-1,2,4-triazin-6-yl)phenyl)ethanone;
(lxxxviii) 4-(3-amino-5-phenyl-1,2,4-triazin-6-yl)benzamide;
(lxxxix) 6-(4-fluoro-3-(trifluoromethyl)phenyl)-5-phenyl-1,2,4-triazin-3-amine;
(xc) 6-(4-fluoromethylphenyl)-5-phenyl-1,2,4-triazin-3-amine;
(xci) 6-(3-bromo-5-chlorophenyl)-5-phenyl-1,2,4-triazin-3-amine:
(xcii) 6-naphthalen-2-yl)-5-phenyl-1,2,4-triazin-3-amine;
(xciii) 5-phenyl-6-m-tolyl-1,2,4-triazin-3-amine;
(xciv) 5-phenyl-6-(pyridin-4-yl)-1,2,4-triazin-3-amine;
(xcv) 4-(3-amino-5-phenyl-1,2,4-triazin-6-yl)phenol;
(xcvi) 6-(2,6-dimethoxypyridin-4-yl)-5-phenyl-1,2,4-triazin-3-amine;
(xcvii) 6-(2,6-dimethylpyridin-4-yl)-5-phenyl-1,2,4-triazin-3-amine:
(xcviii) 5-phenyl-6-(2-(trifluoromethyl)pyridin-4-yl)-1,2,4-triazin-3-amine;
(xcix) 6-(2-cyclopropylpyridin-4-yl)-5-phenyl-1,2,4-triazin-3-amine;
(c) 5-phenyl-6-(2,2,6,6-tetramethyl-3,6-dihydro-2H-pyran-4-yl)-1,2,4-triazin-3-amine;
(ci) 6-(5-chloro-2-fluoro-3-methylphenyl)-5-phenyl-1,2,4-triazin-3-amine;
(cii) 6-(2,6-dichloropyridin-4-yl)-5-phenyl-1,2,4-triazin-3-amine;
(ciii) 6-(3-bromo-5-(trifluoromethoxy)phenyl)-5-phenyl-1,2,4-triazin-3-amine:
(civ) 4-(3-amino-5-phenyl-1,2,4-triazin-6-yl)-2-chloro-6-methoxyphenol;
(cv) 6-(3,5-dichloro-4-ethoxyphenyl)-5-phenyl-1,2,4-triazin-3-amine;
(cvi) 6-(6-amino-5-(trifluoromethyl)pyridin-3-yl)-5-phenyl-1,2,4-triazin-3-amine;
(cvii) 4-(3-amino-5-(3-fluorophenyl)-1,2,4-triazin-6-yl)-2,6-dimethylbenzonitrile;
(cviii) 6-(3-chloro-5-(trifluoromethyl)phenyl)-5-(3-fluorophenyl)-1,2,4-triazin-3-amine;
(cix) 6-(2-chloro-6-methylpyridin-4-yl)-5-(3-fluorophenyl)-1,2,4-triazin-3-amine;
(cx) 4-(3-amino-5-(4-fluorophenyl)-1,2,4-triazin-6-yl)-2,6-dimethylbenzonitrile;
(cxi) 6-(3-chloro-5-propoxyphenyl)-5-phenyl-1,2,4-triazin-3-amine;
(cxii) 6-(3-chloro-5-(trifluoromethyl)phenyl)-5-(4-fluorophenyl)-1,2,4-triazin-3-amine;
(cxiii) 6-(2-chloropyridin-4-yl)-5-(4-fluorophenyl)-1,2,4-triazin-3-amine;
(cxiv) 6-(2-chloro-6-methylpyridin-4-yl)-5-(4-fluorophenyl)-1,2,4-triazin-3-amine;
(cxv) 4-(3-amino-5-(4-chlorophenyl)-1,2,4-triazin-6-yl)-2,6-dimethylbenzonitrile;
(cxvi) 6-(3-chloro-5-(trifluoromethyl)phenyl)-5-(4-chlorophenyl)-1,2,4-triazin-3-amine;
(cxvii) 5-(4-chlorophenyl)-6-(2-chloropyridin-4-yl)-1,2,4-triazin-3-amine;
(cxviii) 6-(2-chloro-6-methylpyridin-4-yl)-5-(4-chlorophenyl)-1,2,4-triazin-3-amine;
(cxix) 4-(3-amino-5-(3-chlorophenyl)-1,2,4-triazin-6-yl)-2,6-dimethylbenzonitriile;
(cxx) 6-(3-chloro-5-(trifluoromethyl)phenyl)-5-(3-chlorophenyl-1,2,4-triazin-3-amine;
(cxxi) 5-(3-chlorophenyl)-6-(2-chloropyridin-4-yl)-1,2,4-triazin-3-amine;
(cxxii) 6-(2-chloro-6-methylpyridin-4-yl)-5-(3-chlorophenyl)-1,2,4-triazin-3-amine;
(cxxiii) 4-(3-amino-6-(3-chloro-5-(trifluoromethyl)phenyl)-1,2,4-triazin-5-yl)benzonitrile;
(cxxiv) 4-(3-amino-6-(2-chloro-6-methylpyridin-4-yl)-1,2,4-triazin-5-yl)benzonitrile;
(cxxv) 4-(3-amino-5-(3-chloro-5-fluorophenyl)-1,2,4-triazin-6-yl)-2,6-dimethylbenzonitrile;
(cxxvi) 5-(3-chloro-5-fluorophenyl)-6-(2-chloro-6-methylpyridin-4-yl)-1,2,4-triazin-3-amine;
(cxxvii) 6-(3-chloro-5-(trifluoromethyl)phenyl)-5-(3-chloro-5-fluorophenyl)-1,2,4-triazin-3-amine;
(cxxviii) 6-(3-chloro-5-(trifluoromethyl)phenyl)-5-(3,5-difluorophenyl)-1,2,4-triazin-3-amine;
(cxxix) 6-(2-chloro-6-methylpyridin-4-yl)-5-(3,5-difluorophenyl)-1,2,4-triazin-3-amine;
(cxxx) 4-(3-amino-5-(3,5-difluorophenyl)-1,2,4-triazin-6-yl)-2,6-dimethylbenzonitrile;
(cxxxi) 4-(3-amino-5-(3-chloro-4-fluorphenyl)-1,2,4-triazin-6-yl)-2,6-dimethylbenzonitrile;
(cxxxii) 5-(3-chloro-4-fluorophenyl)-6-(2-chloro-6-methylpyridin-4-yl-1,2,4-triazin-3-amine;
(cxxxiii) 5-(3-chloro-4-fluorophenyl)-6-(2-chloropyridin-4-yl-1,2,4-triazin-3-amine;
(cxxxiv) 5-(3-chloro-4-fluorophenyl)-6-(3-chloro-5-(trifluoromethyl)phenyl)-1,2,4-triazin-3-amine;
(cxxxv) 4-(3-amino-5-(3,4-difluorophenyl)-1,2,4-triazin-6-yl)-2,6-dimethylbenzonitrile;
(cxxxvi) 6-(2-chloro-6-methylpyridin-4-yl)-5-(3,4-difluorophenyl)-1,2,4-triazin-3-amine;
(cxxxvii) 6-(2-chloropyridin-4-yl)-5-(3,4-difluorophenyl)-1,2,4-triazin-3-amine;
(cxxxviii) 6-(3-chloro-5-(trifluoromethyl)phenyl)-5-(3,4-difluorophenyl)-1,2,4-triazin-3-amine;
(cxxxix) 6-(3-chloro-5-(trifluoromethyl)phenyl)-5-(4-(methoxymethyl)phenyl)-1,2,4-triazin-3-amine;
(cxl) 6-(2-chloro-6-methylpyridin-4-yl)-5-(4-(methoxymethyl)phenyl)-1,2,4-triazin-3-amine;
(cxli) 6-(2,6-dimethylpyridin-4-yl)-5-(4-fluorophenyl)-1,2,4-triazin-3-amine;
(cxlii) 6-(3-chloro-5-methylphenyl)-5-(4-fluorophenyl)-1,2,4-triazin-3-amine;
(cxliii) 6-(6-fluoropyridin-3-yl)-5-phenyl-1,2,4-triazin-3-amine;
(cxliv) 6-(3,5-dimethylisoxazol-4-yl)-5-phenyl-1,2,4-triazin-3-amine;
(cxlv) 6-(3,5-diisopropylphenyl)-5-phenyl-1,2,4-triazin-3-amine;

(cxlvi) 6-3-fluoro-5-(2,2,2-trifluoroethoxy)phenyl)-5-phenyl-1,2,4-triazin-3-amine;
(cxlvii) N-(4-(3-amino-5-phenyl-1,2,4-triazin-6-yl)-2-(trifluoromethyl)phenyl)acetamide;
(cxlviii) 5-(3-amino-5-phenyl-1,2,4-triazin-6-yl)-2-fluorobenzonitrile;
(cxlix) 3-(3-amino-5-phenyl-1,2,4-triazin-6-yl)-N,N-dimethylbenzamide;
(cl) 6-1-methy-1H-pyrazol-4-yl)-5-phenyl-1,2,4-triazin-3-amine;
(cli) 4-(3-amino-5-phenyl-1,2,4-triazin-6-yl)-1-methylpyridin-2(1H)-one;
(clii) 6-(3-(morpholin-4-yl)phenyl)-5-phenyl-1,2,4-triazin-3-amine;
(cliii) 6-(1-benzyl-1H-pyrazol-4-yl)-5-phenyl-1,2,4-triazin-3-amine;
(cliv) 6-(2-methoxypyrimidin-5-yl)-5-phenyl-1,2,4-triazin-3-amine;
(clv) 6-(6-methoxypyridin-3-yl)-5-phenyl-1,2,4-triazin-3-amine;
(clvi) 6-(3-(methylsulfinyl)phenyl)-5-phenyl-1,2,4-triazin-3-amine;
(clvii) 4-(3-amino-6-(2-chloropyridin-4-yl)-1,2,4-triazin-5-yl)benzonitrile;
(clviii) 4-(3-amino-5-(4-(methoxymethyl)phenyl)-1,2,4-triazin-6-yl)-2,6-dimethylbenzonitrile; (clix) 6-(2-chloropyridin-4-yl)-5-(4-(methoxymethyl)phenyl)-1,2,4-triazin-3-amine;
(clx) 6(E)-5-phenyl-6-styryl-1,2,4-triazin-3-amine;
(clxi) 6-(3-amino-5-phenyl-1,2,4-triazin-6-yl)indolin-2-one;
(clxii) tert-butyl 5-(3-amino-5-phenyl-1,2,4-triazin-6-yl)pyridin-2-yl(methyl)carbamate;
(clxiii) 6-(3-methoxypiperidin-1-yl)-5-phenyl-1,2,4-triazin-3-amine;
(clxiv) 6-(3-ethynylpiperidin-1-yl)-5-phenyl-1,2,4-triazin-3-amine;
(clxv) 6-2,6-dimethylmorpholin-4-yl)-5-(4-fluorophenyl)-1,2,4-triazin-3-amine;
(clxvi) 6-(2-ethylmorpholino)-5-phenyl-1,2,4-tiazin-3-amine;
(clxvii) 5-phenyl-6-(6-oxa-9-azaspiro[4.5]decan-9-yl)-1,2,4-triazin-3-amine;
(clxviii) 6-(2,2-diethylmorpholino)-5-phenyl-1,2,4-triazin-3-amine;
(clxix) 6-(2,2-dimethylmorpholino)-5-phenyl-1,2,4-triazin-3-amine;
(clxx) (1-(3-amino-5-phenyl-1,2,4-triazin-6-yl)-3-methylpiperidin-3-yl)methanol;
(clxxi) 6-(3-(methoxymethyl)piperidin-1-yl)-5-phenyl-1,2,4-triazin-3-amine;
(clxxii) 1-(1-(3-amino-5-phenyl-1,2,4-triazin-6-yl)piperidin-3-yl)ethanal;
(cdxxiii) (1-(3-amino-5-phenyl-1,2,4-tiazin-6-yl)piperidin-3-yl)methanol;
(clxxiv) 1-(1-(3-amino-5-phenyl-1,2,4-triazin-6-yl)piperidin-3-yl)ethanone;
(clxxv) 6-(octahydroisoquinolin-2(1H)-yl)-5-phenyl-1,2,4-triazin-3-amine;
(clxxvi) N6-(4-methyl-1,3-thiazol-2-yl)-5-phenyl-1,2,4-triazine-3,6-diamine;
(clxxvii) 5-phenyl-6-[4-(trifluoromethyl)piperidin-1-yl]-1,2,4-triazin-3-amine;
(clxxviii) 5-phenyl-6-(3-phenylpiperidin-1-yl)-1,2,4-triazin-3-amine;
(clxxix) (4-(3-amino-5-phenyl-1,2,4-triazin-6-yl)morpholin-2-yl)methanol;
(clxxx) 5-phenyl-6-(3-(propoxymethyl)pyrrolidin-1-yl)-1,2,4-triazin-3-amine;
(clxxxi) 2-(1-(3-amino-5-phenyl-1,2,4-triazin-6-yl)piperidin-3-yl)propan-2-ol;
(clxxxii) 6-(hexahydropyrrolo[1,2-a]pyrazin-2(1H)-yl)-5-phenyl-1,2,4-triazin-3-amine;
(clxxxiii) 1-(3-amino-5-phenyl-1,2,4-triazin-6-yl)-3-ethylpiperidin-3-ol;
(clxxxiv) 2-(4-(3-amino-5-phenyl-1,2,4-triazin-6-yl)morpholin-2-yl)ethanol;
(clxxxv) 6-(3,5-dimethylphenoxy)-5-phenyl-1,2,4-triazin-3-amine;
(clxxxvi) 6-(3-chloro-5-methoxyphenoxy)-5-phenyl-1,2,4-triazin-3-amine;
(clxxxvii) 1-(3-amino-5-phenyl-1,2,4-triazin-6-yl)pyridin-4(1H)-one;
(clxxxviii) 6-(4-methylphenoxy)-5-phenyl-1,2,4-triazin-3-amine;
(clxxxix) 6-(4-chlorophenoxy)-5-phenyl-1,2,4-triazin-3-amine;
(cxc) 6-(3,4-difluorophenoxy)-5-phenyl-1,2,4-triazin-3-amine;
(cxci) 6-[(6-methoxypyridin-3-yl)oxy]-5-phenyl-1,2,4-triazin-3-amine;
(cxcii) 6-[(2-methylpyridin-3-yl)oxy]-5-phenyl-1,2,4-triazin-3-amine;
(cxciii) 6-[(6-chloropyridin-3-yl)oxy]-5-phenyl-1,2,4-triazin-3-amine;
(cxciv) 4-[(3-amino-5-phenyl-1,2,4-triazin-6-yl)oxy]benzonitrile;
(cxcv) 6-{[1-methyl-3-(trifluoromethyl)-1H-pyrazol-5-yl]oxy}-5-phenyl-1,2,4-triazin-3-amine;
(cxcvi) 6-[(1-methyl-1H-benzimidazol-5-yl)oxy]-5-phenyl-1,2,4-triazin-3-amine;
(cxcvii) 1-(3-amino-5-phenyl-1,2,4-triazin-6-yl)pyridazin-4(1H)-one;
(cxcviii) 1-(3-amino-5-phenyl-1,2,4-triazin-6-yl)-3,5-dichloropyridin-4(1H)-one;
(cxcix) 6-(2,4-difluorophenoxy)-5-phenyl-1,2,4-triazin-3-amine;
(cc) 5-phenyl-6-(pyridin-3-yloxy)-1,2,4-triazin-3-amine;
(cci) 6-[(4-methylpyridin-3-yl)oxy]-5-phenyl-1,2,4-triazin-3-amine;
(ccii) 5-phenyl-6-(p-tolylthio)-1,2,4-triazin-3-amine;
(cciii) 3-(3-amino-5-phenyl-1,2,4-triazin-6-yl)-5-chlorophenol;
(cciv) 6-(3-chloro-5-ethenylphenyl)-5-phenyl-1,2,4-triazin-3-amine;
(ccv) 6-(3-chloro-5-cyclopropylphenyl)-5-phenyl-1,2,4-triazin-3-amine;
(ccvi) 6-(3,5-dichlorophenyl)-5-(3-methylpiperidin-1-yl)-1,2,4-triazin-3-amine;
(ccvii) 6-(6-(methylamino)pyridin-3-yl)-5-phenyl-1,2,4-triazin-3-amine;
(ccviii) 5-(3-chloro-5-fluorophenyl)-8-(2-chloropyridin-4-yl)-1,2,4-triazin-3-amine;
(ccix) 6-(2-chloropyridin-4-yl)-5-(3,5-difluorophenyl)-1,2,4-triazin-3-amine;
(ccx) 4-(3-amino-5-(4-(difluoromethoxy)phenyl)-1,2,4-triazin-6-yl)-2,6-dimethylbenzonitrile;
(ccxi) 6-(2-chloro-6-methylpyridin-4-yl)-5-(4-(difluoromethoxy)phenyl)-1,2,4-triazin-3-amine;
(ccxii) 6-(2-chloropyridin-4-yl)-5-(4-(difluoromethoxy)phenyl)-1,2,4-triazin-3-amine;
(ccxiii) 6-(3-chloro-5-(trifluoromethyl)phenyl)-5-(4-(difluoromethoxy)phenyl)-1,2,4-triazin-3-amine;

(ccxiv) 5-(3-amino-5-(3-fluorophenyl)-1,2,4-triazin-6-yl)-2-chlorophenol;
(ccxv) 4-[3-amino-6-(3-chloro-4-hydroxyphenyl)-1,2,4-triazin-5-yl]benzonitrile;
(ccxvi) 3-(3-amino-5-phenyl-1,2,4-triazin-8-yl)-5-(trifluoromethoxy)phenol;
(ccxvii) 5-(3-chloro-5-fluorophenyl)-6-(2,6-dimethylpyridin-4-yl)-1,2,4-triazin-3-amine;
(ccxviii) 5-3,5-difluorophenyl)-6-(2,6-dimethylpyridin-4-yl)-1,2,4-triazin-3-amine;
(ccxix) 5-(3,4-difluorophenyl)-6-(2,6-dimethylpyridin-4-yl)-1,2,4-triazin-3-amine;
(ccxx) 5-(3-chloro-4-fluorophenyl)-6-(2,6-dimethylpyridin-4-yl)-1,2,4-triazin-3-amine;
(ccxx) 5-(4-(difluoromethoxy)phenyl)-6-(2,6-dimethylpyridin-4-yl)-1,2,4-triazin-3-amine;
(ccxxii) 6-(2,6-dimethylpyridin-4-yl)-5-(3-fluorophenyl)-1,2,4-triazin-3-amine;
(ccxxiii) 5-(4-chlorophenyl)-6-(2,6-dimethylpyridin-4-yl)-1,2,4-triazin-3-amine;
(ccxxiv) 4-(3-amino-6-(2,6-dimethylpyridin-4-yl)-1,2,4-triazin-5-yl)benzonitrile;
(ccxxv) 5-(3-chlorophenyl-6-(2,6-dimethylpyridin-4-yl)-1,2,4-triazin-3-amine;
(ccxxvi) 6-(2,6-dimethylpyridin-4-yl)-5-(4-(methoxymethyl)phenyl)-1,2,4-triazin-3-amine;
(ccxxvii) 4-(3-amino-6-(3-chloro-4-hydroxy-5-methoxyphenyl)-1,2,4-triazin-5-yl)benzonitrile;
(ccxxviii) 5-(3-amino-5-phenyl-1,2,4-triazin-6-yl)-2-chlorophenol;
(ccxxix) 6-(6-chloropyridin-2-yl)-5-phenyl-1,2,4-triazin-3-amine;
(ccxxx) 6-(4-cyclopropylpyridin-2-yl)-5-phenyl-1,2,4-triazin-3-amine;
(ccxxxi) 5-phenyl-6-(6-(trifluoromethyl)pyridin-2-yl)-1,2,4-triazin-3-amine;
(ccxxxii) 5-phenyl-6-(4-(trifluoromethyl)pyridin-2-yl)-1,2,4-triazin-3-amine;
(ccxxxiii) 6-(6-cyclopropylpyridin-2-yl)-5-phenyl-1,2,4-triazin-3-amine;
(ccxxxiv) 5-(3-amino-5-phenyl-1,2,4-triazin-6-yl)pyrazin-2-o;
(ccxxxv) 4-(3-amino-5-phenyl-1,2,4-triazin-6-yl)-2,6-diiodophenol;
(ccxxxvi) 4-(3-amino-5-phenyl-1,2,4-triazin-6-yl)-2-iodophenol;
(ccxxxvii) 6-(3-methoxy-5-(trifluoromethoxy)phenyl)-5-phenyl-1,2,4-triazin-3-amine;
(ccxxxviii) 4-(3-amino-5-phenyl-1,2,4-triazin-6-yl)-2-(propan-2-yloxy)phenol;
(ccxxxix) 5-(3-fluorophenyl)-8-(2-chloropyridin-4-yl)-1,2,4-triazin-3-amine;
(ccxl) 6-(2,4 dichlorophenoxy)-5-phenyl-1,2,4-triazin-3-amine;
(ccxli) 6-[2-chloro-6-(trifluoromethyl)pyridin-4-yl]-5-(3,4-difluorophenyl)-1,2,4-triazin-3-amine;
(ccxlii) 6-[2-chloro-6-(trifluoromethyl)pyridin-4-yl]-5-(3,5-difluorophenyl)-1,2,4-triazin-3-amine;
(ccxliii) 6-[2-(ethylamino)-6-methylpyridin-4-yl]-5-phenyl-1,2,4-triazin-3-amine;
(ccxliv) 6-[2-chloro-6-(trifluoromethyl)pyridin-4-yl]-5-(3-fluorophenyl-1,2,4-tiazin-3-amine;
(ccxlv) 6-[2-chloro-6-(trifluoromethyl)pyridin-4-yl]-5-(4-fluorophenyl)-1,2,4-triazin-3-amine;
(ccxlvi) 6-{2-[ethyl(methyl)amino]-6-methylpyridin-4-yl}-5-phenyl-1,2,4-triazin-3-amine;

(ccxlvii) 6-[2-(dimethylamino)-6-methylpyridin-4-yl]-5-phenyl-1,2,4-triazin-3-amine;
(ccxlviii) 1-[6-(2,6-d6-dimethylpyridin-4-yl)-5-phenyl-1,2,4-triazin-3-amine;
(ccxlix) 6-[2-d3-methyl-6-(trifluoromethyl)pyridin-4-yl]-5-phenyl-1,2,4-triazin-3-amine;
(ccl) 5-(4-fluorophenyl)-6-[2-d3-methyl-6-(trifluoromethyl)pyridin-4-yl]-1,2,4-triazin-3-amine;
(ccli) 6-(2,6-dimethylpyridin-4-yl)-5-(2-fluorophenyl)-1,2,4-triazin-3-amine;
(cclii) 6-(2-chloro-6-methylpyridin-4-yl)-5-(2-fluorophenyl)-1,2,4-triazin-3-amine;
(ccliii) 6-(2,6-dimethylpyridin-4-yl)-5-(4-methoxyphenyl)-1,2,4-triazin-3-amine:
(ccliv) 6-2-chloro-6-methylpyridin-4-yl)-5-(4-methoxyphenyl)-1,2,4-triazin-3-amine;
(cclv) 6-[2-(difluoromethyl-6-methylpyridin-4-yl]-5-phenyl-1,2,4-triazin-3-amine;
(cclvi) 6-[2-chloro-6-(difluoromethyl)pyridin-4-yl]-5-phenyl-1,2,4-triazin-3-amine;
(cclvii) 6-[2-chloro-6-(fluoromethyl)pyridin-4-yl]-5-phenyl-1,2,4-triazin-3-amine;
(cclviii) 6-[2-(difluoromethyl)-6-methylpyridin-4-yl]-5-(4-fluorophenyl)-1,2,4-triazin-3-amine;
(cclix) 6-[2,6-bis(fluoromethyl)pyridine-4-yl]-5-phenyl-1,2,4-triazin-3-amine;
(cclx) 6-[2-(fluoromethyl)-6-methylpyridin-4-yl]-5-phenyl-1,2,4-triazin-3-amine;
(cclxi) 6-2-chloro-6-methylpyridin-4-yl)-5-(2,5-difluorophenyl-1,2,4-triazin-3-amine;
(cclxii) 6-[2-chloro-6-(trifluoromethyl)pyridin-4-yl]-5-(2-fluorophenyl)-1,2,4-triazin-3-amine;
(cclxiii) 6-[2-chloro-6-(trifluoromethyl)pyridin-4-yl]-5-(2,5-difluorophenyl)-1,2,4-triazin-3-amine;
(cclxiv) 6-[2-cyclopropyl-6-(trifluoromethyl)pyridin-4-yl]-5-phenyl-1,2,4-triazin-3-amine;
(cclxv) 6-[2-ethyl-6-(trifluoromethyl)pyridin-4-yl]-5-phenyl-1,2,4-triazin-3-amine;
(cclxvi) 6-(2-cyclopropyl-6-methylpyridin-4-yl)-5-phenyl-1,2,4-triazin-3-amine;
(cclxvii) 5-(2-fluorophenyl)-6-[2-methyl-6-(trifluoromethyl)pyridin-4-yl]-1,2,4-triazin-3-amine;
(cclxviii) 5-(3-fluorophenyl)-6-[2-methyl-6-(trifluoromethyl)pyridin-4-yl]-1,2,4-triazin-3-amine;
(cclxix) 5-(4-fluorophenyl)-6-[2-methyl-6-(trifluoromethyl)pyridin-4-yl]-1,2,4-triazin-3-amine;
(cclxx) 5-(2,5-difluorophenyl)-6-[2-methyl-6-(trifluoromethyl)pyridin-4-yl]-1,2,4-triazin-3-amine;
(cclxxi) 5-(3,4-fluorophenyl)-6-[2-methyl-6-(trifluoromethyl)pyridin-4-yl]-1,2,4-triazin-3-amine;
(cclxxii) 5-(3,5-fluorophenyl)-6-[2-methyl-6-(trifluoromethyl)pyridin-4-yl]-1,2,4-triazin-3-amine;
(cclxxiii) 6-[2-(azetidin-1-yl)-6-(trifluoromethyl)pyridin-4-yl]-5-(4-fluorophenyl)-1,2,4-triazin-3-amine;
(cclxxiv) 6-[2-methyl(morpholin-4-yl)pyridin-4-yl-5-phenyl-1,2,4-triazin-3-amine:
(cclxxv) 6-(2-chloro-6-methylpyridin-4-yl)-5-(4-ethylphenyl)-1,2,4-triazin-3-amine;
(cclxxvi) 5-(2,5-difluorophenyl)-6-(2,6-dimethylpyridin-4-yl)-1,2,4-triazin-3-amine;
(cclxxvii) 6-(2,6-dimethylpyridin-4-yl)-5-(4-methylphenyl)-1,2,4-triazin-3-amine;
(cclxxviii) 6-[2-(difluoromethyl)-6-methylpyridin-4-yl]-5-(3-fluorophenyl)-1,2,4-triazin-3-amine;
(cclxxix) 6-2-(difluoromethyl)-6-methylpyridin-4-yl]-5-(2-fluorophenyl)-1,2,4-triazin-3-amine;

(cclxxx) 6-(3,5-dichlorophenyl)-5-(pyridin-2-yl)-1,2,4-triazin-3-amine;
(cclxxxi) 6-(3-chloro-5-methylphenyl)-5-(pyridin-2-yl)-1,2,4-triazin-3-amine;
(cclxxxii) 6-[2-chloro-6-(trifluoromethyl)pyridin-4-yl]-5-phenyl-1,2,4-triazin-3-amine;
(cclxxxiii) 6-[2,6-bis(trifluoromethyl)pyridin-4-yl]-5-phenyl-1,2,4-triazin-3-amine;
(cclxxxiv) 6-[3-chloro-5-(trifluoromethyl)phenyl]-5-(pyridin-2-yl)-1,2,4-triazin-3-amine;
(cclxxxv) 6-[2-methyl-6-(trifluoromethyl)pyridin-4-yl]-5-phenyl-1,2,4-triazin-3-amine;
(cclxxxvi) 6-3,5-dimethylphenyl)-5-(pyridin-2-yl)-1,2,4-triazin-3-amine;
(cclxxxvii) 6-[2-(dimethylamino)pyridin-4-yl]-5-phenyl-1,2,4-triazin-3-amine;
(cclxxxviii) 6-2-bromo-6-methylpyridin-4-yl)-5-phenyl-1,2,4-triazin-3-amine;
(cclxxxix) 6-(2,6-dimethyl-1-oxidopyridin-4-yl)-5-phenyl-1,2,4-triazin-3-amine;
(ccxc) 4-(3-amino-5-phenyl-1,2,4-triazin-6-yl)-6-methylpyridine-2-carbonitrile;
(ccxci) 6-(3,5-dichlorophenyl)-5-(pyridin-3-yl)-1,2,4-triazin-3-amine;
(ccxcii) 6-(3-chloro-5-methylphenyl)-5-(pyridin-3-yl)-1,2,4-triazin-3-amine;
(ccxciii) 6-(3,5-dichlorophenyl)-5-(pyrimidin-2-yl)-1,2,4-triazin-3-amine;
(ccxciv) 6-[3-chloro-5-(trifluoromethyl)phenyl]-5-(pyrimidin-2-yl-1,2,4-triazin-3-amine;
(ccxcv) 6-[2-bromo-6-(trifluoromethyl)pyridin-4-yl]-5-phenyl-1,2,4-triazin-3-amine;
(ccxcvi) 6-[3-chloro-5-(trifluoromethyl)phenyl]-5-(pyridin-3-yl)-1,2,4-triazin-3-amine;
(ccxcvii) 6-(3-chloro-5-methylphenyl)-5-(pyrimidin-2-yl)-1,2,4-triazin-3-amine;
(ccxcviii) N-[5-(3-amino-5-phenyl-1,2,4-triazin-6-yl)-2-methoxyphenyl]acetamide;
(ccxcix) N-[5-(3-amino-5-phenyl-1,2,4-triazin-6-yl)-2-hydroxyphenyl]acetamide;
(ccc) 6-(2-methyl-6-d3-methylpyridin-4-yl)-5-phenyl-1,2,4-triazin-3-amine;
(ccci) 1-(3-amino-5-phenyl-1,2,4-triazin-6-yl)-3,5-dimethylpyridin-4(1H)-one;
(cccii) 6-[2-(azetidin-1-yl)-6-methylpyridin-4-yl]-5-phenyl-1,2,4-triazin-3-amine;
(ccciii) 6-[2-(azetidin-1-yl)-6-methylpyridin-4-yl]-5-(4-fluorophenyl)-1,2,4-triazin-3-amine; and
(ccciv) 6-[2-(azetidin-1-yl)-6-(trifluoromethyl)pyridin-4-yl]-5-phenyl-1,2,4-triazin-3-amine.

Particular compounds that may be mentioned include compounds (iii), (v), (vi), (xiii), (xix) to (xxi), (xxiii) to (xxv), (xxvii) to (xxxi), (xxxiv), (xxxv), (xxxviii), (xxxix), (xli), (xlv), (xlvi), (xlviii) to (lv), (lvii) to (lxxxvii), (lxxxix) to (xci), (xciii), (xcvi) to (cxlii), (cxlv) to (cxlix), (cli), (clii), (clvi) to (clix) to (clxxiv), (clxxviii), (clxxix), (clxxxi), (clxxxiii), (clxxxiv), (clxxxvii), (cxcvii), (cxcviii), (cciii) to (ccv), (ccviii) to (ccxxxiii), (ccxxxv) to (ccxxxix), and (ccxli) to (ccciv) above.

Other particular compounds that may be mentioned include compounds (iii), (v), (vi), (xiii), (xix) to (xxi), (xxiii) to (xxv), (xxvii) to (xxxi), (xxxiv), (xxxv), (xxxviii), (xxxix), (xli), (xiv), (xlvi), (xlviii) to (lv), (lvii) to (lxxxvii), (lxxxix) to (xci), (xciii), (xcvi) to (cxlii), (cxlv) to (cxlix), (cli), (clii), (clvi) to (clix), (clxiii) to (clxxiv), (clxxviii), (clxxix), (clcxxix), (clxxxi), (clxxxiii), (clxxxiv), (clxxxvii), (cxcvii), (cxcviii), (cciii) to (ccv), (ccviii) to (ccxxxiii), (ccxxxv) to (ccxxxix), and (ccxli) to (ccciv) above.

More particular compounds that may be mentioned include compounds (xxviii), (lix), (lxi), (lxiii), (lxxi), (lxxvi), (lxxxv), (lxxxvi), (xci), (xcvii), (xcviii), (xcix), (cii), (cviii), (cix), (cxii), (cxiv), (cxvi), (cxvii), (cxx), (cxxi), (cxxviii), (cxxxiii), (cxli), (cxlii), (clxxxvii), (ccxvi), (ccxviii), (ccxxii), (ccxxiii), (ccxxvii), (ccxxx), (ccxxxvi), (ccxxxviii), (ccxxxix), (ccxlv), (ccxlix), (ccl), (cclii), (cclv), (cclvi), (cclvii), (cclx), (cclxii), (cclxiii), (cclxvi), (cclxvii), (cclxviii), (cclxix), (cclxxii), (cclxxxi), (cclxxxv), (cclxxxviii), (ccxcv), (ccxcix) and (cccii) above.

Still more particular compounds that may be mentioned include compounds (lxi), (cxiv), (ccl), (cclv) to (cclvii), (cclx), (cclxxxv), (cclxxxvii) and (ccxcix) above.

Other compounds that may be mentioned include:
compounds (ii) to (ccxl) above (e.g. compounds (ii) to (lxvii) above); and
compounds (lxxvi), (cix), (xcvii), (cxiv), (cxli), (ccxvii), (ccxviii), (ccxxii), (ccxxiii) and (ccxxv) above.

For the avoidance of doubt, references herein to compounds of formula I include, where the context permits, references to any of compounds of formula I, A1, Ia, Ib or Ic, Ix, Iy Iz, Ixa, Iya, Iza, Ixb, Iyb, Izb, Ixb1, Iyb1, Izb1, Iyc, Ixd, Iyd or Izd (or, in certain embodiments, to compounds of formula I, Ia, Ib or Ic). Further, references to any of compounds of formula I, A1, Ia, Ib or Ic includes references to such compounds per se, to tautomers of such compounds, as well as to pharmaceutically acceptable salts or solvates, or pharmaceutically functional derivatives of such compounds.

Certain compounds described herein may be novel. Thus, a further aspect of the invention relates to a compound of formula I (or A1, Ia, Ib, Ic, Ix, Iy Iz, Ixa, Iya, Iza, Ixb, Iyb, Izb, Ixb1, Iyb1, Izb1, Iyc, Ixd, Iyd or Izd (or, in certain embodiments, of formula I, A1, Ia, Ib or Ic)), or a pharmaceutically acceptable salt or solvate, or a pharmaceutically functional derivative thereof as described hereinbefore, provided that the compound is not:
(a) 5,6-Diphenyl-[1,2,4]triazin-3-ylamine;
(b) 5-(2-chlorophenyl)-6-(3,4-dimethoxyphenyl)-[1,2,4]triazin-3-ylamine;
(c) 5,6-di-p-tolyl-[1,2,4]triazin-3-ylamine;
(d) 5-(4-dimethylaminophenyl)-6-phenyl-[1,2,4]triazin-3-ylamine;
(e) 6-(4-dimethylaminophenyl)-5-(4-methoxyphenyl)-[1,2,4]triazin-3-ylamine;
(f) 5-(2-chlorophenyl)-6-(3,4,5-trimethoxyphenyl)-[1,2,4]triazin-3-ylamine;
(g) N*5*-(2,4-dichlorophenyl)-6-phenyl-[1,2,4]triazine-3,5-diamine;
(h) N*5'-(4-chlorophenyl)-6-phenyl-[1,2,4]triazine-3,5-diamine;
(i) N*5*-(4-bromophenyl)-6-phenyl-[1,2,4]triazine-3,5-diamine;
(j) 6-phenyl-N*5'-p-tolyl-[1,2,4]triazine-3,5-diamine;
(k) N*5'-(4-methoxyphenyl)-6-phenyl-[1,2,4]triazine-3,5-diamine;
(l) 2-[5,6-bis-(4-methoxyphenyl)-[1,2,4]triazin-3-ylamino]-ethanol;
(m) 1-[5-(4-dimethylaminophenyl)-6-(4-methanesulfinylphenyl)-[1,2,4]triazin-3-ylamino]-butan-2-ol;
(n) 2-[5-(4-dimethylaminophenyl)-6-(4-methoxyphenyl)-[1,2,4]triazin-3-ylamino]-ethanol;
(o) 2-[6-(4-fluorophenyl)-5-(4-propoxyphenyl)-[1,2,4]triazin-3-ylamino]-ethanol;

(p) 1-[5-(4-dimethylaminophenyl)-6-(4-methoxyphenyl)-[1,2,4]triazin-3-ylamino]-butan-2-ol;
(q) 2-[5-(4-dimethylaminophenyl)-6-(4-methanesulfinylphenyl)-[1,2,4]triazin-3-ylamino]-ethanol;
(r) 1-[6-(4-ethoxyphenyl)-5-(4-methanesulfinylphenyl)-[1,2,4]triazin-3-ylamino]-butan-2-ol;
(s) 1-[5,6-bis-(4-methanesulfinylphenyl)-[1,2,4]triazin-3-ylamino]-propan-2-ol;
(t) 1-[5,6-bis-(4-methanesulfinylphenyl)-[1,2,4]triazin-3-ylamino]-butan-2-ol;
(u) 2-[5-(4-dimethylaminophenyl-6-(4-fluorophenyl)-[1,2,4]triazin-3-ylamino]-ethanol;
(v) 6-benzyl-5-piperidin-1-yl-[1,2,4]triazin-3-ylamine;
(w) 6-benzyl-N*5*-phenyl-[1,2,4]triazine-3,5-diamine;
(x) 5-benzyl-6-phenyl-[1,2,4]triazin-3-ylamine;
(y) N*5*-(2,4-dichlorophenyl)-6-phenyl-[1,2,4]triazine-3,5-diamine;
(z) 6-phenyl-N*5*-o-tolyl-[1,2,4]triazine-3,5-diamine;
(aa) N*5*(4-bromophenyl)-6-phenyl-[1,2,4]triazine-3,5-diamine;
(bb) N*5*(3-chloro-4-fluorophenyl)-6-phenyl-[1,2,4]triazine-3,5-diamine;
(cc) N*5*-(2-bromophenyl)-6-phenyl-[1,2,4]triazine-3,5-diamine;
(dd) N*5*(2-chlorophenyl)-6-phenyl-[1,2,4]triazine-3,5-diamine;
(ee) N*5*-(4-iodophenyl)-6-phenyl-[1,2,4]triazine-3,5-diamine;
(ff) N*5*-(4-chlorophenyl)-6-phenyl-[1,2,4]triazine-3,5-diamine;
(gg) N*5*-(4-fluorophenyl)-6-phenyl-[1,2,4]triazine-3,5-diamine;
(hh) N*5*(4-chlorophenyl)-6-phenyl-[1,2,4]triazine-3,5-diamine;
(ii) N*5*(4-methoxyphenyl)-6-phenyl-[1,2,4]triazine-3,5-diamine;
(jj) N*5*(4-methylphenyl)-6-phenyl-[1,2,4]triazine-3,5-diamine;
(kk) 6,N*5*-diphenyl-[1,2,4]triazine-3,5-diamine;
(ll) (2S,3S,4S,5R,6R)-6-[3-amino-6-(2,3-dichlorophenyl)-[1,2,4]triazin-5-ylamino]-3,4,5-trihydroxytetrahydropyran-2-carboxylic acid;
(mm) (5,6-diphenyl-[1,2,4]triazin-3-yl)-methylamine;
(nn) (5,6-difuran-2-yl-[1,2,4]triazin-3-yl)-methylamine;
(oo) 5,6-bis-(4-methoxyphenyl)-[1,2,4]triazin-3-ylamine;
(pp) butyl-(5,6-diphenyl-[1,2,4]triazin-3-yl)-amine;
(qq) N*4*-[5,6-bis-(4-chlorophenyl)-[1,2,4]triazin-3-yl]-N*1*,N*1*-diethylpentane-1,4-diamine;
(rr) N'-[5,6-bis-(4-chlorophenyl)-[1,2,4]triazin-3-yl]-N,N-dibutylpropane-1,3-diamine;
(ss) N'-[5,6-bis-(4-chlorophenyl)-[1,2,4]triazin-3-yl]-N,N-diethylpropane-1,3-diamine;
(tt) 3-[5,6-bis-(4-chlorophenyl)-[1,2,4]triazin-3-ylamino]-propan-1-ol;
(uu) N,N-dibutyl-N'-(5,6-diphenyl-[1,2,4]triazin-3-yl)-propane-1,3-diamine;
(vv) N'-(5,6-diphenyl-[1,2,4]triazin-3-yl)-N,N-diethylpropane-1,3-diamine; and
(ww) 3-(5,6-diphenyl-[1,2,4]triazin-3-ylamino)-propan-1-ol.

In this aspect of the invention the compound may be a compound of formula I (or A1 or, particularly, Ia, Ib, Ic, Ix, Iy Iz, Ixa, Iya, Iza, Ixb, Iyb, Izb, Ixb1, Iyb1, Izb1, Iyc, Ixd, Iyd or Izd (or, in certain embodiments, of formula I, Ia, Ib or Ic)), or a pharmaceutically acceptable salt or solvate, or a pharmaceutically functional derivative thereof as described hereinbefore, provided that the compound is not (a) 2-(5,6-diphenyl-[1,2,4]triazin-3-ylamino)-ethan-1-ol;
(b) 3-amino-5,6-bis(2-chlorophenyl)-1,2,4-triazine; and
(c) 3-amino-5,6-bis(furan-2-yl)-1,2,4-triazine.

Similarly, other compounds of formula I may be novel. In this respect, other aspects of the invention relate to compounds of formula I (or Ia, Ib, Ic, Ix, Iy Iz, Ixa, Iya, Iza, Ixb, Iyb, Izb, Ixb1, Iyb1, Izb1, Iyc, Ixd, Iyd or Izd (or, in certain embodiments, of formula I, Ia, Ib or Ic)) as described hereinbefore, wherein, (i) when $L^1$ represents a bond or $CH_2$, $L^2$ represents a bond, $CH_2$ or NH, B represents unsubstituted phenyl and A represents phenyl, then A is substituted by one or more $R^{4a}$ substituents;

(ii) when $L^1$ represents a bond, $L^2$ represents a bond or NH, B represents phenyl monosubstituted by $CH_3$, $OCH_3$, $N(CH_3)_2$ or Cl in the para-position, Cl in the ortho-position or disubstituted by Cl in the ortho- and para-position, and A represents phenyl, then A is substituted by one or more $R^{4a}$ substituents provided that A is not monosubstituted by $CH_3$, $OCH_3$, $N(CH_3)_2$ or Cl in the para-position;

(iii) when $L^1$ represents a bond, $L^2$ represents a bond, $R^1$ represents —$CH_2CH_2OH$, —$CH_2CH(OH)CH_3$ or —$CH_2CH(OH)CH_2CH_3$, A represents phenyl substituted in the para-position with $OR^7$, $N(CH_3)_2$, F or $S(O)CH_3$ and B represents phenyl, then B is not substituted in the pare position of the phenyl ring by $OR^7$, $N(CH_3)_2$, F or $S(O)CH_3$;

(iv) when $L^1$ represents $CH_2$, $L^2$ represents a bond, B represents unsubstituted piperidinyl linked to the rest of the molecule via the nitrogen atom of the piperidinyl group and A represents phenyl, then A is substituted by one or more $R^{4a}$ substituents;

(v) when $L^1$ represents a bond, $L^2$ represents NH, B represents phenyl optionally substituted by one or more groups selected from halo, $CH_3$ and $OCH_3$ and A represents phenyl, then A is substituted by one or more $R^{4a}$ substituents;

(vi) when $L^1$ represents a bond, $L^2$ represents NH and A represents 2,3-dichlorophenyl then B does not represent 3,4,5-trihydroxytetrahydropyran-2-carboxylic acid;

(vii) when $L^1$ represents a bond, $L^2$ represents a bond, B represents unsubstituted furanyl and A represents furanyl, then A is substituted by one or more $R^{4a}$ substituents;

(viii) when A is a phenyl ring bearing substituents $R^{4a}$ at both meta-positions and is unsubstituted at the para-position, relative to the point of attachment of A to the rest of the molecule, then B can be unsubstituted phenyl.

Still further compounds of formula I may be novel. In this respect, still further aspects of the invention relate to compounds of formula I (or A1 or, particularly, Ia, Ib, Ic, Ix, Iy Iz, Ixa, Iya, Iza, Ixb, Iyb, Izb, Ixb1, Iyb1, Izb1, Iyc, Ixd, Iyd or Izd (or, in certain embodiments, of formula I, Ia, Ib or Ic)) as described hereinbefore, wherein when $L^1$ represents a bond or $CH_2$, $L^2$ represents a bond or NH, then at least one of A and B is not phenyl.

Still further compounds of formula I may be novel. Thus, according to a further aspect of the invention, there is provided a compound of formula I, which relate to compounds of formula I in which:

(1) $R^1$ represents H;
(2) $L^1$ represents $CH_2$, $NR^{3a}$, $S(O)_p$ or, particularly, a direct bond, O, or C(O);
(3) $L^2$ represents $CH_2$, $S(O)_p$, or, particularly, a direct bond, O, or C(O);
(4) A represents a group selected from cyclopentyl, dihydrofuranyl (e.g 2,3-dihydrofuranyl, 2,5-dihydrofuranyl), 4,5-dihydro-1H-maleimido, dioxanyl, furazanyl, hydantoinyl, imidazolyl, isoxazolyl, isoxazolidinyl, isothiaziolyl, oxadiazolyl, oxazolyl, pyrazolyl, pyrrolinyl (e.g. 3-pyrrolinyl), pyrrolyl, pyrrolidinonyl, sulfolanyl, 3-sulfolenyl, tetrahydrofuranyl, tetramethylenesulfoxide, tetrazolyl, thiadiazolyl, thiazolyl, thiazolidinyl, thienyl, triazolyl, particularly 2-azabicyclo[4.1.0]heptanyl, 1-azabicyclo-[2.2.2]octanyl, benzimidazolyl, benzisothiazolyl, benzisoxazolyl, benzodioxanyl, benzofuranyl, benzofurazanyl, benzo[c]isoxazolidinyl, benzomorpholinyl, 2,1,3-benzoxadiazolyl, benzoxazinyl (including 3,4-dihydro-2H-1,4-benzoxazinyl), benzoxazolidinyl, benzopyrazolyl, benzo[e]pyrimidine, 2,1,3-benzothiadiazolyl, benzothiazolyl, benzothienyl, benzotriazolyl, carbazolyl, chromanyl, chromenyl, cinnolinyl, (1Z,2Z,4Z,6Z,8Z)-cyclodecapentaenyl, cyclohexyl, cyclopentenyl, decahydroisoquinolenyl, 2,3-dihydrobenzimidazolyl, 1,3-dihydrobenzo-[c]furanyl, 1,3-dihydro-2,1-benzisoxazolyl, dihydropyranyl (e.g. 3,4-dihydropyranyl, 3,6-dihydropyranyl), 2,3-dihydropyrrolo[2,3-b]pyridinyl, dioxolanyl, hexahydropyrimidinyl, imidazo[2,3-b]thiazolyl, indanyl, indazolyl, indenyl, indolinyl, isobenzofuranyl, isochromanyl, isoindolinyl, isoindolyl, isothiochromanyl, ketopiperidinyl (e.g. 2-ketopiperidinyl, 3-ketopiperidinyl or 4-ketopiperidinyl), naphtho[1,2-b]furanyl, naphthyridinyl (including 1,6-naphthyridinyl or, particularly, 1,5-naphthyridinyl and 1,8-naphthyridinyl), 1,2- or 1,3-oxazinanyl, oxazolidinyl, phenazinyl, phenothiazinyl, phthalazinyl, piperazinyl, pteridinyl, purinyl, pyranyl, pyridazinyl, pyrrolo[2,3-b]pyridinyl, pyrrolo[5,1-b]pyridinyl, pyrrolo[2,3-c]pyridinyl, quinazolinyl, quinolizinyl, quinoxalinyl, 4,5,6,7-tetrahydrobenzimidazolyl, 4,5,6,7-tetrahydrobenzopyrazolyl, 5,6,7,8-tetrahydrobenzo[e]pyrimidine, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrahydropyranyl, tetrahydropyridinyl (e.g. 3,4,5,6-tetrahydropyridinyl), 1,2,3,4-tetrahydropyrimidinyl, 3,4,5,6-tetrahydropyrimidinyl, tetrahydrothiophenyl, thieno[5,1-c]pyridinyl, thiochromanyl, thiophenetyl, triazinanyl, 1,3,4-triazolo[2,3-b]pyrimidinyl, particularly, benzoxazolyl, benzodioxolyl, 2,3-dihydrobenzo[b]furanyl, cyclohexyl, furanyl, imidazo[1,2-a]pyridinyl, imidazo[1,5-a]pyridinyl, indolyl, isoquinolinyl, morpholinyl, napthalenyl (e.g. 1-napthalenyl, 2-napthalenyl, 1,2,3,4-tetrahydronaphthyl), piperidinyl, pyrimidinyl, pyrrolidinyl pyrrolo[1,5-a]pyridinyl, pyrazinyl, pyridinonyl (such as 1-1H-pyridin-2-onyl, 3-1H-pyridin-2-onyl, 4-1H-pyridin-2-onyl, 6-1H-pyridin-2-onyl, or, particularly, 4-pyridinonyl), quinolinyl, more particularly, pyridinyl (e.g. 2-pyridinyl, 3-pyridinyl, 4-pyridinyl), which are optionally substituted by one or more $R^{4a}$ or $R^{4b}$ substituents, as appropriate, and phenyl substituted by one or more $R^{4a}$ substituents;

(5) B represents piperidine or, particularly, phenyl substituted by one or more $R^{4c}$ substituents;

(6) $R^{4c}$ represents, independently at each occurrence,
Cl or, particularly, Br, F, I,
CN,
$C_{2-12}$ alkyl, $C_{2-12}$ alkenyl, $C_{2-12}$ alkynyl, which latter three groups are optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{5a}$, $S(O)_qR^{5b}$, $S(O)_2N(R^{5c})(R^{5d})$, $N(R^{5e})S(O)_2R^{5f}$, $N(R^{5g})(R^{5h})$, $B^1$—C($G^1$)-$B^2$—$R^{5i}$, aryl and $Het^1$, $Cy^3$, which $Cy^3$ group is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{6a}$, $S(O)_qR^{6b}$, $S(O)_2N(R^{6c})(R^{6d})$, $N(R^{6e})S(O)_2R^{6f}$, $N(R^{6g})(R^{6h})$, $B^3$—C($G^1$)-$B^4$—$R^{6i}$, aryl and $Het^2$, $Het^a$, which $Het^a$ group is optionally substituted by one or more substituents selected from halo, nitro, CN, $C_{1-6}$ alkyl, $C_{2-6}$ alkenyl, $C_{2-6}$ alkynyl (which latter three groups are optionally substituted by one or more substituents selected from OH, =O, halo, $C_{1-4}$ alkyl and $C_{1-4}$ alkoxy), $OR^{7a}$, $S(O)_qR^{7b}$, $S(O)_2N(R^{7c})(R^{7d})$, $N(R^{7e})S(O)_2R^{7f}$, $N(R^{7g})(R^{7h})$, $B^5$—C($G^1$)-$B^6$—$R^{7i}$, aryl and $Het^3$, $OR^8$, meta- or ortho-methoxy relative to the point of attachment of B to the rest of the molecule;
$S(O)_rR^{9a}$,
$S(O)_2N(R^{9b})(R^{9c})$,
$N(R^{9d})S(O)_2R^{9e}$,
$N(R^{9f})(R^{9g})$
$B^7$—C($G^1$)-$B^8$—$R^{9h}$,
=O,
=S, or when two $R^{4c}$ groups are attached to the same carbon atom in a non-aromatic portion of a $Cy^1$, $Het^A$, $Cy^2$ or $Het^B$ group, they may form, together with the carbon atom to which they are attached, a saturated or unsaturated 3 to 6-membered ring, which ring optionally contains one to three heteroatoms selected from O, S and N, and which ring is optionally substituted by one or more $R^a$ substituents;

(7) $R^8$ represents, independently at each occurrence,
H,
$Cy^3$, $Het^a$, $aryl^a$, $C_{1-8}$ alkyl, $C_{2-8}$ alkenyl, $C_{2-8}$ alkynyl, $C_{3-8}$ cycloalkyl, which latter seven groups are optionally substituted by one or more substituents selected from halo, —CN, $C_{3-6}$ cycloalkyl, aryl, $Het^4$, —C(O)$OR^{10}$, —C(O)$R^{11}$, —C(O)N($R^{N1}$)($R^{N2}$), S(O)$_sR^{9aa}$, S(O)$_2$N($R^{9ba}$)($R^{9ca}$), N($R^{9da}$)S(O)$_2R^{9ea}$ and N($R^{9fd}$)($R^{9ga}$).

Further embodiments of the invention, include those in which $L^1$ represents a direct bond, O, NH, S, $SO_2$ or C(O) and $L^2$ represents a direct bond (e.g. $L^1$ represents a direct bond or O, and $L^2$ represents a direct bond.)

Still further compounds of formula I may be novel. Thus, according to a further aspect of the invention, there is provided a compound of formula I, which relate to compounds of formula I in which:

(1) $L^1$ represents a direct bond, O, $NR^{3a}$, $S(O)_p$ or C(O);
(2) $L^2$ represents a direct bond, O, $S(O)_p$, NR, $CH_2$ or C(O);
(3) B represents a group, selected from 2-azabicyclo[4.1.0]heptanyl, 1-azabicyclo-[2.2.2]octanyl, benzimidazolyl, benzisothiazolyl, benzisoxazolyl, benzodioxanyl, benzodioxolyl, benzofurazanyl, benzo[c]isoxazolidinyl, 2,1,3-benzoxadiazolyl, benzoxazolidinyl, benzoxazolyl, benzopyrazolyl, 2,1,3-benzothiadiazolyl, benzothiazolyl, benzothienyl, benzotriazolyl, cyclopentyl, cyclohexyl, cyclopentenyl, cyclohexenyl, 2,3-dihydrobenzimidazolyl, dihydrofuranyl (e.g. 2,3-dihydrofuranyl, 2,5-dyhdrofuranyl), 2,3-dihydrobenzo[b]furanyl, 1,3-dihydrobenzo-[c]furanyl, dihydropyranyl (e.g. 3,4-dihydropyranyl, 3,6- dihydropyranyl), 4,5-dihydro-1H-maleimido, 1,3-dihydro-2,1-benzisoxazolyl 2,3-dihydropyrrolo[2,3-b]pyridinyl, dioxanyl, dioxolanyl, furazanyl, hexahydropyrimidinyl, hydantoinyl, imidazolyl, imidazo[1,2-a]pyridinyl, imidazo[2,3-b]thiazolyl, indanyl, indenyl, indolinyl, isobenzofuranyl, isoindolinyl, isoindolyl, isothiazolyl, isoxazolyl, isoxazolidinyl, ketopiperidinyl (e.g. 2-ketopiperidinyl, 3-ketopiperidinyl or 4-ketopiperidinyl), morpholinyl, oxadiazolyl, 1,2- or 1,3-oxazinanyl, oxazolidinyl, oxazolyl, piperidinyl (e.g. piperidin-1-yl or, particularly, piperidin-2-yl, piperidin-3-yl, piperidin-4-yl, piperidin-5-yl or piperidin-6-yl), piperazinyl, phthalazinyl, pteridinyl, purinyl, pyranyl, pyridazinyl, pyrrolidinonyl, pyrrolinyl (e.g. 3-pyrrolinyl), pyrrolyl, pyrrolo[2,3-b]pyridinyl, pyrrolo[5,1-b]pyridinyl, pyrrolo[2,3-c]pyridinyl, sulfolanyl, 3-sulfolenyl, tetrahydrofuranyl, tetrahydropyranyl, 3,4,5,6-tetrahydropyridinyl, 1,2,3,4-tetrahydropyrimidinyl, 3,4,5,6-tetrahydropyrimidinyl, tetrahydrothiophenyl, 4,5,6,7-tetrahydrobenzimidazolyl, 4,5,6,7-tetrahydrobenzopyrazolyl, tetramethylenesulfoxide, tetrazolyl, thiazolidinyl, thiazolyl, thienyl, thieno[5,1-c]pyridinyl, thiophenethyl, triazinanyl, triazoly, 1,3,4-triazolo[2,3-b]pyrimidinyl, more particularly, benzofuranyl, indazolyl, indolyl, pyrazinyl, pyrazolyl, pyridinyl (e.g. 2-pyridinyl, 3-pyridinyl, 4-pyridinyl), pyridinonyl, pyrimidinyl and pyrrolo[1,5-a]pyridinyl, wherein B is optionally substituted by one or more $R^{4c}$ or $R^{4d}$ substituents, as appropriate.

The invention encompasses (in respect of the invention described herein) embodiments in which the compound of formula A1 or, particularly, I, Ia, Ib, Ic, Ix, Iy Iz, Ixa, Iya, Iza, Ixb, Iyb, Izb, Ixb1, Iyb1, Izb1, Iyc, Ixd, Iyd or Izd (or, in certain embodiments, of formula I, Ia, Ib or Ic) has definitions of A, B, $L^1$, $L^2$ and $R^1$ that are derived from any mutually compatible combination of any of the substituent definitions listed above in respect of compounds of formulae A1 or, particularly, I, Ia, Ib, Ic, Ix, Iy Iz, Ixa, Iya, Iza, Ixb, Iyb, Izb, Ixb1, Iyb1, Izb1, Iyc, Ixd, Iyd or Izd (or, in certain embodiments, of formula I, Ia, Ib or Ic).

In accordance with the invention, compounds of formula I (e.g. formula A1) may be administered alone (i.e. as a monotherapy, such as a monotherapy of a condition or disorder ameliorated by inhibition of the $A_1$ or, particularly, $A_{2a}$ receptor). In alternative embodiments of the invention, however, compounds of formula I (e.g. formula A1) may be administered in combination with another therapeutic agent (e.g. another therapeutic agent for the treatment of a condition or disorder ameliorated by inhibition of the $A_1$ or, particularly, $A_{2a}$ receptor).

Thus further aspects of the invention relate to the following.
(a) A compound of formula I (e.g. formula A1), as hereinbefore defined, and another therapeutic agent for use in the treatment of a condition or disorder ameliorated by the inhibition of the $A_1$ or, particularly, the $A_{2a}$ receptor.
In this aspect of the invention, the compound of formula I, as hereinbefore defined, may be administered sequentially, simultaneously or concomitantly with the other therapeutic agent
(b) A compound of formula I (e.g. formula A1), as hereinbefore defined, for use in the treatment of a condition or disorder ameliorated by the inhibition of the $A_1$ or, particularly, the $A_{2a}$ receptor, wherein the compound of formula I is administered sequentially, simultaneously or concomitantly with another therapeutic agent.
(c) Use of a compound of formula I (e.g. formula A1), as hereinbefore defined, and another therapeutic agent for the preparation of a medicament for the treatment of a condition or disorder ameliorated by the inhibition of the $A_1$ or, particularly, the $A_{2a}$ receptor, wherein the compound of formula I is administered sequentially, simultaneously or concomitantly with the other therapeutic agent.
(d) Use of a compound of formula I (e.g. formula A1), as hereinbefore defined, for the preparation of a medicament for the treatment of a condition or disorder ameliorated by the inhibition of the $A_1$ receptor or, particularly, the $A_{2a}$ receptor, wherein the medicament is administered in combination with another therapeutic agent.
(e) A method of treatment of a disorder or condition ameliorated by antagonising the $A_1$ receptor or, particularly, the $A_{2a}$ receptor, which method comprises the administration of an effective amount of a compound of formula I (e.g. formula A1), as hereinbefore defined, and another therapeutic agent to a patient in need of such treatment.
(f) A combination product comprising
 (A) a compound of formula I (e.g. formula A1), as hereinbefore defined, and
 (B) another therapeutic agent,
 wherein each of components (A) and (B) is formulated in admixture with a pharmaceutically-acceptable adjuvant, diluent or carrier.
(g) A combination product as defined at (f) above for use in the treatment of a condition or disorder ameliorated by the inhibition of the $A_1$ receptor or, particularly, the $A_{2a}$ receptor.
(h) The use of a combination product as defined at (f) above for the manufacture of a medicament for the treatment of a condition or disorder ameliorated by the inhibition of the $A_1$ receptor or, particularly, the $A_{2a}$ receptor.
(i) A method of treatment of a disorder or condition ameliorated by antagonising the $A_1$ receptor or, particularly, the $A_{2a}$ receptor, which method comprises the administration of an effective amount of a combination product as defined at (f) above.

When used herein, the term "another therapeutic agent" includes references to one or more (e.g. one) therapeutic agents (e.g. one therapeutic agent) that are known to be useful for (e.g. that are known to be effective in) the treatment of: heart failure (such as acute decompensated heart failure and congestive heart failure); kidney failure (e.g. caused by heart failure); oedema; cancer (such as prostate, rectal, renal, ovarian, endometrial, thyroid, pancreatic, particularly breast, colon, bladder, brain, glia, melanoma, pineal gland cancer and, more particularly, Lewis lung carcinoma; diabetes; diarrhea; macular degeneration (such as macular degeneration caused by angiogenesis (e.g. retinal angiogenesis); or particularly a disease of the central nervous system such as depression, a cognitive function disease, a neurodegenerative disease (such as Parkinson's disease, Huntington's disease, Alzheimer's disease, amyotrophic lateral sclerosis) and psychoses; an attention related disorder (such as attention deficit disorder (ADD) and attention deficit hyperactivity disorder (ADHD)); extra pyramidal syndrome (e.g. dystonia, akathisia, pseudoparkinsonism and tardive dyskinesia); a disorder of abnormal movement (such as restless leg syndrome (RLS) and periodic limb movement in sleep (PLMS)); cirrhosis; liver fibrosis; fatty liver; dermal fibrosis (e.g. in diseases such as scleroderma); a sleep disorder; stroke; and addictive behaviour. In particular embodiments of the invention that may be mentioned, the one or more other therapeutic agents do not exert their therapeutic effect by way of binding to an adenosine receptor (e.g. the $A_{2a}$ receptor).

Particular other therapeutic agents that may be mentioned include, for example, levodopa (L-DOPA), dopamine agonists (e.g. pramipexole, ropinirole or rotigotine), monoamine oxidase B inhibitors (e.g. selegiline or rasagiline), catechol O-methyl transferase inhibitors (e.g. entacapone or tolcapone), amantadine, acetylcholinesterase inhibitors (e.g. donepezil, rivastigmine or galantamine) and glutamate inhibitors (e.g. memantine).

When used herein, the term "administered sequentially, simultaneously or concomitantly" includes references to:
- administration of separate pharmaceutical formulations (one containing the compound of formula I and one or more others containing the one or more other therapeutic agents); and
- administration of a single pharmaceutical formulation containing the compound of formula I and the other therapeutic agent(s).

The combination product described above provides for the administration of component (A) in conjunction with component (B), and may thus be presented either as separate formulations, wherein at least one of those formulations comprises component (A) and at least one comprises component (B), or may be presented (i.e. formulated) as a combined preparation (i.e. presented as a single formulation including component (A) and component (B)).

Thus, there is further provided:
(I) a pharmaceutical formulation including a compound of formula I (e.g. formula A1), as hereinbefore defined and another therapeutic agent, in admixture with a pharmaceutically-acceptable adjuvant, diluent or carrier (which formulation is hereinafter referred to as a "combined preparation"); and
(II) a kit of parts comprising components:
 (i) a pharmaceutical formulation including a compound of formula I (e.g. formula A1), as hereinbefore defined, in admixture with a pharmaceutically-acceptable adjuvant, diluent or carrier; and
 (ii) a pharmaceutical formulation including another therapeutic agent, in admixture with a pharmaceutically-acceptable adjuvant, diluent or carrier,
 which components (i) and (ii) are each provided in a form that is suitable for administration in conjunction with the other.

Component (i) of the kit of parts is thus component (A) in admixture with a pharmaceutically-acceptable adjuvant, diluent or carrier. Similarly, component (ii) is component (B) in admixture with a pharmaceutically-acceptable adjuvant, diluent or carrier.

Compounds of formula I (e.g. formula A1) may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration Compounds of formula I (e.g. formula A1) will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy,* 19th ed., Mack Printing Company, Easton, Pa. (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable formulations may be achieved routinely by the skilled person using routine techniques and/or in accordance with standard and/or accepted pharmaceutical practice.

The amount of compound of formula I (e.g. formula A1) in any pharmaceutical formulation used in accordance with the present invention will depend on various factors, such as the severity of the condition to be treated, the particular patient to be treated, as well as the compound(s) which is/are employed. In any event, the amount of compound of formula I in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compounds of formula I (e.g. formula A1) may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I (e.g. formula A1).

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

As mentioned above, compounds of formula A1 or, particularly, Ix, Iy, Iz, Ixa, Iya, Iza, Ixb, Iyb, Izb, Ixb1, Iyb1, Izb1, Iyc, Ixd, Iyd or Izd (or, particularly, formula I, Ia, Ib or Ic) may bind selectively to $A_1$ or, particularly, $A_{2a}$ receptors, and may therefore have utility as diagnostic agents for determining the presence and/or location (either in vivo or in vitro) of adenosine $A_1$ or, particularly, $A_{2a}$ receptors.

Thus, according to a further aspect of the invention there is provided a method (e.g. an in vivo or, particularly, an ex vivo method) of determining the presence and/or location of adenosine $A_{2a}$ receptors in a tissue sample, said method comprising contacting the tissue sample with a compound of formula A1 or, particularly, Ix, Iy, Iz, Ixa, Iya, Iza, Ixb, Iyb, Izb, Ixb1, Iyb1, Izb1, Iyc, Ixd, Iyd or Izd (or, particularly, formula I, Ia, Ib or Ic) and then detecting by a visualising method the location of the compound of formula I in the sample.

Visualising methods that may be mentioned include spectroscopic detection methods (e.g. fluorescence detection, magnetic resonance imaging, etc.) or, when the compound of formula I is isotopically labelled or enriched with a radioisotope (such as $^3H$, $^{11}C$, $^{35}S$, $^{18}F$, or $^{125}I$), radioactivity detection methods (e.g. alpha-, beta- or gamma-detection by standard autoradiography, phosphor or scintillation methods known to those skilled in the art, or positron emission tomography (which latter method may be employed, for example, when the compound of formula I is isotopically labelled or enriched with $^{11}C$, or, particularly, $^{13}F$)).

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, or may have other useful pharmacological properties over, similar compounds, combinations, methods (treatments) or uses known in the prior art for use in the treatment of those conditions or otherwise.

Side effects that may be mentioned in this respect include side effects caused by $A_3$ receptor antagonism (such as an increased propensity for tissue damage following ischaemia (e.g. in the CNS, heart, kidney, lung and eye), increased reperfusion injury, increased neurodegeneration in response to hypoxia, potentially deleterious effects on motor function or pain thresholds, immunosuppression or immunostimulation).

Compounds of formula I may be known and/or may be commercially available. Other compounds of formula I (e.g. that are not commercially available) may be prepared in accordance with techniques that are well known to those skilled in the art, for example as described hereinafter.

According to a further aspect of the invention there is provided a process for the preparation of a compound of formula I which process comprises:

(ia) for compounds of formula I in which $R^1$ represents $CH_2$—$R^{1a}$, wherein $R^{1a}$ represents a $C_{1-5}$ alkyl optionally substituted by one or more halo atoms, reaction of a compound of formula I in which $R^1$ represents H, with a compound of formula IIa,

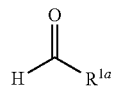

IIa wherein $R^{1a}$ represents H or a $C_{1-5}$ alkyl which may be optionally substituted by one or more halo atoms, followed by reduction of the resulting imine by a suitable reducing agent (e.g. $LiBH_4$, $NaBH_4$, $NaBH(OAc)_3$, $LiAlH_4$), under reaction conditions well known to those skilled in the art, for example under such conditions that the two steps may be performed with or without the separation or purification of the reaction mixture;

(ib) for compounds of formula I in which $R^1$ represents $C_{1-6}$ alkyl optionally substituted by one or more of halo $OR^{2a}$ or $NR^{2b}R^{2c}$, reaction of a compound of formula I in which $R^1$ represents H, with a compound of formula IIb, $$L^{xaa}\text{-}R^{1x}$$ IIb wherein $L^{xaa}$ represents a suitable leaving group (such as chloro, bromo, or preferably iodo) and $R^{1x}$ represents $C_{1-6}$ alkyl optionally substituted by one or more of halo $OR^{2a}$ or $NR^{2b}R^{2c}$, under reaction conditions known to those skilled in the art, for example in the presence of an appropriate base (such as Hunig's base, triethylamine, pyridine), in a suitable solvent (e.g. pyridine, triethylamine, dichloromethane, tetrahydrofuran) and at a suitable temperature (e.g. from room temperature to about 180° C.);

(ii) for compounds of formula I in which $L^1$ represents a direct bond, (a) reaction of a compound of formula III,

III wherein $L^{x1a}$ represents a metal halide (for example a zinc halide (e.g. —ZnCl) or a magnesium halide (e.g. —MgBr)), —Sn$(R^{x1})_3$, an organoboronic acid (e.g. an alkyl-cyclotriboroxane derivative or, particularly, —B(OH)$_2$ or —B(OR$^{x1}$)$_2$), or an organosilane (e.g. —Si(OEt)$_3$), wherein each $R^{x1}$ mentioned herein independently represents a $C_{1-6}$ alkyl group, or, in the case of —B(OR$^{x1}$)$_2$, the two $R^{x1}$ groups may be linked together to form a 4- to 6-membered cyclic group (such as a 4,4,5,5-tetramethyl-1,3,2-dioxaborolan-2-yl group), and $L^2$, B, and $R^1$ are as defined hereinbefore, with a compound of formula IV, $$A\text{-}X^{1a}$$ IV wherein $X^{1a}$ represents a suitable leaving group (such as chloro, bromo, or preferably iodo), and A is as defined hereinbefore, under reaction conditions known to those skilled in the art, for example in the presence of an appropriate metal catalyst (or a salt or complex thereof, such as Cu, Cu(OAc)$_2$, CuI (or CuI/diamine complex), copper tris(triphenyl-phosphine)bromide, Pd(OAc)$_2$, Pd$_2$(dba)$_3$ or NiCl$_2$) and an optional additive (such as Ph$_3$P, 2,2'-bis(diphenylphosphino)-1,1'-binaphthyl, xantphos, NaI or an appropriate crown ether such as 18-crown-6-benzene), in the presence of an appropriate base (such as NaH, Et$_3$N, pyridine, N,N'-dimethylethylenediamine, triethanolamine. N-methyldiethanolamine, N,N-diisopropylethanolamine, triisopropanolamine, Na₂CO₃, K₂CO₃, K₃PO₄, Cs₂CO₃, t-BuONa or t-BuOK or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, propionitrile, dimethylacetamide, N-methylpyrrolidinone, tetrahydrofuran, diethyl ether or a mixture thereof) and at a suitable temperature (e.g. from room temperature to about 180° C.);

(b) reaction of a compound of formula V,

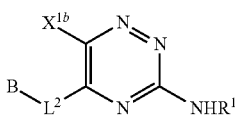

V wherein $X^{1b}$ represents a suitable leaving group (such as chloro, bromo, or preferably iodo), and $L^2$, B, and $R^1$ are as defined hereinbefore, with a compound of formula VI, A-$L^{x1b}$   VI wherein $L^{x1b}$ represents a metal halide (for example a zinc halide (e.g. —ZnCl) or a magnesium halide (e.g. —MgBr)), —Sn($R^{x1}$)₃, an organoboronic acid (e.g. an alkyl-cyclotriboroxane derivative or, particularly, —B(OH)₂ or —B(O$R^{x1}$)₂), or an organosilane (e.g. —Si(OEt)₃), wherein each $R^{x1}$ is a defined above, and A is as defined hereinbefore, under reaction conditions known to those skilled in the art, for example such as those described in respect of process step (ii)(a) above;

(iii) for compounds of formula I in which $L^1$ represents —$NR^{3a}$—, (a) reaction of a compound of formula VII,

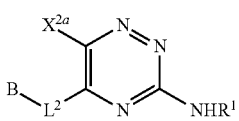

VII wherein $X^{2a}$ represents a suitable leaving group (such as chloro, bromo, iodo or a sulfonate group (e.g. —OS(O)₂CF₃, —OS(O)₂CH₃ or —OS(O)₂PhMe)), and $L^2$, B, and $R^1$ are as defined hereinbefore with a compound of formula VIII, A-NH$R^{3a}$   VIII wherein A and $R^{3a}$ are as defined hereinbefore, under reaction conditions known to those skilled in the art, for example in the presence of an appropriate base (such as NaH, Et₃N, pyridine, N,N'-dimethylethylenediamine, Na₂CO₃, K₂CO₃, K₃PO₄, Cs₂CO₃, t-BuONa or t-BuOK or a mixture thereof, optionally in the presence of 4 Å molecular sieves), optionally in the presence of a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof) and at a suitable temperature (e.g. from room temperature to about 180° C.);

(b) reaction of a compound of formula IX,

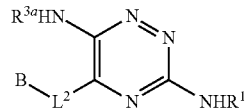

IX wherein $R^{3a}$, $L^2$, B, and $R^1$ are as defined hereinbefore, with a compound of formula X, A-$X^{2b}$   X wherein $X^{2b}$ represents a suitable leaving group (such as chloro, bromo, iodo or a sulfonate group (e.g. —OS(O)₂CF₃, —OS(O)₂CH₃ or —OS(O)₂PhMe)), and A represents $Cy^1$ or $Het^4$, as defined hereinbefore, except that the $Cy^1$ or $Het^4$ group contains a fully saturated carbon atom that is attached to $X^{2b}$, under reaction conditions known to those skilled in the art, for example such as those described in respect of process step (iii)(a) above;

(c) reaction of a compound of formula IX as defined above, with a compound of formula XI, A-$L^{x2a}$   XI wherein $L^{x2a}$ represents a suitable leaving group (such as chloro, bromo, iodo or a sulfonate group (e.g. —OS(O)₂CF₃, —OS(O)₂CH₃ or —OS(O)₂PhMe), —B(OH)₂ or —B(O$R^{x1}$)₂, in which each $R^{x1}$ is as defined above, and A represents $Cy^1$ or $Het^4$, as defined hereinbefore, except that $Cy^1$ or $Het^4$ contains an aromatic ring that is attached to $L^{x2a}$ via a carbon atom, under reaction conditions known to those skilled in the art, for example in the presence of an appropriate metal catalyst (or a salt or complex thereof, such as Cu, Cu(OAc)₂, CuI (or CuI/diamine complex), copper tris(triphenyl-phosphine)bromide), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof), and at a suitable temperature (e.g. from room temperature to about 180° C.), e.g. as described in Quach et al. *Org. Lett.*, 2003, 5, 4397-4400 or Wolfe et al. 2004. *Org. Synth.: Coll. Vol.* 10: 423;

(d) reaction of a compound of formula XII,

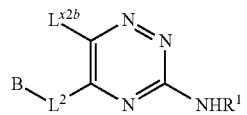

XII wherein $L^{x2b}$ represents a suitable leaving group (such as chloro, bromo, iodo or a sulfonate group (e.g. —OS(O)₂CF₃, —OS(O)₂CH₃ or —OS(O)₂PhMe), —B(OH)₂ or —B(O$R^{x1}$)₂ in which each $R^{x1}$ is as defined above, and $L^2$, B, and $R^1$ are as defined hereinbefore, with a compound of formula VIII as defined above, under reaction conditions known to those skilled in the art, for example such as those described in respect of process step (iii)(c) above;

(iv) for compounds of formula I in which $L^1$ represents —O— or —S—, (a) reaction of a compound of formula VII as defined above, with a compound of formula XIII, A-$Q^a$-H   XIII wherein $Q^a$ is O or S, and A is as defined hereinbefore, under reaction conditions known to those skilled in the art, for example the reaction may be performed at a suitable temperature (e.g. from room temperature to about 180° C.), in the presence of a suitable base (e.g. caesium carbonate, sodium hydride, sodium bicarbonate, potassium carbonate, pyrrolidinopyridine, pyridine, triethylamine, tributylamine, trimethylamine, dimethylaminopyridine, diisopropylamine, diisopropylethylamine, 1,8-diazabicycbo[5.4.0]undec-7-ene, sodium hydroxide, N-ethyldiisopropylamine, N-(methylpolystyrene)-4-(methylamino)pyridine, potassium bis(trimethylsilyl)amide, sodium bis(trimethylsilyl)amide, potassium tert-butoxide, lithium diisopropylamide, lithium 2,2,6,6-tetramethylpiperidine or mixtures thereof), or alternatively in the presence of a suitable coupling agent (such as a dialkylazodicarboxylate (e.g. diethylazodicarboxylate) together with a trialkyl or triaryl phosphine (e.g. $PPh_3$)), and an appropriate solvent (e.g. dimethylsulfoxide, tetrahydrofuran, pyridine, toluene, dichloromethane, chloroform, acetonitrile, dimethylformamide, trifluoromethylbenzene, dioxane or triethylamine);

(b) reaction of a compound of formula XIV,

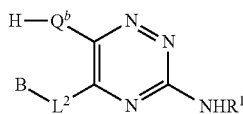

XIV wherein $Q^b$ is O or S, and $L^2$, B and $R^1$ are as defined hereinbefore, with a compound of formula X as defined above, under reaction conditions known to those skilled in the art, for example such as those described in respect of process step (iv(a)) above;

(v) for compounds of formula I in which $L^1$ represents —O— and A represents $Cy^1$ or $Het^4$ as defined hereinbefore, except that the $Cy^1$ or $Het^4$ group is directly attached to the rest of the molecule via a fully saturated carbon atom, reaction of a compound of formula XIII, wherein $Q^a$ is O and A is as defined hereinbefore, with a compound of formula XIV wherein $Q^b$ is O and $L^2$, B and $R^1$ are as defined hereinbefore, under reaction conditions known to those skilled in the art, for example the reaction may be performed at a suitable temperature (e.g. from room temperature to about 180° C.), in the presence of a suitable coupling agent (such as a dialkylazodicarboxylate (e.g. diethylazodicarboxylate) together with a trialkyl or triaryl phosphine (e.g. $PPh_3$)), and an appropriate solvent (e.g. tetrahydrofuran, dimethylsulfoxide, pyridine, toluene, dichloromethane, chloroform, acetonitrile, dimethylformamide, trifluoromethylbenzene, dioxane or triethylamine);

(vi) for compounds of formula I in which $L^1$ represents —S(O)— or —S(O)$_2$—, oxidation of a compound of formula I in which $L^1$ represents —S—, in the presence of a suitable oxidising agent, (for example meta-chloroperoxybenzoic acid, $KMnO_4$, t-butylammoniumperiodate and/or potassium peroxymonosulfate (e.g. Oxone®)). In order to provide selective oxidisation to provide either compounds of formula I in which $L^1$ represents —S(O)— or —S(O)$_2$—, the skilled person will appreciate that the length of time (and the number of equivalents of the oxidising agent) or the use of certain oxidising agents may provide for better selectivity. For example, for the formation of compounds of formula I in which $L^1$ represents —S(O)—, the oxidising agent of choice is preferably t-butylammoniumperiodate (and preferably one equivalent, or a slight excess, is employed). Such a reaction may be performed in the presence of a suitable solvent such as dichloromethane, and optionally in the presence of a catalyst such as 5,10,15,20-tetraphenyl-21H,23H-porphine iron(III)chloride, under an inert atmosphere. For the formation of compounds of formula I in which $L^1$ represents —S(O)$_2$—, the oxidising agent is preferably potassium peroxymonosulfate (e.g. Oxone®), which reaction may be performed in the presence of a suitable solvent such as tetrahydrofuran;

(vii) for compounds of formula I in which $L^2$ represents a direct bond, (a) reaction of a compound of formula XV,

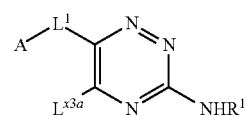

XV wherein $L^{x3a}$ represents a metal halide (for example a zinc halide (e.g. —ZnCl) or a magnesium halide (e.g. —MgBr)), —Sn($R^{x1}$)$_3$, an organoboronic acid (e.g. an alkyl-cyclotriboroxane derivative or, particularly, —B(OH)$_2$ or —B(O$R^{x1}$)$_2$), or an organosilane (e.g. —Si(EtO)$_3$), in which each $R^{x1}$ is as defined above, and $L^1$, A, and $R^1$ are as defined hereinbefore, with a compound of formula XVI, B—$X^{3a}$  XVI wherein $X^{3a}$ represents a suitable leaving group such as chloro, bromo, or preferably iodo, and B is as defined hereinbefore, under reaction conditions known to those skilled in the art, for example such as those described in respect of process step (ii)(a) above;

(b) reaction of a compound of formula XVII,

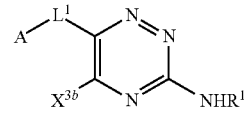

XVII wherein $X^{3b}$ represents a suitable leaving group such as chloro, bromo, or preferably iodo, and $L^1$, A, and $R^1$ are as defined hereinbefore, with a compound of formula XVIII, B-$L^{x3b}$  XVIII wherein $L^{x3b}$ represents a metal halide (for example a zinc halide (e.g. —ZnCl), or a magnesium halide (e.g. —MgBr)), —Sn($R^{x1}$)$_3$, an organoboronic acid (e.g. an alkyl-cyclotriboroxane derivative or, particularly, —B(OH)$_2$ or —B(O$R^{x1}$)$_2$), or an organosilane (e.g. —Si(EtO)$_3$), in which each $R^{x1}$ is as defined above, and B is as defined hereinbefore, under reaction conditions known to those skilled in the art, for example such as those described in respect of process step (ii)(a) above;

(viii) for compounds of formula I in which $L^2$ represents —$NR^{3a}$—,
(a) reaction of a compound of formula XIX,

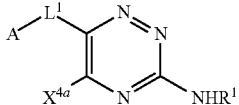

XIX wherein $X^{4a}$ represents a suitable leaving group (such as chloro, bromo, iodo or a sulfonate group (e.g. —$OS(O)_2CF_3$, —$OS(O)_2CH_3$ or —$OS(O)_2PhMe$)), and $L^1$, A, and $R^1$ are as defined hereinbefore, with a compound of formula XX, B—$NHR^{3a}$  XX wherein B and $R^{3a}$ are as defined hereinbefore, under reaction conditions known to those skilled in the art, for example such as those described in respect of process step (iii)(a) above;
(b) reaction of a compound of formula XXI,

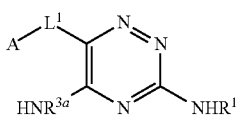

XXI wherein $R^{3a}$, $L^1$, A, and $R^1$ are as defined hereinbefore, with a compound of formula XXII, B—$X^{4b}$  XXII wherein $X^{4b}$ represents a suitable leaving group (such as chloro, bromo, iodo or a sulfonate group (e.g. —$OS(O)_2CF_3$, —$OS(O)_2CH_3$ or —$OS(O)_2PhMe$)), and B represents $Cy^2$ or $Het^B$, as defined hereinbefore, except that the $Cy^2$ or $Het^B$ group contains a fully saturated carbon atom that is attached to $X^{4b}$, under reaction conditions known to those skilled in the art, for example such as those described in respect of process step (iii)(a) above;
(c) reaction of a compound of formula XXI as defined above, with a compound of formula XXIII, B-$L^{x4a}$  XXIII wherein $L^{x4a}$ represents a suitable leaving group, —$B(OH)_2$ or —$B(OR^{x1})_2$ in which each $R^{x1}$ is as defined above, and B is as defined hereinbefore, except that $Cy^2$ or $Het^B$ contains an aromatic ring that is attached to $L^{x4a}$ via a carbon atom, under reaction conditions known to those skilled in the art, for example such as those described in respect of process step (iii)(c) above;
(d) reaction of a compound of formula XXIV,

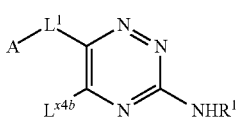

XXIV wherein $L^{x4b}$ represents —$B(OH)_2$ or —$B(OR^{x1})_2$ in which each $R^{x1}$ is as defined above, and $L^1$, A, and $R^1$ are as defined hereinbefore, with a compound of formula XX as defined above, under reaction conditions known to those skilled in the art, for example such as those described in respect of process step (iii)(c) above;
(ix) for compounds of formula I in which $L^2$ represents —O— or —S—,
(a) reaction of a compound of formula XIX as defined above, with a compound of formula XXV, B-$Q^c$-H  XXV wherein $Q^c$ represents O or S, and B is as defined hereinbefore, under reaction conditions known to those skilled in the art, for example such as those described in respect of process step (iv)(a) above;
(b) reaction of a compound of formula XXVI,

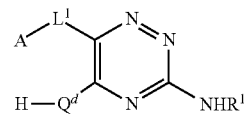

XXVI wherein $Q^d$ represents O or S, and $L^1$, A and $R^1$ are as defined hereinbefore, with a compound of formula XXII as defined above, under reaction conditions known to those skilled in the art, for example such as those described in respect of process step (iv)(a) above;
(x) for compounds of formula I in which $L^2$ represents —O— and B represents $Cy^2$ or $Het^B$ as defined hereinbefore, except that the $Cy^2$ or $Het^B$ group is directly attached to the rest of the molecule via a fully saturated carbon atom, reaction of a compound of formula XXV, wherein $Q^c$ is O and B is as defined hereinbefore, with a compound of formula XXVI wherein $Q^d$ is O and $L^1$, A and $R^1$ are as defined hereinbefore, under reaction conditions known to those skilled in the art, for example the reaction may be performed at a suitable temperature (e.g. from room temperature to about 180° C.), in the presence of a suitable coupling agent (such as a dialkylazodicarboxylate (e.g. diethylazodicarboxylate) together with a trialkyl or triaryl phosphine (e.g. $PPh_3$)), and an appropriate solvent (e.g. tetrahydrofuran, dimethylsulfoxide, pyridine, toluene, dichloromethane, chloroform, acetonitrile, dimethylformamide, trifluoromethylbenzene, dioxane or triethylamine);
(xi) for compounds of formula I in which $L^2$ represents —S(O)— or —$S(O)_2$—, oxidation of a compound of formula I in which $L^2$ represents —S— wherein A, $L^1$, B, and $R^1$ are as defined hereinbefore, in the presence of a suitable oxidising agent, under reaction conditions known to those skilled in the art, for example such as those described in respect of process step (vi) above;
(xii) for compounds of formula I in which $L^1$ and/or $L^2$ represents $N(R^{3x})$, wherein $R^{3x}$ takes the same definition as $R^{3a}$ above, except that $R^{3x}$ does not represent H, reaction of a corresponding compound of formula I in which $L^1$ and/or $L^2$ is NH, with a compound of formula XXVII, $X^{5a}$—$R^{3x}$  XXVII wherein $X^{5a}$ represents a suitable leaving group such as one defined hereinbefore in respect of $X^{2a}$ or —$Sn(R^{x1})_3$ in which $R^{3x}$ and each $R^{x1}$ are as defined above, under reaction conditions known to those skilled in the art, for example in the case where $X^{5a}$ represents a leaving group (such as iodo, bromo, chloro or a sulfonate group), the reaction may be performed at a suitable temperature (e.g. from room temperature to about 180° C.), optionally in the presence of a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, diisopropylethylamine, 1,8-diazabicyclo[5.4.0]undec-7-ene, sodium hydroxide, N-ethyldiisopropylamine, N-(methylpolystyrene)-4-(methylamino)pyridine, potassium bis(trimethylsilyl)amide, sodium bis(trimethylsilyl)amide, potassium tert-butoxide, lithium diisopropylamide, lithium 2,2,6,6-tetramethylpiperidine or mixtures thereof) and an appropriate solvent (e.g. tetrahydrofuran, pyridine, toluene, dichloromethane, chloroform, acetonitrile, dimethylformamide, trifluoromethylbenzene, dioxane or triethylamine). In the case when X represents —B(OH)$_2$ or —Sn(alkyl)$_3$, the reaction may be performed in the presence of a suitable catalyst system, (e.g. a metal (or a salt or complex thereof) such as CuI (or CuI/diamine complex), Cu, Cu(OAc)$_2$, copper tris(triphenyl-phosphine)bromide, Pd/C, PdCl$_2$, Pd(OAc)$_2$, Pd(Ph$_3$P)$_2$Cl$_2$, Pd(Ph$_3$P)$_4$, Pd$_2$(dba)$_3$ or NiCl$_2$ and a ligand such as t-Bu$_3$P, (C$_6$H$_{11}$)$^3$P, Ph$_3$P, AsPh$_3$, P(o-Tol)$_3$, 1,2-bis(diphenylphosphino) ethane, 2,2'-bis(di-tert-butylphosphino)-1,1'-bi-phenyl, 2,2'-bis(diphenylphosphino)-1,1'-binaphthyl, 1,1'-bis(diphenylphosphinoferrocene), 1,3-bis(diphenylphosphino)-propane, xantphos, or a mixture thereof), together with a suitable base (such as, Na$_2$CO$_3$, K$_3$PO$_4$, Cs$_2$CO$_3$, NaOH, KOH, K$_2$CO$_3$, CsF, Et$_3$N, (i-Pr)$_2$NEt, t-BuONa or t-BuOK, NaH, Et$_3$N, pyridine, N,N'-dimethylethylenediamine, (or mixtures thereof, optionally in the presence of 4 Å molecular sieves)) in a suitable solvent (such as dioxane, toluene, ethanol, isopropanol, ethylene glycol, dimethylformamide, ethylene glycol dimethyl ether, water, dimethylsulfoxide, acetonitrile, dimethylacetamide, N-methylpyrrolidinone, tetrahydrofuran or mixtures thereof);

(xiii) reaction of a compound of formula XXVIII,

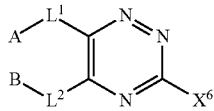

XXVIII wherein $X^6$ represents a suitable leaving group (such as chloro, bromo, iodo, a sulfonate group (e.g. —OS(O)$_2$CF$_3$, —OS(O)$_2$CH$_3$ or —OS(O)$_2$PhMe), a sulfone group (e.g. —S(O)$_2$CH$_3$, —S(O)$_2$CF$_3$ or —S(O)$_2$-PhMe) or —OR$^{4x}$, wherein R$^{4x}$ represents an aryl or heteroaryl group), and A, B, L$^1$ and L$^2$ are as defined hereinbefore, with a compound of formula XXIX,

R$^1$NH$_2$     XXIX wherein R$^1$ is as defined hereinbefore, under reaction conditions known to those skilled in the art, for example such as those described in respect of process step (iii)(a) above;

(xiv) for compounds of formula I, reaction of a compound of formula XXX,

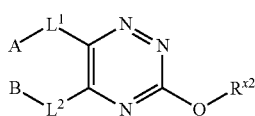

XXX wherein $R^{x2}$ represents a suitable leaving group (e.g. a tosyl, mesylate group or an electron deficient aryl or heteroaryl group (such as pentafluorophenyl)) and A, B, L$^1$ and L$^2$ are as defined hereinbefore, or a protected derivative thereof, with a compound of formula XXIX, wherein R$^1$ is as defined hereinbefore, under conditions known to those skilled in the art, for example the reaction may be performed at around room temperature or above (e.g. up to 40-180° C.), in a suitable solvent such as dioxane, ethanol, isopropanol, dimethylformamide, acetonitrile, tetrahydrofuran or mixtures thereof;

(xv) for compounds of formula I in which both L$^1$ and L$^2$ represent direct bonds, reaction of a compound of formula XXXI,

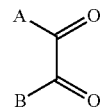

XXXI wherein A and B are as defined hereinbefore, with a compound of formula XXXII,

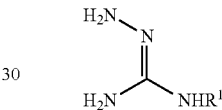

XXXII wherein R$^1$ is as defined hereinbefore, under reaction conditions known to those skilled in the art, for example as described in WO 92/02513;

(xvi) for compounds of formula I in which L$^1$ represents a direct bond and A represents a nitrogen-containing Het$^4$ group that is attached via a nitrogen atom within the ring system, reaction of a compound of formula VII as defined above, with a compound of formula XXXIII.

Het$^{41}$-H     XXXIII wherein Het$^{41}$ takes the same definition as Het$^4$ as defined above, except that Het$^{41}$ is a nitrogen-containing heterocycle that is attached to the H-atom depicted for the compound of formula XXXIII via a nitrogen atom in the heterocycle, under reaction conditions known to those skilled in the art, for example such as those described in respect of process step (iii)(a) above;

(xvii) for compounds of formula I in which L$^2$ represents a direct bond and B represents a nitrogen-containing Het$^B$ group that is attached via a nitrogen atom within the ring system, reaction of a compound of formula XIX as defined above, with a compound of formula XXXIV, Het$^{B2}$-H     XXXIV wherein Het$^{B2}$ takes the same definition as Het$^B$ as defined above, except that Het$^{B2}$ is a nitrogen-containing heterocycle that is attached to the H-atom depicted for the compound of formula XXXIV via a nitrogen atom in the heterocycle, under reaction conditions known to those skilled in the art, for example such as those described in respect of process step (iii)(a) above;

(xviii) for compounds of formula I in which L$^1$ represents a direct bond and A represents a phenyl group optionally substituted by one or more R$^{4a}$ groups, reaction of a compound of formula XXXV,

XXXV

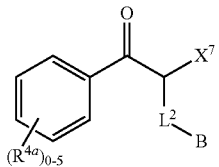

wherein X$^7$ represents a suitable leaving group (such as chloro, bromo, iodo, a sulfonate group (e.g. —OS(O)$_2$CF$_3$, —OS(O)$_2$CH$_3$ or —OS(O)$_2$PhMe), and L$^2$, B and R$^{4a}$ are as defined hereinbefore, with a compound of formula XXXVI,

XXXVI

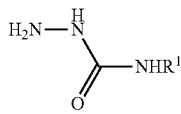

wherein R$^1$ is as defined hereinbefore, under reaction conditions known to those skilled in the art, for example as described in WO 00/66568;

(xix) for compounds of formula I in which L$^1$ represents —CH=CH—, reaction of a compound of formula V as defined above, with a compound of formula XXXVII, A-CH=CH-L$^{x5a}$   XXXVII wherein L$^{x5a}$ represents a metal halide (for example a zinc halide (e.g. —ZnCl) or a magnesium halide (e.g. —MgBr)), —Sn(R$^{x1}$)$_3$, —B(OH)$_2$, —B(OR$^{x1}$)$_2$, or an organosilane (e.g. —Si(OEt)$_3$), wherein each R$^{x1}$ is as defined above, and A is as defined hereinbefore, under reaction conditions known to those skilled in the art, for example such as those described in respect of process step (ii)(a) above; and (xx) for compounds of formula I in which one of R$^{4a}$ to R$^{4d}$ represents —OH, reaction of a compound of formula I in which one of R$^{4a}$ to R$^{4d}$ represents —OR$^{4y}$, wherein R$^{4y}$ represents a C$_{1-6}$ alkyl, C$_{2-6}$ alkenyl, C$_{2-6}$ alkynyl, C$_{3-6}$ cycloalkyl, which groups are optionally substituted by one or more substituents selected from halo, C$_{1-4}$ alkyl and aryl, with an appropriate dealkylating agent (such as boron tribromide, 2-(diethylamino)ethanethiol or a hydrogen halide (e.g. HBr)), under reaction conditions known to those skilled in the art, for example in a suitable solvent (e.g. dichloromethane, dimethylformamide, dioxane, toluene, ethanol, isopropanol, dimethylsulfoxide, acetonitrile, dimethylacetamide, tetrahydrofuran or a mixture thereof, or an ionic liquid (e.g. [bmim][BF$_4$])), and at a suitable temperature (e.g. from room temperature to about 180° C.), e.g. as described in I. Ryu et al., *J. Am. Chem. Soc.*, 2002, 124, 12946-12947; J. Magano et al., *J. Org. Chem.*, 2006, 71, 7103-7105; or S. K. Boovanahalli et al., *J. Org. Chem.*, 2004, 69, 3340-3344.

Compounds of formula XXVIII wherein X$^6$ represents OR$^{4x}$, may be prepared by reaction of a compound of formula XXXVIII.

XXXVIII

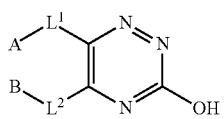

wherein A, B, L$^1$ and L$^2$ are as defined hereinbefore, with a compound of formula XXXIXa, R$^{4x}$—OH   XXXIXa wherein R$^{4x}$ is as described hereinbefore, under reaction conditions known to those skilled in the art, for example as described in French patent no. 2,485,531.

Compounds of formula XXVIII wherein L$^1$ represents a direct bond and X$^6$ represents a sulfone group (e.g. —S(O)$_2$CH$_3$, —S(O)$_2$CF$_3$ or —S(O)$_2$-PhMe), may be prepared by reaction of a compound of formula XXXIXb, XXXIXb

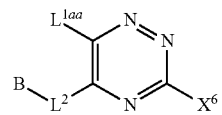

wherein L$^{1aa}$ represents a halogen atom (such as chloro, bromo or, preferably, iodo), X$^6$ represents a sulfone group, and A, B and L$^2$ are as defined hereinbefore, with a compound of formula VI as defined hereinbefore, under reaction conditions known to those skilled in the art, for example such as those described in respect of process step (ii)(a) above).

Compounds of formula XXVIII wherein L$^2$ represents a direct bond and X$^6$ represents a sulfone group (e.g. —S(O)$_2$CH$_3$, —S(O)$_2$CF$_3$ or —S(O)$_2$-PhMe), may be prepared by reaction of a compound of formula XXXIXc, XXXIXc

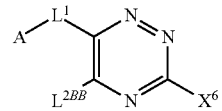

wherein L$^{2aa}$ represents a halogen atom (such as chloro, bromo or, preferably, iodo), X$^6$ represents a sulfone group, and A, B and L$^1$ are as defined hereinbefore, with a compound of formula XVIII as defined hereinbefore, under reaction conditions known to those skilled in the art, for example such as those described in respect of process step (ii)(a) above).

Other intermediate compounds (e.g. intermediate XXVIII) which contain the 1,2,4-triazine core common to the compounds of formula I, may be prepared by reaction of a compound of formula XXXI as defined above, with a compound of formula XL,

XL

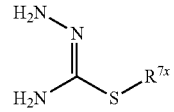

wherein R$^{7x}$ represents a corresponding C$_{1-6}$ alkyl or aryl group, under reaction conditions known to those skilled in the art, for example as described in WO 92/02513, optionally followed by oxidation of the sulfur atom to the desired oxidation state.

Compounds of formula VI wherein $L^{x1b}$ represents $B(OH)_2$, may be prepared by reaction of a compound of formula XLI,

A-H    XLI wherein A is as defined hereinbefore, with a boronic acid derivative (such as bis(pinacolato)diboron, trimethylborate), under reaction conditions known to those skilled in the art, for example in the presence of an appropriate metal catalyst (or a salt or complex thereof, such as $[Ir(COD)(OMe)]_2$, $[Rh(COD)(OMe)]_2$, $[Rh(COD)Cl]_2$, Cu, $Cu(OAc)_7$, CuI (or CuI/diamine complex), copper tris(triphenyl-phosphine) bromide, $Pd(OAc)_2$ or $Pd_2(dba)_3$) and an optional additive (such as 4,4'-di-tert-butyl-2,2'-bipyridine(dtbpy), $Ph_3P$, 2,2'-bis(diphenylphosphino)-1,1'-binaphthyl, xantphos, NaI or an appropriate crown ether such as 18-crown-6-benzene), in the presence of an appropriate base (such as NaH, $Et_3N$, pyridine, N,N'-dimethylethylenediamine, triethanolamine. N-methyldiethanolamine, N,N-diisopropylethanolamine, triisopropanolamine, $Na_2CO_3$, $K_2CO_3$, $K_3PO_4$. $Cs_2CO_3$, t-BuONa or t-BuOK or a mixture thereof, optionally in the presence of 4 Å molecular sieves), in a suitable solvent (e.g. dichloromethane, dimethylformamide, dioxane, toluene, ethanol, isopropanol, dimethylsulfoxide, acetonitrile, dimethylacetamide, tetrahydrofuran or a mixture thereof, or an ionic liquid (e.g. $[bmim][BF_4]$)), and at a suitable temperature (e.g. from room temperature to about 180° C.), e.g. as described in J. M. Murphy, C. C. Tzschucke, J. F. Hartwig, *Org. Lett.*, 2007, 9, 757-760.

Compounds of formulae IIa, IIb, III, IV, VI, VII, VIII, IX, X, XI, XII, XIII, XIV, XV, XVI, XVII, XVIII, XIX, XX, XXI, XXII, XXIII, XXIV, XXV, XXVI, XXVII, XXIX, XXX, XXXI, XXXII, XXXIV, XXXV, XXXVI, XXXVII, XXXVIII, XXXIXa, XXXIXb, XXXIXc, XL and XLI are either commercially available, are known in the literature, or may be obtained either by analogy with the processes described herein (or processes described in references contained herein), or by conventional synthetic procedures, in accordance with standard techniques, from available starting materials using appropriate reagents and reaction conditions.

Substituents, such as $R^{3a}$, $R^{4a}$, $R^{4b}$, $R^{4c}$ and $R^{4d}$ in final compounds of formula I (or precursors thereto and other relevant intermediates) may be modified one or more times, after or during the processes described above by way of methods that are well known to those skilled in the art. Examples of such methods include palladium-mediated cross couplings or, particularly, substitutions, reductions (e.g. carbonyl bond reductions in the presence of suitable and, if necessary, chemoselective, reducing agents such as $LiBH_4$ or $NaBH_4$), oxidations, alkylations, acylations, hydrolyses, esterifications and etherifications. The precursor groups can be changed to a different such group, or to the groups defined in formula I, at any time during the reaction sequence.

Compounds of the invention may be isolated from their reaction mixtures using conventional techniques (e.g. recrystallisation, column chromatography, preparative HPLC, etc.).

In the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", $3^{rd}$ edition, T. W. Greene & P. G. M. Wutz, Wiley-Interscience (1999).

As used herein, the term "functional groups" means, in the case of unprotected functional groups, hydroxy-, thiolo-, aminofunction, carboxylic acid and, in the case of protected functional groups, lower alkoxy, N-, O-, S-acetyl, carboxylic acid ester.

Some of the intermediates referred to hereinbefore are novel. According to a further aspect of the invention there is thus provided: (a) a compound of formula XXVIII, or a protected derivative thereof, in which $X^6$ represents $SO_2R^{x6}$, wherein $R^{x6}$ represents $C_{1-12}$ alkyl optionally substituted by one or more halo (e.g. fluoro) atoms, or $R^{x6}$ represents phenyl optionally substituted by one or more substituents selected from $C_{1-6}$ alkyl (e.g. methyl), nitro and halo (e.g. bromo); (b) a compound of formula XXXIXb, or a protected derivative thereof; and (c) a compound of formula XXXIXc, or a protected derivative thereof.

Biological Tests

The cell lines mentioned below were all purchased from the European Collection of Cell Cultures (ECACC: http://www.hpacultures.org.uk/collections/ecacc.jsp).

Test A

HEK293-h$A_{2a}$ [$^3$H]-ZM241385/CHO-h$A_1$ [$^3$H]DPCPX Binding Assay

Test Compounds

All test compounds were prepared as a stock solution of 10 mM in 100% DMSO.

Inhibition binding assays were performed using 2.5 µg of membranes prepared from HEK293 cells transiently transfected with human adenosine $A_{2a}$ receptor or 10 µg of membranes prepared from CHO cells stably transfected with human adenosine $A_1$ receptor. Membranes were incubated in 50 mM Tris-HCl (HEK293-h$A_{2a}$; pH 7.4) or 20 mM HEPES, 100 mM NaCl, 10 mM $MgCl_2$ (CHO-h$A_1$; pH 7.4) in the presence of varying concentrations of test compound and 1 nM [$^3$H]ZM241385 (HEK293-h$A_{2a}$) or [$^3$H]DPCPX (CHO-h$A_1$) at 25° C. for 1 h. The assay was then terminated by rapid filtration onto GF/B grade Unifilter plates using a TomTec cell harvester, followed by 5×0.5 ml washes with double distilled $H_2O$. Nonspecific binding was defined in the presence of 1 µM CGS15943 (HEK293-h$A_{2a}$) or 1 µM DPCPX (CHO-h$A_1$). Bound radioactivity was determined by liquid scintillation counting (Trilux Microbeta® Counter) and inhibition curves were analysed using a four-parameter logistic equation. $IC_{50}$ values were converted to $K_i$ values with the Cheng-Prusoff equation using a $K_D$ value derived from saturation binding studies.

Test B

Catalepsy Reversal Test

The dopamine $D_2$ receptor antagonist, haloperidol, induces Parkinsonism in humans and induces motor effects in rats such as catalepsy. There is considerable evidence that adenosine $A_{2A}$ receptor antagonists reverse haloperidol-induced motor effects in preclinical studies. Suggested mechanisms by which these effects are mediated include the hypothesis that $A_{2A}$ receptor antagonism modulates $D_2$ receptor sensitivity such that $D_2$ receptors exhibit increased sensitivity to striatal dopamine in the presence of an $A_{2A}$ receptor antagonist. The present study determines the ability of haloperidol-induced catalepsy in rats to be reversed by novel $A_{2A}$ receptor antagonists.

Catalepsy was monitored individually in Sprague-Dawley rats (Charles River, UK; 200-250 g; n=8/group) by gently placing each paw in turn on a large rubber bung. A score of 1 is given for each paw which remains in position for 15 seconds, giving each rat a maximum score of 4. Haloperidol (0.82 mg/kg, i.p.; 150 min pre-test time) induces significant cataleptic behaviour in rats (average score 3.1). The effect of selected compounds of the invention (2-10 mg/kg or 0.3-3 mg/kg, p.o.; 120 min pre-test time) on catalepsy was established by administration of said compounds to rats pre-treated with haloperidol as described above.

Details of a similar test may be found in, for example, Hodgson et al., *J. Pharmacol. Exp. Ther.* 330, 2009, 294-303.

EXAMPLES

Where no preparative routes are included, the relevant intermediate is commercially available (e.g. from Sigma Aldrich or Manchester Organics Ltd).

General Procedures

Commercial reagents were utilized without further purification. Room temperature refers to 20-27° C. Melting points, wherever reported, are uncorrected. $^1$H-NMR spectra were recorded at 400 MHz on a Bruker instrument. Chemical shift values are expressed in parts per million, i.e. (δ)-values. The following abbreviations are used for the multiplicity for the NMR signals: s=singlet, b=broad, d=doublet, t=triplet, q=quartet, qui=quintet, h=heptet, dd=doublet of doublets, dt=double of triplets, m=multiplet Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. The TLC for monitoring the reaction means the TLC run using the specified mobile phase and the Silica gel F254 as a stationary phase from Merck. Microwave-mediated reactions were performed in a Biotage Initiator.

HPLC purities were measured under the following conditions:

Instrument: Waters Alliance 2695. Column: Sunfire C-18, 250×4.6 mm, 5 µm, or equivalent. Gradient [time (min)/% solvent B in A]: 0.00/10, 9.00/90, 11.00/100, 20.00/100, 20.01/10, 25.00/10 (solvent A=0.1% formic acid in water; solvent B=0.1% formic acid in acetonitrile), 1 mL/min; detection wavelength specified for each compound in the detailed experimental section.

Mass spectroscopy was carried out on a Shimadzu LCMS-2010 EV, using electrospray conditions as specified for each compound in the detailed experimental section.

LCMS experiments were carried out with methods A-C, as specified for each compound in the detailed experimental section, using the following conditions:

LCMS method A: Instruments: Waters Alliance 2795. Waters 2996 PDA detector, Micromass ZQ. Column: Waters X-Bridge C-18, 2.5 micron, 2.1×20 mm or Phenomenex Gemini-NX C-18, 3 micron, 2.0×30 mm. Gradient [time (min)/solvent D in C (%)]: 0.00/2, 0.10/2, 2.50/95, 3.50/95, 3.55/2, 4.00/2 (solvent C=1.58 g ammonium formate in 2.5 L water+2.7 mL ammonia solution; solvent D=2.5 L Acetonitrile+132 mL (5%) solvent C+2.7 mL ammonia solution). Injection volume 5 uL; UV detection 230 to 400 nM; column temperature 45° C.

LCMS method B: Instrument: Waters Semi-Prep LCMS with ZQ MS. Column: Agilent Prep-C18 Scalar, 5 µm, 4.6×50 mm Detection wavelength: 254 nm and 215 nm. Gradient [time (min)/solvent B in A (%), flow rate]: 0.00/5 (2.5 mL/min), 0.10/5 (2.5 mL/min), 5.0/95 (2.5 mL/min), 5.50/95 (2.5 mL/min), 5.60/95 (3.5 mL/min), 6.60/95 (3.5 mL/min), 6.75/5 (3.5 mL/min) 6.90/5 (3.5 mL/min), 7.00/5 (2.5 mL/min), (solvent A: water with 0.1% $NH_4OH$; solvent B: MeOH with 0.1% $NH_4OH$).

LCMS method C: Instruments: Waters Alliance 2795. Waters 2996 PDA detector, Micromass ZQ. Column: Waters X-Bridge C-18, 2.5 micron, 2.1×20 mm or Phenomenex Gemini-NX C-18, 3 micron, 2.0×30 mm. Gradient [time (min)/solvent D in C (%)]: 0.00/2, 0.10/2, 8.40/95, 9.40/95, 9.50/2, 10.00/2 (solvent C=1.58 g ammonium formate in 2.5 L water+2.7 mL ammonia solution; solvent D=2.5 L Acetonitrile+132 mL (5%) solvent C+2.7 mL ammonia solution). Injection volume 5 uL; UV detection 230 to 400 nM; column temperature 45° C.: 1.5 mL/min.

Preparative HPLC was typically carried out with instrument A or B using an acidic method (gradients of acetonitrile and water, each containing 0.1% formic acid) or a basic method (gradients of methanol and water, each containing 0.1% $NH_4OH$) Instrument A conditions: Waters delta 600 HPLC. Column: X-bridge C-18, 250×19 mm, 5 µm, or equivalent Flow rate: 19 mL/min.

Instrument B: Gilson HPLC. Column: Agilent Zorbax Extend Cartridge, 5 µm, 21.2×100 mm. Guard Column: Agilent Prep-C18 Guard Cartridge, 10 µm. Flow rate: 28 mL/min.

Preparation 1

Procedure for the Preparation of Methyl Hydrazinecarbimidothioate

Methyl hydrazinecarbimidothioate was prepared by drop wise addition of methyl iodide (2.80 g, 19.8 mmol) to a solution of thiosemicarbazide (1.80 g, 19.75 mmol) in ethanol (50 mL). The resulting mixture was refluxed for 2.5 hrs with TLC monitoring (methanol/DCM, 1:9). The reaction mixture was then concentrated in vacuo and the crude compound (1.80 g, 90%) was used in the next step without any further purification.

Mass spectroscopy: (ESI+ve) 106 [M–H]$^+$

Typical Procedure for the Preparation of Arylglyoxal Derivatives, as Exemplified with (i) 4-fluorophenylglyoxal Selenium dioxide (6.70 g, 61.0 mmol) was added to a solution of 4-fluoroacetophenone (8.43 g, 61.0 mmol) in dioxane (100 mL) and water (3 mL), and the resulting mixture was heated at 55° C. until complete dissolution of selenium dioxide had occurred. The reaction mass was then refluxed for 5-6 hrs. After completion of the reaction (TLC), the mixture was filtered and the filtrate was concentrated in vacuo affording a viscous oil. Water (50 mL) was added and the resulting mixture was stirred for 12 hrs, after which time the solid was collected on a filter, washed with water (25 mL) and dried in vacuo, affording 4-fluorophenylglyoxal (6.60 g, 85%).

$^1$H NMR: (400 MHz, CDCl$_3$) δ: 7.18 (m, 2H), 8.11 (d, 2H), aldehyde CHO signal not observed.

(ii) (3-Chloro-5-fluorophenyl)(oxo)acetaldehyde (3-Chloro-5-fluorophenyl)(oxo)acetaldehyde (27 g, 84%) was prepared from 3-chloro-5-fluoro acetophenone (30.0 g, 174.4 mmol) and selenium dioxide (21.28 g, 191.8 mmol) according to the typical procedure used for Preparation 1.

(iii) (3,5-Difluorophenyl)(oxo)acetaldehyde (3,5-Difluorophenyl)(oxo)acetaldehyde (28 g, 84%) was prepared from 3,5-difluoro acetophenone (30.0 g, 192.3 mmol) and selenium dioxide (23.55 g, 214.0 mmol) according to the typical procedure used for Preparation 1.

(iv) 4-(Methoxymethyl)phenylglyoxal

Step 1: Preparation of 4-(Methoxymethyl)benzonitrile 4-(Hydroxymethyl) benzonitrile (6.0 g, 45.09 mmol) was dissolved in THF (60 mL), cooled to −5° C. to −10° C. and treated with sodium hydride (2.16 g, 90.19 mmol). The resulting mixture was stirred for 30 minutes then treated with methyl iodide (9.6 g, 67.65 mmol) at RT for 2 hours. After completion of the reaction (TLC: ethyl acetate/Hexane, 5:5), the mixture was poured into water (50 mL) and extracted with ethyl acetate (3×25 mL). The separated organic layers were combined, dried over $Na_2SO_4$ and concentrated in vacuo. The crude compound was purified by gradient flash chromatography, eluting with 5% ethyl acetate in hexane to afford 4-(methoxymethyl)benzonitrile (6.7 g, 90%).

HPLC purity: 99.20% (232 nm)
Mass spectroscopy: (ESI+ve) 148.0 $[M+H]^+$.

Step 2: Preparation of 1-[4-(methoxymethyl)phenyl]ethanone 4-(Methoxymethyl)benzonitrile (6.0 g, 40.82 mmol) was dissolved in THF/diethyl ether (1:1, 60 mL) and the resulting solution was cooled to −10° C. 3 M solution of methyl magnesium iodide (13.57 g, 81.63 mmol) was added and the resulting mixture was stirred at this temperature for 5 hours. After completion of the reaction (TLC; toluene/methanol, 97:3), the mixture was poured into acidified water (50 mL; pH 3-4) and extracted with ethyl acetate (3×50 mL). The separated organic layers were combined, dried over $Na_2SO_4$ and concentrated in vacuo. The crude compound was purified by gradient flash chromatography, eluting with 8% ethyl acetate in hexane to afford the target compound (3.7 g, 55%).

Mass spectroscopy: (ESI+ve) 165.0 $[M+H]^+$.

Step 3: Preparation of 4-(methoxymethyl)phenylglyoxal

Selenium dioxide (3.53 g, 31.84 mmol) was dissolved in 1,4-dioxane (50 mL) and water (0.5 mL). The solution was warmed to 40° C. and treated with 1-(4-(methoxymethyl)phenyl)ethanone (3.9 g, 26.53 mmol); the resulting mixture was refluxed for 6 hours and monitored by TLC (chloroform/methanol, 95:5). After completion of the reaction, the mixture was filtered through celite and concentrated in vacuo. The crude compound was purified by column chromatography eluting with up to 15% ethyl acetate in hexane, affording the target glyoxal (4.0 g, 85%).

Mass spectroscopy: (ESI+ve) 179.0$[M-H]^-$ (v) 2-Pyrimidineglyoxal

Step 1: Preparation of 1-(pyrimidin-2-yl)ethanone

A solution of 2-cyano-pyrimidine (10.0 g, 95.2 mmol) in THF (100 mL) was cooled to −5° C. and treated with a 3 M solution of methyl magnesium bromide in THF (38.0 mL, 98.4 mmol). The reaction was stirred at 0° C. for two hours until completion was observed by TLC (chloroform/methanol, 9:1). The reaction mixture was poured in water; the pH was adjusted to 5-6 and the aqueous layer was extracted with ethyl acetate (3×150 mL). The combined organic layers were concentrated under reduced pressure and the crude compound was purified by column chromatography, eluting with chloroform to afford the target compound (6.5 g, 48%).

HPLC purity: 97.2% (223 nm).
Mass spectroscopy: (ESI+ve) 123.1 $[M+H]^+$

Step 2: Preparation of 2-pyrimidineglyoxal

A solution of selenium dioxide (15 g, 135 mmol) in ethanol (150 mL) was stirred at 50° C. until a clear solution was obtained, 1-(Pyrimidin-2-yl)ethanone (10 g, 82.0 mmol) was added to the resulting mixture which was stirred for 6 hrs at 78° C. with TLC monitoring. This crude mixture was then used in next step without further purification.

Mass spectroscopy: (ESI+ve) 137.1 $[M+H]^+$
TLC $R_f$: 0.3 (chloroform/methanol, 9:1)

(vi) 2-Pyridylglyoxal

2-Pyridylglyoxal (8.0 g, crude) was prepared from selenium dioxide (15 g, 135 mmol) and 2-acetyl pyridine (10 g, 82 mmol) according to the typical procedure used for Preparation 1.

TLC $R_f$: 0.1 (ethyl acetate)
Mass spectroscopy: (ESI+ve) 136.1 [M+H].

(vii) 3-pyridylglyoxal

3-Pyridylglyoxal (5.0 g, crude) was prepared from selenium dioxide (6.82 g, 61.4 mmol) and 3-acetyl pyridine (5.0 g, 41.0 mmol) according to the typical procedure used for Preparation 1.

Mass spectroscopy: (ESI+ve) 136.1 $[M+H]^+$.
TLC $R_f$: 0.1 (ethyl acetate)

Phenylglyoxal monohydrate is commercially available from Sigma Aldrich. 2,4-difluorophenylglyoxal and 3-methoxyphenylglyoxal are commercially available from Manchester Organics Ltd.

Preparation 2 intermediate A

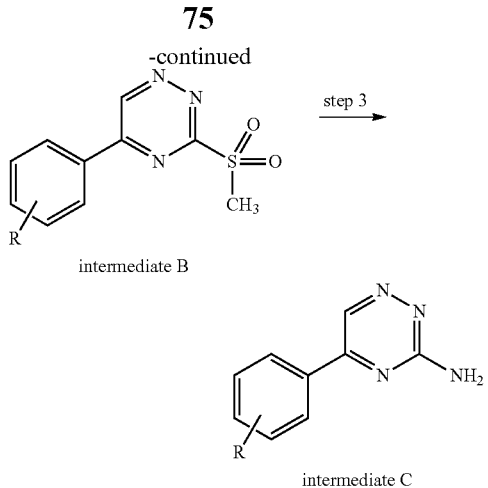

intermediate B intermediate C

General Procedure for the Preparation of 5-Aryl-1,2,4-Triazin-3-Amine Derivatives from Arylglyoxal Derivatives Step 1: A solution of an arylglyoxal derivative (19.7 mmol) in ethanol (50 mL) is treated successively with sodium bicarbonate (3.32 g, 39.5 mol) and methyl hydrazinecarbimidothioate (19.7 mmol) and the resulting mixture is refluxed for 3 hrs. After completion of the reaction (TLC), the mixture is concentrated in vacuo, poured into water (50 mL), and extracted with DCM or ethyl acetate (2×25 mL). The combined organic extracts are then dried over $Na_2SO_4$, concentrated in vacuo, and purified by gradient flash chromatography, affording intermediate A, a 3-(methylsulfanyl)-5-aryl-1,2,4-triazine derivative.

Step 2: m-CPBA (7.44 g, 43.3 mmol) is added to a solution of intermediate A (14.4 mmol) in DCM (50 mL) at −20 to −15° C. and the resulting mixture is stirred at this temperature until the reaction is judged to be complete by TLC (typically 8 hrs). The reaction is then quenched with saturated aqueous $NaHCO_3$ solution (100 mL) and extracted with ethyl acetate (2×25 mL). The combined organic extracts are dried over $Na_2SO_4$ and evaporated under reduced pressure. The crude product, intermediate B, a 3-(methylsulfonyl)-5-aryl-1,2,4-triazine derivative, is purified by gradient flash chromatography.

Step 3: 0.5 M ammonia in THF (100 mL, 500 mmol) is cooled to −33° C. and treated with ferric nitrate (5.50 g, 13.6 mmol) for 10 minutes. A solution of intermediate B (13.6 mmol) in THF (15 mL) is then introduced by drop wise addition and the mixture is stirred for 4 hrs with monitoring by TLC (methanol/DCM, 1:9). After completion of the reaction, the mixture is poured into water (150 mL) and extracted with DCM or ethyl acetate (2×50 mL). The combined organic extracts are then dried over $Na_2SO_4$, concentrated in vacuo and treated with 4N aqueous HCl solution (40-50 mL) for 10 minutes. The aqueous phase is then extracted with ethyl acetate (150 mL), neutralized with aqueous $K_2CO_3$ solution (90-100 mL), and re-extracted with ethyl acetate (100 mL). All of the organic extracts are then combined, dried over $Na_2SO_4$ and concentrated in vacuo, affording intermediate C, a 5-aryl-1,2,4-triazin-3-amine derivative.

(i) 5-Phenyl-1,2,4-triazin-3-amine

Step 1: 3-(Methylsulfanyl)-5-phenyl-1,2,4-triazine (2.93 g, 73%) was prepared from methyl hydrazinecarbimidothioate (2.07 g, 19.7 mmol) and phenylglyoxal monohydrate (2.89 g, 19.7 mmol) according to the general procedure of Preparation 2.

Mass spectroscopy: (ESI+ve) 204 [M+H]$^+$
$^1$H NMR: (400 MHz, CDCl$_3$) δ: 2.73 (s, 3H), 7.53-7.60 (m, 3H), 8.14-8.17 (m, 2H), 9.38 (s, 1H).

Step 2: 3-(Methylsulfonyl)-5-phenyl-1,2,4-triazine (3.20 g, 96%) was prepared from 3-(methylsulfanyl)-5-phenyl-1,2,4-triazine (2.93 g, 14.4 mmol) and m-CPBA (7.44 g, 43.3 mmol) according to the general procedure of Preparation 2.

Mass spectroscopy: (ESI+ve) 236.9 [M+H]$^+$

Step 3: 5-Phenyl-1,2,4-triazin-3-amine (1.70 g, 73%) was prepared from 3-(methylsulfonyl)-5-phenyl-1,2,4-triazine (3.20 g, 13.6 mmol) and 0.5 M ammonia in THF (100 mL, 500 mmol) according to the general procedure of Preparation 2.

Mass spectroscopy: (ESI+ve) 172.9 [M+H]$^+$
$^1$H NMR: (400 MHz, CDCl$_3$) δ: 7.30 (br s, 2H), 7.53-7.60 (m, 3H), 8.19-8.21 (dd, 2H), 9.20 (s, 1H).

(ii) 5-(2,4-Difluorophenyl)-1,2,4-triazin-3-amine

Step 1: 3-(Methylsulfanyl)-5-(2,4-difluorophenyl)-1,2,4-triazine (1.00 g, 78%) was prepared from methyl hydrazinecarbimidothioate (0.63 g, 6.0 mmol) and 2,4-difluorophenylglyoxal monohydrate (1.00 g, 6.0 mmol) according to the general procedure of Preparation 2.

Mass spectroscopy: (ESI+ve) 239.9 [M+H]$^+$
$^1$H NMR: (400 MHz, CDCl$_3$) δ: 2.69 (s, 3H), 6.96-7.02 (m, 1H), 7.06-7.11 (m, 1H), 8.27-8.33 (m, 1H), 9.46 (s, 1H).

Step 2: 3-(Methylsulfonyl)-5-(2,4-difluorophenyl)-1,2,4-triazine (1.1 g, 97%) was prepared from 3-(methylsulfanyl)-5-(2,4-difluorophenyl)-1,2,4-triazine (1.00 g, 4.17 mmol) and m-CPBA (2.16 g, 4.17 mmol) according to the general procedure of Preparation 2.

Mass spectroscopy: (ESI+ve) 271.9 [M+H]$^+$

Step 3: 5-(2,4-Difluorophenyl)-1,2,4-triazin-3-amine (0.45 g, 53%) was prepared from 3-(methylsulfonyl)-5-(2,4-difluorophenyl)-1,2,4-triazine (1.10 g, 4.05 mmol) and 0.5 M ammonia in THF (50 mL, 25 mmol) according to the general procedure of Preparation 2.

Mass spectroscopy: (ESI+ve) 208.9 [M+H]$^+$ (iii) 5-(3-Methoxyphenyl)-1,2,4-triazin-3-amine Step 1: 3-(Methylsulfanyl)-5-(3-methoxyphenyl)-1,2,4-triazine (1.01 g, 79%) was prepared from methyl hydrazinecarbimidothioate (0.58 g, 5.50 mmol) and 3-methoxyphenylglyoxal monohydrate (1.00 g, 5.50 mmol) according to the general procedure of Preparation 2.

Mass spectroscopy: (ESI+ve) 233.9 [M+H]$^+$

Step 2: 3-(Methylsulfonyl)-5-(3-methoxyphenyl)-1,2,4-triazine (0.90 g, 79%) was prepared from 3-(methylsulfanyl)-5-(3-methoxyphenyl)-1,2,4-triazine (1.00 g, 4.20 mmol) and m-CPBA (2.30 g, 12.8 mmol) according to the general procedure of Preparation 2.

Mass spectroscopy: (ESI+ve) 265.9 [M+H]$^+$

Step 3: 5-(3-Methoxyphenyl)-1,2,4-triazin-3-amine (0.31 g, 45%) was prepared from 3-(methylsulfonyl)-5-(3-methoxyphenyl)-1,2,4-triazine (0.90 g, 3.39 mmol) and 0.5 M ammonia in THF (50 mL, 25.0 mmol) according to the general procedure of Preparation 2.

Mass spectroscopy: (ESI+ve) 202.9 [M+H]$^+$ (iv) 5-(4-Fluorophenyl)-1,2,4-triazin-3-amine Step 1: 3-(Methylsulfanyl)-5-(4-fluorophenyl)-1,2,4-triazine (6.00 g, 69%) was prepared from methyl hydrazinecarbimidothioate (4.51 g, 43.0 mmol) and 4-fluorophenylglyoxal monohydrate (6.60 g, 43.0 mmol) according to the general procedure of Preparation 2.

Mass spectroscopy: (ESI+ve) 221.9 [M+H]$^+$
$^1$H NMR: (400 MHz, CDCl$_3$) δ: 2.73 (s, 3H), 7.24 (d, 2H), 8.18 (d, 2H), 9.34 (s, 1H).

Step 2: 3-(Methylsulfonyl)-5-(4-fluorophenyl)-1,2,4-triazine (5.00 g, 72%) was prepared from 3-(methylsulfanyl)-5-(4-fluorophenyl)-1,2,4-triazine (6.00 g, 27.0 mmol) and m-CPBA (12.4 g, 81.0 mmol) according to the general procedure of Preparation 2.

Mass spectroscopy: (ESI+ve) 253.9 [M+H]$^+$
$^1$H NMR: (400 MHz, CDCl$_3$) δ: 3.55 (s, 3H), 7.34 (d, 2H), 8.33 (d, 2H), 9.82 (s, 1H).

Step 3: 5-(4-Fluorophenyl)-1,2,4-triazin-3-amine (2.80 g, 74%) was prepared from 3-(methylsulfonyl)-5-(4-fluorophenyl)-1,2,4-triazine (5.00 g, 19.7 mmol) and 0.5 M ammonia in THF (100 mL, 50.0 mmol) according to the general procedure of Preparation 2.

Mass spectroscopy: (ESI+ve) 191.0[M+H]$^+$
$^1$H NMR: (400 MHz, CDCl$_3$) δ: 6.79 (s, 2H), 7.40 (m, 2H), 8.23 (m, 2H), 9.21 (s, 1H).

(v) 5-[4-(methoxymethyl)phenyl]-1,2,4-triazin-3-amine

Step 1: 5-[4-(methoxymethyl)phenyl]-3-(methylsulfanyl)-1,2,4-triazine (4.0 g, 72%) was prepared from methyl hydrazinecarbimidothioate (7.33 g, 31.46 mmol) and 4-(methoxymethyl)phenylglyoxal (4 g, 22.47 mmol) according to the general procedure of Preparation 2.

Mass spectroscopy: (ESI+ve) 248.0 [M−H]$^+$

Step 2: 5-[4-(methoxymethyl)phenyl]-3-(methylsulfonyl)-1,2,4-triazine (3.5 g, 83%) was prepared from 5-[4-(methoxymethyl)phenyl]-3-(methylsulfanyl)-1,2,4-triazine (3.75 g, 15.2 mmol) and m-CPBA (7.92 g, 45.6 mmol) according to the general procedure of Preparation 2.

Mass spectroscopy: (ESI+ve) 279.9 [M−H]$^+$

Step 3: 5-[4-(methoxymethyl)phenyl]-1,2,4-triazin-3-amine (2.2 g, 85%) was prepared from 5-[4-(methoxymethyl)phenyl]-3-(methylsulfonyl)-1,2,4-triazine (3.40 g, 12.2 mmol) in THF (35 mL) and treated with NH$_3$ gas by purging for 30 minutes, similarly to the general procedure of Preparation 2.

Mass spectroscopy: (ESI+ve) 217.0 [M+H]$^+$.
$^1$H NMR: (400 MHz, DMSO) δ: 3.32 (s, 3H), 4.48 (s, 2H), 7.22 (s, 2H), 7.47 (d, 2H), 8.14 (d, 2H), 9.2 (s, 1H).

(vi) 5-(3-chloro-5-fluorophenyl)-1,2,4-triazin-3-amine

Step 1: 3-(methylsulfanyl)-5-(3-chloro-5-fluorophenyl)-1,2,4-triazine (16 g, 38.4%) was prepared from methyl hydrazinecarbimidothioate (25.5 g, 243 mmol) and 2-(3-chloro-5-fluorophenyl)-2-oxoacetaldehyde (30 g, 162 mmol) according to the general procedure of Preparation 2.

Mass spectroscopy: (ESI+ve) 255.9 [M−H]$^+$

Step 2: 3-(methylsulfonyl)-5-(3-chloro-5-fluorophenyl)-1,2,4-triazine (16 g, 88%) was prepared from 3-(methylsulfanyl)-5-(3-chloro-5-fluorophenyl)-1,2,4-triazine (16 g, 62.7 mmol) and m-CPBA (16.18 g, 94.11 mmol) according to the general procedure of Preparation 2.

Mass spectroscopy: (ESI+ve) 287.9 [M−H]$^+$

Step 3: 5-(3-chloro-5-fluorophenyl)-1,2,4-triazin-3-amine (1.70 g, 73%) was prepared from 3-(methylsulfonyl)-5-(3-chloro-5-fluorophenyl)-1,2,4-triazine (16.0 g, 55.5 mmol) and ammonia gas according to the general procedure of Preparation 2.

Mass spectroscopy: (ESI+ve) 224.9 [M−H]$^+$ (vii) 5-(3,5-difluorophenyl)-1,2,4-triazin-3-amine Step-1: 3-(methylsulfanyl)-5-(3,5-difluorophenyl)-1,2,4-triazine (28 g, 80.0%) was prepared from methyl hydrazine carbimidothioate (20.68 g, 197.4 mmol) and 2-(3,5-difluorophenyl)-2-oxoacetaldehyde (25 g, 147.0 mmol) according to the general procedure of Preparation 2.

Mass spectroscopy: (ESI+ve) 240.0 [M−H]$^+$
$^1$H NMR: (400 MHz, CDCl$_3$) δ: 2.74 (s, 3H), 7.02-7.07 (m, 1H), 7.69 (d, 2H), 9.32 (s, 1H).

Step-2: 3-(methylsulfonyl)-5-(3,5-difluorophenyl)-1,2,4-triazine (31 g, 97.7%) was prepared from 3-(methylsulfanyl)-5-(3-chloro-5-fluorophenyl)-1,2,4-triazine (28.0 g, 117.0 mmol) and m-chloro perbenzoic acid (40 g, 234 mmol) according to the general procedure of Preparation 2.

Mass spectroscopy: (ESI+ve) 271.9 [M−H]$^+$

Step-3: 5-(3,5-difluorophenyl)-1,2,4-triazin-3-amine (18 g, 74%) was prepared from 3-(methylsulfonyl)-5-(3,5-difluorophenyl)-1,2,4-triazine (31.0 g, 115.0 mmol) and ammonia gas according to the general procedure of Preparation 2.

Mass spectroscopy: (ESI+ve) 209.0 [M+H]$^+$.
$^1$H NMR: (400 MHz, DMSO) δ: 7.37 (bs, 2H), 7.4 (m, 3H), 9.29 (s, 1H).

(viii) 5-(Pyrimidin-2-yl)-1,2,4-triazin-3-amine

Step 1: 3-(Methylsulfanyl)-5-(pyrimidin-2-yl)-1,2,4-triazine (5.0 g, 67%) was prepared from methylhydrazinecarbimidothioate (4.8 g 44.1 mmol) and 2-pyrimidineglyoxal (5.0 g, 37 mmol) according to the general procedure of Preparation 2.

Mass spectroscopy: (ES+I+ve) 206.0 [M+H]$^+$.

Step 2: 3-(Methylsulfonyl)-5-(pyrimidin-2-yl)-1,2,4-triazine (5.0 g, crude) was prepared from 3-(methylsulfanyl)-5-(pyrimidin-2-yl)-1,2,4-triazine (5.0 g, 24.3 mmol) and m-CPBA (10.5 g, 58.0 mmol) according to the general procedure of Preparation 2, without chromatographic purification.

Mass spectroscopy: (ESI+ve) 237.0 [M+H]$^+$.
TLC R$_f$: 0.5 (chloroform/methanol, 9:1)

Step 3: 5-(Pyrimidin-2-yl)-1,2,4-triazin-3-amine (1.0 g, 23%) was prepared from 3-(methylsulfonyl)-5-(pyrimidin-2-yl)-1,2,4-triazine (5.0 g. crude) and 0.5 M ammonia in THF (20 mL) according to the general procedure of Preparation 2.

Mass spectroscopy: (ESI+ve) 175 [M+H]$^+$.

The following triazine intermediates were prepared from arylglyoxal derivatives in one step by condensation with aminoguanidine:

(ix) 5-(Pyridin-2-yl)-1,2,4-triazin-3-amine (1.5 g, 8% over 2 steps) was prepared from a crude sample of 2-pyridylglyoxal (8.0 g) and aminoguanidine hydrogen carbonate (6.0 g, 44 mmol). The reagents were refluxed in EtOH (100 mL) for 4 hours. The reaction mixture was then cooled, concentrated under reduced pressure and purified by gradient flash chromatography (eluting with 0-30% ethyl acetate/hexane). The sample contained a mixture of isomers at this stage and was used without further purification.

HPLC purity: 35%, (265 nm)
Mass spectroscopy: (ESI+ve) 174 [M+H]$^+$.

(x) 5-(Pyridin-3-yl)-1,2,4-triazin-3-amine (1.5 g, 16% over 2 steps) was prepared from a crude sample of 3-pyridylglyoxal (10.0 g) and aminoguanidine hydrogen carbonate (3.0 g, 22 mmol). The reagents were refluxed in EtOH (100 mL) for 4 hours. The reaction mixture was then cooled, concentrated under reduced pressure and purified by gradient flash chromatography (eluting with 0-30% ethyl acetate/hexane).

Mass spectroscopy: (ESI+ve) 174 [M+H]$^+$
TLC R$_f$=0.2 (ethyl acetate)

The following 3-amino-5-aryl-1,2,4-triazine compounds are commercially available from UkrOrgSynth:
5-[4-(difluoromethoxy)phenyl]-1,2,4-triazin-3-amine;
5-(3-chloro-4-fluorophenyl)-1,2,4-triazin-3-amine;
5-(3-chlorophenyl)-1,2,4-triazin-3-amine;
5-(4-chlorophenyl)-1,2,4-triazin-3-amine;
5-(3,4-difluorophenyl)-1,2,4-triazin-3-amine;
5-(3-fluorophenyl)-1,2,4-triazin-3-amine;
4-(3-amino-1,2,4-triazin-5-yl)benzonitrile;
5-(4-ethylphenyl)-1,2,4-triazin-3-amine;
5-(4-methylphenyl)-1,2,4-triazin-3-amine;
5-(2-fluorophenyl)-1,2,4-triazin-3-amine;
5-(4-methoxyphenyl)-1,2,4-triazin-3-amine and
5-(2,5-difluorophenyl)-1,2,4-triazin-3-amine.

Preparation 3

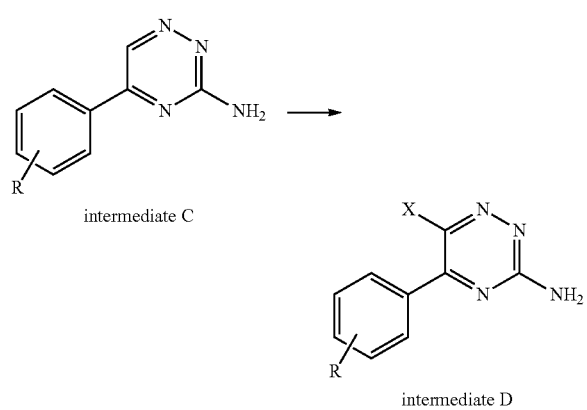

General Procedure for the Halogenation of 5-Aryl-1,2,4-Triazin-3-Amine Derivatives
Method 1

A solution of intermediate C, a 5-aryl-1,2,4-triazin-3-amine derivative (8.70 mmol) in DMF (15 mL) is cooled to −25° C. and treated with a solution of N-chlorosuccinimide or N-bromosuccinimide (26.6 mmol) in DMF (10 mL) by drop wise addition. The reaction is stirred overnight and monitored by TLC (methanol/DCM, 1:9). After completion of the reaction, the mixture is poured into saturated bicarbonate solution (50 mL) and extracted with diethyl ether (25×3 mL). The organic phases are combined, dried over Na$_2$SO$_4$ and concentrated in vacuo. The crude compound is purified by gradient flash chromatography, eluting with mixtures of ethyl acetate in hexane (e.g. 10% ethyl acetate in hexane) to afford the target compound, intermediate D.

Method 2

A solution of intermediate C, a 5-aryl-1,2,4-triazin-3-amine derivative (8.70 mmol) in DMF (15 mL) is cooled to −25° C. and treated with a solution of N-chlorosuccinimide or N-bromosuccinimide (26.6 mmol) in DMF (10 mL) by drop wise addition. The reaction is stirred at room temperature and monitored by TLC or LCMS. After completion of the reaction, the mixture is poured into saturated bicarbonate solution (50 mL) and extracted with an organic solvent such as diethyl ether or ethyl acetate. The organic phases are combined, dried over Na$_2$SO$_4$ and concentrated in vacuo. The crude compound is purified by gradient flash chromatography, eluting with mixtures of ethyl acetate in hexane, or methanol in DCM, to afford the target compound, intermediate D.

(i) 6-Bromo-5-phenyl-1,2,4-triazin-3-amine

6-Bromo-5-phenyl-1,2,4-triazin-3-amine (1.40 g, 64%) was prepared from 5-phenyl-1,2,4-triazin-3-amine (1.50 g, 8.70 mmol) and N-bromosuccinimide (4.50 g, 26.6 mmol) according to the general procedure of Preparation 3.

Mass spectroscopy: (ESI+ve) 251.9 [M+H]$^+$
$^1$H NMR: (400 MHz, CDCl$_1$) δ: 5.49 (s, 2H), 7.49-7.58 (m, 3H), 7.82-7.85 (m, 2H).

(ii) 6-Chloro-5-phenyl-1,2,4-triazin-3-amine

6-Chloro-5-phenyl-1,2,4-triazin-3-amine (0.38 g, 65%) was prepared from 5-phenyl-1,2,4-triazin-3-amine (0.50 g, 1.99 mmol) and N-chlorosuccinimide (0.50 g, 3.7 mmol) according to the general procedure of Preparation 3.

Mass spectroscopy: (ESI+ve) 207.9 [M+H]$^+$ (iii) 6-Bromo-5-(2,4-difluorophenyl)-1,2,4-triazin-3-amine 6-Brom-5-(2,4-difluorophenyl)-1,2,4-triazin-3-amine (0.13 g, 21%) was prepared from 5-(2,4-difluorophenyl)-1,2,4-triazin-3-amine (0.45 g, 2.1 mmol) and N-bromosuccinimide (0.49 g, 2.80 mmol) according to the general procedure of Preparation 3.

Mass spectroscopy: (ESI+ve) 286.8 [M+H]$^+$ (iv) 6-Bromo-5-(3-methoxyphenyl)-1,2,4-triazin-3-amine 6-Bromo-5-(3-methoxyphenyl)-1,2,4-triazin-3-amine (0.18 g, 42%) was prepared from 5-(3-methoxyphenyl)-1,2,4-triazin-3-amine (0.31 g, 1.50 mmol) and N-bromosuccinimide (0.35 g, 1.99 mmol) according to the general procedure of Preparation 3.

Mass spectroscopy: (ESI+ve) 280.9 [M+H]$^+$ (v) 6-Bromo-5-(4-fluorophenyl)-1,2,4-triazin-3-amine 6-Bromo-5-(4-fluorophenyl)-1,2,4-triazin-3-amine (1.95 g, 49%) was prepared from 5-(4-fluorophenyl)-1,2,4-triazin-3-amine (2.8 g, 14.00 mmol) and N-bromosuccinimide (7.87 g, 44.00 mmol) according to the general procedure of Preparation 3.

Mass spectroscopy: (ESI+ve) 268.9 [M+H]$^+$
$^1$H NMR: (400 MHz, CDCl$_3$) δ: 5.43 (s, 2H), 7.19 (d, 2H), 7.87 (d, 2H).

The following intermediate compounds were also prepared according to the general procedure of Preparation 3:

| No. | Product (yield) | Prepared From | LCMS | NMR |
|---|---|---|---|---|
| (vi) | 6-bromo-5-(3,4-difluorophenyl)-1,2,4-triazin-3-amine (1.71 g, 44%) | 5-(3,4-difluorophenyl)-1,2,4-triazin-3-amine (2.8 g, 13.45 mmol) | Mass spectroscopy: m/z 287, 289 (M + H)$^+$ (ES$^+$); 285, 287 (M − H)$^−$ (ES$^−$), at 4.07 min, 100% (method B). | (400 MHz, DMSO) δ: 7.58-7.66 (m, 3H), 7.77-7.98 (m, 2H). |

| No. | Product (yield) | Prepared From | LCMS | NMR |
|---|---|---|---|---|
| (vii) | 6-bromo-5-(3-fluorophenyl)-1,2,4-triazin-3-amine (1.27 g, 44.9%) | 5-(3-fluorophenyl)-1,2,4-triazin-3-amine (2.00 g, 10.52 mmol) | Mass spectroscopy: m/z (Br) 269.6/271.7 (M + H)+ (ES+); 267.9/269.9 (M − H)− (ES−), at 3.85 min, 100% (method B). | (400 MHz, DMSO) δ: 7.38-7.47 (m, 1H), 7.51-7.70 (m, 5H). |
| (viii) | 6-bromo-5-(3-chlorophenyl)-1,2,4-triazin-3-amine (1.1 g, 40%) | 5-(3-chlorophenyl)-1,2,4-triazin-3-amine (2.00 g, 9.68 mmol) | Mass spectroscopy: m/z (Br, Cl) 285.7/287.7/289.7 (M + H)+ (ES+); 283.9/285.9/288.0 (M − H)− (ES−), at 4.32 min, 100% (method B). | (400 MHz, DMSO) δ: 7.52-7.66 (m, 4H), 7.69-7.73 (m, 1H), 7.79 (t, J 1.7 Hz, 1H). |
| (ix) | 4-(3-amino-6-bromo-1,2,4-triazin-5-yl)benzonitrile (605 mg, 21%) | 4-(3-amino-1,2,4-triazin-5-yl)benzonitrile (2.00 g, 10.14 mmol) | Mass spectroscopy: m/z (Br) 276.6/278.6 (M + H)+ (ES+); 274.9/276.9 (M − H)− (ES−), at 3.42 min, 98.6% (method B). | (400 MHz, DMSO) δ: 7.66 (s, 2H), 7.86-7.94 (m, 2H), 7.99-8.06 (m, 2H). |
| (x) | 6-bromo-5-(4-chlorophenyl)-1,2,4-triazin-3-amine (890 mg, 32%) | 5-(4-chlorophenyl)-1,2,4-triazin-3-amine (2.00 g, 9.68 mmol) | Mass spectroscopy: m/z (Br, Cl) 285.0/287.0/289.0 (M + H)+ (ES+); 283.2/285.2/287.2 (M − H)− (ES−), at 4.32 min, 98.0% (method B). | (400 MHz, DMSO) δ: 7.58 (s, 2H), 7.60-7.65 (m, 2H), 7.74-7.81 (m, 2H). |
| (xi) | 6-bromo-5-(4-(difluoromethoxy)phenyl)-1,2,4-triazin-3-amine (1.32 g, 50%) | 5-(4-(difluoromethoxy)phenyl)-1,2,4-triazin-3-amine (2 g, 8.40 mmol) | Mass spectroscopy: m/z 317, 319 (M + H)+ (ES+); 315-, 317 (M − H)− (ES−), at 3.98 min, 100% purity method B. | (400 MHz, DMSO) δ: 7.30-7.36 (m, 2H), 7.39 (t, 2JHF 72 Hz, 1H), 7.57 (s, 2H), 7.81-7.87 (m, 2H). |
| (xii) | 6-bromo-5-[4-(methoxymethyl)phenyl]-1,2,4-triazin-3-amine (1.3 g, 43%) | 5-[4-(methoxymethyl)phenyl]-1,2,4-triazin-3-amine (2.2 g, 15.2 mmol) | HPLC purity: 98.35% (242 nm); Mass spectroscopy: (ESI +ve) 295.0 [M + H]+. | (400 MHz, DMSO) δ: 3.33 (s, 3H), 4.48 (s, 2H), 7.44 (d, 2H), 7.54 (b s, 2H), 7.72 (d, 2H). |
| (xiii) | 6-bromo-5-(3-chloro-4-fluorophenyl)-1,2,4-triazin-3-amine (1.12 g, 36%) | 5-(3-chloro-4-fluorophenyl)-1,2,4-triazin-3-amine (2.2 g, 9.79 mmol) | Mass spectroscopy: m/z 303, 305 (M + H)+ (ES+); 301, 303 (M − H)− (ES−), at 4.35 min, 100% purity method B. | (400 MHz, DMSO) δ: 7.54-7.70 (m, 3H), 7.80 (ddd, J 8.6, 4.7, 2.2 Hz, 1H), 7.99 (dd, J 7.2, 2.2 Hz, 1H). |
| (xiv) | 6-bromo-5-(3-chloro-5-fluorophenyl)-1,2,4-triazin-3-amine (8.0 g, 38%) | 5-(3-chloro-5-fluorophenyl)-1,2,4-triazin-3-amine (16.0 g, 55.55 mmol) | HPLC purity: 99.01% (247 nm); Mass spectroscopy: (ESI +ve) 304.0 [M + H]+. | (400 MHz, CDCl3) δ: 5.53 (bs, 2H), 7.27 (m, 1H), 7.48 (m, 1H), 7.64 (m, 1H). |
| (xv) | 6-bromo-5-(3,5-difluorophenyl)-1,2,4-triazin-3-amine (6.0 g, 24%) | 5-(3,5-difluorophenyl)-1,2,4-triazin-3-amine (18.0 g, 62.0 mmol) | HPLC purity: 97.88% (247 nm); Mass spectroscopy: (ESI +ve) 286.8 [M + H]+. | (400 MHz, CDCl3) δ: 7.48 (m, 3H), 7.62 (s, 2H). |
| (xvi) | 6-bromo-5-(pyrimidin-2-yl)-1,2,4-triazin-3-amine (0.90 g, 64%) | 5-(pyrimidin-2-yl)-1,2,4-triazin-3-amine (1.0 g, 5.75 mmol) and N-bromosuccinimide (1.53 g, 8.60 mmol) | HPLC purity: 99.08% Mass spectroscopy: (ESI +ve) 253. [M + H]+. | (400 MHz, DMSO) δ: 7.73 (t, 1H), 7.79 (s, 2H), 9.04 (d, 2H) |
| (xvii) | 6-bromo-5-(pyridin-2-yl)-1,2,4-triazin-3-amine (0.18 g, 41%) | 5-(pyridin-2-yl)-1,2,4-triazin-3-amine (0.30 g, 1.73 mmol) and N-bromosuccinimide (0.46 g, 2.60 mmol) | Mass spectroscopy: (ESI +ve) 253. [M + H]+. TLC Rf: 0.6 (ethyl acetate) | |
| (xviii) | 6-bromo-5-(pyridin-3-yl)-1,2,4-triazin-3-amine (0.19 g, 33%) | 5-(pyridin-3-yl)-1,2,4-triazin-3-amine (0.4 g, 2.3 mmol) and N-bromosuccinimide (0.61 g, 3.4 mmol) | TLC Rf: 0.6 (ethyl acetate) Mass spectroscopy: (ESI +ve) 253. [M + H]+. | |
| (xix) | 6-bromo-5-(4-methylphenyl)-1,2,4-triazin-3-amine (450 mg, 34%) | 5-(4-methylphenyl)-1,2,4-triazin-3-amine (930 mg, 5.0 mmol) and N-bromosuccinimide (2.67 g, 15.0 mmol) | Mass spectroscopy: m/z 265.0/267.0 (M + H)+ (ESI+) at 3.0 min, >95% (method C). | (400 MHz, DMSO) δ: 3.35 (s, 3H), 7.41 (m, 2H), 7.74 (m, 2H) (NH2 not observed). |

-continued

| No. | Product (yield) | Prepared From | LCMS | NMR |
|---|---|---|---|---|
| (xx) | 6-bromo-5-(4-ethylphenyl)-1,2,4-triazin-3-amine (500 mg, crude; used without chromatographic purification) | 5-(4-ethylphenyl)-1,2,4-triazin-3-amine (930 mg, 5.0 mmol) and N-bromosuccinimide (2.67 g, 15.0 mmol) | Mass spectroscopy: m/z 279.0/281.0 (M + H)$^+$ (ESI+) at 3.48 min, 90% (method C). TLC R$_f$: 0.11 (MeOH/DCM, 3:97) | |
| (xxi) | 6-bromo-5-(2-fluorophenyl)-1,2,4-triazin-3-amine (700 mg, 20%) | 5-(2-fluorophenyl)-1,2,4-triazin-3-amine (2.5 g, 13.2 mmol) and N-bromosuccinimide (7.05 g, 39.6 mmol) | TLC R$_f$: 0.4 (EtOAc:isohexane 1:1) | (400 MHz, DMSO) δ: 7.32-7.42 (m, 2H), 7.54-7.67 (m, 4H) |
| (xxii) | 6-bromo-5-(2,5-difluorophenyl)-1,2,4-triazin-3-amine (800 mg, 27%) | 5-(2,5-difluorophenyl)-1,2,4-triazin-3-amine (2.5 g, 10.4 mmol) and N-bromosuccinimide (7.05 g, 39.6 mmol) | Mass spectroscopy: m/z 288.9 ($^{81}$Br) (M + H)$^+$ (ES$^+$), at 1.29 min, 100% (method A) | (400 MHz, DMSO) δ: 7.43-7.86 (m, 5H) |
| (xxiii) | 6-bromo-5-(4-methoxyphenyl)-1,2,4-triazin-3-amine (600 mg, 17%) | 5-(4-methoxyphenyl)-1,2,4-triazin-3-amine (2.5 g, 12.4 mmol) and N-bromosuccinimide (7.05 g, 39.6 mmol) | TLC R$_f$: 0.4 (EtOAc:isohexane 1:1) | (400 MHz, DMSO) δ: 3.83 (s, 3H), 7.08 (d, J 9.0, 2H), 7.47-7.54 (bs, 2H), 7.80 (d, J 9.0, 2H) |

Preparation 4

4a: General Procedure for S$_N$Ar Displacements of 2-Chloropyridine Derivatives with Amines A 2-chloropyridine derivative (1 equivalent) and an amine (typically 5 equivalents) were dissolved in MeCN and sealed in a microwave vial. The mixture was heated under microwave irradiation (typically 160-180° C.) for up to 1 hour with LCMS monitoring. If necessary, further equivalents of amine were added and the procedure repeated. Upon completion of the reaction, the mixture was evaporated under reduced pressure and purified by flash column chromatography, eluting with ethyl acetate/hexane mixtures, or by preparative HPLC.

The following intermediate compounds were prepared according to the general procedure of Preparation 4a:

| No. | Product (yield) | Prepared from | LC/MS | NMR |
|---|---|---|---|---|
| (i) | 2-ethyl(methyl)amino-6-methylpyridine (534 mg, 45%) | 2-Chloro-6-methylpyridine (0.87 mL, 7.84 mmol) and ethylmethylamine (3.37 mL, 39.2 mmol) | Mass spectroscopy: m/z 151 (M + H)$^+$ (ES+) at 1.56 min, 95% (method A) TLC R$_f$: 0.55 (EtOAc/isohexane, 1:20) | |
| (ii) | 2-dimethylamino-6-methylpyridine (93 mg, 21%). | 2-Chloro-6-methylpyridine (0.35 mL, 3.20 mmol) and dimethylamine (2.0M solution in THF, 8.0 mL, 16.0 mmol) | Mass spectroscopy: m/z 137 (M + H)$^+$ (ES)$^+$ at 1.37 min (method A) TLC R$_f$: 0.38 (Et$_2$O/isohexane, 1:20) | |
| (iii) | 2-(azetidin-1-yl)-6-(trifluoromethyl)pyridine (807 mg, 72%) | 2-Chloro-6-trifluoromethylpyridine (1.00 g, 5.51 mmol) and azetidine (1.57 g, 1.86 ml, 27.5 mmol) | Mass spectroscopy: m/z (ES$^+$) 223.0 (M + H)$^+$ at 1.68 min, 90% (method A) | (400 MHz, CDCl$_3$) δ: 2.41 (quint., J7.5, 2H), 4.08 (t, J7.5, 4H), 6.36-6.39 (m, 1H), 6.89-6.91 (m, 1H), 7.49-7.53 (m, 1H). |
| (iv) | 4-(6-methylpyridin-2-yl)morpholine (693 mg, 50%) | 2-Chloro-6-methylpyridine (1.00 g, 0.87 ml, 7.84 mmol) and morpholine (3.41 g, 3.45 ml, 39.2 mmol) | Mass spectroscopy: m/z (ES$^+$) 179.0 (M + H)$^+$ at 1.26 min, 90% (method A). | (400 MHz, CDCl$_3$) δ: 2.41 (s, 3H), 3.48-3.50 (m, 4H), 3.81-3.84 (m, 4H), 6.42-6.44 (m, 1H), 6.53-6.55 (m, 1H), 7.38-7.42 (m, 1H). |

4b: Preparation of Other Pyridine Derivatives (i) Preparation of 2,6-de-dimethylpyridine Methyl-$d_3$-magnesium iodide solution (9.60 mL, 1 M in diethyl ether, 9.60 mmol) was added drop-wise over 10 mins to a solution of 2,6-dibromopyridine (947 mg, 4.00 mmol) and iron(III)acetylacetonate (141 mg, 0.40 mmol) in THF (30 mL) and NMP (3 mL) under $N_2$. After stirring at ambient temperature for 40 mins, 1 M aqueous HCl (10 mL) was added and the mixture stirred for 5 mins. Diethyl ether (20 mL) was added and the phases were separated. The organic phase was extracted with water (2×10 mL) and the combined aqueous phases were then basified by the addition of 1M aqueous NaOH (15 mL). The aqueous phase was extracted with DCM (3×25 mL) and the combined organic phases concentrated in vacuo. Purification by gradient flash chromatography ($SiO_2$, 5 to 20% EtOAc in isohexane) yielded the title compound as a clear oil (430 mg, 95%).

$^1$H NMR: (400 MHz, $CDCl_3$) δ: 6.95 (d, J=7.8, 2H), 7.45 (t, J=7.8, 1H).

TLC $R_f$: 0.30 (EtOAc/isohexane, 1:4)

(ii) Preparation of 2-$d_3$-methyl-6-(trifluoromethyl) pyridine

A mixture of 2-chloro-6-(trifluoromethyl)pyridine (2.69 g, 14.8 mmol) and iron(III)acetylacetonate (523 mg, 1.48 mmol) in THF (100 mL) and NMP (10 mL) was stirred at 0° C. under $N_2$ for 5 mins. Methyl-$d_3$-magnesium iodide solution (18.0 mL, 1M in diethyl ether, 18.0 mmol) was added drop-wise over 10 mins, and the mixture was stirred under $N_2$ at 0° C. for 5 mins, then ambient temperature for 75 mins, 1 M aqueous HCl (50 mL) was added and the mixture was stirred for 5 mins before addition of diethyl ether (50 mL) and separation of the phases. The organic phase was washed with 0.5 M aqueous HCl (50 mL) and water (50 mL) and the combined aqueous phases were extracted with diethyl ether (2×50 mL). The combined organic phases were concentrated to a volume of approximately 25 mL and short path distillation (bp 28-30° C. at 35 mbar) yielded a clear oil to which was added DCM (5 mL) and $H_2O$ (5 mL). The phases were separated and the aqueous phase was extracted with DCM (2×5 mL); the combined organic phases were concentrated in vacuo to yield the title compound (639 mg, 26%) as a clear oil.

$^1$H NMR: (400 MHz, $CDCl_3$) δ: 7.34 (d, J 7.8, 1H), 7.49 (d, J 7.8, 1H), 7.75 (t, J 7.8, 1H).

Bp: 28-30° C. at 35 mbar (iii) Preparation of 2-cyclopropyl-6-(trifluoromethyl)pyridine 2-Chloro-6-trifluoromethyl pyridine (451 mg, 2.5 mmol), cyclopropyltrifluoroborate potassium salt (373 mg, 2.52 mmol), palladium acetate (11 mg, 0.05 mmol), di(1-adamantyl)-n-butylphosphine (27 mg, 0.075 mmol), and cesium carbonate (2.4 g, 7.5 mmol) were suspended in a mixture of toluene and water (10:1, 10 mL). After flushing the vessel under a stream of nitrogen gas for 5 minutes, the reaction tube was sealed and then heated at 100° C. for 18 hours. On cooling, the mixture was partitioned between DCM (15 mL) and water (15 mL). The separated aqueous phase was extracted with DCM (2×15 mL) and the combined organic phases were passed through a phase separator and concentrated in vacuo, affording a yellow oil which was used without further purification (423 mg, crude).

LCMS: major peak observed at 1.77 min; poor ionisation (method A)

TLC $R_f$: 0.6 (EtOAc/hexane, 1:9).

(iv) Preparation of 2-ethyl-6-(trifluoromethyl)pyridine

2-Chloro-6-trifluoromethyl pyridine (451 mg, 2.5 mmol), ethyltrifluoroborate potassium salt (374 mg, 2.75 mmol), palladium acetate (11 mg, 0.05 mmol), di(1-adamantyl)-n-butylphosphine (27 mg, 0.075 mmol), and cesium carbonate (2.4 g, 7.5 mmol) were suspended in a mixture of toluene and water (10:1, 10 mL). After flushing the vessel under a stream of nitrogen gas for 5 minutes, the reaction tube was sealed and then heated at 100° C. for 18 hours. On cooling, the mixture was partitioned between DCM (15 mL) and water (15 mL). The separated aqueous phase was extracted with DCM (2×15 mL) and the combined organic phases were passed through a phase separator and concentrated in vacuo, affording a yellow oil which was used without further purification (460 mg, crude)

LCMS: major peak observed at 1.53 min; poor ionisation (method A)

TLC $R_f$: 0.55 (EtOAc/hexane, 1:9).

(v) Preparation of 2-ethylamino-6-methylpyridine

2-Amino-6-methylpyridine (1.00 g, 9.25 mmol) and acetaldehyde (0.52 mL, 9.34 mmol) were stirred together in anhydrous methyl alcohol for 1 hour at room temperature under a nitrogen atmosphere. The mixture was then treated with sodium triacetoxyborohydride (7.84 g, 37.0 mmol) and five drops of acetic acid and all was allowed to continue stirring for 4 hours. The reaction mixture was concentrated in vacuo. The residue was partitioned between water and DCM, and the separated aqueous phase was extracted twice with DCM. The combined organics were dried over $MgSO_4$, filtered and concentrated in vacuo to give a mobile oil which was purified by flash column chromatography, eluting with 2% MeOH/DCM, to give 2-ethylamino-6-methylpyridine (636 mg, 51%).

LCMS: 137.0 $[M+H]^+$ (ES+) at 1.17 min, 100% (method A).

Preparation 5

General Procedure for the Preparation of 2-Fluoromethyl-pyridine Derivatives (Diethylamino)sulfur trifluoride (1.0 mL, 7.7 mmol) was added to a solution of a 2-pyridinylmethanol derivative (7.0 mmol) in DCM (30 mL, anhydrous), drop-wise, under nitrogen in an acetone/$CO_2$ bath at −20° C. The resultant solution was allowed to warm to ambient temperature and then stirred until complete conversion was observed by TLC. The reaction was quenched with ice and then basified to pH 8-10 with solid sodium hydrogen carbonate. The layers were then separated, and the organic phase washed successively with water and then saturated brine solution, then dried ($MgSO_4$), concentrated in vacuo and purified by gradient flash chromatography, affording the 2-fluoromethylpyridine derivative.

The following intermediate compounds were prepared according to the general procedure of Preparation 5:

| No. | Product (yield) | Prepared from | LCMS/TLC | NMR |
|---|---|---|---|---|
| (i) | 2-(fluoromethyl)-6-methylpyridine (850 mg, 84%) | 6-methyl-2-pyridine methanol (1.0 g, 8.1 mmol) | TLC $R_f$: 0.9 (EtOAc/iso-hexane 1:9) | (400 MHz, DMSO) δ: 2.48 (s, 3H), 5.43 (d, J 47.2 2H), 7.23 (d, J 7.8, 1H), 7.29 (d, J 7.8, 1H), 7.76 (t, J 7.8, 1H) |
| (ii) | 2-chloro-6-(fluoromethyl)pyridine (200 mg, 17%) | (6-chloro-2-pyridinyl)methanol (1.0 g, 7.0 mmol) | TLC $R_f$: 0.9 (EtOAc/iso-hexane 1:9) | (400 MHz, DMSO) δ: 5.51 (d, J 46.7 Hz, 2H), 7.55 (d, J 7.78, 1H), 7.57 (d, J 7.78, 1H), 8.00 (t, J 7.78, 1H) |
| (iii) | 2,6-bis-(fluoromethyl)pyridine (850 mg, 41%) | 2,6-bis(hydroxymethyl)pyridine (2.0 g, 14.4 mmol) | TLC $R_f$: 0.9 (EtOAc/iso-hexane 1:9) | (400 MHz, DMSO) δ: 5.50 (d, J 46.6, 2H), (d, J 7.78, 2H), 7.98 (t, J 7.78, 1H) |

Preparation 6
General Procedure for the Preparation of 2-Difluoromethylpyridine Derivatives (Diethylamino)sulfur trifluoride (2.4 mL, 18.3 mmol) was added to a solution of a 2-pyridinecarboxaldehyde derivative (8.3 mmol) in DCM (30 mL, anhydrous), drop-wise, under nitrogen in an acetone/$CO_2$ bath at −20° C. The resultant solution was allowed to warm to ambient temperature and then stirred until complete conversion was observed by TLC. The reaction was quenched with ice and then basified to pH 8-10 with solid sodium hydrogen carbonate. The layers were then separated, and the organic phase washed successively with water and then saturated brine solution, then dried ($MgSO_4$), concentrated in vacuo and purified by gradient flash chromatography, affording the 2-fluoromethylpyridine derivative.

The following intermediate compounds were prepared according to the general procedure of Preparation 6:

| No. | Product (yield) | Prepared from | LCMS/TLC | NMR |
|---|---|---|---|---|
| (i) | 2-chloro-6-(difluoromethyl)pyridine (1.1 g, 86%) | 6-chloro-2-pyridinecarboxaldehyde (1.0 g, 7.07 mmol) | TLC $R_f$: 0.9 (EtOAc/isohexane 1:9) | (400 MHz, DMSO), δ: 4.69 (s, 1H), 7.50 (m, 2H), 7.91 (m, 1H) |
| (ii) | 2-(difluoromethyl)-6-methylpyridine (410 mg, 35%) | 6-methyl-2-pyridinecarboxaldehyde (1.0 g, 8.26 mmol) | TLC $R_f$: 0.9 (EtOAc/isohexane 1:9) | (400 MHz, DMSO), δ: 2.53 (3H, s) 6.90 (d, J 55.2, 1H), 7.47 (m, 2H), 7.89 (m, 1H) |

Preparation 7
General Procedure for the 4-Borylation of 2,6-Disubstituted Pyridine Derivatives Methoxy(cyclooctadiene)rhodium(I) dimer (0.05 molar equivalents Rh), 4,4'-di-tert-butyl-2,2'-bipyridine(dtbpy) (0.05 molar equivalents), and bis(pinacolato)diboron (2 molar equivalents) were added to a flask which had been thoroughly purged with nitrogen. The flask was once more purged before adding hexane via syringe (final concentration of pyrine approximately 0.5 mM). The resulting mixture was heated at 50° C. for 10 minutes until the appearance of a dark red solution was observed. A pyridine derivative (1 molar equivalent) was then added by syringe and heating continued for a further 6 hours. After cooling to room temperature, the crude reaction mixture concentrated under reduced pressure. The resulting residue was purified by column chromatography, eluting with ethyl acetate/hexane mixtures to afford the target compound.

The following compounds were prepared according to the general procedure of Preparation 7, by reacting the indicated starting materials for 6 hours at 50° C., unless otherwise stated:

| No. | Product (yield) | Prepared from | LCMS/TLC | NMR |
|---|---|---|---|---|
| (i) | 2,6-$d_6$-dimethyl-4-(4,4,5,5-tetramethyl-1,3,2-dioxaborolan-2-yl)pyridine (1.56 g, crude) used without chromatographic purification | bis(pinacolato)diboron (1.93 g, 7.60 mmol) and 2,6-$d_6$-dimethylpyridine (430 mg, 3.80 mmol) were heated at 70° C. for 105 minutes according to the typical procedure. | Mass spectroscopy: m/z 240.1 $[M + H]^+$ (ESI +ve) at 0.1 min, 100% (method A). | |

-continued

| No. | Product (yield) | Prepared from | LCMS/TLC | NMR |
|---|---|---|---|---|
| (ii) | 2-$d_3$-methyl-4-(4,4,5,5-tetramethyl-1,3,2-dioxaborolan-2-yl)-6-(trifluoromethyl)pyridine (716 mg, 32%) | 2-$d_3$-methyl-6-(trifluoromethyl)pyridine (639 mg, 3.89 mmol) and bis(pinacolato)diboron (1.98 g, 7.80 mmol) were heated at 70° C. for 3.5 hours according to the typical procedure. | Mass spectroscopy: m/z: 291.1 [M + H]$^+$ (ESI +ve) at 0.15 min, 100% (method A) | (400 MHz, CDCl$_3$) δ: 1.37 (s, 12H), 7.70 (s, 1H), 7.82 (s, 1H). |
| (iii) | 2-ethylamino-4-(4,4,5,5-tetramethyl-1,3,2-dioxaborolan-2-yl)-6-methylpyridine (crude sample used without chromatographic purification) | bis(pinacolato) diborane (776 mg, 3.06 mmol) and 2-ethylamino-6-methylpyridine (277 mg, 2.04 mmol) were heated to 55° C. for 6 hours according to the typical procedure. | Mass spectroscopy: m/z 263.2 [M + H]$^+$ (ESI+) at 0.10 min, (method A). | |
| (iv) | 2-ethyl(methyl)amino-4-(4,4,5,5-tetramethyl-1,3,2-dioxaborolan-2-yl)-6-methylpyridine (2.04 g, crude) used without chromatographic purification. | bis(pinacolato)diboron (1.81 g, 7.11 mmol) and 2-ethyl(methyl)amino-6-methylpyridine (534 mg, 3.55 mmol) were heated at 65° C. for 3 hours according to the typical procedure. | Mass spectroscopy: m/z 277 (M + H)$^+$ (ES)$^+$ at 1.11 min, (method A). | |
| (v) | 2-dimethylamino-4-(4,4,5,5-tetramethyl-1,3,2-dioxaborolan-2-yl)-6-methylpyridine (414 mg, crude) used without chromatographic purification. | 2-dimethylamino-6-methylpyridine (93 mg, 0.68 mmol) and bis(pinacolato)diboron (348 mg g, 1.37 mmol) were heated at 70° C. for 2 hours according to the typical procedure. | No ionisation observed by LCMS, major peak at 0.8 min (method A). | |
| (vi) | 2-chloro-4-(4,4,5,5-tetramethyl-1,3,2-dioxaborolan-2-yl)-6-methylpyridine (46.9 g, 94%) | 2-methyl-6-chloro pyridine (25 g, 195.9 mmol) and bis(pinacolato)diboron (32.3 g, 127 mmol) according to the typical procedure. | HPLC purity: 99.33% (282 nm) Mass spectroscopy: (ESI +ve) 254.1 [M + H]$^+$. | (400 MHz, DMSO) δ: 1.30 (s, 12 H), 2.50 (s, 3H), 7.35 (s, 1H), 7.44 (s, 1H). |
| (vii) | 2,6-dimethyl-4-(4,4,5,5-tetramethyl-1,3,2-dioxaborolan-2-yl)pyridine (1.0 g, 30%) | 2,6-dimethyl pyridine (1.5 g, 13.9 mmol) and bis(pinacolato)diboron (1.9 g, 7.69 mmol) according to the typical procedure. | HPLC purity: 93.33% (268 nm) Mass spectroscopy: (ESI +ve) 234.1 [M + H]$^+$. | (400 MHz, DMSO) δ: 1.27 (s, 12 H), 2.48 (s, 6H), 7.20 (s, 2H). |
| (viii) | 2-(trifluoromethyl)-4-(4,4,5,5-tetramethyl-1,3,2-dioxaborolan-2-yl)-6-methylpyridine (5.9 g, 83%) | 2-trifluoromethyl-6-methyl pyridine (4.0 g, 24.8 mmol) and bis(pinacolato)diboron (4.09 g, 16.1 mmol) according to the typical procedure. | HPLC purity: 95.65% (210 nm) Mass spectroscopy: (ESI +ve) 287.8 [M + H]$^+$. | (400 MHz, DMSO) δ: 1.31 (s, 12 H), 2.51 (s, 3H), 7.70 (s, 1H), 7.76 (s, 1H). |
| (ix) | 2-dimethylamino-4-(4,4,5,5-tetramethyl-1,3,2-dioxaborolan-2-yl)pyridine (0.98 g, 53%) | N,N-dimethylpyridine-2-amine (0.9 g, 7.4 mmol) and bis(pinacolato)diboron (1.12 g, 4.4 mmol) according to the typical procedure. | Mass spectroscopy: (ESI +ve) 248.9 [M]$^+$). TLC R$_f$: 0.10 (ethyl acetate/ hexane, 5:5) | |
| (x) | 2-bromo-4-(4,4,5,5-tetramethyl-1,3,2-dioxaborolan-2-yl)-6-methylpyridine (0.70 g, 81%) | 2-methyl-6-bromo pyridine (0.50 g, 2.90 mmol) and bis(pinacolato)diboron (0.48 g, 1.8 mmol) according to the typical procedure. | Mass spectroscopy: (ESI +ve) 299.7 [M + H]$^+$ TLC R$_f$: 0.15 (ethyl acetate/ hexane, 5:5) | |
| (xi) | 2-cyano-4-(4,4,5,5-tetramethyl-1,3,2-dioxaborolan-2-yl)-6-methylpyridine (0.70 g, 70%) | 2-methyl-6-cyano pyridine (0.5 g, 4.2 mmol) and bis(pinacolato)diboron (0.69 g, 2.7 mmol), | Mass spectroscopy: (ESI +ve) 244.9 [M + H]$^+$ TLC R$_f$: 0.15, (ethyl acetate/ hexane, 5:5) | |

| No. | Product (yield) | Prepared from | LCMS/TLC | NMR |
|---|---|---|---|---|
| (xii) | 1-oxo-2,6-dimethyl-4-(4,4,5,5-tetramethyl-1,3,2-dioxaborolan-2-yl)pyridine (1.8 g, 90%) | 2,6-dimethyl pyridine-N-oxide (1.0 g, 8.12 mmol) and bis(pinacolato)diboron (1.34 g, 5.27 mmol) | Mass spectroscopy: (ESI +ve) 249.9 $[M]^+$ TLC $R_f$: 0.12 (ethyl acetate/hexane, 5:5) | |
| (xiii) | 2-bromo-4-(4,4,5,5-tetramethyl-1,3,2-dioxaborolan-2-yl)-6-trifluoromethylpyridine (0.5 g, 64%) | 2-trifluoro methyl 6-bromo pyridine (0.5 g, 2.20 mmol) and bis(pinacolato)diboron (0.36 g, 1.4 mmol) according to the typical procedure. | Mass spectroscopy: (ESI +ve) 352.9 $[M]^+$). TLC $R_f$: 0.18 (ethyl acetate/hexane, 5:5) | |
| (xiv) | 2-chloro-4-(4,4,5,5-tetramethyl-1,3,2-dioxaborolan-2-yl)-6-(difluoromethyl)pyridine (310 mg, 13%) | 2-chloro-6-(difluoromethyl)pyridine (1.4 g, 8.56 mmol) and bis(pinacolato)diboron (10.1 g, 42.8 mmol) were heated at 60° C. for 2 hours according to the typical procedure. | TLC $R_f$: streak from baseline to 0.3 (EtOAc/isohexane, 1:9) | (400 MHz, DMSO) δ: 1.33 (s, 12H), 7.03 (t, J 54.5, 1H), 7.75 (s, 1H), 7.80 (s, 1H) |
| (xv) | 2-(fluoromethyl)-4-(4,4,5,5-tetramethyl-1,3,2-dioxaborolan-2-yl)-6-methylpyridine (1.1 g, 26%) | 2-(fluoromethyl)-6-methylpyridine (2.1 g, 16.8 mmol) and bis(pinacolato)diboron (8.5 g, 33.6 mmol) were heated at 60° C. for 48 hours according to the typical procedure. | Mass spectroscopy: (ESI +ve) 252.1 $[M + H]^+$ at 0.13 mins, (method A). | (400 MHz, DMSO) δ: 1.32 (s, 12H), 2.55 (s, 3H), 5.45 (d, J 47.2, 2H), 7.45 (s, 1H), 7.47 (s, 1H) |
| (xvi) | 2-chloro-4-(4,4,5,5-tetramethyl-1,3,2-dioxaborolan-2-yl)-6-(fluoromethyl)pyridine (450 mg, 24%) | 2-chloro-6-(fluoromethyl)pyridine (1.0 g, 6.9 mmol) and bis(pinacolato)diboron (3.5 g, 13.8 mmol) were heated at 60° C. for 2 hours according to the typical procedure. | TLC $R_f$: streak from baseline to 0.3 (EtOAc/isohexane, 1:9) | (400 MHz, DMSO) δ: 1.33 (s, 12H), 5.50(d, J 46.7, 2H), 7.57 (s, 1H), 7.65 (s, 1H) |
| (xvii) | 2,6-bis-(fluoromethyl)-4-(4,4,5,5-tetramethyl-1,3,2-dioxaborolan-2-yl)-pyridine (1.6 g, 88%) | 2,6-bis-fluoromethylpyridine (1.2 g, 6.8 mmol) and bis(pinacolato)diboron (3.5 g, 13.6 mmol) were heated at 65° C. for 2 hours according to the typical procedure. | TLC $R_f$: streak from baseline to 0.3 (EtOAc/isohexane, 1:9) | (400 MHz, DMSO) δ: 1.22 (s, 12H), 5.50 (d, J 46.7, 4H), 7.51 (s, 2H) |
| (xviii) | 2-(difluoromethyl)-4-(4,4,5,5-tetramethyl-1,3,2-dioxaborolan-2-yl)-6-methylpyridine (500 mg, 22%) | 2-(difluoromethyl)-6-methylpyridine (1.2 g, 8.4 mmol) and bis(pinacolato)diboron (4.3 g, 16.8 mmol) were heated at 60° C. for 2 hours according to the typical procedure. | TLC $R_f$: streak from baseline to 0.3 (EtOAc/isohexane, 1:9) | (400 MHz, DMSO) δ: 1.32 (s, 12H), 2.55 (s, 3H), 6.94 (t, J 55, 1H), 7.61 (s, 1H), 7.63 (s, 1H) |
| (xix) | 2-ethyl-4-(4,4,5,5-tetramethyl-1,3,2-dioxaborolan-2-yl)-6-(trifluoromethyl)pyridine (551 mg, 73%) | 2-ethyl-6-(trifluoromethyl)pyridine (440 mg, 2.50 mmol) and bis(pinacolato)diboron (1.27 g, 5.00 mmol) according to the typical procedure. | Mass spectroscopy: m/z 302.1 $(M + H)^+$ (ES+); at 0.93 min (method A). | (400 MHz, DMSO) δ: 1.25 (t, 3H, J 8.0), 1.33 (s, 12H), 2.88 (q, 2H, J 8.0), 7.74 (s, 1H), 7.77 (s, 1H). |
| (xx) | 2-cyclopropyl-4-(4,4,5,5-tetramethyl-1,3,2-dioxaborolan-2-yl)-6-(trifluoromethyl)pyridine (473 mg, 67%) | 2-cyclopropyl-6-(trifluoromethyl)pyridine (423 mg, 2.25 mmol) and bis(pinacolato)diboron (1.14 g, 4.50 mmol) according to the typical procedure. | Mass spectroscopy: m/z 314.1 $(M + H)^+$ (ES+); at 1.02 min (method A). | (400 MHz, DMSO) δ: 0.92-0.97 (m, 2H), 1.02-1.08 (m, 2H), 1.33 (s, 12H), 2.29-2.36 (m, 1H), 7.63 (s, 1H), 7.79 (s, 1H). |
| (xxi) | 2-(azetidin-1-yl)-6-trifluoromethyl-4-(4,4,5,5-tetramethyl-1,3,2-dioxaborolan-2-yl)pyridine (68%) | 2-(azetidin-1-yl)-6-(trifluoromethyl)pyridine (807 mg, 3.99 mmol) and bis(pinacolato)diboron (2.03 g, 7.98 mmol) were heated at 70° C. for 2.0 | Mass spectroscopy: m/z 329.0 $(M + H)^+$ (ES+), at 1.00 min, 98% (method | (400 MHz, CDCl$_3$) δ: 1.31 (s, 12H), 2.35 (quint, J 7.5, 2H), 4.03 (t, J 7.5 Hz, 4H), |

| No. | Product (yield) | Prepared from | LCMS/TLC | NMR |
| --- | --- | --- | --- | --- |
| (xxii) | 2-methyl-6-(morpholin-4-yl)-4-(4,4,5,5-tetramethyl-1,3,2-dioxaborolan-2-yl)pyridine (1.09 g, 92%) | hours according to the typical procedure. 4-(6-methylpyridin-2-yl)morpholine (693 mg, 3.89 mmol) and bis(pinacolato)diboron (1.97 g, 7.78 mmol) were heated at 70° C. for 4.0 hours according to the typical procedure | A). Mass spectroscopy: m/z 305.0 $(M + H)^+$ $(ES^+)$, at 2.02 min, ~80% (method A). TLC $R_f$: 0.3 (DCM/MeOH, 1:9 (5% $NH_3$)) | 6.74 (s, 1H), 7.06 (s, 1H). |
| (xxiii) | 2-chloro-4-(4,4,5,5-tetramethyl-1,3,2-dioxaborolan-2-yl)-6-trifluoromethylpyridine (2.6 g, 68%). | bis(pinacolato)diboron (1.99 g, 7.9 mmol) and 2-trifluoromethyl-6-chloropyridine (2.2 g, 12.1 mmol) | HPLC purity: purity: 95.87% (273 nm) Mass spectroscopy: (ESI +ve) 308.1$[M + H]^+$. | (400 MHz, DMSO) δ: 1.31 (s, 12 H), 7.88 (s, 1H), 7.89 (s, 1H). |

Example 1

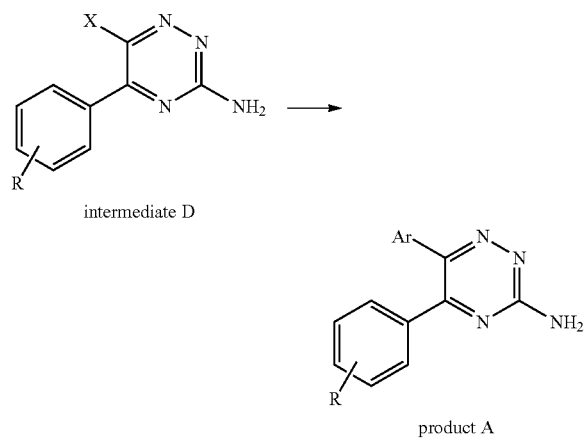

intermediate D product A

General Procedure for the Preparation of 5,6-Biaryl-3-amino-1,2,4-triazines

A solution of intermediate D, a 6-halo-5-aryl-1,2,4-triazin-3-amine derivative, (0.80 mmol) in dioxane (2 mL) is treated with an arylboronic acid (0.92 mmol) and $K_2CO_3$ (0.23 g, 1.67 mmol). The resulting mixture is diluted with water (1.0 mL), degassed, treated with tetrakis triphenylphosphine palladium (0.05 g, 0.04 mmol) and stirred at 150° C. for 2.25 hrs with monitoring by TLC (hexane/ethyl acetate, 5:5). Upon completion of the reaction, the mixture is diluted with water (30 mL) and extracted with ethyl acetate (3×20 mL); the combined organic extracts are then dried over $Na_2SO_4$ and concentrated under reduced pressure. The crude compound, product A, is purified by gradient flash chromatography or preparative HPLC.

(i) 5,6-Diphenyl-1,2,4-triazin-3-amine 5,6-Diphenyl-1,2,4-triazin-3-amine (86.0 mg, 42%) was prepared from 6-bromo-5-phenyl-1,2,4-triazin-3-amine (0.21 g, 0.8 mmol) and phenyl boronic acid (0.11 g, 0.92 mmol) according to the general procedure of Example 1.

HPLC purity: 99.6% (261 nm)

Mass spectroscopy: (ESI+ve) 249.0 $[M+H]^+$.

$^1$H NMR: (400 MHz. $CDCl_3$) δ: 5.49 (s, 2H), 7.30-7.37 (m, 5H), 7.40-7.43 (m, 3H,) 7.45-7.46 (m, 1H), 7.47-7.51 (m, 1H).

(ii) 6-(3-Methoxyphenyl)-5-phenyl-1,2,4-triazin-3-amine 6-(3-Methoxyphenyl)-5-phenyl-1,2,4-triazin-3-amine (106 mg, 47%) was prepared from 6-bromo-5-phenyl-1,2,4-triazin-3-amine (0.21 g, 0.8 mmol) and 3-methoxyphenyl boronic acid (0.137 g, 0.90 mmol) according to the general procedure of Example 1.

HPLC purity: 99.58% (223 nm)

Mass spectroscopy: (ESI+ve) 278.9 $[M+H]^+$.

$^1$H NMR: (400 MHz, $CDCl_3$) δ: 3.72 (s, 3H), 5.47 (s, 2H), 6.88-6.94 (m, 2H), 7.03 (m, 1H), 7.20 (t, 1H), 7.33 (m, 2H), 7.40 (m, 1H), 7.44 (m, 2H).

(iii) 6-(4-Fluorophenyl)-5-phenyl-1,2,4-triazin-3-amine 6-(4-Fluorophenyl)-5-phenyl-1,2,4-triazin-3-amine (99 mg, 46%) was prepared from 6-bromo-5-phenyl-1,2,4-triazin-3-amine (0.21 g, 0.80 mmol) and 4-fluorophenylboronic acid (0.112 g, 0.80 mmol) according to the general procedure of Example 1.

HPLC purity: 99.93% (261 nm)

Mass spectroscopy: (ESI+ve) 267.0 $[M+H]^+$.

$^1$H NMR: (400 MHz, $CDCl_3$) δ: 5.49 (s, 2H), 6.99 (m, 2H), 7.31-7.37 (m, 2H), 7.37-7.46 (m, 5H).

(iv) 6(5-Chloro-2-methoxyphenyl)-5-phenyl-1,2,4-triazin-3-amine 6-(5-Chloro-2-methoxyphenyl)-5-phenyl-1,2,4-triazin-3-amine (57 mg, 22%) was prepared from 6-bromo-5-phenyl-1,2,4-triazin-3-amine (0.21 g, 0.80 mmol) and 5-chloro-2-methoxyphenylboronic acid (0.15 g, 0.80 mmol) according to the general procedure of Example 1.

HPLC purity: 98.73% (229 nm)

Mass spectroscopy: (ESI+ve) 312.9 $[M]^+$.

¹H NMR: (400 MHz, CDCl₃) δ: 3.16 (s, 3H), 5.46 (s, 2H), 6.62 (d, 1H), 7.26-7.33 (m, 3H), 7.37 (m, 1H), 7.44 (m, 2H), 7.66 (d, 1H).

(v) 6-(2-Chlorophenyl)-5-phenyl-1,2,4-triazin-3-amine 6-(2-Chlorophenyl)-5-phenyl-1,2,4-triazin-3-amine (103 mg, 45%) was prepared from 6-bromo-5-phenyl-1,2,4-triazin-3-amine (0.21 g, 0.80 mmol) and 2-chlorophenylboronic acid (0.125 g, 0.80 mmol) according to the general procedure of Example 1.
HPLC purity: 99.27% (245 nm)
Mass spectroscopy: (ESI+ve) 282.9 [M]⁺.
¹H NMR: (400 MHz, CDCl₃) δ: 5.62 (s, 2H), 7.26-7.32 (m, 2H), 7.33-7.36 (m, 4H) 7.43-7.45 (m, 2H), 7.52 (m, 1H).

(vi) 6-(3-Chlorophenyl)-5-phenyl-1,2,4-triazin-3-amine 6-(3-Chlorophenyl)-5-phenyl-1,2,4-triazin-3-amine (110 mg, 49%) was prepared from 6-bromo-5-phenyl-1,2,4-triazin-3-amine (0.21 g, 0.80 mmol) and 3-chlorophenylboronic acid (0.12 g, 0.80 mmol) according to the general procedure of Example 1.
HPLC purity: 93.7% (261 nm)
Mass spectroscopy: (ESI+ve) 282.9 [M]⁺.
¹H NMR: (400 MHz, CDCl₃) δ: 5.50 (s, 2H), 7.18-7.26 (m, 2H), 7.30-7.36 (m, 3H) 7.42-7.47 (m, 3H), 7.53 (s, 1H).

(vii) 6-(4-Chlorophenyl)-5-phenyl-1,2,4-triazin-3-amine 6-(4-Chlorophenyl)-5-phenyl-1,2,4-triazin-3-amine (125 mg, 56%) was prepared from 6-bromo-5-phenyl-1,2,4-triazin-3-amine (0.21 g, 0.80 mmol) and 4-chlorophenylboronic acid (0.12 g, 0.80 mmol) according to the general procedure of Example 1.
HPLC purity: 97.7% (264 nm)
Mass spectroscopy: (ESI+ve) 282.9 [M]⁺
¹H NMR: (400 MHz, CDCl₃) δ: 5.46 (s, 2H), 7.28-7.33 (m, 2H), 7.35-7.38 (m, 5H) 7.42-7.46 (m, 2H).

(viii) 6-(Furan-2-yl)-5-phenyl-1,2,4-triazin-3-amine 6-(Furan-2-yl)-5-phenyl-1,2,4-triazin-3-amine (100 mg, 35%) was prepared from 6-bromo-5-phenyl-1,2,4-triazin-3-amine (0.3 g, 1.19 mmol) and 2-furanboronic acid (0.16 g, 1.428 mmol) according to the general procedure of Example 1.
HPLC purity: 95.03% (290 nm)
Mass spectroscopy: (ESI+ve) 239.0 [M+H]⁺
¹H NMR: (400 MHz. CDCl₃) δ: 5.58 (s, 2H), 6.43 (m, 1H), 6.55 (m, 1H) 7.40-7.47 (m, 3H), 7.47-7.59 (m, 3H).

(ix) 5-Phenyl-6-[3-(trifluoromethyl)phenyl]-1,2,4-triazin-3-amine

5-Phenyl-6-[3-(trifluoromethyl)phenyl]-1,2,4-triazin-3-amine (120 mg, 31%) was prepared from 6-bromo-5-phenyl-1,2,4-triazin-3-amine (0.30 g, 1.19 mmol) and 3-trifluoromethylphenylboronic acid (0.25 g, 1.30 mmol) according to the general procedure of Example 1.
HPLC purity: 99.4% (262 nm)
Mass spectroscopy: (ESI+ve) 316.9 [M+H]⁺
¹H NMR: (400 MHz, DMSO) δ: 7.36 (m, 4H), 7.42 (m, 2H), 7.51 (s, 2H) 7.56 (m, 1H), 7.63 (m, 3H).

(x) 6-[3-Fluoro-5-(trifluoromethyl)phenyl]-5-phenyl-1,2,4-triazin-3-amine

6-[3-Fluoro-5-(trifluoromethyl)phenyl-5-phenyl]-5-phenyl-1,2,4-triazin-3-amine (149 mg, 37%) was prepared from 6-bromo-5-phenyl-1,2,4-triazin-3-amine (0.30 g, 1.19 mmol) and 3-fluoro-5-(trifluoromethyl)phenylboronic acid (0.27 g, 1.30 mmol) according to the general procedure of Example 1.
HPLC purity: 94.3% (265 nm)
Mass spectroscopy: (ESI+ve) 335.0 [M+H]⁺
¹H NMR: (400 MHz, DMSO) δ: 7.36 (m, 4H), 7.45 (m, 3H), 7.61 (s, 2H) 7.64 (d, 1H).

(xi) 5-Phenyl-6-(3,4,5-trifluorophenyl)-1,2,4-triazin-3-amine

5-Phenyl-6-(3,4,5-trifluorophenyl)-1,2,4-triazin-3-amine (131 mg, 37%) was prepared from 6-bromo-5-phenyl-1,2,4-triazin-3-amine (0.30 g, 1.19 mmol) and 3,4,5-trifluorophenylboronic acid (0.23 g, 1.30 mmol) according to the general procedure of Example 1.
HPLC purity: 99.6% (262 nm)
Mass spectroscopy: (ESI+ve) 303.0 [M+H]⁺, (ESI−ve) 301.2 [M−H]⁻
¹H NMR: (400 MHz, DMSO) δ: 7.24 (t, 2H), 7.38 (m, 4H), 7.44 (m, 1H), 7.56 (s, 2H).

(xii) 6-(3,5-Difluorophenyl)-5-phenyl-1,2,4-triazin-3-amine 6-(3,5-Difluorophenyl)-5-phenyl-1,2,4-triazin-3-amine (160 mg, 47%) was prepared from 6-bromo-5-phenyl-1,2,4-triazin-3-amine (0.30 g, 1.19 mmol) and 3,5-difluorophenylboronic acid (0.20 g, 1.30 mmol) according to the general procedure of Example 1.
HPLC purity: 99.3% (262 nm)
Mass spectroscopy: (ESI+ve) 284.9[M+H], (ESI−ve) 283.1 [M−H]⁻
¹H NMR: (400 MHz, DMSO) δ: 6.99 (d, 2H), 7.12 (t, 1H), 7.40 (m, 5H) 7.56 (s, 2H).

(xiii) 6-(3,5-Dichlorophenyl)-5-phenyl-1,2,4-triazin-3-amine 6-(3,5-Dichlorophenyl)-5-phenyl-1,2,4-triazin-3-amine (130 mg, 34%) was prepared from 6-bromo-5-phenyl-1,2,4-triazin-3-amine (0.30 g, 1.19 mmol) and 3,5-dichlorophenylboronic acid (0.42 g, 2.19 mmol) according to the general procedure of Example 1.
HPLC purity: 90% (245 nm)
Mass spectroscopy: (ESI+ve) 316.9[M+H]⁺, (ESI−ve) 315.1 [M−H]⁻
¹H NMR: (400 MHz, CDCl₃) δ: 5.55 (s, 2H), 7.33 (m, 3H), 7.38 (m, 2H) 7.49 (m, 3H).

(xiv) 6-(5-Chloropyridin-3-yl)-5-phenyl-1,2,4-triazin-3-amine 6-(5-Chloropyridin-3-yl)-5-phenyl-1,2,4-triazin-3-amine (35 mg, 10%) was prepared from 6-bromo-5-phenyl-1,2,4-triazin-3-amine (0.30 g, 1.19 mmol) and 5-chloropyridine-3-ylboronic acid (0.20 g, 1.30 mmol) according to the general procedure of Example 1.

HPLC purity: 98.9% (262 nm)
Mass spectroscopy: (ESI+ve) 283.9 [M+H]+.
$^1$H NMR: (400 MHz, DMSO) δ: 7.38 (m, 4H), 7.45 (m, 1H), 7.61 (s, 2H), 7.87 (t, 1H), 8.35 (d, 1H), 8.55 (d, 1H).

(xv) 6-(3-Chloro-4-fluorophenyl)-5-phenyl-1,2,4-triazin-3-amine 6-(3-Chloro-4-fluorophenyl)-5-phenyl-1,2,4-triazin-3-amine (140 mg, 29%) was prepared from 6-bromo-5-phenyl-1,2,4-triazin-3-amine (0.40 g, 1.59 mmol) and 3-chloro-4-fluorophenylboronic acid (0.33 g, 1.91 mmol) according to the general procedure of Example 1.
HPLC purity: 93.7% (261 nm)
Mass spectroscopy: (ESI+ve) 300.9 [M+H]+.
$^1$H NMR: (400 MHz, CDCl$_3$) δ: 5.49 (s, 2H), 7.04 (t, 1H), 7.18 (m, 1H), 7.37 (m, 2H), 7.45 (m, 3H), 7.60 (dd, 1H).

(xvi) 6-(3-Chloro-5-methoxyphenyl)-5-phenyl-1,2,4-triazin-3-amine 6-(3-Chloro-5-methoxyphenyl)-5-phenyl-1,2,4-triazin-3-amine (36 mg, 9%) was prepared from 6-bromo-5-phenyl-1,2,4-triazin-3-amine (0.30 g, 1.19 mmol) and 3-chloro-5-methoxyphenylboronic acid (0.27 g, 1.43 mmol) according to the general procedure of Example 1.
HPLC purity: 99% (254 nm)
Mass spectroscopy: (ESI+ve) 312.9 [M+H]+.
$^1$H NMR: (400 MHz. DMSO) δ: 3.63 (s, 3H), 6.78 (m, 1H), 6.94 (m, 2H), 7.34-7.45 (m, 5H), 7.49 (bs, 2H).

(xvii) 6-(3-Fluoro-5-methoxyphenyl)-5-phenyl-1,2,4-triazin-3-amine 6-(3-Fluoro-5-methoxyphenyl)-5-phenyl-1,2,4-triazin-3-amine (193 mg, 32%) was prepared from 6-bromo-5-phenyl-1,2,4-triazin-3-amine (0.50 g, 1.99 mmol) and 3-fluoro-5-methoxy phenylboronic acid (0.37 g, 2.19 mmol) according to the general procedure of Example 1.
HPLC purity: 99.6% (263 nm)
Mass spectroscopy: (ESI+ve) 296.9 [M+H]+.
$^1$H NMR: (400 MHz, CDCl$_3$) δ: 3.69 (s, 3H), 5.56 (s, 2H), 6.59 (d, 1H) 6.70 (d, 1H), 6.78 (s, 1H), 7.35 (m, 2H), 7.45 (m, 3H).

(xviii) 6-(1H-Indol-6-yl)-5-phenyl-1,2,4-triazin-3-amine 6-(1H-Indol-6-yl)-5-phenyl-1,2,4-triazin-3-amine (107 mg, 23%) was prepared from 6-bromo-5-phenyl-1,2,4-triazin-3-amine (0.4 g, 1.59 mmol) and indol-6-boronic acid (0.256 g, 1.59 mmol) according to the general procedure of Example 1.
HPLC purity: 97.75% (222 nm)
Mass spectroscopy: (ESI+ve) 288.0 [M+H]+
$^1$H NMR: (400 MHz, DMSO) δ: 6.38 (m, 1H), 6.89 (dd, 1H), 7.26-7.40 (m, 3H), 7.42-7.62 (m, 5H), 11.12 (s, 1H).

(xix) 6-(3-Bromophenyl)-5-phenyl-1,2,4-triazin-3-amine 6-(3-Bromophenyl)-5-phenyl-1,2,4-triazin-3-amine (218 mg, 52%) was prepared from 6-bromo-5-phenyl-1,2,4-triazin-3-amine (0.4 g, 1.59 mmol) and 3-bromophenylboronic acid (0.32 g, 1.59 mmol) according to the general procedure of Example 1.
HPLC purity: 95.65% (262 nm)
Mass spectroscopy: (ESI+ve) 326.9 [M+H]+
$^1$H NMR: (400 MHz, CDCl$_3$) δ: 5.61 (s, 2H), 7.15 (t, 1H), 7.24 (m, 1H), 7.35 (m, 2H), 7.47 (m, 4H), 7.69 (t, 1H).

(xx) 6-(3,4-Dichlorophenyl)-5-phenyl-1,2,4-triazin-3-amine 6-(3,4-Dichlorophenyl)-5-phenyl-1,2,4-triazin-3-amine (52 mg, 54%) was prepared from 6-bromo-5-phenyl-1,2,4-triazin-3-amine (75 mg, 0.299 mmol) and 3,4-dichlorophenylboronic acid (65.5 mg, 0.344 mmol) according to the general procedure of Example 1.
HPLC purity: 99.2% (254 nm)
Mass spectroscopy: (ESI+ve) 317.1/319.1/321.1 (M+H)+
$^1$H NMR: (400 MHz, d6-DMSO) δ: 7.24 (dd, 1H), 7.35-7.47 (m, 5H), 7.53 (bs, 2H), 7.57 (m, 1H), 7.63 (d, 1H).

(xxi) 6-(3-Fluorophenyl)-5-phenyl-1,2,4-triazin-3-amine 6-(3-Fluorophenyl)-5-phenyl-1,2,4-triazin-3-amine (49 mg, 62%) was prepared from 6-bromo-5-phenyl-1,2,4-triazin-3-amine (75 mg, 0.299 mmol) and 3-fluorophenylboronic acid (48.1 mg, 0.344 mmol) according to the general procedure of Example 1.
HPLC purity: 100% (254 nm)
Mass spectroscopy: (ESI+ve) 267.1 (M+H)+
$^1$H NMR: (400 MHz, d6-DMSO) 5:7.10-7.20 (m, 3H), 7.31-7.44 (m, 6H), 7.45 (bs, 2H).

(xxii) 6-(1,3-Benzodioxol-5-yl)-5-phenyl-1,2,4-triazin-3-amine 6-(1,3-Benzodioxol-5-yl)-5-phenyl-1,2,4-triazin-3-amine (54 mg, 62%) was prepared from 6-bromo-5-phenyl-1,2,4-triazin-3-amine (75 mg, 0.299 mmol) and benzo[d][1,3]dioxol-5-ylboronic acid (57.0 mg, 0.344 mmol) according to the general procedure of Example 1.
HPLC purity: 100% (254 nm)
Mass spectroscopy: 293.2 (M+H)+
$^1$H NMR: (400 MHz, d6-DMSO) δ: 6.05 (s, 2H), 6.52 (dd, 1H), 6.83 (m, 1H), 6.87 (m, 1H), 7.32 (bs, 2H), 7.35-7.43 (m, 5H).

(xxiii) 3-(3-Amino-5-phenyl-1,2,4-triazin-6-yl)benzonitrile 3-(3-Amino-5-phenyl-1,2,4-triazin-6-yl)benzonitrile (20 mg, 25%) was prepared from 6-bromo-5-phenyl-1,2,4-triazin-3-amine (75 mg, 0.299 mmol) and 3-cyanophenylboronic acid (50.5 mg, 0.344 mmol) according to the general procedure of Example 1.
HPLC purity: 96.0% (254 nm)
Mass spectroscopy: (ESI+ve) 274.2 (M+H)+
$^1$H NMR: (400 MHz, d6-DMSO) δ: 7.30-7.35 (m, 4H), 7.52 (m, 1H), 7.52 (m, 1H), 7.54 (bs, 2H), 7.63 (m, 1H), 7.82 (m, 2H).

(xxiv) 6-(3,5-Dimethoxyphenyl)-5-phenyl-1,2,4-triazin-3-amine 6-(3,5-Dimethoxyphenyl)-5-phenyl-1,2,4-triazin-3-amine (55 mg, 60%) was prepared from 6-bromo-5-phenyl-1,2,4-triazin-3-amine (75 mg, 0.299 mmol) and 3,5-dimethoxyphenylboronic acid (62.5 mg, 0.344 mmol) according to the general procedure of Example 1.

HPLC purity: 100% (254 nm)
Mass spectroscopy: (ESI+ve) 309.2 (M+H)+
$^1$H NMR: (400 MHz, d6-DMSO) δ: 3.70 (s, 6H), 6.54 (m, 3H), 7.42-7.54 (m, 7H).

(xxv) 6-(3,5-Dimethylphenyl)-5-phenyl-1,2,4-triazin-3-amine 6-(3,5-Dimethylphenyl)-5-phenyl-1,2,4-triazin-3-amine (54 mg, 65%) was prepared from 6-bromo-5-phenyl-1,2,4-triazin-3-amine (75 mg, 0.299 mmol) and 3,5-dimethylphenylboronic acid (51.5 mg, 0.344 mmol) according to the general procedure of Example 1.
HPLC purity: 100% (254 nm)
Mass spectroscopy: (ESI+ve) 277.2 (M+H)+
$^1$H NMR: (400 MHz, d6-DMSO) δ: 2.06 (s, 6H), 6.82 (m, 3H), 7.18-7.27 (m, 7H).

(xxvi) 6-(3,4-Dimethylphenyl)-5-phenyl-1,2,4-triazin-3-amine 6-(3,4-Dimethylphenyl)-5-phenyl-1,2,4-triazin-3-amine (55 mg, 67%) was prepared from 6-bromo-5-phenyl-1,2,4-triazin-3-amine (75 mg, 0.299 mmol) and 3,4-dimethylphenylboronic acid (51.5 mg, 0.344 mmol) according to the general procedure of Example 1.
HPLC purity: 100% (254 nm)
Mass spectroscopy: (ESI+ve) 277.2 (M+H)+
$^1$H NMR: (400 MHz, d6-DMSO) δ: 2.15 (s, 3H), 2.17 (s, 3H), 6.88 (m, 1H), 7.02 (m, 1H), 7.23 (m, 1H), 7.32 (bs, 2H), 7.34 (m, 2H), 7.87-7.42 (m, 3H).

(xxvii) 6-[3-(Dimethylamino)phenyl]-5-phenyl-1,2,4-triazin-3-amine

6-[3-(Dimethylamino)phenyl]-5-phenyl-5-phenyl-1,2,4-triazin-3-amine (53 mg, 60%) was prepared from 6-bromo-5-phenyl-1,2,4-triazin-3-amine (75 mg, 0.299 mmol) and 3-(dimethylamino)phenylboronic acid (56.7 mg, 0.344 mmol) according to the general procedure of Example 1.
HPLC purity: 98.3% (254 nm)
Mass spectroscopy: (ESI+ve) 292.2 (M+H)+
$^1$H NMR: (400 MHz, d6-DMSO) δ: 2.77 (s, 6H), 6.58 (m, 1H), 6.67 (m, 2H), 7.09 (m, 1H), 7.32 (bs, 2H), 7.34 (m, 2H), 7.40 (m, 3H).

(xxviii) N-[3-(3-Amino-5-phenyl-1,2,4-triazin-6-yl)phenyl]acetamide

N-[3-(3-Amino-5-phenyl-1,2,4-triazin-6-yl)phenyl]acetamide (59 mg, 62%) was prepared from 6-bromo-5-phenyl-1,2,4-triazin-3-amine (75 mg, 0.299 mmol) and 3-acetamidophenylboronic acid (61.5 mg, 0.344 mmol) according to the general procedure of Example 1.
HPLC purity: 100% (254 nm)
Mass spectroscopy: (ESI+ve) 306.2 (M+H)+
$^1$H NMR: (400 MHz, d6-DMSO) δ: 1.95 (s, 3H), 6.70 (m, 1H), 7.07 (m, 1H), 7.25-7.35 (m, 6H), 7.52 (m, 2H), 7.64 (m, 1H), 9.89 (s, 1H).

(xxix) N-[3-(3-Amino-5-phenyl-1,2,4-triazin-6-yl)phenyl]methanesulfonamide

N-[3-(3-Amino-5-phenyl-1,2,4-triazin-6-yl)phenyl]methanesulfonamide (42 mg, 41%) was prepared from 6-bromo-5-phenyl-1,2,4-triazin-3-amine (75 mg, 0.299 mmol) and N-(3-(4,4,5,5-tetramethyl-1,3,2-dioxaborolan-2-yl)phenyl) methanesulfonamide (102 mg, 0.344 mmol) according to the general procedure of Example 1.
HPLC purity: 100% (254 nm)
Mass spectroscopy: (ESI+ve) 342.2 (M+H)+
$^1$H NMR: (400 MHz, d6-DMSO) δ: 2.79 (s, 3H), 7.02 (m, 1H), 7.36 (m, 1H), 7.26 (m, 2H), 7.35-7.48 (m, 7H), 9.78 (s, 1H).

(xxx) 6-(3-Chlorophenyl)-5(2,4-difluorophenyl)-1,2,4-triazin-3-amine 6-(3-Chlorophenyl)-5-(2,4-difluorophenyl)-1,2,4-triazin-3-amine (23 mg, 15%) was prepared from 6-bromo-5-(2,4-difluorophenyl)-1,2,4-triazin-3-amine (0.13 g, 0.40 mmol) and 3-chlorophenylboronic acid (0.07 g, 0.40 mmol) according to the general procedure of Example 1.
HPLC purity: 98.7% (260 nm)
Mass spectroscopy: (ESI+ve) 318.9 [M+H]+, 317.1 [M−H]−.
$^1$H NMR: (400 MHz, CDCl$_3$) δ: 5.64 (s, 2H), 6.75 (m, 1H), 7.01 (m, 1H), 7.20 (m, 2H), 7.32 (m, 1H), 7.48 (s, 1H), 7.54 (m, 1H).

(xxxi) 6-(3-Chlorophenyl)-5-(3-methoxyphenyl)-1,2,4-triazin-3-amine 6-(3-Chlorophenyl)-5-(3-methoxyphenyl)-1,2,4-triazin-3-amine (18 mg 9%) was prepared from 6-bromo-5-(3-methoxyphenyl)-1,2,4-triazin-3-amine (0.18 g, 0.60 mmol) and 3-chlorophenylboronic acid (0.10 g, 0.60 mmol) according to the general procedure of Example 1.
HPLC purity: 88% (258 nm)
Mass spectroscopy: (ESI+ve) 313.0 [M+H]+, 311.1 [M−H]−.
$^1$H NMR: (400 MHz, CDCl$_3$) δ: 3.72 (s, 3H), 6.53 (s, 2H), 7.04 (m, 3H), 7.23-7.30 (m, 3H), 7.37 (d, 1H), 7.49 (s, 1H).

(xxxii) 6-(3-Chlorophenyl)-5-(4-fluorophenyl)-1,2,4-triazin-3-amine 6-(3-Chlorophenyl)-5-(4-fluorophenyl)-1,2,4-triazin-3-amine (65.0 mg, 19%) was prepared from 6-bromo-5-(4-fluorophenyl)-1,2,4-triazin-3-amine (0.30 g, 1.11 mmol) and 3-chlorophenylboronic acid (0.19 g, 1.23 mmol) according to the general procedure of Example 1.
HPLC purity: 98% (261 nm)
Mass spectroscopy: (ESI+ve) 300.9 [M+H]+.
$^1$H NMR: (400 MHz, CDCl$_3$) δ: 5.47 (s, 2H), 7.03 (m, 2H), 7.19-7.26 (m, 3H), 7.33 (m, 1H), 7.47 (m, 2H), 7.53 (m, 1H).

(xxxiii) 6-(2-Methoxyphenyl)-5-phenyl-1,2,4-triazin-3-amine 6-(2-Methoxyphenyl)-5-phenyl-1,2,4-triazin-3-amine (108 mg, 48%) was prepared from 6-bromo-5-phenyl-1,2,4-triazin-3-amine (0.21 g, 0.80 mmol) and 2-methoxyphenyl boronic acid (0.137 g, 0.90 mmol) according to the general procedure of Example 1.
HPLC purity: 99.28% (223 nm)
Mass spectroscopy: (ESI+ve) 278.9 [M+H]+.
$^1$H NMR: (400 MHz, CDCl$_3$) δ: 3.20 (s, 3H), 5.49 (s, 2H), 6.70 (t, 1H) 7.10 (m, 2H), 7.26 (m, 1H), 7.32-7.39 (m, 2H), 7.43 (m, 2H), 7.64 (dd, 1H).

(xxxiv) 6-(3-trifluoromethoxyphenyl)-5-phenyl-1,2,4-triazin-3-amine 6-(3-trifluoromethoxyphenyl)-5-phenyl-1,2,4-triazin-3-amine (170 mg, 25%) was prepared from 6-bromo-5-phenyl-1,2,4-triazin-3-amine (0.50 g, 1.99 mmol) and 3-(trifluoromethoxy)phenyl boronic acid (0.44 g, 2.13 mmol) according to the general procedure of Example 1.

HPLC purity: 99% (262 nm)
Mass spectroscopy: (ESI+ve) 332.9 [M+H]$^+$
$^1$H NMR: (400 MHz, CDCl3) δ: 5.46 (s, 2H), 7.19 (m, 1H), 7.25 (m, 1H) 7.36 (m, 3H), 7.43 (t, 4H).

(xxxv) 6-(1-benzofuran-5-yl)-5-phenyl-1,2,4-triazin-3-amine 6-(1-benzofuran-5-yl)-5-phenyl-1,2,4-triazin-3-amine (225 mg, 47%) was prepared from 6-bromo-5-phenyl-1,2,4-triazin-3-amine (0.50 g, 1.99 mmol) and benzofuran-5 boronic acid (0.32 g, 1.99 mmol) according to the general procedure of Example 1.

HPLC purity: 99.61% (245 nm)
Mass spectroscopy: (ESI+ve) 288.9 [M+H]$^+$
$^1$H NMR: (400 MHz, DMSO) δ: 6.92 (m, 1H), 7.20 (m, 1H), 7.27 (m, 2H), 7.36 (m, 5H), 7.52 (d, 1H), 7.66 (d, 1H), 7.98 (d, 1H).

(xxxvi) 5-phenyl-6-[3-(propan-2-yl)phenyl]-1,2,4-triazin-3-amine 5-phenyl-6-[3-(propan-2-yl)phenyl]-1,2,4-triazin-3-amine (110 mg, 33%) was prepared from 6-bromo-5-phenyl-1,2,4-triazin-3-amine (0.3 g, 1.19 mmol) and 3-isopropyl phenyl boronic acid (0.215 g, 1.31 mmol) according to the general procedure of Example 1.

HPLC purity: 99.78% (262 nm)
Mass spectroscopy: (ESI+ve) 291.0 [M+H]$^+$
$^1$H NMR: (400 MHz, CDCl$_3$) δ: 1.09 (d, 6H), 2.79 (m, 1H), 5.48 (bs, 2H), 7.19 (m, 2H), 7.31 (m, 4H), 7.44 (m, 3H).

(xxxvii) 6-(3,5-dichlorophenyl)-5-(4-fluorophenyl)-1,2,4-triazin-3-amine 6-(3,5-dichlorophenyl)-5-(4-fluorophenyl)-1,2,4-triazin-3-amine (0.11 g, 17.6%) was prepared from 6-Bromo-5-(4-fluorophenyl)-1,2,4-triazin-3-amine (0.5 g, 1.18 mmol) and 3,5-dichloro phenylboronic acid (0.47 mg, 2.4 mmol) according to the general procedure of Example 1.

HPLC purity: 97.46% (225 nm)
Mass spectroscopy: (ESI+ve) 334.9 [M]$^+$.
$^1$H NMR: (400 MHz, DMSO) δ: 7.24 (m, 2H), 7.34 (m, 2H), 7.45 (m, 2H), 7.58 (m, 3H).

(xxxviii) 4-(3-amino-5-phenyl-1,2,4-triazin-6-yl)-2-(propan-2-yloxy)phenol 4-(3-amino-5-phenyl-1,2,4-triazin-6-yl)-2-(propan-2-yloxy)phenol (0.450 g, 18%) was prepared from 6-bromo-5-phenyl-1,2,4-triazin-3-amine (1.9 g, 7.52 mmol) and 3-isopropoxy-4-hydroxyphenylboronic acid pinacol ester (2.5 g, 9.02 mmol) according to the general procedure of Example 1.

HPLC purity: 94.14% (290 nm)
Mass spectroscopy: (ESI+ve) 323.1 [M+H]$^+$ (ESI−ve) 321.1 [M+H]$^+$.
$^1$H NMR: (400 MHz, DMSO) δ: 1.04 (d, 6H), 4.20 (m, 1H), 6.68 (m, 1H), 6.70 (m, 1H), 6.84 (m, 1H), 7.26 (bs, 2H), 7.32-7.44 (m, 5H), 9.01 (s, 1H).

The compounds in the following table were prepared using the general procedure outlined for Example 1, by reacting the corresponding starting materials at 140° C. for 1 hour.

| No. | Product (yield) | Prepared From | LCMS | NMR |
|---|---|---|---|---|
| (xxxix) | 6-(3,5-bis(trifluoromethyl)phenyl)-5-phenyl-1,2,4-triazin-3-amine (50.2 mg, 0.131 mmol, 36.4%) | 6-bromo-5-phenyl-1,2,4-triazin-3-amine (90 mg, 0.358 mmol) and 3,5-bis(trifluoromethyl)phenylboronic acid (106 mg, 0.412 mmol) | Mass spectroscopy: m/z 385.3 (M + H)$^+$ (ES$^+$); 383.5 (M − H)$^-$ (ES$^-$), at 4.89 min, 100% (method B). | (400 MHz, DMSO) δ: 7.35-7.43 (m, 4H), 7.44-7.50 (m, 1H), 7.68 (s, 2H), 7.94 (s, 2H), 8.06 (s, 1H). |
| (xl) | 4-(3-amino-5-phenyl-1,2,4-triazin-6-yl)-2-methoxyphenol (42.5 mg, 0.139 mmol, 38.7%) | 6-bromo-5-phenyl-1,2,4-triazin-3-amine (90 mg, 0.358 mmol) and -methoxy-4-(4,4,5,5-tetramethyl-1,3,2-dioxaborolan-2-yl)phenol (103 mg, 0.412 mmol) | Mass spectroscopy: m/z 295.2 (M + H)$^+$ (ES$^+$); 293.4 (M − H)$^-$ (ES$^-$), at 2.70 min, 96.0% (method B). | (400 MHz, DMSO) δ: 3.55 (s, 3H), 6.65-6.76 (m, 2H), 6.85 (d, J 1.8, 1H), 7.28 (s, 2H), 7.33-7.45 (m, 5H), 9.18 (s, 1H). |
| (xli) | 4-(3-amino-5-phenyl-1,2,4-triazin-6-yl)-2,6-dimethylphenol (41.3 mg, 0.141 mmol, 39.4%) | 6-bromo-5-phenyl-1,2,4-triazin-3-amine (90 mg, 0.358 mmol) and 2,6-dimethyl-4-(4,4,5,5-tetramethyl-1,3,2-dioxaborolan-2-yl)phenol (102 mg, 0.412 mmol) | Mass spectroscopy: m/z 293.2 (M + H)$^+$ (ES$^+$); 291.4 (M − H)$^-$ (ES$^-$), at 3.57 min, 100% (method B). | (400 MHz, DMSO) δ: 2.06 (s, 6H), 6.87 (s, 2H), 7.31-7.64 (m, 7H), 8.46 (s, 1H). |
| (xlii) | 4-(3-amino-5-phenyl-1,2,4-triazin-6-yl)-2-chlorophenol (26.8 mg, 0.085 mmol, 23.78%) | 6-bromo-5-phenyl-1,2,4-triazin-3-amine (90 mg, 0.358 mmol) and 3-chloro-4-hydroxyphenylboronic acid (64.9 mg, 0.376 mmol) | Mass spectroscopy: m/z (Cl) 299.2/301.2 (M + H)$^+$ (ES$^+$); 297.4/299.4 (M − H)$^-$ (ES$^-$), at 2.15 min, 97.1% (method B). | (400 MHz, DMSO) δ: 6.87 (d, J 8.4, 1H), 7.03 (dd, J 8.4, 2.2, 1H), 7.31 (d, J 2.2, 1H), 7.33-7.47 (m, 7H), 10.38 (s, 1H). |

-continued

| No. | Product (yield) | Prepared From | LCMS | NMR |
|---|---|---|---|---|
| (xliii) | 6-(2-chloropyridin-4-yl)-5-phenyl-1,2,4-triazin-3-amine (22.5 mg, 0.079 mmol, 22.12%) | 6-bromo-5-phenyl-1,2,4-triazin-3-amine (90 mg, 0.358 mmol) and 2-chloropyridin-4-ylboronic acid (59.2 mg, 0.376 mmol) | Mass spectroscopy: m/z (Cl) 284.1/286.1 (M + H)$^+$ (ES$^+$); 282.3/284.3 (M − H)$^-$ (ES$^-$), at 3.55 min, 100% (method B). | (400 MHz, DMSO) δ: 7.28 (dd, J 5.2, 1.5, 1H), 7.38-7.53 (m, 6H), 7.74 (s, 2H), 8.33 (dd, J 5.2, 0.6, 1H). |
| (xliv) | 6-(3-(methylsulfonyl)phenyl)-5-phenyl-1,2,4-triazin-3-amine (78.8 mg, 0.241 mmol, 67.4%) | 6-bromo-5-phenyl-1,2,4-triazin-3-amine (90 mg, 0.358 mmol) and 3-(methylsulfonyl)phenylboronic acid (82 mg, 0.412 mmol) | Mass spectroscopy: m/z 327.2 (M + H)$^+$ (ES$^+$); 325.4 (M − H)$^-$ (ES$^-$), at 3.12 min, 100% (method B). | (400 MHz, DMSO) δ: 3.10 (s, 3H), 7.33-7.48 (m, 5H), 7.50-7.68 (m, 4H), 7.83-7.91 (m, 2H). |
| (xlv) | 6-(3,5-dichloro-4-methoxyphenyl)-5-phenyl-1,2,4-triazin-3-amine (52 mg, 0.147 mmol, 41.1%) | 6-bromo-5-phenyl-1,2,4-triazin-3-amine (90 mg, 0.358 mmol) and 3,5-dichloro-4-methoxyphenylboronic acid (83 mg, 0.376 mmol) | Mass spectroscopy: m/z (2Cl) 347.2/349.2/351.2 (M + H)$^+$ (ES$^+$); 345.3/347.3/349.4 (M − H)$^-$ (ES$^-$), at 4.57 min, 91.0% (method B). | (400 MHz, DMSO) δ: 3.83 (s, 3H), 7.37-7.50 (m, 7H), 7.55 (s, 2H). |
| (xlvi) | 6-(4-methoxy-3-(trifluoromethyl)phenyl)-5-phenyl-1,2,4-triazin-3-amine (53.4 mg, 0.154 mmol, 51.6%) | 6-bromo-5-phenyl-1,2,4-triazin-3-amine (75 mg, 0.299 mmol) and 4-methoxy-3-(trifluoromethyl)phenylboronic acid (76 mg, 0.344 mmol) | Mass spectroscopy: m/z 347.2 (M + H)$^+$ (ES$^+$); 345.4 (M − H)$^-$ (ES$^-$), at 4.25 min, 100% (method B). | (400 MHz, DMSO) δ: 3.88 (s, 3H), 7.21 (d, J 8.6, 1H), 7.33-7.50 (m, 7H), 7.51-7.59 (m, 2H). |
| (xlvii) | 6-(3-chloro-5-(dimethylamino)phenyl)-5-phenyl-1,2,4-triazin-3-amine (68.3 mg, 0.204 mmol, 57.0%) | 6-bromo-5-phenyl-1,2,4-triazin-3-amine (90 mg, 0.358 mmol) and 3-chloro-N,N-dimethyl-5-(4,4,5,5-tetramethyl-1,3,2-dioxaborolan-2-yl)aniline (106 mg, 0.376 mmol) | Mass spectroscopy: m/z (Cl) 326.3/328.2 (M + H)$^+$ (ES$^+$); 324.4/326.4 (M − H)$^-$ (ES$^-$), at 4.53 min, 100% (method B). | (400 MHz, DMSO) δ: 2.75 (s, 6H), 6.47-6.53 (m, 1H), 6.61-6.68 (m, 2H), 7.30-7.54 (m, 7H). |
| (xlviii) | 3-(3-amino-5-phenyl-1,2,4-triazin-6-yl)-5-(trifluoromethyl)benzonitrile (47.5 mg, 0.137 mmol, 38.2%) | 6-bromo-5-phenyl-1,2,4-triazin-3-amine (90 mg, 0.358 mmol) and 3-(4,4,5,5-tetramethyl-1,3,2-dioxaborolan-2-yl)-5-(trifluoromethyl)benzonitrile (122 mg, 0.412 mmol) | Mass spectroscopy: m/z 342.9 (M + H)$^+$ (ES$^+$); 341.0 (M − H)$^-$ (ES$^-$), at 4.25 min, 98.4% (method B). | (400 MHz, DMSO) δ: 7.36-7.42 (m, 4H), 7.43-7.51 (m, 1H), 7.69 (s, 2H), 7.90 (s, 1H), 8.09 (s, 1H), 8.31 (s, 1H). |
| (xlix) | 4-(3-amino-5-phenyl-1,2,4-triazin-6-yl)-2,6-dimethylbenzonitrile (72.4 mg, 0.233 mmol, 65.0%) | 6-bromo-5-phenyl-1,2,4-triazin-3-amine (90 mg, 0.358 mmol) and 2,6-dimethyl-4-(4,4,5,5-tetramethyl-1,3,2-dioxaborolan-2-yl)benzonitrile (106 mg, 0.412 mmol) | Mass spectroscopy: m/z 302.2 (M + H)$^+$ (ES$^+$); 300.4 (M − H)$^-$ (ES$^-$), at 4.14 min, 100% (method B). | (400 MHz, DMSO) δ: 2.37 (s, 6H), 7.22 (s, 2H), 7.35-7.42 (m, 4H), 7.43-7.49 (m, 1H), 7.57 (s, 2H). |
| (l) | 6-(3-chloro-5-(trifluoromethyl)phenyl)-5-phenyl-1,2,4-triazin-3-amine (42.5 mg, 0.117 mmol, 32.6%) | 6-bromo-5-phenyl-1,2,4-triazin-3-amine (90 mg, 0.358 mmol) and 2-(3-chloro-5-(trifluoromethyl)phenyl)-4,4,5,5-tetramethyl-1,3,2-dioxaborolane (115 mg, 0.376 mmol) | Mass spectroscopy: m/z 351.9 (M + H)$^+$ (ES$^+$); 350.0 (M − H)$^-$ (ES$^-$), at 4.80 min, 96.4% (method B). | (400 MHz, DMSO) δ: 7.35-7.43 (m, 4H), 7.44-7.49 (m, 1H), 7.55 (s, 1H), 7.63 (s, 2H), 7.72 (s, 1H), 7.82 (s, 1H). |
| (li) | 6-(3-chloro-5-methylphenyl)-5-phenyl-1,2,4-triazin-3-amine (65.1 mg, 0.219 mmol, 61.2%) | 6-bromo-5-phenyl-1,2,4-triazin-3-amine (90 mg, 0.358 mmol) and 3-chloro-5-methylphenylboronic acid (64.1 mg, 0.376 mmol) | Mass spectroscopy: m/z (Cl) 297.1/299.3 (M + H)$^+$ (ES$^+$); 295.3/297.3 (M − H)$^-$ (ES$^-$), at 4.55 min, 100% (method B). | (400 MHz, DMSO) δ: 2.24 (s, 3H), 7.07-7.12 (m, 1H), 7.13-7.17 (m, 1H), 7.21-7.25 (m, 1H), 7.33-7.57 (m, 7H). |
| (lii) | 6-(3-(methylthio)-5-(trifluoromethyl)phenyl)-5-phenyl-1,2,4-triazin-3-amine (66 | from 6-bromo-5-phenyl-1,2,4-triazin-3-amine (90 mg, 0.358 mmol) and 3- | Mass spectroscopy: m/z 363.2 (M + H)$^+$ (ES$^+$); 361.4 (M − H)$^-$ | (400 MHz, DMSO) δ: 2.33 (s, 3H), 7.35-7.43 (m, 6H), 7.43-7.47 (m, 1H), 7.57 (s, |

-continued

| No. | Product (yield) | Prepared From | LCMS | NMR |
|---|---|---|---|---|
| | mg, 0.181 mmol, 50.5%) | (methylthio)-5-(trifluoromethyl)phenylboronic acid (97 mg, 0.412 mmol) | (ES⁻), at 4.75 min, 99.4% (method B). | 2H), 7.49 (s, 1H). |
| (liii) | 6-(3-methoxy-5-(trifluoromethyl)phenyl)-5-phenyl-1,2,4-triazin-3-amine (62.9 mg, 0.179 mmol, 49.9%) | 6-bromo-5-phenyl-1,2,4-triazin-3-amine (90 mg, 0.358 mmol) and 3-methoxy-5-(trifluoromethyl)phenylboronic acid (91 mg, 0.412 mmol) | Mass spectroscopy: m/z 347.2 (M + H)⁺ (ES⁺); 345.4 (M − H)⁻ (ES⁻), at 4.52 min, 99.5% (method B). | (400 MHz, DMSO) δ: 3.71 (s, 3H), 7.14-7.22 (m, 3H), 7.35-7.42 (m, 4H), 7.42-7.47 (m, 1H), 7.55 (s, 2H). |
| (liv) | 6-(3-ethoxy-5-(trifluoromethyl)phenyl)-5-phenyl-1,2,4-triazin-3-amine (76.4 mg, 0.211 mmol, 58.8%) | 6-bromo-5-phenyl-1,2,4-triazin-3-amine (90 mg, 0.358 mmol) and 3-ethoxy-5-(trifluoromethyl)phenylboronic acid (96 mg, 0.412 mmol) | Mass spectroscopy: m/z 361.2 (M + H)⁺ (ES⁺); 359.5 (M − H)⁻ (ES⁻), at 4.74 min, 99.4% (method B). | (400 MHz, DMSO) δ: 1.23 (t, J 7.0, 3H), 3.97 (q, J 7.0, 2H), 7.12-7.15 (m, 1H), 7.15-7.17 (m, 1H), 7.18-7.21 (m, 1H), 7.34-7.48 (m, 5H), 7.54 (s, 2H). |
| (lv) | 6-(3-tert-butyl-5-methylphenyl)-5-phenyl-1,2,4-triazin-3-amine (80 mg, 0.249 mmol, 69.5%) | 6-bromo-5-phenyl-1,2,4-triazin-3-amine (90 mg, 0.358 mmol) and with 3-tert-butyl-5-methylphenylboronic acid (79 mg, 0.412 mmol) | Mass spectroscopy: m/z 319.5 (M + H)⁺ (ES⁺); 317.5 (M − H)⁻ (ES⁻), at 4.99 min, 99.1% (method B). | (400 MHz, DMSO) δ: 1.03 (s, 9H), 2.31 (s, 3H), 6.80-6.85 (m, 1H), 7.11-7.15 (m, 1H), 7.24-7.28 (m, 1H), 7.30-7.44 (m, 7H). |
| (lvi) | 6-(2-chloro-6-methylpyridin-4-yl)-5-phenyl-1,2,4-triazin-3-amine (52.5 mg, 0.170 mmol, 47.3%) | 6-bromo-5-phenyl-1,2,4-triazin-3-amine (90 mg, 0.358 mmol) and 2-chloro-6-methyl-4-(4,4,5,5-tetramethyl-1,3,2-dioxaborolan-2-yl)pyridine (100 mg, 0.394 mmol) | Mass spectroscopy: m/z (Cl) 298.1/300.1 (M + H)⁺ (ES⁺); 296.3/298.3 (M − H)⁻ (ES⁻), at 3.73 min, 99.6% (method B). | (400 MHz, DMSO) δ: 2.39 (s, 3H), 7.08-7.13 (m, 1H), 7.24-7.30 (m, 1H), 7.39-7.45 (m, 4H), 7.46-7.53 (m, 1H), 7.71 (s, 2H). |
| (lvii) | 4-(3-amino-5-phenyl-1,2,4-triazin-6-yl)-2-chlorobenzonitrile (29 mg, 0.092 mmol, 25.7%) | 6-bromo-5-phenyl-1,2,4-triazin-3-amine (90 mg, 0.358 mmol) and 3-chloro-4-cyanophenylboronic acid (71.5 mg, 0.394 mmol) | Mass spectroscopy: m/z (Cl) 308.1/310.1 (M + H)⁺ (ES⁺); 306.3/308.3 (M − H)⁻ (ES⁻), at 4.02 min, 97.9% (method B). | (400 MHz, DMSO) δ: 7.36-7.44 (m, 5H), 7.44-7.50 (m, 1H), 7.69 (s, 2H), 7.73 (d, J 1.3, 1H), 7.91 (d, J 8.2, 1H). |
| (lviii) | 6-(3-ethylphenyl)-5-phenyl-1,2,4-triazin-3-amine (70 mg, 0.252 mmol, 70.3%) | 6-bromo-5-phenyl-1,2,4-triazin-3-amine (90 mg, 0.358 mmol) and 3-ethylphenylboronic acid (61.8 mg, 0.412 mmol) | Mass spectroscopy: m/z 277.2 (M + H)⁺ (ES⁺); 275.4 (M − H)⁻ (ES⁻), at 4.49 min, 99.5% (method B). | (400 MHz, DMSO) δ: 1.03 (t, J 7.6, 3H), 2.51 (q, J 7.6, 2H), 7.12-7.18 (m, 3H), 7.20-7.26 (m, 1H), 7.31-7.45 (m, 7H). |
| (lix) | 6-(2-methoxy-6-(trifluoromethyl)pyridin-4-yl)-5-phenyl-1,2,4-triazin-3-amine (61.6 mg, 0.176 mmol, 49.2%) | 6-bromo-5-phenyl-1,2,4-triazin-3-amine (90 mg, 0.358 mmol) and 2-methoxy-4-(4,4,5,5-tetramethyl-1,3,2-dioxaborolan-2-yl)-6-(trifluoromethyl)pyridine (125 mg, 0.412 mmol) | Mass spectroscopy: m/z 348.2 (M + H)⁺ (ES⁺); 346.4 (M − H)⁻ (ES⁻), at 4.47 min, 99.4% (method B). | (400 MHz, DMSO) δ: 3.86 (s, 3H), 7.00-7.04 (m, 1H), 7.34 (d, J 1.1, 1H), 7.38-7.46 (m, 4H), 7.46-7.52 (m, 1H), 7.75 (s, 2H). |
| (lx) | 6-(3-methyl-5-(trifluoromethoxy)phenyl)-5-phenyl-1,2,4-triazin-3-amine (41 mg, 0.116 mmol, 32.3%) | 6-bromo-5-phenyl-1,2,4-triazin-3-amine (90 mg, 0.358 mmol) and 4,4,5,5-tetramethyl-2-(3-methyl-5-(trifluoromethoxy)phenyl)-1,3,2-dioxaborolane (125 mg, 0.412 mmol) | Mass spectroscopy: m/z 347.2 (M + H)⁺ (ES⁺); 345.4 (M − H)⁻ (ES⁻), at 4.72 min, 97.7% (method B). | (400 MHz, DMSO) δ: 2.32 (s, 3H), 6.85-6.91 (m, 1H), 7.12-7.18 (m, 1H), 7.32-7.41 (m, 5H), 7.41-7.47 (m, 1H), 7.51 (s, 2H). |
| (lxi) | 6-(3-(1,3-dioxolan-2-yl)-5-(trifluoromethyl)phenyl)-5-phenyl-1,2,4-triazin- | from 6-bromo-5-phenyl-1,2,4-triazin-3-amine (90 mg, 0.358 mmol) and 3- | Mass spectroscopy: m/z 389.3 (M + H)⁺ (ES⁺); 387.5 (M − H)⁻ | (400 MHz, DMSO) δ: 3.92 (s, 4H), 5.81 (s, 1H), 7.34-7.41 (m, 4H), 7.41-7.48 (m, |

-continued

| No. | Product (yield) | Prepared From | LCMS | NMR |
|---|---|---|---|---|
| | triazin-3-amine (76 mg, 0.194 mmol, 54.2%) | (1,3-dioxolan-2-yl)-5-(trifluoromethyl)phenylboronic acid (108 mg, 0.412 mmol) | (ES$^-$), at 4.32 min, 95.3% (method B). | 1H), 7.57 (s, 2H), 7.60 (s, 1H), 7.68 (s, 1H), 7.73 (s, 1H). |
| (lxii) | 5-phenyl-6-(3-(2,2,2-trifluoroethoxy)phenyl)-1,2,4-triazin-3-amine (86 mg, 0.246 mmol, 68.6%) | 6-bromo-5-phenyl-1,2,4-triazin-3-amine (90 mg, 0.358 mmol) and 3-(2,2,2-trifluoroethoxy)phenylboronic acid (91 mg, 0.412 mmol) | Mass spectroscopy: m/z 347.2 (M + H)$^+$ (ES$^+$); 345.4 (M − H)$^-$ (ES$^-$), at 4.30 min, 99.0% (method B). | (400 MHz, DMSO) δ: 4.69 (q, J 8.9, 2H), 6.87-6.93 (m, 1H), 7.02 (ddd, J 8.3, 2.7, 0.8, 1H), 7.07-7.12 (m, 1H), 7.25 (t, J 8.0, 1H), 7.31-7.52 (m, 7H). |
| (lxiii) | 6-(3-(methoxymethyl)phenyl)-5-phenyl-1,2,4-triazin-3-amine (76 mg, 0.256 mmol, 71.4%) | 6-bromo-5-phenyl-1,2,4-triazin-3-amine (90 mg, 0.358 mmol) and 3-(methoxymethyl)phenylboronic acid (68.4 mg, 0.412 mmol) | Mass spectroscopy: m/z 293.0 (M + H)$^+$ (ES$^+$); 291.3 (M − H)$^-$ (ES$^-$), at 3.85 min, 98.5% (method B). | (400 MHz, DMSO) δ: 3.16 (s, 3H), 4.35 (s, 2H), 7.16-7.22 (m, 1H), 7.25-7.30 (m, 2H), 7.30-7.37 (m, 3H), 7.36-7.49 (m, 5H). |
| (lxiv) | 5-(3-amino-5-phenyl-1,2,4-triazin-6-yl)-1-methylpyridin-2(1H)-one (50 mg, 0.177 mmol, 49.2%) | 6-bromo-5-phenyl-1,2,4-triazin-3-amine (90 mg, 0.358 mmol) and 1-methyl-5-(4,4,5,5-tetramethyl-1,3,2-dioxaborolan-2-yl)pyridin-2(1H)-one (97 mg, 0.412 mmol) | Mass spectroscopy: m/z 280.0 (M + H)$^+$ (ES$^+$); 278.2 (M − H)$^-$ (ES$^-$), at 2.73 min, 98.6% (method B). | (400 MHz, DMSO) δ: 3.44 (s, 3H), 6.23 (d, J 9.4, 1H), 7.03 (dd, J 9.4, 2.6, 1H), 7.33-7.50 (m, 5H), 7.51-7.57 (m, 2H), 7.97 (d, J 2.5, 1H). |
| (lxv) | 6-(3-methyl-5-(trifluoromethyl)phenyl)-5-phenyl-1,2,4-triazin-3-amine (79 mg, 0.239 mmol, 66.6%) | 6-bromo-5-phenyl-1,2,4-triazin-3-amine (90 mg, 0.358 mmol) and 3-methyl-5-(trifluoromethyl)phenylboronic acid (84 mg, 0.412 mmol) | Mass spectroscopy: m/z 331.1 (M + H)$^+$ (ES$^+$); 329.3 (M − H)$^-$ (ES$^-$), at 4.62 min, 99.8% (method B). | (400 MHz, DMSO) δ: 2.33 (s, 3H), 7.32 (s, 1H), 7.34-7.41 (m, 4H), 7.41-7.47 (m, 1H), 7.48-7.60 (m, 4H). |
| (lxvi) | 6-(2-methoxypyridin-4-yl)-5-phenyl-1,2,4-triazin-3-amine (39 mg, 39%) | 6-bromo-5-phenyl-1,2,4-triazin-3-aimine (90 mg, 0.358 mmol) and 2-methoxy-4-(4,4,5,5-tetramethyl-1,3,2-dioxaborolan-2-yl)pyridine (97 mg, 0.412 mmol) | Mass spectroscopy: m/z 280.1 (M + H)$^+$ (ES$^+$); 278.4 (M − H)$^-$ (ES$^-$), at 3.60 min, 99.4% (method B). | (400 MHz, DMSO) δ: 3.81 (s, 3H), 6.75 (dd, J 1.4, 0.7, 1H), 6.88 (dd, J 5.3, 1.5, 1H), 7.34-7.51 (m, 5H), 7.61 (s, 2H), 8.08 (dd, J 5.3, 0.7, 1H). |
| (lxvii) | 1-(3-(3-amino-5-phenyl-1,2,4-triazin-6-yl)phenyl)ethanone (71 mg, 0.243 mmol, 67.8%) | 6-bromo-5-phenyl-1,2,4-triazin-3-amine (90 mg, 0.358 mmol) and 3-acetylphenylboronic acid (67.6 mg, 0.412 mmol) | Mass spectroscopy; m/z 291.1 (M + H)$^+$ (ES$^+$); 289.3 (M − H)$^-$ (ES$^-$), at 3.62 min, 99.4% (method B). | (400 MHz, DMSO) δ: 2.46 (s, 3H), 7.32-7.52 (m, 8H), 7.52-7.57 (m, 1H), 7.87-7.93 (m, 1H), 7.93-7.98 (m, 1H). |
| (lxviii) | 4-(3-amino-5-phenyl-1,2,4-triazin-6-yl)benzamide (73 mg, 0.243 mmol, 67.7%) | 6-bromo-5-phenyl-1,2,4-triazin-3-amine (90 mg, 0.358 mmol) and 4-carbamoylphenylboronic acid (68.0 mg, 0.412 mmol) | Mass spectroscopy: m/z 292.2 (M + H)$^+$ (ES$^+$); 290.4 (M − H)$^-$ (ES$^-$), at 2.93 min, 96.9% (method B). | (400 MHz, DMSO) δ: 7.31-7.46 (m, 8H), 7.48 (s, 2H), 7.81 (d, J 8.5, 2H), 7.98 (s, 1H). |
| (lxix) | 6-(4-fluoro-3-(trifluoromethyl)phenyl)-5-phenyl-1,2,4-triazin-3-amine (83 mg, 0.244 mmol, 68.0%) | 6-bromo-5-phenyl-1,2,4-triazin-3-amine (90 mg, 0.358 mmol) and 2-(4-fluoro-3-(trifluoromethyl)phenyl)-4,4,5,5-tetramethyl-1,3,2-dioxaborolane (120 mg, 0.412 mmol) | Mass spectroscopy: m/z 335.2 (M + H)$^+$ (ES$^+$); 333.4 (M − H)$^-$ (ES$^-$), at 4.42 min, 98.2% (method B). | (400 MHz, DMSO) δ: 7.32-7.51 (m, 6H), 7.55 (s, 2H), 7.63-7.68 (m, 1H), 7.70 (dd, J 7.0, 2.1, 1H). |
| (lxx) | 6-(4-fluoro-3-methylphenyl)-5-phenyl-1,2,4-triazin-3-amine (72 mg, 0.257 mmol, 71.7%) | 6-bromo-5-phenyl-1,2,4-triazin-3-amine (90 mg, 0.358 mmol) and 4-fluoro-3-methylphenylboronic acid (63.5 mg, 0.412 mmol) | Mass spectroscopy: m/z 281.1 (M + H)$^+$ (ES$^+$); 279.3 (M − H)$^-$ (ES$^-$), at 4.32 min, 100% (method B). | (400 MHz, DMSO) δ: 2.19 (s, 3H), 7.00-7.09 (m, 2H), 7.32-7.46 (m, 8H). |
| (lxxi) | 6-(3-bromo-5-chlorophenyl)-5-phenyl-1,2,4-triazin-3-amine (30 mg, 0.083 mmol, 23.14%) | 6-bromo-5-phenyl-1,2,4-triazin-3-amine (90 mg, 0.358 mmol) and 2-(3-bromo-5-chlorophenyl)- | Mass spectroscopy: m/z (Br) 361.2/363.1/365.1 (M + H)$^+$ (ES$^+$); | (400 MHz, DMSO) δ: 7.36-7.38 (m, 1H), 7.39-7.44 (m, 4H), 7.44-7.50 (m, 2H), 7.59 (s, 2H), 7.69 (t, J |

| No. | Product (yield) | Prepared From | LCMS | NMR |
|---|---|---|---|---|
| | | 4,4,5,5-tetramethyl-1,3,2-dioxaborolane (116 mg, 0.366 mmol) | 359.3/361.3/363.3 (M − H)⁻ (ES⁻), at 5.07 min, 100% (method B). | 1.9, 1H). |
| (lxxii) | 6-(naphthalen-2-yl)-5-phenyl-1,2,4-triazin-3-amine (83 mg, 0.278 mmol, 77%) | from 6-bromo-5-phenyl-1,2,4-triazin-3-amine (90 mg, 0.358 mmol) and naphthalen-2-ylboronic acid (70.9 mg, 0.412 mmol) | Mass spectroscopy: m/z 299.2 (M + H)⁺ (ES⁺), at 4.67 min, 99.8% (method B). | (400 MHz, DMSO) δ: 7.28-7.36 (m, 3H), 7.37-7.48 (m, 5H), 7.48-7.56 (m, 2H), 7.81 (d, J 8.7, 1H), 7.83-7.92 (m, 2H), 8.02 (s, 1H). |
| (lxxiii) | 5-phenyl-6-m-tolyl-1,2,4-triazin-3-amine (73.4 mg, 0.278 mmol, 78%) | 6-bromo-5-phenyl-1,2,4-triazin-3-amine (90 mg, 0.358 mmol) and m-tolylboronic acid (56.0 mg, 0.412 mmol) | Mass spectroscopy: m/z 263.2 (M + H)⁺ (ES⁺); 261.3 (M − H)⁻ (ES⁻), at 4.43 min, 99.4% (method B). | (400 MHz, DMSO) δ: 2.26 (s, 3H), 6.97-7.02 (m, 1H), 7.11-7.20 (m, 2H), 7.26 (s, 1H), 7.30-7.45 (m, 7H). |
| (lxxiv) | 5-phenyl-6-(pyridin-4-yl)-1,2,4-triazin-3-amine (16 mg, 0.064 mmol, 17.78%) | 6-bromo-5-phenyl-1,2,4-triazin-3-amine (90 mg, 0.358 mmol) and pyridin-4-ylboronic acid (50.7 mg, 0.412 mmol) | Mass spectroscopy: m/z 250.2 (M + H)⁺ (ES⁺); 248.3 (M − H)⁻ (ES⁻), at 3.34 min, 99.3% (method B). | (400 MHz, DMSO) δ: 7.32 (dd, J 4.4, 1.7, 2H), 7.34-7.43 (m, 4H), 7.43-7.50 (m, 1H), 7.63 (s, 2H), 8.51 (dd, J 4.5, 1.6, 2H). |
| (lxxv) | 4-(3-amino-5-phenyl-1,2,4-triazin-6-yl)phenol (21 mg, 0.078 mmol, 21.81%) | 6-bromo-5-phenyl-1,2,4-triazin-3-amine (90 mg, 0.358 mmol) and 4-(4,4,5,5-tetramethyl-1,3,2-dioxaborolan-2-yl)phenol (91 mg, 0.412 mmol) | Mass spectroscopy: m/z 265.1 (M + H)⁺ (ES⁺); 263.4 (M − H)⁻ (ES⁻), at 2.77 min, 98.4% (method B). | (400 MHz, DMSO) δ: 6.69 (d, J 8.7, 2H), 7.12 (d, J 8.6, 2H), 7.26 (s, 2H), 7.31-7.44 (m, 5H), 9.59 (s, 1H). |
| (lxxvi) | 6-(2,6-dimethoxypyridin-4-yl)-5-phenyl-1,2,4-triazin-3-amine (61 mg, 0.196 mmol, 54.8%) | 6-bromo-5-phenyl-1,2,4-triazin-3-amine (90 mg, 0.358 mmol) and 2,6-dimethoxy-4-(4,4,5,5-tetramethyl-1,3,2-dioxaborolan-2-yl)pyridine (109 mg, 0.412 mmol) | Mass spectroscopy: m/z 310.2 (M + H)⁺ (ES⁺); 308.4 (M − H)⁻ (ES⁻), at 4.27 min, 99.6% (method B). | (400 MHz, DMSO) δ: 3.79 (s, 6H), 6.29 (s, 2H), 7.35-7.49 (m, 5H), 7.58 (s, 2H). |
| (lxxvii) | 6-(2,6-dimethylpyridin-4-yl)-5-phenyl-1,2,4-triazin-3-amine (44 mg, 0.154 mmol, 42.8%) | from 6-bromo-5-phenyl-1,2,4-triazin-3-amine (90 mg, 0.358 mmol) and 2,6-dimethyl-4-(4,4,5,5-tetramethyl-1,3,2-dioxaborolan-2-yl)pyridine (96 mg, 0.412 mmol) | Mass spectroscopy: m/z 278.2 (M + H)⁺ (ES⁺); 276.4 (M − H)⁻ (ES⁻), at 3.77 min, 96.8% (method B). | (400 MHz, DMSO) δ: 2.33 (s, 6H), 6.97 (s, 2H), 7.35-7.43 (m, 4H), 7.43-7.50 (m, 1H), 7.58 (s, 2H). |
| (lxxviii) | 5-phenyl-6-(2-(trifluoromethyl)pyridin-4-yl)-1,2,4-triazin-3-amine (31 mg, 0.098 mmol, 27.3%) | 6-bromo-5-phenyl-1,2,4-triazin-3-amine (90 mg, 0.358 mmol) and 2-(trifluoromethyl)pyridin-4-ylboronic acid (79 mg, 0.412 mmol) | Mass spectroscopy: m/z 318.2 (M + H)⁺ (ES⁺); 316.4 (M − H)⁻ (ES⁻), at 4.03 min, 100% (method B). | (400 MHz, DMSO) δ: 7.37-7.45 (m, 4H), 7.46-7.53 (m, 1H), 7.63 (dd, J 5.0, 1.2, 1H), 7.75 (s, 1H), 7.77 (s, 2H), 8.70 (d, J 5.1, 1H). |
| (lxxix) | 6-(2-cyclopropylpyridin-4-yl)-5-phenyl-1,2,4-triazin-3-amine (61 mg, 0.206 mmol, 57.3%) | 6-bromo-5-phenyl-1,2,4-triazin-3-amine (90 mg, 0.358 mmol) and 2-cyclopropyl-4-(4,4,5,5-tetramethyl-1,3,2-dioxaborolan-2-yl)pyridine (101 mg, 0.412 mmol) | Mass spectroscopy: m/z 290.1 (M + H)⁺ (ES⁺); 288.4 (M − H)⁻ (ES⁻), at 3.92 min, 97.5% (method B). | (400 MHz, DMSO) δ: 0.76-0.83 (m, 2H), 0.87-0.93 (m, 2H), 1.96-2.06 (m, 1H), 6.97 (dd, J 5.1, 1.7, 1H), 7.25 (dd, J 1.6, 0.8, 1H), 7.35-7.44 (m, 4H), 7.44-7.51 (m, 1H), 7.60 (s, 2H), 8.28 (dd, J 5.1, 0.6, 1H). |
| (lxxx) | 5-phenyl-6-(2,2,6,6-tetramethyl-3,6-dihydro-2H-pyran-4-yl)-1,2,4-triazin-3-amine (85 mg, 0.269 mmol, 75%) | 6-bromo-5-phenyl-1,2,4-triazin-3-amine (90 mg, 0.358 mmol) and 4,4,5,5-tetramethyl-2-(2,2,6,6-tetramethyl-3,6-dihydro-2H-pyran-4-yl)-1,3,2-dioxaborolane (110 mg, 0.412 mmol) | Mass spectroscopy: m/z 311.2 (M + H)⁺ (ES⁺); 309.4 (M − H)⁻ (ES⁻), at 4.40 min, 98.2% (method B). | (400 MHz, DMSO) δ: 1.01 (s, 6H), 1.16 (s, 6H), 2.28 (d, J 1.3, 2H), 5.46 (t, J 1.4, 1H), 7.29 (s, 2H), 7.43-7.50 (m, 3H), 7.56-7.61 (m, 2H). |

| No. | Product (yield) | Prepared From | LCMS | NMR |
|---|---|---|---|---|
| (lxxxi) | 6-(5-chloro-2-fluoro-3-methylphenyl)-5-phenyl-1,2,4-triazin-3-amine (10 mg, 0.031 mmol, 8.64%) | 6-bromo-5-phenyl-1,2,4-triazin-3-amine (90 mg, 0.358 mmol) and 5-chloro-2-fluoro-3-methylphenylboronic acid (78 mg, 0.412 mmol) | Mass spectroscopy: m/z (Cl) 315.8/317.8 (M + H)+ (ES+), at 4.67 min, 97.5% (method B). | (400 MHz, DMSO) δ: 2.07 (d, J 1.9, 3H), 7.33-7.47 (m, 6H), 7.50 (dd, J 5.9, 2.8, 1H), 7.60 (s, 2H). |
| (lxxxii) | 6-(2,6-dichloropyridin-4-yl)-5-phenyl-1,2,4-triazin-3-amine (7 mg, 0.022 mmol, 2.205%) | 6-bromo-5-phenyl-1,2,4-triazin-3-amine (250 mg, 0.996 mmol) and 2,6-dichloro-4-(4,4,5,5-tetramethyl-1,3,2-dioxaborolan-2-yl)pyridine (286 mg, 1.045 mmol) | Mass spectroscopy: m/z (2 Cl) 318.0/320.1/322.1 (M + H)+ (ES+); 316.3/318.2/320.2 (M − H)− (ES−), at 4.34 min, 94.8% (method B). | (400 MHz, DMSO) δ: 7.41-7.48 (m, 6H), 7.48-7.55 (m, 1H), 7.85 (s, 2H). |
| (lxxxiii) | 6-(3-bromo-5-(trifluoromethoxy)phenyl)-5-phenyl-1,2,4-triazin-3-amine (23 mg, 0.055 mmol, 16.47%) | 6-iodo-5-phenyl-1,2,4-triazin-3-amine (100 mg, 0.335 mmol) and 3-bromo-5-(trifluoromethoxy)phenylboronic acid (119 mg, 0.419 mmol) | Mass spectroscopy: m/z (Br) 411.8/413.8 (M + H)+ (ES+): 410.0/412.0 (M − H)− (ES−), at 5.15 min, 98.8% (method B). | (400 MHz, DMSO) δ: 7.14-7.19 (m, 1H), 7.36-7.42 (m, 4H), 7.42-7.49 (m, 1H), 7.57-7.66 (m, 2H), 7.63-7.66 (m, 1H), 7.67-7.70 (m, 1H). |
| (lxxxiv) | 4-(3-amino-5-phenyl-1,2,4-triazin-6-yl)-2-chloro-6-methoxyphenol (72 mg, 0.215 mmol, 28.4%) | 6-bromo-5-phenyl-1,2,4-triazin-3-amine (90 mg, 0.358 mmol) and 2-chloro-6-methoxy-4-(4,4,5,5-tetramethyl-1,3,2-dioxaborolan-2-yl)phenol (248 mg, 0.870 mmol) | Mass spectroscopy: m/z (Cl) 329.0/331.1 (M + H)+ (ES+); 327.2/329.0 (M − H)− (ES−), at 2.61 min, 98.2% (method B). | (400 MHz, DMSO) δ: 3.58 (s, 3H), 6.80 (d, J 2.0, 1H), 6.92 (d, J 2.0, 1H), 7.34-7.47 (m, 7H), 9.62 (s, 1H). |
| (lxxxv) | 6-(3,5-dichloro-4-ethoxyphenyl)-5-phenyl-1,2,4-triazin-3-amine (81 mg, 0.214 mmol, 59.8%) | 6-bromo-5-phenyl-1,2,4-triazin-3-amine (90 mg, 0.358 mmol) and 2-(3,5-dichloro-4-ethoxyphenyl)-4,4,5,5-tetramethyl-1,3,2-dioxaborolane (131 mg, 0.412 mmol) | Mass spectroscopy: m/z (2 Cl) 361.8/363.9 (M + H)+ (ES+); 360.1/362.1 (M − H)− (ES−), at 5.02 min, 95.6% (method B). | (400 MHz, DMSO) δ: 1.36 (t, J 7.0, 3H), 4.05 (q, J 7.0, 2H), 7.36-7.50 (m, 7H), 7.55 (s, 2H). |
| (lxxxvi) | 6-(6-amino-5-(trifluoromethyl)pyridin-3-yl)-5-phenyl-1,2,4-triazin-3-amine (30 mg, 0.089 mmol, 24.78%) | 6-bromo-5-phenyl-1,2,4-triazin-3-amine (90 mg, 0.358 mmol) and 5-(4,4,5,5-tetramethyl-1,3,2-dioxaborolan-2-yl)-3-(trifluoromethyl)pyridin-2-amine (119 mg, 0.412 mmol) | Mass spectroscopy: m/z 333.7 (M + H)+ (ES+); 331.8 (M − H)− (ES−), at 3.80 min, 98.4% (method B). | (400 MHz, DMSO) δ: 6.66 (s, 2H), 7.32-7.50 (m, 7H), 7.62-7.67 (m, 1H), 8.01-8.09 (m, 1H). |
| (lxxxvii) | 4-(3-amino-5-(3-fluorophenyl)-1,2,4-triazin-6-yl)-2,6-dimethylbenzonitrile (70 mg, 0.219 mmol, 65.5%) | 6-bromo-5-(3-fluorophenyl)-1,2,4-triazin-3-amine (90 mg, 0.334 mmol) and 2,6-dimethyl-4-(4,4,5,5-tetramethyl-1,3,2-dioxaborolan-2-yl)benzonitrile (99 mg, 0.385 mmol) | Mass spectroscopy: m/z 320.9 (M + H)+ (ES+); 319.1 (M − H)− (ES−), at 4.37 min, 99.9% (method B). | (400 MHz, DMSO) δ: 2.39 (s, 6H), 7.11-7.17 (m, 1H), 7.25 (s, 2H), 7.26-7.35 (m, 2H), 7.37-7.44 (m, 1H), 7.64 (s, 2H). |
| (lxxxviii) | 6-(3-chloro-5-(trifluoromethyl)phenyl)-5-(3-fluorophenyl)-1,2,4-triazin-3-amine (54 mg, 0.141 mmol, 42.1%) | 6-bromo-5-phenyl-1,2,4-triazin-3-amine (90 mg, 0.358 mmol) and 2-(3-chloro-5-(trifluoromethyl)phenyl)-4,4,5,5-tetramethyl-1,3,2-dioxaborolane (118 mg, 0.385 mmol) | Mass spectroscopy: m/z (Cl) 369.8/371.9 (M + H)+ (ES+); 368.0/370.0 (M − H)− (ES−), at 4.99 min, 96.1% (method B). | (400 MHz, DMSO) δ: 7.15-7.21 (m, 1H), 7.25-7.36 (m, 2H), 7.39-7.46 (m, 1H), 7.55-7.60 (m, 1H), 7.70 (s, 2H), 7.73-7.77 (m, 1H), 7.84-7.88 (m, 1H). |
| (lxxxix) | 6-(2-chloropyridin-4-yl)-5-(3-fluorophenyl)-1,2,4-triazin-3-amine (28 | 6-bromo-5-phenyl-1,2,4-triazin-3-amine (90 mg, 0.358 mmol) and 2-chloro-4- | Mass spectroscopy: m/z (Cl) 302.8/304.8 (M + H)+ (ES+); | (400 MHz, DMSO) δ: 7.16-7.23 (m, 1H), 7.27-7.38 (m, 3H), 7.41-7.48 (m, 1H), |

| No. | Product (yield) | Prepared From | LCMS | NMR |
| --- | --- | --- | --- | --- |
| | mg, 0.090 mmol, 26.9%) | (4,4,5,5-tetramethyl-1,3,2-dioxaborolan-2-yl)pyridine (92 mg, 0.385 mmol) | 301.0/303.0 (M − H)− (ES−), at 3.87 min, 97.1% (method B). | 7.49 (dd, J 1.5, 0.7, 1H), 7.80 (s, 2H), 8.35 (dd, J 5.2, 0.7, 1H). |
| (xc) | 6-(2-chloro-6-methylpyridin-4-yl)-5-(3-fluorophenyl)-1,2,4-triazin-3-amine (54 mg, 0.171 mmol, 51.1%) | 6-bromo-5-(3-fluorophenyl)-1,2,4-triazin-3-amine (90 mg, 0.334 mmol) and 2-chloro-6-methyl-4-(4,4,5,5-tetramethyl-1,3,2-dioxaborolan-2-yl)pyridine (98 mg, 0.385 mmol) | Mass spectroscopy: m/z (Cl) 316.6/318.6 (M + H)+ (ES+); 314.8/316.8 (M − H)− (ES−), at 4.05 min, 99.9% (method B). | (400 MHz, DMSO) δ: 2.40 (s, 3H), 7.13-7.16 (m, 1H), 7.16-7.21 (m, 1H), 7.27-7.29 (m, 1H), 7.29-7.39 (m, 2H), 7.40-7.48 (m, 1H), 7.78 (s, 2H). |
| (xci) | 4-(3-amino-5-(4-fluorophenyl)-1,2,4-triazin-6-yl)-2,6-dimethylbenzonitrile (66 mg, 0.206 mmol, 61.7%) | 6-bromo-5-(4-fluorophenyl)-1,2,4-triazin-3-amine (90 mg, 0.334 mmol) and 2,6-dimethyl-4-(4,4,5,5-tetramethyl-1,3,2-dioxaborolan-2-yl)benzonitrile (99 mg, 0.385 mmol) | Mass spectroscopy: m/z 320.7 (M + H)+ (ES+); 318.9 (M − H)− (ES−), at 4.40 min, 99.8% (method B). | (400 MHz, DMSO) δ: 2.39 (s, 6H), 7.19-7.28 (m, 4H), 7.46 (dd, J 8.8, 5.5, 2H), 7.59 (s, 2H). |
| (xcii) | 6-(3-chloro-5-propoxyphenyl)-5-phenyl-1,2,4-triazin-3-amine (71 mg, 0.202 mmol, 56.3%) | 6-bromo-5-phenyl-1,2,4-triazin-3-amine (90 mg, 0.358 mmol) and 2-(3-chloro-5-propoxyphenyl)-4,4,5,5-tetramethyl-1,3,2-dioxaborolane (106 mg, 0.358 mmol) | Mass spectroscopy: m/z (Cl) 341.6/343.6 (M + H)+ (ES+); 339.8/341.8 (M − H)− (ES−), at 5.14 min, 96.9% (method B). | (400 MHz, DMSO) δ: 0.88 (t, J 7.4, 3H), 1.52-1.64 (m, 2H), 3.80 (t, J 6.6, 2H), 6.75-6.80 (m, 1H), 6.94-6.99 (m, 2H), 7.35-7.47 (m, 5H), 7.50 (s, 2H). |
| (xciii) | 6-(3-chloro-5-(trifluoromethyl)phenyl)-5-(4-fluorophenyl)-1,2,4-triazin-3-amine (65 mg, 0.169 mmol, 50.5%) | 6-bromo-5-(4-fluorophenyl)-1,2,4-triazin-3-amine (90 mg, 0.334 mmol) and 2-(3-chloro-5-(trifluoromethyl)phenyl)-4,4,5,5-tetramethyl-1,3,2-dioxaborolane (118 mg, 0.385 mmol) | Mass spectroscopy: m/z (Cl) 369.4/371.5 (M + H)+ (ES+); 367.7/369.7 (M − H)− (ES−), at 5.03 min, 95.8% (method B). | (400 MHz, DMSO) δ: 7.25 (t, J 8.9, 2H), 7.47 (dd, J 8.8, 5.5, 2H), 7.57 (s, 1H), 7.64 (s, 2H), 7.74 (s, 1H), 7.84 (s, 1H). |
| (xciv) | 6-(2-chloropyridin-4-yl)-5-(4-fluorophenyl)-1,2,4-triazin-3-amine (14 mg, 0.046 mmol, 13.76%) | 6-bromo-5-(4-fluorophenyl)-1,2,4-triazin-3-amine (90 mg, 0.334 mmol) and 2-chloro-4-(4,4,5,5-tetramethyl-1,3,2-dioxaborolan-2-yl)pyridine (92 mg, 0.385 mmol) | Mass spectroscopy: m/z (Cl) 302.7/304.7 (M + H)+ (ES+); 300.9/302.9 (M − H)− (ES−), at 3.90 min, 99.2% (method B). | (400 MHz, DMSO) δ: 7.21-7.33 (m, 3H), 7.44-7.53 (m, 3H), 7.75 (s, 2H), 8.35 (d, J 5.1, 1H). |
| (xcv) | 6-(2-chloro-6-methylpyridin-4-yl)-5-(4-fluorophenyl)-1,2,4-triazin-3-amine (37 mg, 0.117 mmol, 34.9%) | 6-bromo-5-(4-fluorophenyl)-1,2,4-triazin-3-amine (90 mg, 0.334 mmol) and 2-chloro-6-methyl-4-(4,4,5,5-tetramethyl-1,3,2-dioxaborolan-2-yl)pyridine (98 mg, 0.385 mmol) | Mass spectroscopy: m/z (Cl) 316.7/318.7 (M + H)+ (ES+); 314.9/316.9 (M − H)− (ES−), at 4.05 min, 99.5% (method B). | (400 MHz, DMSO) δ: 2.40 (s, 3H), 7.15 (s, 1H), 7.23-7.31 (m, 3H), 7.48 (dd, J 8.9, 5.5, 2H), 7.72 (s, 2H). |
| (xcvi) | 4-(3-amino-5-(4-chlorophenyl)-1,2,4-triazin-6-yl)-2,6-dimethylbenzonitrile (61 mg, 0.181 mmol, 57.4%) | 6-bromo-5-(4-chlorophenyl)-1,2,4-triazin-3-amine (90 mg, 0.315 mmol) and 2,6-dimethyl-4-(4,4,5,5-tetramethyl-1,3,2-dioxaborolan-2-yl)benzonitrile (81 mg, 0.315 mmol) | Mass spectroscopy: m/z (Cl) 336.6/338.6 (M + H)+ (ES+); 334.8/336.8 (M − H)− (ES−), at 4.67 min, 99.6% (method B). | (400 MHz, DMSO) δ: 2.40 (s, 6H), 7.25 (s, 2H), 7.40-7.50 (m, 4H), 7.61 (s, 2H). |
| (xcvii) | 6-(3-chloro-5-(trifluoromethyl)phenyl)-5-(4-chlorophenyl)-1,2,4-triazin-3-amine (62.5 | 6-bromo-5-(4-chlorophenyl)-1,2,4-triazin-3-amine (90 mg, 0.315 mmol) and 2-(3-chloro-5- | Mass spectroscopy: m/z (2 Cl) 385.3/387.4 (M + H)+ (ES+); 383.5/385.5 (M − H)− | (400 MHz, DMSO) δ: 7.40-7.51 (m, 4H), 7.59 (s, 1H), 7.67 (s, 2H), 7.74 (s, 1H), 7.85 (s, 1H). |

| No. | Product (yield) | Prepared From | LCMS | NMR |
|---|---|---|---|---|
| | mg, 0.157 mmol, 49.7%) | (trifluoromethyl)phenyl)-4,4,5,5-tetramethyl-1,3,2-dioxaborolane (111 mg, 0.362 mmol) | (ES⁻), at 5.25 min, 96.6% (method B). | |
| (xcviii) | 5-(4-chlorophenyl)-6-(2-chloropyridin-4-yl)-1,2,4-triazin-3-amine (12.7 mg, 0.039 mmol, 12.44%) | 6-bromo-5-(4-chlorophenyl)-1,2,4-triazin-3-amine (90 mg, 0.315 mmol) and 2-chloro-4-(4,4,5,5-tetramethyl-1,3,2-dioxaborolan-2-yl)pyridine (87 mg, 0.362 mmol) | Mass spectroscopy: m/z (2 Cl) 318.6/320.6 (M + H)⁺ (ES⁺); 316.8/318.8 (M − H)⁻ (ES⁻), at 4.22 min, 98.2% (method B). | (400 MHz, DMSO) δ: 7.27 (dd, J 5.2, 1.5, 1H), 7.41-7.54 (m, 5H), 7.77 (s, 2H), 8.35 (dd, J 5.2, 0.6, 1H). |
| (xcix) | 6-(2-chloro-6-methylpyridin-4-yl)-5-(4-chlorophenyl)-1,2,4-triazin-3-amine (46.1 mg, 0.138 mmol, 43.9%) | 6-bromo-5-(4-chlorophenyl)-1,2,4-triazin-3-amine (90 mg, 0.315 mmol) and 2-chloro-6-methyl-4-(4,4,5,5-tetramethyl-1,3,2-dioxaborolan-2-yl)pyridine (92 mg, 0.362 mmol) | Mass spectroscopy: m/z (2 Cl) 332.5/334.6 (M + H)⁺ (ES⁺); 330.8/332.7 (M − H)⁻ (ES⁻), at 4.37 min, 99.6% (method B). | (400 MHz, DMSO) δ: 2.41 (s, 3H), 7.14-7.18 (m, 1H), 7.27-7.31 (m, 1H), 7.42-7.54 (m, 4H), 7.74 (s, 2H). |
| (c) | 4-(3-amino-5-(3-chlorophenyl)-1,2,4-triazin-6-yl)-2,6-dimethylbenzonitrile (64.3 mg, 0.190 mmol, 60.3%) | 6-bromo-5-(3-chlorophenyl)-1,2,4-triazin-3-amine (90 mg, 0.315 mmol) and 2,6-dimethyl-4-(4,4,5,5-tetramethyl-1,3,2-dioxaborolan-2-yl)benzonitrile (81 mg, 0.315 mmol) | Mass spectroscopy: m/z (Cl) 336.6/338.6 (M + H)⁺ (ES⁺); 334.8/336.8 (M − H)⁻ (ES⁻), at 4.59 min, 99.3% (method B). | (400 MHz, DMSO) δ: 2.40 (s, 6H), 7.20 (ddd, J 7.8, 1.6, 1.0, 1H), 7.26 (s, 2H), 7.9, 1H), 7.53 (ddd, J 8.0, 2.2, 1.0, 1H), 7.59 (app t, J 1.7, 1H), 7.64 (s, 2H). |
| (ci) | 6-(3-chloro-5-(trifluoromethyl)phenyl)-5-(3-chlorophenyl)-1,2,4-triazin-3-amine (67.6 mg, 0.169 mmol. 53.7%) | 6-bromo-5-(3-chlorophenyl)-1,2,4-triazin-3-amine (90 mg, 0.315 mmol) and 2-(3-chloro-5-(trifluoromethyl)phenyl)-4,4,5,5-tetramethyl-1,3,2-dioxaborolane (111 mg, 0.362 mmol) | Mass spectroscopy: m/z (2 Cl) 385.3/387.4 (M + H)⁺ (ES⁺); 383.5/385.6 (M − H)⁻ (ES⁻), at 5.20 min, 96.4% (method B). | (400 MHz, DMSO) δ: 7.24-7.29 (m, 1H), 7.39 (app td, J 7.8, 0.6, 1H), 7.51-7.57 (m, 2H), 7.57-7.61 (m, 1H), 7.69 (s, 2H), 7.75-7.79 (m, 1H), 7.84-7.88 (m, 1H). |
| (cii) | 5-(3-chlorophenyl)-6-(2-chloropyridin-4-yl)-1,2,4-triazin-3-amine (32.4 mg, 0.101 mmol, 32.0%) | 6-bromo-5-(3-chlorophenyl)-1,2,4-triazin-3-amine (90 mg, 0.315 mmol) and 2-chloro-4-(4,4,5,5-tetramethyl-1,3,2-dioxaborolan-2-yl)pyridine (87 mg, 0.362 mmol) | Mass spectroscopy: m/z (2 Cl) 318.6/320.6 (M + H)⁺ (ES⁺); 316.8/318.8 (M − H)⁻ (ES⁻), at 4.17 min, 99.0% (method B). | (400 MHz, DMSO) δ: 7.25-7.29 (m, 1H), 7.31 (dd, J 5.2, 1.5, 1H), 7.40 (app t, J 11.9, 1H), 7.49-7.53 (m, 1H), 7.54-7.61 (m, 2H), 7.80 (s, 2H), 8.36 (dd, J 5.2, 0.6, 1H). |
| (ciii) | 6-(2-chloro-6-methylpyridin-4-yl)-5-(3-chlorophenyl)-1,2,4-triazin-3-amine (51.3 mg, 0.154 mmol, 49.0%) | 6-bromo-5-(3-chlorophenyl)-1,2,4-triazin-3-amine (90 mg, 0.315 mmol) and 2-chloro-6-methyl-4-(4,4,5,5-tetramethyl-1,3,2-dioxaborolan-2-yl)pyridine (92 mg, 0.362 mmol) | Mass spectroscopy: m/z (2 Cl) 332.5/334.6 (M + H)⁺ (ES⁺); 330.8/332.7 (M − H)⁻ (ES⁻), at 4.30 min, 100% (method B). | (400 MHz, DMSO) δ: 2.41 (s, 3H), 7.19-7.15 (m, 1H), 7.26 (ddd, J 7.8, 1.6, 1.1, 1H), 7.33-7.29 (m, 1H), 7.41 (app t, J 7.9, 1H), 7.57 (ddd, J 8.0, 2.2, 1.0, 1H), 7.60 (app t, J 1.7, 1H), 7.78 (s, 2H). |
| (civ) | 4-(3-amino-6-(3-chloro-5-(trifluoromethyl)phenyl)-1,2,4-triazin-5-yl)benzonitrile (64.7 mg, 0.171 mmol, 52.5%) | 4-(3-amino-6-bromo-1,2,4-triazin-5-yl)benzonitrile (90 mg, 0.326 mmol) and 2-(3-chloro-5-(trifluoromethyl)phenyl)-4,4,5,5-tetramethyl-1,3,2-dioxaborolane (115 mg, 0.375 mmol) | Mass spectroscopy: m/z (Cl) 376.4/378.4 (M + H)⁺ (ES⁺); 374.6/376.6 (M − H)⁻ (ES⁻), at 4.67 min, 99.4% (method B). | (400 MHz, DMSO) δ: 7.54-7.58 (m, 1H), 7.57-7.62 (m, 2H), 7.65-7.81 (m, 3H), 7.83-7.87 (m, 1H), 7.87-7.93 (m, 2H). |
| (cv) | 4-(3-amino-6-(2-chloro-6-methylpyridin-4-yl)-1,2,4-triazin-5-yl)benzonitrile (30.5 | 4-(3-amino-6-bromo-1,2,4-triazin-5-yl)benzonitrile (90 mg, 0.326 mmol) and 2-chloro-6- | Mass spectroscopy: m/z (Cl) 323.6/325.6 (M + H)⁺ (ES⁺); 321.8/323.8 (M − H)⁻ | (400 MHz, DMSO) δ: 2.40 (s, 3H), 7.16 (s, 1H), 7.26 (s, 1H), 7.58-7.64 (m, 2H), 7.82 (s, 2H), 7.88- |

| No. | Product (yield) | Prepared From | LCMS | NMR |
|---|---|---|---|---|
| | mg, 0.093 mmol, 28.6%) | methyl-4-(4,4,5,5-tetramethyl-1,3,2-dioxaborolan-2-yl)pyridine (95 mg, 0.375 mmol) | (ES$^-$), at 3.65 min, 98.6% (method B). | 7.94 (m, 2H). |
| (cvi) | 4-(3-amino-5-(3-chloro-5-fluorophenyl)-1,2,4-triazin-6-yl)-2,6-dimethylbenzonitrile (57 mg, 52%) | 6-bromo-5-(3-chloro-5-fluorophenyl)-1,2,4-triazin-3-amine (90 mg, 0.297 mmol) and 2,6-dimethyl-4-(4,4,5,5-tetramethyl-1,3,2-dioxaborolan-2-yl)benzonitrile (88 mg, 0.341 mmol) | Mass spectroscopy: m/z 354, 356 (M + H)$^+$ (ES$^+$); 352, 354 (M − H)$^-$ (ES$^-$), at 4.72 min, 95% (method B). | (400 MHz, DMSO) δ: 2.41 (s, 6H), 7.11-7.19 (m, 1H), 7.27 (s, 2H), 7.34-7.38 (m, 1H), 7.55-7.62 (m, 1H), 7.70 (s, 2H). |
| (cvii) | 5-(3-chloro-5-fluorophenyl)-6-(2-chloro-6-methylpyridin-4-yl)-1,2,4-triazin-3-amine (18 mg, 16%) | 6-bromo-5-(3-chloro-5-fluorophenyl)-1,2,4-triazin-3-amine (90 mg, 0.297 mmol) and 2-chloro-6-methylpyridin-4-ylboronic acid (58.4 mg, 0.341 mmol) | Mass spectroscopy: m/z 350, 352 (M + H)$^+$ (ES$^+$); 348, 350 (M − H)$^-$ (ES$^-$), at 4.2 min, 95% (method B). | (400 MHz, DMSO) δ: 2.42 (s, 3H), 7.19 (s, 1H), 7.20-7.26 (m, 1H), 7.30 (s, 1H), 7.38 (s, 1H), 7.58-7.66 (m, 1H), 7.84 (s, 2H). |
| (cviii) | 6-(3-chloro-5-(trifluoromethyl)phenyl)-5-(3-chloro-5-fluorophenyl)-1,2,4-triazin-3-amine (28 mg, 22%) | 6-bromo-5-(3-chloro-5-fluorophenyl)-1,2,4-triazin-3-amine (90 mg, 0.297 mmol) and 2-(3-chloro-5-(trifluoromethyl)phenyl)-4,4,5,5-tetramethyl-1,3,2-dioxaborolane (105 mg, 0.341 mmol) | Mass spectroscopy: m/z 403, 405 (M + H)$^+$ (ES$^+$); 401, 403 (M − H)$^-$ (ES$^-$), at 5.28 min, 93% (method B). | (400 MHz, DMSO) δ: 7.22 (ddd, J 9.3, 2.4, 1.4, 1H), 7.34-7.39 (m, 1H), 7.58-7.64 (m, 2H), 7.76 (s, 2H), 7.79 (s, 1H), 7.89 (s, 1H). |
| (cix) | 6-(3-chloro-5-(trifluoromethyl)phenyl)-5-(3,5-difluorophenyl)-1,2,4-triazin-3-amine (54 mg, 43%) | 6-bromo-5-(3,5-difluorophenyl)-1,2,4-triazin-3-amine (90 mg, 0.314 mmol) and 2-(3-chloro-5-(trifluoromethyl)phenyl)-4,4,5,5-tetramethyl-1,3,2-dioxaborolane (96 mg, 0.314 mmol) | Mass spectroscopy: m/z 387, 389 (M + H)$^+$ (ES$^+$); 385, 387 (M − H)$^-$ (ES$^-$), at 5.09 min, 96% (method B). | (400 MHz, DMSO) δ: 7.08-7.20 (m, 2H), 7.42 (tt, J 9.3, 2.4, 1H), 7.58 (s, 1H), 7.66-7.86 (m, 3H), 7.89 (s, 1H). |
| (cx) | 6-(2-chloro-6-methylpyridin-4-yl)-5-(3,5-difluorophenyl)-1,2,4-triazin-3-amine (29 mg, 27%) | 6-bromo-5-(3,5-difluorophenyl)-1,2,4-triazin-3-amine (90 mg, 0.314 mmol) and 2-chloro-6-methylpyridin-4-ylboronic acid (61.8 mg, 0.361 mmol) | Mass spectroscopy: m/z 334, 336 (M + H)$^+$ (ES$^+$); 332, 334 (M − H)$^-$ (ES$^-$), at 4.17 min, 98% (method B). | (400 MHz, DMSO) δ: 2.42 (s, 3H), 7.11-7.18 (m, 1H), 7.17-7.20 (m, 1H), 7.25-7.31 (m, 1H), 7.44 (tt, J 9.3, 2.4, 1H), 7.82 (s, 2H). |
| (cxi) | 4-(3-amino-5-(3,5-difluorophenyl)-1,2,4-triazin-6-yl)-2,6-dimethylbenzonitrile (48 mg, 45%) | 6-bromo-5-(3,5-difluorophenyl)-1,2,4-triazin-3-amine (90 mg, 0.314 mmol) and 2,6-dimethyl-4-(4,4,5,5-tetramethyl-1,3,2-dioxaborolan-2-yl)benzonitrile (93 mg, 0.361 mmol) | Mass spectroscopy: m/z 338 (M + H)$^+$ (ES$^+$); 336 (M − H)$^-$ (ES$^-$), at 4.45 min, 100% (method B). | (400 MHz, DMSO) δ: 2.41 (s, 6H), 7.05-7.14 (m, 2H), 7.26 (s, 2H), 7.40 (tt, J 9.3, 2.4, 1H), 7.69 (s, 2H). |
| (cxii) | 4-(3-amino-5-(3-chloro-4-fluorophenyl)-1,2,4-triazin-6-yl)-2,6-dimethylbenzonitrile (35 mg, 33%) | 6-bromo-5-(3-chloro-4-fluorophenyl)-1,2,4-triazin-3-amine (90 mg, 0.297 mmol) and 2,6-dimethyl-4-(4,4,5,5-tetramethyl-1,3,2-dioxaborolan-2-yl)benzonitrile (88 mg, 0.341 mmol) | Mass spectroscopy: m/z 354, 356 (M + H)$^+$ (ES$^+$); 352, 354 (M − H)$^-$ (ES$^-$), at 4.67 min, 98% (method B). | (400 MHz, DMSO) δ: 2.41 (s, 6H), 7.22-7.28 (m, 1H), 7.28 (s, 2H), 7.37-7.44 (m, 1H), 7.66 (s, 2H), 7.75 (dd, J 7.2, 2.2, 1H). |
| (cxiii) | 5-(3-chloro-4-fluorophenyl)-6-(2-chloro-6-methylpyridin-4-yl)-1,2,4-triazin-3-amine (40 mg, 38%) | 6-bromo-5-(3-chloro-4-fluorophenyl)-1,2,4-triazin-3-amine (90 mg, 0.297 mmol) and 2-chloro-6-methylpyridin-4-ylboronic acid (61.8 mg, 0.361 mmol) | Mass spectroscopy: m/z 350, 352 (M + H)$^+$ (ES$^+$); 348, 350 (M − H)$^-$ (ES$^-$), at 4.39 min, 99% (method B). | (400 MHz, DMSO) δ: 2.42 (s, 3H), 7.21 (s, 1H), 7.30 (s, 1H), 7.30-7.35 (m, 1H), 7.46 (app t, J 8.9, 1H), 7.66-7.91 (m, 3H). |

-continued

| No. | Product (yield) | Prepared From | LCMS | NMR |
|---|---|---|---|---|
| (cxiv) | 5-(3-chloro-4-fluorophenyl)-6-(2-chloropyridin-4-yl)-1,2,4-triazin-3-amine (9 mg, 9%) | 6-bromo-5-(3,5-difluorophenyl)-1,2,4-triazin-3-amine (90 mg, 0.314 mmol) and 2-chloropyridin-4-ylboronic acid (61.8 mg, 0.361 mmol) | Mass spectroscopy: m/z 336, 338 (M + H)$^+$ (ES$^+$); 334, 336 (M − H)$^-$ (ES$^-$), at 4.2 min, 98% (method B). | (400 MHz, DMSO) δ: 7.30 (dd, J 5.2, 1.5, 1H), 7.34 (ddd, J 8.6, 4.7, 2.2, 1H), 7.42-7.51 (m, 1H), 7.53-7.57 (m, 1H), 7.75 (dd, J 7.2, 2.1, 1H), 7.82 (s, 2H), 8.37 (dd, J 5.2, 0.6, 1H). |
| (cxv) | 5-(3-chloro-4-fluorophenyl)-6-(3-chloro-5-(trifluoromethyl)phenyl)-1,2,4-triazin-3-amine (50 mg, 42%) | 6-bromo-5-(3-chloro-4-fluorophenyl)-1,2,4-triazin-3-amine (90 mg, 0.297 mmol) and 2-(3-chloro-5-(trifluoromethyl)phenyl)-4,4,5,5-tetramethyl-1,3,2-dioxaborolane (91 mg, 0.297 mmol) | Mass spectroscopy: m/z 403, 405 (M + H)$^+$ (ES$^+$); 401, 403 (M − H)$^-$ (ES$^-$), at 5.22 min, 100% (method B). | (400 MHz, DMSO) δ: 7.33 (ddd, J 8.6, 4.7, 2.2, 1H), 7.45 (app t, J 8.9, 1H), 7.61 (s, 1H), 7.63-7.76 (m, 3H), 7.78 (s, 1H), 7.88 (s, 1H). |
| (cxvi) | 4-(3-amino-5-(3,4-difluorophenyl)-1,2,4-triazin-6-yl)-2,6-dimethylbenzonitrile (35 mg, 33%) | 6-bromo-5-(3,4-difluorophenyl)-1,2,4-triazin-3-amine (90 mg, 0.314 mmol) and 2,6-dimethyl-4-(4,4,5,5-tetramethyl-1,3,2-dioxaborolan-2-yl)benzonitrile (93 mg, 0.361 mmol) | Mass spectroscopy: m/z 338 (M + H)$^+$ (ES$^+$); 336 (M − H)$^-$ (ES$^-$), at 4.49 min, 99% (method B). | (400 MHz, DMSO) δ: 2.41 (s, 6H), 7.10-7.20 (m, 1H), 7.26 (s, 2H), 7.40-7.50 (m, 1H), 7.54 (ddd, J 11.4, 7.8, 2.1, 1H), 7.65 (s, 2H). |
| (cxvii) | 6-(2-chloro-6-methylpyridin-4-yl)-5-(3,4-difluorophenyl)-1,2,4-triazin-3-amine (28 mg, 27%) | 6-bromo-5-(3,4-difluorophenyl)-1,2,4-triazin-3-amine (90 mg, 0.314 mmol) and 2-chloro-6-methylpyridin-4-ylboronic acid (61.8 mg, 0.361 mmol) | Mass spectroscopy: m/z 334, 336 (M + H)$^+$ (ES$^+$); 332, 334 (M − H)$^-$ (ES$^-$), at 4.15 min, 99% (method B). | (400 MHz, DMSO) δ: 2.41 (s, 3H), 7.20 (s, 1H), 7.20-7.24 (m, 1H), 7.28 (s, 1H), 7.44-7.62 (m, 2H), 7.79 (s, 2H). |
| (cxviii) | 6-(2-chloropyridin-4-yl)-5-(3,4-difluorophenyl)-1,2,4-triazin-3-amine (10 mg, 10%) | 6-bromo-5-(3,4-difluorophenyl)-1,2,4-triazin-3-amine (90 mg, 0.314 mmol) and 2-chloropyridin-4-ylboronic acid (56.7 mg, 0.361 mmol) | Mass spectroscopy: m/z 320, 322 (M + H)$^+$ (ES$^+$); 318, 320 (M − H)$^-$ (ES$^-$), at 4.0 min, 96% (method B). | (400 MHz, DMSO) δ: 7.18-7.26 (m, 1H), 7.28 (dd, J 5.2, 1.5, 1H), 7.44-7.62 (m, 3H), 7.79 (s, 2H), 8.36 (dd, J 5.2, 0.6, 1H). |
| (cxix) | 6-(3-chloro-5-(trifluoromethyl)phenyl)-5-(3,4-difluorophenyl)-1,2,4-triazin-3-amine (16 mg, 13%) | 6-bromo-5-(3,4-difluorophenyl)-1,2,4-triazin-3-amine (90 mg, 0.314 mmol) and 2-(3-chloro-5-(trifluoromethyl)phenyl)-4,4,5,5-tetramethyl-1,3,2-dioxaborolane (96 mg, 0.314 mmol) | Mass spectroscopy: m/z 387, 389 (M + H)$^+$ (ES$^+$); 385, 387 (M − H)$^-$ (ES$^-$), at 5.07 min, 95% (method B). | (400 MHz, DMSO) δ: 7.17-7.26 (m, 1H), 7.43-7.57 (m, 2H), 7.59 (s, 1H), 7.71 (s, 2H), 7.76 (s, 1H), 7.87 (s, 1H). |
| (cxx) | 6-(3-chloro-5-(trifluoromethyl)phenyl)-5-(4-(methoxymethyl)phenyl)-1,2,4-triazin-3-amine (36 mg, 0.087 mmol, 28.7%) | 6-bromo-5-(4-(methoxymethyl)phenyl)-1,2,4-triazin-3-amine (90 mg, 0.305 mmol) and 2-(3-chloro-5-(trifluoromethyl)phenyl)-4,4,5,5-tetramethyl-1,3,2-dioxaborolane (107 mg, 0.351 mmol) | Mass spectroscopy: m/z (Cl) 395.3/397.3 (M + H)$^+$ (ES$^+$); 393.5/395.5 (M − H)$^-$ (ES$^-$), at 4.93 min, 95.9% (method B). | (400 MHz, DMSO) δ: 3.26 (s, 3H), 4.43 (s, 2H), 7.33 (d, J 8.5, 2H), 7.39 (d, J 8.4, 2H), 7.57 (s, 1H), 7.64 (s, 2H), 7.72 (s, 1H), 7.83 (s, 1H). |
| (cxxi) | 6-(2-chloro-6-methylpyridin-4-yl)-5-(4-(methoxymethyl)phenyl)-1,2,4-triazin-3-amine (23 mg, 0.066 mmol, 21.49%) | 6-bromo-5-(4-(methoxymethyl)phenyl)-1,2,4-triazin-3-amine (90 mg, 0.305 mmol) and 2-chloro-6-methyl-4-(4,4,5,5-tetramethyl-1,3,2-dioxaborolan-2-yl)pyridine (89 mg, 0.351 mmol) | Mass spectroscopy: m/z (Cl) 342.6/344.5 (M + H)$^+$ (ES$^+$); 340.8/342.8 (M − H)$^-$ (ES$^-$), at 3.93 min, 97.4% (method B). | (400 MHz, DMSO) δ: 2.39 (s, 3H), 3.28 (s, 3H), 4.45 (s, 2H), 7.08-7.14 (m, 1H), 7.25-7.31 (m, 1H), 7.35 (d, J 8.5, 2H), 7.41 (d, J 8.4, 2H), 7.72 (s, 2H). |
| (cxxii) | 6-(2,6-dimethylpyridin-4-yl)-5-(4-fluorophenyl)- | 6-bromo-5-(4-fluorophenyl)-1,2,4-triazin-3-amine (90 | Mass spectroscopy: m/z 296.8 (M + H)$^+$ | (400 MHz, DMSO) δ: 2.40 (s, 6H), 7.10 (s, 2H), 7.20-7.31 (m, |

| No. | Product (yield) | Prepared From | LCMS | NMR |
|---|---|---|---|---|
| | 1,2,4-triazin-3-amine (23 mg, 0.078 mmol, 23.19%) | mg, 0.334 mmol) and 2,6-dimethylpyridin-4-ylboronic acid (58.1 mg, 0.385 mmol) | (ES⁺); 295.0 (M − H)⁻ (ES⁻), at 3.85 min, 99.6% (method B). | 2H), 7.40-7.53 (m, 2H), 7.68 (s, 2H). |
| (cxxiii) | 6-(3-chloro-5-methylphenyl)-5-(4-fluorophenyl)-1,2,4-triazin-3-amine (67 mg, 0.212 mmol, 63.3%) | 6-bromo-5-(4-fluorophenyl)-1,2,4-triazin-3-amine (90 mg, 0.334 mmol) and 3-chloro-5-methylphenylboronic acid (65.5 mg, 0.385 mmol) | Mass spectroscopy: m/z (Cl) 315.6/317.6 (M + H)⁺ (ES⁺); 313.8/315.8 (M − H)⁻ (ES⁻), at 4.82 min, 99.4% (method B). | (400 MHz, DMSO) δ: 2.25 (s, 3H), 7.10-7.17 (m, 2H), 7.19-7.28 (m, 3H), 7.42-7.49 (m, 2H), 7.51 (s, 2H). |
| (cxxiv) | 6-(6-fluoropyridin-3-yl)-5-phenyl-1,2,4-triazin-3-amine (47 mg, 0.173 mmol, 58.0%) | 6-bromo-5-phenyl-1,2,4-triazin-3-amine (75 mg, 0.299 mmol) and 2-fluoro-5-(4,4,5,5-tetramethyl-1,3,2-dioxaborolan-2-yl)pyridine (77 mg, 0.344 mmol) | Mass spectroscopy: m/z 268.2 (M + H)⁺ (ES⁺); 266.3 (M − H)⁻ (ES⁻), at 3.54 min, 98.5% (method B). | (400 MHz, DMSO) δ: 7.17 (ddd, J 8.5, 2.8, 0.5, 1H), 7.53 (s, 2H), 7.35-7.48 (m, 5H), 7.86-7.94 (m, 1H), 8.13-8.19 (m, 1H). |
| (cxxv) | 6-(3,5-dimethylisoxazol-4-yl)-5-phenyl-1,2,4-triazin-3-amine (8 mg, 0.030 mmol, 10.02%) | 6-bromo-5-phenyl-1,2,4-triazin-3-amine (75 mg, 0.299 mmol) and 5-dimethylisoxazol-4-ylboronic acid (42.1 mg, 0.299 mmol) | Mass spectroscopy: m/z 268.2 (M + H)⁺ (ES⁺); 266.4 (M − H)⁻ (ES⁻), at 3.48 min, 96.2% (method B). | (400 MHz, DMSO) δ: 1.85 (s, 3H), 2.02 (s, 3H), 7.38-7.55 (m, 7H). |
| (cxxvi) | 6-(3,5-diisopropylphenyl)-5-phenyl-1,2,4-triazin-3-amine (84.5 mg, 0.254 mmol, 70.9%) | 6-bromo-5-phenyl-1,2,4-triazin-3-amine (90 mg, 0.358 mmol) and 2-(3,5-diisopropylphenyl)-4,4,5,5-tetramethyl-1,3,2-dioxaborolane (119 mg, 0.412 mmol) | Mass spectroscopy: m/z 333.3 (M + H)⁺ (ES⁺); 331.5 (M − H)⁻ (ES⁻), at 5.24 min, 100% (254 nm). | (400 MHz, DMSO) δ: 1.06 (d, J 6.9, 12H), 2.78 (hept, J 6.8, 2H), 6.96-7.06 (m, 3H), 7.31-7.45 (m, 7H). |
| (cxxvii) | 6-(3-fluoro-5-(2,2,2-trifluoroethoxy)phenyl)-5-phenyl-1,2,4-triazin-3-amine (80 mg, 0.214 mmol, 59.7%) | 6-bromo-5-phenyl-1,2,4-triazin-3-amine (90 mg, 0.358 mmol) and 3-fluoro-5-(2,2,2-trifluoroethoxy)phenylboronic acid (98 mg, 0.412 mmol) | Mass spectroscopy: m/z 365.2 (M + H)⁺ (ES⁺); 363.4 (M − H)⁻ (ES⁻), at 4.43 min, 97.4% (method B). | (400 MHz, DMSO) δ: 4.73 (q, J 8.8, 2H), 6.76 (ddd, J 9.5, 2.3, 1.4, 1H), 6.89-6.94 (m, 1H), 6.99 (dt, J 10.7, 2.3, 1H), 7.52 (s, 2H), 7.34-7.48 (m, 5H). |
| (cxxviii) | N-(4-(3-amino-5-phenyl-1,2,4-triazin-6-yl)-2-(trifluoromethyl)phenyl)acetamide (99 mg, 0.255 mmol, 71.0%) | 6-bromo-5-phenyl-1,2,4-triazin-3-amine (90 mg, 0.358 mmol) and N-(4-(4,4,5,5-tetramethyl-1,3,2-dioxaborolan-2-yl)-2-(trifluoromethyl)phenyl)acetamide (136 mg, 0.412 mmol) | Mass spectroscopy: m/z 374.1 (M + H)⁺ (ES⁺); 372.3 (M − H)⁻ (ES⁻), at 3.52 min, 98.9% (method B). | (400 MHz, DMSO) δ: 2.04 (s, 3H), 7.34-7.48 (m, 5H), 7.49-7.68 (m, 5H), 9.55 (s, 1H). |
| (cxxix) | 5-(3-amino-5-phenyl-1,2,4-triazin-6-yl)-2-fluorobenzonitrile (43 mg, 0.147 mmol, 40.9%) | 6-bromo-5-phenyl-1,2,4-triazin-3-amine (90 mg, 0.358 mmol) and 3-cyano-4-fluorophenylboronic acid (68.0 mg, 0.412 mmol) | Mass spectroscopy: m/z 292.1 (M + H)⁺ (ES⁺); 290.3 (M − H)⁻ (ES⁻), at 3.79 min, 99.3% (method B). | (400 MHz, DMSO) δ: 7.34-7.42 (m, 4H), 7.42-7.47 (m, 1H), 7.50 (t, J 9.2, 1H), 7.57 (s, 2H), 7.67 (ddd, J 8.8, 5.3, 2.3, 1H), 7.89 (dd, J 6.2, 2.3, 1H). |
| (cxxx) | 3-(3-amino-5-phenyl-1,2,4-triazin-6-yl)-N,N-dimethylbenzamide (80 mg, 0.251 mmol, 69.9%) | 6-bromo-5-phenyl-1,2,4-triazin-3-amine (90 mg, 0.358 mmol) and 3-(dimethylcarbamoyl)phenylboronic acid (80 mg, 0.412 mmol) | Mass spectroscopy: m/z 320.2 (M + H)⁺ (ES⁺); 318.4 (M − H)⁻ (ES⁻), at 3.30 min, 100% (method B). | (400 MHz, DMSO) δ: 2.60 (s, 3H), 2.89 (s, 3H), 7.19-7.24 (m, 1H), 7.31-7.38 (m, 3H), 7.38-7.47 (m, 6H), 7.48-7.52 (m, 1H). |
| (cxxxi) | 6-(1-methyl-1H-pyrazol-4-yl)-5-phenyl-1,2,4-triazin-3-amine (43 mg, 0.168 mmol, 47.0%) | 6-bromo-5-phenyl-1,2,4-triazin-3-amine (90 mg, 0.358 mmol) and 1-methyl-4-(4,4,5,5-tetramethyl-1,3,2-dioxaborolan-2-yl)-1H-pyrazole (86 mg, 0.412 mmol) | Mass spectroscopy: m/z 253.2 (M+H)⁺ (ES⁺); 251.4 (M − H)⁻ (ES⁻), at 3.15 min, 98.8% (method B). | (400 MHz, DMSO) δ: 3.77 (s, 3H), 7.04 (d, J 0.7, 1H), 7.24 (s, 2H), 7.43-7.56 (m, 5H), 7.64 (s, 1H). |

-continued

| No. | Product (yield) | Prepared From | LCMS | NMR |
|---|---|---|---|---|
| (cxxxii) | 4-(3-amino-5-phenyl-1,2,4-triazin-6-yl)-1-methylpyridin-2(1H)-one (33 mg, 0.115 mmol, 32.1%) | 6-bromo-5-phenyl-1,2,4-triazin-3-amine (90 mg, 0.358 mmol) and 1-methyl-4-(4,4,5,5-tetramethyl-1,3,2-dioxaborolan-2-yl)pyridin-2(1H)-one (97 mg, 0.412 mmol) | Mass spectroscopy: m/z 280.1 (M + H)$^+$ (ES$^+$); 278.4 (M − H)$^−$ (ES$^−$), at 2.92 min, 97.4% (method B). | (400 MHz, DMSO) δ: 3.39 (s, 3H), 6.14 (dd, J 7.0, 2.0, 1H), 6.32 (d, J 1.7, 1H), 7.38-7.54 (m, 5H), 7.56-7.70 (m, 3H). |
| (cxxxiii) | 6-(3-morpholinophenyl)-5-phenyl-1,2,4-triazin-3-amine (65 mg, 0.192 mmol, 53.6%) | 6-bromo-5-phenyl-1,2,4-triazin-3-amine (90 mg, 0.358 mmol) and 4-(3-(4,4,5,5-tetramethyl-1,3,2-dioxaborolan-2-yl)phenyl)morpholine (119 mg, 0.412 mmol) | Mass spectroscopy: m/z 334.3 (M + H)$^+$ (ES$^+$); 332.4 (M − H)$^−$ (ES$^−$), at 4.07 min, 98.6% (method B). | (400 MHz, DMSO) δ: 2.87-3.02 (m, 4H), 3.58-3.72 (m, 4H), 6.74 (d, J 7.7, 1H), 6.86-6.94 (m, 2H), 7.16 (t, J 7.6, 1H), 7.28-7.45 (m, 7H). |
| (cxxxiv) | 6-(1-benzyl-1H-pyrazol-4-yl)-5-phenyl-1,2,4-triazin-3-amine (78 mg, 0.237 mmol, 66.1%) | 6-bromo-5-phenyl-1,2,4-triazin-3-amine (90 mg, 0.358 mmol) and 1-benzyl-4-(4,4,5,5-tetramethyl-1,3,2-dioxaborolan-2-yl)-1H-pyrazole (117 mg, 0.412 mmol) | Mass spectroscopy: m/z 329.3 (M + H)$^+$ (ES$^+$); 327.5 (M − H)$^−$ (ES$^−$), at 4.07 min, 99.8% (method B). | (400 MHz, DMSO) δ: 5.26 (s, 2H), 7.12-7.18 (m, 2H), 7.20 (d, J 0.7, 1H), 7.26 (s, 2H), 7.27-7.37 (m, 3H), 7.40-7.53 (m, 5H), 7.67 (d, J 0.7, 1H). |
| (cxxxv) | 6-(2-methoxypyrimidin-5-yl)-5-phenyl-1,2,4-triazin-3-amine (34 mg, 0.119 mmol, 33.2%) | 6-bromo-5-phenyl-1,2,4-triazin-3-amine (90 mg, 0.358 mmol) and 2-methoxypyrimidin-5-ylboronic acid (63.5 mg, 0.412 mmol) | Mass spectroscopy: m/z 281.2 (M + H)$^+$ (ES$^+$); 279.4 (M − H)$^−$ (ES$^−$), at 3.42 min, 98.2% (method B). | (400 MHz, DMSO) δ: 3.91 (s, 3H), 7.38-7.49 (m, 5H), 7.55 (s, 2H), 8.50 (s, 2H). |
| (cxxxvi) | 6-(6-methoxypyridin-3-yl)-5-phenyl-1,2,4-triazin-3-amine (50 mg, 0.176 mmol, 49.1%) | 6-bromo-5-phenyl-1,2,4-triazin-3-amine (90 mg, 0.358 mmol) and 6-methoxypyridin-3-ylboronic acid (63.0 mg, 0.412 mmol) | Mass spectroscopy: m/z 280.1 (M + H)$^+$ (ES$^+$); 278.4 (M − H)$^−$ (ES$^−$), at 3.88 min, 98.3% (method B). | (400 MHz, DMSO) δ: 3.84 (s, 3H), 6.78 (dd, J 8.6, 0.7, 1H), 7.34-7.48 (m, 7H), 7.60 (dd, J 8.6, 2.5, 1H), 8.10 (dd, J 2.5, 0.7, 1H). |
| (cxxxvii) | 6-(3-(methylsulfinyl)phenyl)-5-phenyl-1,2,4-triazin-3-amine (70 mg, 0.217 mmol, 60.4%) | 6-bromo-5-phenyl-1,2,4-triazin-3-amine (90 mg, 0.358 mmol) and with 3-(methylsulfinyl)phenylboronic acid (76 mg, 0.412 mmol) | Mass spectroscopy: m/z 311.1 (M + H)$^+$ (ES$^+$); 309.3 (M − H)$^−$ (ES$^−$), at 3.29 min, 96.0% (method B). | (400 MHz, DMSO) δ: 2.58 (s, 3H), 7.32-7.47 (m, 5H), 7.47-7.57 (m, 4H), 7.58-7.60 (m, 1H), 7.63 (dt, J 7.3, 1.7, 1H). |
| (cxxxviii) | 4-(3-amino-6-(2-chloropyridin-4-yl)-1,2,4-triazin-5-yl)benzonitrile (11.3 mg, 0.036 mmol, 10.93%) | 4-(3-amino-6-bromo-1,2,4-triazin-5-yl)benzonitrile (90 mg, 0.326 mmol) and 2-chloro-4-(4,4,5,5-tetramethyl-1,3,2-dioxaborolan-2-yl)pyridine (90 mg, 0.375 mmol) | Mass spectroscopy: m/z (Cl) 309.6/311.7 (M + H)$^+$ (ES$^+$); 307.9/309.9 (M − H)$^−$ (ES$^−$), at 3.50 min, 97.3% (method B). | (400 MHz, DMSO) δ: 7.25 (dd, J 5.2, 1.5, 1H), 7.51 (dd, J 1.5, 0.7, 1H), 7.58-7.65 (m, 2H), 7.85 (s, 2H), 7.89-7.94 (m, 2H), 8.34 (dd, J 5.2, 0.6, 1H). |
| (cxxxix) | 4-(3-amino-5-(4-(methoxymethyl)phenyl)-1,2,4-triazin-6-yl)-2,6-dimethylbenzonitrile (47 mg, 0.132 mmol, 43.2%) | 6-bromo-5-(4-(methoxymethyl)phenyl)-1,2,4-triazin-3-amine (90 mg, 0.305 mmol) and 2,6-dimethyl-4-(4,4,5,5-tetramethyl-1,3,2-dioxaborolan-2-yl)benzonitrile (78 mg, 0.305 mmol) | Mass spectroscopy: m/z 346.6 (M + H)$^+$ (ES$^+$); 344.8 (M − H)$^−$ (ES$^−$), at 4.25 min, 96.7% (method B). | (400 MHz, DMSO) δ: 2.38 (s, 6H), 4.43 (s, 2H), 7.23 (s, 2H), 7.32 (d, J 8.5, 2H), 7.39 (d, J 8.4, 2H), 7.67 (s, 2H). |
| (cxl) | 6-(2-chloropyridin-4-yl)-5-(4-(methoxymethyl)phenyl)-1,2,4-triazin-3-amine (26 mg, 0.077 mmol, 25.3%) | 6-bromo-5-(4-(methoxymethyl)phenyl)-1,2,4-triazin-3-amine (90 mg, 0.305 mmol) and 2-chloro-4-(4,4,5,5-tetramethyl-1,3,2-dioxaborolan-2-yl)pyridine (84 mg, 0.351 mmol) | Mass spectroscopy: m/z (Cl) 328.6/330.5 (M + H)$^+$ (ES$^+$); 326.8/328.8 (M − H)$^−$ (ES$^−$), at 3.79 min, 97.4% (method B). | (400 MHz, DMSO) δ: 3.29 (s, 3H), 4.45 (s, 2H), 7.28 (dd, J 5.2, 1.5, 1H), 7.35 (d, J 8.5, 2H), 7.42 (d, J 8.4, 2H), 7.48 (dd, J 1.5, 0.7, 1H), 7.74 (s, 2H), 8.33 (dd, J 5.2, 0.7, 1H). |

-continued

| No. | Product (yield) | Prepared From | LCMS | NMR |
|---|---|---|---|---|
| (cxli) | 6(E)-5-phenyl-6-styryl-1,2,4-triazin-3-amine (27 mg, 0.098 mmol, 27.5%) | 6-bromo-5-phenyl-1,2,4-triazin-3-amine (90 mg, 0.358 mmol) and (E)-styrylboronic acid (61.0 mg, 0.412 mmol) | Mass spectroscopy: m/z z 275.1 (M + H)$^+$ (ES$^+$), at 4.78 min, 93.2% (method B). | (400 MHz, DMSO) δ: 7.09 (d, J 16.0, 1H), 7.28 (t, J 7.3, 1H), 7.36 (t, J 7.5, 2H), 7.44 (s, 2H), 7.49 (d, J 7.3, 2H), 7.55-7.62 (m, 4H), 7.64-7.70 (m, 2H). |
| (cxlii) | 6-(3-amino-5-phenyl-1,2,4-triazin-6-yl)indolin-2-one (34 mg, 0.111 mmol, 31.0%) | 6-bromo-5-phenyl-1,2,4-triazin-3-amine (90 mg, 0.358 mmol) and 2-oxoindolin-6-ylboronic acid (72.9 mg, 0.412 mmol) | Mass spectroscopy: m/z 304.7 (M + H)$^+$ (ES$^+$); 302.9 (M − H)$^-$ (ES$^-$), at 3.47 min, 99.1% (method B). | (400 MHz, DMSO) δ: 3.48 (s, 2H), 6.80 (dd, J 7.6, 1.6, 1H), 6.86-6.90 (m, 1H), 7.11 (d, J 7.7, 1H), 7.31-7.47 (m, 7H), 10.38 (s, 1H). |
| (cxliii) | tert-butyl 5-(3-amino-5-phenyl-1,2,4-triazin-6-yl)pyridin-2-yl(methyl)carbamate (120 mg, 0.308 mmol, 42.9%) | 6-bromo-5-phenyl-1,2,4-triazin-3-amine (90 mg, 0.358 mmol) and 6-(tert-butoxycarbonyl(methyl)amino)pyridin-3-ylboronic acid (181 mg, 0.717 mmol) | Mass spectroscopy: m/z 379.5 (M + H)$^+$ (ES$^+$); 377.8 (M − H)$^-$ (ES$^-$), at 4.53 min, 97.1% (method B). | (400 MHz, DMSO) δ: 1.45 (s, 9H), 3.28 (s, 3H), 7.35-7.48 (m, 5H), 7.49 (s, 2H), 7.60 (d, J 8.7, 0.8, 1H), 7.66 (dd, J 8.7, 2.4, 1H), 8.30 (dd, J 2.4, 0.8, 1H). |
| (cxliv) | 5-(3-chloro-5-fluorophenyl)-6-(2-chloropyridin-4-yl)-1,2,4-triazin-3-amine (22 mg, 22%) | 6-bromo-5-(3-chloro-5-fluorophenyl)-1,2,4-triazin-3-amine (90 mg, 0.297 mmol), 2-chloropyridin-4-ylboronic acid (53.7 mg, 0.341 mmol) | Mass spectroscopy: m/z 336, 338 (M + H)$^+$ (ES$^+$); 334, 336 (M − H)$^-$ (ES$^-$), at 4.27 min, 100% purity (method B). | (400 MHz, DMSO) δ: 7.24 (ddd, J 9.2, 2.4, 1.4 Hz, 1H), 7.30 (dd, J 5.2, 1.4 Hz, 1H), 7.39 (t, J 1.4 Hz, 1H), 7.53 (dd, J 1.4, 0.6 Hz, 1H), 7.59-7.65 (m, 1H), 7.85 (s, 2H), 8.38 (dd, J 5.2, 0.6 Hz, 1H). |
| (cxlv) | 6-(2-chloropyridin-4-yl)-5-(3,5-difluorophenyl)-1,2,4-triazin-3-amine (22 mg, 22%) | 6-bromo-5-(3,5-difluorophenyl)-1,2,4-triazin-3-amine (90 mg, 0.314 mmol), 2-chloropyridin-4-ylboronic acid (56.7 mg, 0.361 mmol) | Mass spectroscopy: m/z 320, 322 (M + H)$^+$ (ES$^+$); 318, 320 (M − H)$^-$ (ES$^-$), at 3.98 min, 98% purity (method B) | ((400 MHz, DMSO) δ: 7.11-7.24 (m, 2H), 7.30 (d, J 5.1, 1.4 Hz, 1H), 7.43 (tt, J 9.3, 2.4 Hz, 1H), 7.53 (dd, J 1.4, 0.6 Hz, 1H), 7.84 (s, 2H), 8.38 (dd, J 5.1, 0.6 Hz, |
| (cxlvi) | 4-(3-amino-5-(4-(difluoromethoxy)phenyl)-1,2,4-triazin-6-yl)-2,6-dimethylbenzonitrile (32 mg, 30%) | 6-bromo-5-(4-(difluoromethoxy)phenyl)-1,2,4-triazin-3-amine (90 mg, 0.284 mmol), 2,6-dimethyl-4-(4,4,5,5-tetramethyl-1,3,2-dioxaborolan-2-yl)benzonitrile (84 mg, 0.326 mmol) | Mass spectroscopy: m/z 368 (M + H)$^+$ (ES$^+$); 366 (M − H)$^-$ (ES$^-$), at 4.42 min, 99% purity (method B). | (400 MHz, DMSO) δ: 2.39 (s, 6H), 7.15-7.21 (m, 2H), 7.24 (s, 2H), 7.31 (t, $^2J_{HF}$ 72 Hz, 1H), 7.43-7.48 (m, 2H), 7.57 (s, 2H). |
| (cxlvii) | 6-(2-chloro-6-methylpyridin-4-yl)-5-(4-(difluoromethoxy)phenyl)-1,2,4-triazin-3-amine (15 mg, 14%) | 6-bromo-5-(4-(difluoromethoxy)phenyl)-1,2,4-triazin-3-amine (90 mg, 0.284 mmol), 2-chloro-6-methylpyridin-4-ylboronic acid (55.9 mg, 0.326 mmol) | Mass spectroscopy: m/z 364, 366 (M + H)$^+$ (ES$^+$); 362, 364 (M − H)$^-$ (ES$^-$), at 4.14 min, 98% purity (method B). | (400 MHz, DMSO) δ: 2.40 (s, 3H), 7.17 (s, 1H), 7.22 (d, J 8.7 Hz, 2H), 7.27 (d, J 0.7 Hz, 1H), 7.33 (t, $^2J_{HF}$ 72 Hz, 1H), 7.46-7.51 (m, 2H), 7.71 (s, 2H). |
| (cxlviii) | 6-(2-chloropyridin-4-yl)-5-(4-(difluoromethoxy)phenyl)-1,2,4-triazin-3-amine (17 mg, 17%) | 6-bromo-5-(4-(difluoromethoxy)phenyl)-1,2,4-triazin-3-amine (90 mg, 0.284 mmol), 2-chloropyridin-4-ylboronic acid (51.4 mg, 0.326 mmol) | Mass spectroscopy: m/z 350, 352 (M + H)$^+$ (ES$^+$); 348, 350 (M − H)$^-$ (ES$^-$), at 4.0 min, 98% purity (method B) | (400 MHz, DMSO) δ: 7.21 (d, J 8.7 Hz, 2H), 7.29 (dd, J 5.2, 1.5 Hz, 1H), 7.34 (t, $^2J_{HF}$ 72 Hz, 1H), 7.46-7.55 (m, 3H), 7.73 (s, 2H), 8.35 (dd, J 5.2, 0.6 Hz, 1H). |
| (cxlix) | 6-(3-chloro-5-(trifluoromethyl)phenyl)-5-(4-(difluoromethoxy)phe- | 6-bromo-5-(4-(difluoromethoxy)phenyl)-1,2,4-triazin-3-amine (90 mg, 0.284 | Mass spectroscopy: m/z 417, 419 (M + H)$^+$ (ES$^+$); 415, 417 (M − | (400 MHz, DMSO) δ: 7.17-7.23 (m, 2H), 7.31 (t, $^2J_{HF}$ 72 Hz, 1H), 7.44-7.50 (m, |

| No. | Product (yield) | Prepared From | LCMS | NMR |
|---|---|---|---|---|
| | nyl)-1,2,4-triazin-3-amine (67 mg, 54%) | mmol), 2-(3-chloro-5-(trifluoromethyl)phenyl)-4,4,5,5-tetramethyl-1,3,2-dioxaborolane (87 mg, 0.284 mmol) | H)⁻ (ES⁻), at 5.02 min, 95% purity (method B). | 2H), 7.56-7.59 (m, 1H), 7.63 (s, 2H), 7.74-7.75 (m, 1H), 7.84-7.85 (m, 1H). |
| (cl) | 5-(3-amino-5-(3-fluorophenyl)-1,2,4-triazin-6-yl)-2-chlorophenol (16 mg, 15%) | 6-bromo-5-(3-fluorophenyl)-1,2,4-triazin-3-amine (90 mg, 0.334 mmol), 4-chloro-3-hydroxyphenylboronic acid (57.7 mg, 0.334 mmol) | Mass spectroscopy: m/z 317, 319 (M + H)⁺ (ES⁺); 315, 317 (M − H)⁻ (ES⁻), at 2.68 min, 97% purity (method B). | (400 MHz, DMSO) δ: 6.64 (dd, J 8.2, 2.0 Hz, 1H), 7.07 (d, J 2.0 Hz, 1H), 7.23 (d, J 8.2 Hz, 1H), 7.34-7.48 (m, 7H), 10.26 (s, 1H). |
| (cli) | 4-(3-amino-6-(3-chloro-4-hydroxyphenyl)-1,2,4-triazin-5-yl)benzonitrile (21 mg, 23%) | 4-(3-amino-6-bromo-1,2,4-triazin-5-yl)benzonitrile (75 mg, 0.272 mmol) and 2-chloro-4-(4,4,5,5-tetramethyl-1,3,2-dioxaborolan-2-yl)phenol (76 mg, 0.299 mmol) | Mass spectroscopy: m/z (Cl) 324.2/326.3 (M + H)⁺ (ES+); 322.1/324.2 (M − H)− (ES−), at 2.48 min, 95.4% purity (method B). | (400 MHz, DMSO) δ: 6.80-6.93 (m, 1H), 6.99 (dd, J 8.4, 2.2 Hz, 1H), 7.36 (d, J 2.2 Hz, 1H), 7.53-7.64 (m, 2H), 7.84 (s, 2H), 7.84-7.93 (m, 2H), 10.44 (s, 1H). |
| (clii) | 3-(3-amino-5-phenyl-1,2,4-triazin-6-yl)-5-(trifluoromethoxy)phenol (180 mg, 65%) | 6-bromo-5-phenyl-1,2,4-triazin-3-amine (200 mg, 0.797 mmol), 3-hydroxy-5-(trifluoromethoxy)phenylboronic acid (265 mg, 1.195 mmol) | Mass spectroscopy: m/z 349 (M + H)⁺ (ES⁺); 347 (M − H)⁻ (ES⁻), at 3.22 min, 100% purity (method B). | (400 MHz, DMSO) δ: 6.55-6.56 (m, 1H), 6.64-6.65 (m, 1H), 6.87-6.91 (m, 1H), 7.31-7.53 (m, 7H), 10.15 (s, 1H). |
| (cliii) | 5-(3-chloro-5-fluorophenyl)-6-(2,6-dimethylpyridin-4-yl)-1,2,4-triazin-3-amine (40 mg, 40%) | 6-bromo-5-(3-chloro-5-fluorophenyl)-1,2,4-triazin-3-amine (90 mg, 0.297 mmol), 2,6-dimethyl-4-(4,4,5,5-tetramethyl-1,3,2-dioxaborolan-2-yl)pyridine (79 mg, 0.341 mmol) | Mass spectroscopy: m/z 330(M + H)⁺ (ES⁺); 328 (M − H)⁻ (ES⁻), at 4.27 min, 98% purity (method B). | (400 MHz, DMSO) δ: 2.37 (s, 6H), 7.02 (s, 2H), 7.18 (ddd, J = 9.3, 2.4, 1.4 Hz, 1H), 7.36 (t, J 1.4 Hz, 1H), 7.56-7.61 (m, 1H), 7.70 (s, 2H). |
| (cliv) | 5-(3,5-difluorophenyl)-6-(2,6-dimethylpyridin-4-yl)-1,2,4-triazin-3-amine (50 mg, 49%) | 6-bromo-5-(3,5-difluorophenyl)-1,2,4-triazin-3-amine (90 mg, 0.314 mmol), 2,6-dimethyl-4-(4,4,5,5-tetramethyl-1,3,2-dioxaborolan-2-yl)pyridine (84 mg, 0.361 mmol) | Mass spectroscopy: m/z 314 (M + H)⁺ (ES⁺); 312 (M − H)⁻ (ES⁻), at 3.95 min, 97% purity (method B) | (400 MHz, DMSO) δ: 2.37 (s, 6H), 7.01 (s, 2H), 7.04-7.16 (m, 2H), 7.38-7.44 (m, 1H), 7.70 (s, 2H). |
| (clv) | 5-(3,4-difluorophenyl)-6-(2,6-dimethylpyridin-4-yl)-1,2,4-triazin-3-amine | 6-bromo-5-(3,4-difluorophenyl)-1,2,4-triazin-3-amine (90 mg, 0.314 mmol), 2,6-dimethyl-4-(4,4,5,5-tetramethyl-1,3,2-dioxaborolan-2-yl)pyridine (84 mg, 0.361 mmol) | Mass spectroscopy: m/z 314(M + H)⁺ (ES⁺); 313 (M − H)⁻ (ES⁻), at 3.97 min, 99% purity (method B). | (400 MHz, DMSO) δ: 2.37 (s, 6H), 7.01 (s, 2H), 7.15-7.23 (m, 1H), 7.42-7.56 (m, 2H), 7.65 (s, 2H). |
| (clvi) | 5-(3-chloro-4-fluorophenyl)-6-(2,6-dimethylpyridin-4-yl)-1,2,4-triazin-3-amine (38 mg, 38%) | 6-bromo-5-(3-chloro-4-fluorophenyl)-1,2,4-triazin-3-amine (90 mg, 0.297 mmol), 2,6-dimethyl-4-(4,4,5,5-tetramethyl-1,3,2-dioxaborolan-2-yl)pyridine (79 mg, 0.341 mmol) | Mass spectroscopy: m/z 330(M + H)⁺ (ES⁺); 328 (M − H)⁻ (ES⁻), at 4.2 min, 97% purity (method B). | (400 MHz, DMSO) δ: 2.37 (s, 6H), 7.02 (s, 2H), 7.29 (ddd, J 8.6, 4.7, 2.2 Hz, 1H), 7.40-7.45 (m, 1H), 7.65 (s, 2H), 7.73 (dd, J 7.2, 2.2 Hz, 1H). |
| (clvii) | 5-(4-(difluoromethoxy)phenyl)-6-(2,6-dimethylpyridin-4-yl)-1,2,4-triazin-3-amine (36 mg, 37%) | 6-bromo-5-(4-(difluoromethoxy)phenyl)-1,2,4-triazin-3-amine (90 mg, 0.284 mmol), 2,6-dimethyl-4-(4,4,5,5-tetramethyl-1,3,2-dioxaborolan-2-yl)pyridine (76 mg, 0.326 mmol) | Mass spectroscopy: m/z 344(M + H)⁺ (ES⁺); 342 (M − H)⁻ (ES⁻), at 3.93 min, 99% purity (method B). | (400 MHz, DMSO) δ: 2.35 (s, 6H), 6.99 (s, 2H), 7.15-7.23 (m, 2H), 7.32 (t, $^2J_{HF}$ 72 Hz, 1H), 7.43-7.49 (m, 2H), 7.58 (s, 2H). |

| No. | Product (yield) | Prepared From | LCMS | NMR |
|---|---|---|---|---|
| (clviii) | 6-(2,6-dimethylpyridin-4-yl)-5-(3-fluorophenyl)-1,2,4-triazin-3-amine (42 mg, 41%) | 6-bromo-5-(3-fluorophenyl)-1,2,4-triazin-3-amine (90 mg, 0.334 mmol) and 2,6-dimethyl-4-(4,4,5,5-tetramethyl-1,3,2-dioxaborolan-2-yl)pyridine (78 mg, 0.334 mmol) | Mass spectroscopy: m/z 295.0 (M − H)⁻ (ES⁻), at 3.82 min, 98.1% purity (method B). | (400 MHz, DMSO) δ: 2.36 (s, 6H), 7.02 (s, 2H), 7.17 (d, J 7.7 Hz, 1H), 7.25-7.36 (m, 2H), 7.38-7.45 (m, 1H), 7.66 (s, 2H). |
| (clix) | 5-(4-chlorophenyl)-6-(2,6-dimethylpyridin-4-yl)-1,2,4-triazin-3-amine (33 mg, 34%) | 6-bromo-5-(4-chlorophenyl)-1,2,4-triazin-3-amine (90 mg, 0.315 mmol) and 2,6-dimethyl-4-(4,4,5,5-tetramethyl-1,3,2-dioxaborolan-2-yl)pyridine (73.5 mg, 0.315 mmol) | Mass spectroscopy: m/z 312.7/314.7 (M + H)⁺ (ES⁺); 310.9/312.9 (M − H)⁻ (ES⁻), at 4.17 min, 100% purity (method B). | (400 MHz, DMSO) δ: 2.39 (s, 6H), 7.07 (s, 2H), 7.41-7.51 (m, 4H), 7.67 (s, 2H). |
| (clx) | 4-(3-amino-6-(2,6-dimethylpyridin-4-yl)-1,2,4-triazin-5-yl)benzonitrile (27 mg, 27%) | 4-(3-amino-6-bromo-1,2,4-triazin-5-yl)benzonitrile (90 mg, 0.326 mmol) and 2,6-dimethyl-4-(4,4,5,5-tetramethyl-1,3,2-dioxaborolan-2-yl)pyridine (76 mg, 0.326 mmol) | Mass spectroscopy: m/z 303.8 (M + H)⁺ (ES⁺); 302.0 (M − H)⁻ (ES⁻), at 3.47 min, 98.5% purity (method B). | (400 MHz, DMSO) δ: 2.36 (s, 6H), 7.01 (s, 2H), 7.55-7.64 (m, 2H), 7.73 (s, 2H), 7.85-7.95 (m, 2H). |
| (clxi) | 5-(3-chlorophenyl)-6-(2,6-dimethylpyridin-4-yl)-1,2,4-triazin-3-amine (31 mg, 32%) | 6-bromo-5-(3-chlorophenyl)-1,2,4-triazin-3-amine (90 mg, 0.315 mmol) and 2,6-dimethyl-4-(4,4,5,5-tetramethyl-1,3,2-dioxaborolan-2-yl)pyridine (73.5 mg, 0.315 mmol) | Mass spectroscopy: m/z 312.7/314.7 (M + H)⁺ (ES⁺); 310.9/312.9 (M − H)⁻ (ES⁻), at 4.10 min, 100% purity (method B). | (400 MHz, DMSO) δ: 2.35 (s, 6H), 7.00 (s, 2H), 7.22-7.25 (m, 1H), 7.37 (dd, J 11.9, 4.2 Hz, 1H), 7.51-7.60 (m, 2H), 7.65 (s, 2H). |
| (clxii) | 6-(2,6-dimethylpyridin-4-yl)-5-(4-(methoxymethyl)phenyl)-1,2,4-triazin-3-amine (32 mg, 32%) | 6-bromo-5-(4-(methoxymethyl)phenyl)-1,2,4-triazin-3-amine (90 mg, 0.305 mmol) and 2,6-dimethyl-4-(4,4,5,5-tetramethyl-1,3,2-dioxaboralan-2-yl)pyridine (71.1 mg, 0.305 mmol) | Mass spectroscopy: m/z 322.7 (M + H)⁺ (ES⁺); 320.9 (M − H)⁻ (ES⁻), at 3.72 min, 98.5% purity (method B). | (400 MHz, DMSO) δ: 2.36 (s, 6H), 3.28 (s, 3H), 4.44 (s, 2H), 7.03 (s, 2H), 7.31-7.34 (m, 2H), 7.37-7.43 (m, 2H), 7.62 (s, 2H). |
| (clxiii) | 4-(3-amino-6-(3-chloro-4-hydroxy-5-methoxyphenyl)-1,2,4-triazin-5-yl)benzonitrile (10 gm, 10%) | 4-(3-amino-6-bromo-1,2,4-triazin-5-yl)benzonitrile (75 mg, 0.272 mmol) and 2-chloro-6-methoxy-4-(4,4,5,5-tetramethyl-1,3,2-dioxaborolan-2-yl)phenol (85 mg, 0.299 mmol) | Mass spectroscopy: m/z (Cl) 354.2/356.0 (M + H)⁺ (ES⁺); 352.1/354.0 (M − H)⁻ (ES⁻), at 2.56 min, 94.6% purity (method B). | (400 MHz, DMSO) δ: 3.60 (s, 3H), 6.81 (d, J 2.0 Hz, 1H), 6.92 (d, J 2.0 Hz, 1H), 7.45 (s, 2H), 7.56-7.64 (m, 2H), 7.84-7.93 (m, 2H), 9.67 (s, 1H). |
| (clxiv) | 5-(3-amino-5-phenyl-1,2,4-triazin-6-yl)-2-chlorophenol (43 mg, 40%) | 6-bromo-5-phenyl-1,2,4-triazin-3-amine (90 mg, 0.358 mmol), 4-chloro-3-hydroxyphenylboronic acid (61.8 mg, 0.358 mmol) | Mass spectroscopy: m/z 299, 301 (M + H)⁺ (ES⁺); 297, 299 (M − H)⁻ (ES⁻), at 2.55 min, 99% purity (method B). | (400 MHz, DMSO) δ: 6.64 (dd, J = 8.2, 2.0 Hz, 1H), 7.07 (d, J = 2.0 Hz, 1H), 7.23 (d, J = 8.2 Hz, 1H), 7.34-7.47 (m, 7H), 10.26 (s, 1H). |
| (clxv) | 6-[2-chloro-6-(trifluoromethyl)pyridin-4-yl]-5-(3,4-difluorophenyl)-1,2,4-triazin-3-amine (20 mg, 13%) | 6-bromo-5-(3,4-difluorophenyl)-1,2,4-triazin-3-amine (115 mg, 0.40 mmol) and 2-chloro-4-(4,4,5,5-tetramethyl-1,3,2-dioxaborolan-2-yl)-6-(trifluoromethyl)pyridine (129 mg, 0.421 mmol) | Mass spectroscopy: m/z 387.84/389.77 [M + H]⁺(ES)⁺ 99.70% at 4.60 mnin (method B). | (400 MHz DMSO) δ: 7.25-7.32 (m, 1H), 7.48-7.57 (q, 1H), 7.58-7.66 (m, 1H), 7.78(s, 1H), 7.82 (s, 1H), 7.93-7.99 (bs, 2H) |
| (clxvi) | 6-[2-chloro-6-(trifluoromethyl)pyridin-4-yl]-5-(3,5- | 6-bromo-5-(3,5-difluorophenyl)-1,2,4-triazin-3-amine (115 | Mass spectroscopy: m/z 387.87/389.78 | (400 MHz DMSO) δ: 7.20-7.25 (m, 2H), 7.46-7.51 (m, 1H), |

-continued

| No. | Product (yield) | Prepared From | LCMS | NMR |
|---|---|---|---|---|
| | difluorophenyl)-1,2,4-triazin-3-amine (26 mg, 17%) | mg, 0.40 mmol) and 2-chloro-4-(4,4,5,5-tetramethyl-1,3,2-dioxaborolan-2-yl)-6-(trifluoromethyl)pyridine (129 mg, 0.421 mmol) | [M + H]+ (ES)+ 99.17% at 4.59 min (method B). | 7.77 (s, 1H), 7.81 (s, 1H), 8.00 (bs, 2H) |
| (clxvii) | 6-[2-(ethylamino)-6-methylpyridin-4-yl]-5-phenyl-1,2,4-triazin-3-amine (6 mg, 0.2%) | 6-bromo-5-phenyl-1,2,4-triazin-3-amine and 2-ethylamino-4-(4,4,5,5-tetramethyl-1,3,2-dioxaborolan-2-yl)-6-methylpyridine used crude from borylation step) | Mass spectroscopy: m/z 307.1 [M + H]+ (ES)+ 93.7% at 1.024 min (method B). | (400 MHz DMSO) δ: 1.03 (t, 3H), 2.18 (s, 3H), 3.94 (s, 2H), 6.28 (s, 1H), 6.34 (s, 1H) 7.37-7.50 (m, 5H). |
| (clxviii) | 6-[2-chloro-6-(trifluoromethyl)pyridin-4-yl]-5-(3-fluorophenyl)-1,2,4-triazin-3-amine (16 mg, 11%) | 6-bromo-5-(3-fluorophenyl)-1,2,4-triazin-3-amine (108 mg, 0.40 mmol) and 2-chloro-4-(4,4,5,5-tetramethyl-1,3,2-dioxaborolan-2-yl)-6-(trifluoromethyl)pyridine (129 mg, 0.42 mmol) | Mass spectroscopy: m/z 370/372 (M + H)+ (ES+); 368/370 (M − H)− (ES−), at 3.83 min, 100% (method C). | (400 MHz, DMSO) δ: 7.24 (d, J7.5 Hz, 1 H), 7.33-7.43 (m, 2 H), 7.43-7.53 (m, 1 H), 7.76 (s, 1 H), 7.79 (s, 1 H), 7.96 (bs, 2 H). |
| (clxix) | 6-[2-chloro-6-(trifluoromethyl)pyridin-4-yl]-5-(4-fluorophenyl)-1,2,4-triazin-3-amine (13 mg, 9%) | 6-bromo-5-(4-fluorophenyl)-1,2,4-triazin-3-amine (108 mg, 0.40 mmol) and 2-chloro-4-(4,4,5,5-tetramethyl-1,3,2-dioxaborolan-2-yl)-6-(trifluoromethyl)pyridine (129 mg, 0.42 mmol) | Mass spectroscopy: m/z 370/372 (M + H)+ (ES+); 368/370 (M − H)− (ES−), at 3.84 min, 100% (method C). | (400 MHz, DMSO) δ: 7.23-7.41 (m, 2 H), 7.46-7.65 (m, 2 H), 7.76 (s, 1 H), 7.79 (1 H, s), 7.90 (bs, 2 H). |
| (clxx) | 6-{2-[ethyl(methyl)amino]-6-methylpyridin-4-yl}-5-phenyl-1,2,4-triazin-3-amine (16 mg, 10%) | 6-bromo-5-phenyl-1,2,4-triazin-3-amine (126 mg, 0.5 mmol) and 2-ethyl(methyl)amino-4-(4,4,5,5-tetramethyl-1,3,2-dioxaborolan-2-yl)-6-methylpyridine (276 mg, crude) | Mass spectroscopy: m/z 321 (M + H)+ (ES+), at 3.88 min, 100% (method C). | (400 MHz, DMSO) δ: 0.86 (t, J8 Hz, 3H) 2.25 (s, 3 H) 2.81 (s, 3 H) 4.11 (q, J8 Hz, 2 H) 6.17 (s, 1 H) 6.49 (s, 1 H) 7.32-7.47 (m, 5 H) 7.50 (bs, 2 H). |
| (clxxi) | 6-[2-(dimethylamino)-6-methylpyridin-4-yl]-5-phenyl-1,2,4-triazin-3-amine (13 mg, 8%) | 6-bromo-5-phenyl-1,2,4-triazin-3-amine (126 mg, 0.5 mmol) and crude 2-dimethylamino-4-(4,4,5,5-tetramethyl-1,3,2-dioxaborolan-2-yl)-6-methylpyridine (234 mg, crude) | Mass spectroscopy: m/z 307 (M + H)+ (ES+), at 3.43 min, >99% (method C). | (400 MHz, DMSO) δ: 2.24 (s, 3 H) 2.86 (s, 6 H) 6.25 (s, 1 H) 6.46 (s, 1 H) 7.34-7.47 (m, 5 H) 7.47-7.57 (m, 2 H). |
| (clxxii) | 1-[6-(2,6-d6-dimethylpyridin-4-yl)-5-phenyl-1,2,4-triazin-3-amine (13.3 mg, 4%) | 6-bromo-5-phenyl-1,2,4-triazin-3-amine (310 mg, 1.24 mmol) and 1-[6-(2,6-d6-dimethylpyridin-4-yl)-5-phenyl-1,2,4-triazin-3-amine (crude, 1.17 g) | Mass spectroscopy: m/z 284.1 (M + H)+ (ES+) at 2.48 min, 100% (method C). | (400 MHz, CDCl3) δ: 5.49 (s, 2H), 7.02 (s, 2H), 7.33-7.39 (m, 2H), 7.43-7.49 (m, 3H). |
| (clxxiii) | 6-[2-d3-methyl-6-(trifluoromethyl)pyridin-4-yl]-5-phenyl-1,2,4-triazin-3-amine (28.5 mg, 12%) | 6-bromo-5-phenyl-1,2,4-triazin-3-amine (178 mg, 0.71 mmol) and 2-(d3)methyl-4-(4,4,5,5-tetramethyl-1,3,2-dioxaborolan-2-yl)-6-(trifluoromethyl)pyridine (226 mg, 0.78 mmol) | Mass spectroscopy: m/z 335.1 (M + H)+ (ES+); 333.1 (M − H)− (ES−) at 3.56 min, 100% (method C). | (400 MHz, CDCl3) δ: 5.57 (s, 2H), 7.37-7.52 (m, 7H). |
| (clxxiv) | 5-(4-fluorophenyl)-6-[2-d3-methyl-6- | 6-bromo-5-(4-fluorophenyl)-1,2,4- | Mass spectroscopy: m/z | (400 MHz, CDCl3) δ: 5.57 (s, 2H), 7.06- |

| No. | Product (yield) | Prepared From | LCMS | NMR |
|---|---|---|---|---|
| | (trifluoromethyl)pyridin-4-yl]-1,2,4-triazin-3-amine (93.3 mg, 38%) | triazin-3-amine (189 mg, 0.70 mmol) and 2-(d₃)methyl-4-(4,4,5,5-tetramethyl-1,3,2-dioxaborolan-2-yl)-6-(trifluoromethyl)pyridine (225 mg, 0.78 mmol) | 353.1 (M + H)⁺ (ES⁺); 351.1 (M − H)⁻ (ES⁻) at 3.68 min, 100% (method C). | 7.12 (m, 2H), 7.45-7.50 (m, 3H), 7.51-7.53 (m, 1H). |
| (clxxv) | 6-(2,6-dimethylpyridin-4-yl)-5-(2-fluorophenyl)-1,2,4-triazin-3-amine (32 mg, 57%) | 6-bromo-5-(2-fluoropheny)-1,2,4-triazin-3-amine (50 mg, 0.19 mmol) and 2,6-dimethyl-4-(4,4,5,5-tetramethyl-1,3,2-dioxaborolan-2-yl)-pyridine (68 mg, 0.29 mmol) | Mass spectroscopy: m/z 296.0 (M + H)⁺ (ES⁺), at 2.20 min, 100% (method C). | (400 MHz, DMSO), δ: 2.31 (s, 6H), 6.93 (s, 2H), 7.18 (t, J 7.8, 1H), 7.37 (t, J 6.5, 1H), 7.54-7.66 (m, 6H) |
| (clxxvi) | 6-(2-chloro-6-methylpyridin-4-yl)-5-(2-fluorophenyl)-1,2,4-triazin-3-amine (21 mg, 35%) | 6-bromo-5-(2-fluoropheny)-1,2,4-triazin-3-amine (50 mg, 0.19 mmol) and 2-chloro-4-(4,4,5,5-tetramethyl-1,3,2-dioxaborolan-2-yl)-6-methylpyridine (74 mg, 0.29 mmol) | Mass spectroscopy: m/z 315.9 (M + H)⁺ (ES⁺), at 2.66 min, 100% (method C). | (400 Mhz, DMSO) δ: 2.31 (s, 3H), 7.06 (s, 1H). 7.21 (t, J 7.8, 1H), 7.27 (s, 1H), 7.40 (t, J 6.5, 1H), 7.56-7.63 (m, 1H), 7.64-7.69 (m, 1H), 7.80-7.90 (bs, 2H) |
| (clxxvii) | 6-(2,6-dimethylpyridin-4-yl)-5-(4-methoxyphenyl)-1,2,4-triazin-3-amine (20 mg, 36%) | 6-bromo-5-(4-methoxypheny)-1,2,4-triazin-3-amine (50 mg, 0.18 mmol) and 2,6-dimethyl-4-(4,4,5,5-tetramethyl-1,3,2-dioxaborolan-2-yl)-pyridine (63 mg, 0.27 mmol) | Mass spectroscopy: m/z 308.0 (M + H)⁺ (ES⁺), at 2.31 min, 100% (method C). | (400 MHz, DMSO) δ: 2.37 (s, 6H), 3.78 (s, 3H), 6.95 (d, J 9.0, 2H), 7.02 (s, 2H), 7.39 (d, J 9.0, 2H), 7.45-7.55 (bs, 2H) |
| (clxxviii) | 6-(2-chloro-6-methylpyridin-4-yl)-5-(4-methoxyphenyl)-1,2,4-triazin-3-amine (10 mg, 17%) | 6-bromo-5-(4-methoxypheny)-1,2,4-triazin-3-amine (50 mg, 0.18 mmol) and 2-chloro-4-(4,4,5,5-tetramethyl-1,3,2-dioxaborolan-2-yl)-6-methylpyridine (68 mg, 0.27 mmol) | Mass spectroscopy: m/z 328.0 (M + H)⁺ (ES⁺), at 2.72 min, 100% (method C). | (400 MHz, DMSO) δ: 2.42 (s, 3H), 3.80 (s, 3H) 6.98 (d, J 8.8, 2H), 7.18 (s, 1H), 7.31 (s, 1H), 7.41 (d, J 8.8, 2H), 7.37-7.43 (s, 2H) |
| (clxxix) | 6-[2-(difluoromethyl)-6-methylpyridin-4-yl]-5-phenyl-1,2,4-triazin-3-amine (42 mg, 32%) | 6-bromo-5-phenyl-1,2,4-triazin-3-amine (100 mg, 0.40 mmol) and (2-(difluoromethyl)-4-(4,4,5,5-tetramethyl-1,3,2-dioxaborolan-2-yl)-6-methylpyridine (108 mg, 0.40 mmol) | Mass spectroscopy: m/z 314.1 (M + H)⁺ (ES⁺), at 1.38 min, 100% (method A). | (400 MHz, DMSO) δ: 2.46 (s, 3H), 6.83 (t, J 55.0, 1H), 7.33 (s, 1H), 7.38-7.45 (m, 5H), 7.47-7.52 (m, 1H), 7.62-7.75 (bs, 2H) |
| (clxxx) | 6-[2-chloro-6-(difluoromethyl)pyridin-4-yl]-5-phenyl-1,2,4-triazin-3-amine (27 mg, 20%) | 6-bromo-5-phenyl-1,2,4-triazin-3-amine (100 mg, 0.40 mmol) and 2-chloro-4-(4,4,5,5-tetramethyl-1,3,2-dioxaborolan-2-yl)-6-(difluoromethyl)-pyridine (151 mg, 0.52 mmol) | Mass spectroscopy: m/z 333.9 (M + H)⁺ (ES⁺), at 1.56 min, 100% (method C). | (400 MHz, DMSO) δ: 6.94 (t, J 54.5, 1H), 7.41-7.48(m, 4H), 7.50-7.56 (m, 1H), 7.57 (s, 1H), 7.62 (s, 1H) |
| (clxxxi) | 6-[2-chloro-6-(fluoromethyl)pyridin-4-yl]-5-phenyl-1,2,4-triazin-3-amine (13 mg, 10%) | 6-bromo-5-phenyl-1,2,4-triazin-3-amine (100 mg, 0.40 mmol) and 2-chloro-4-(4,4,5,5-tetramethyl-1,3,2-dioxaborolan-2-yl)-6-(fluoromethyl)-pyridine (141 mg, 0.52 mmol) | Mass spectroscopy: m/z 316.0 (M + H)⁺ (ES⁺), at 3.12 min, 100% (method C). | (400 MHz, DMSO) δ: 5.43 (d, J 46.4, 2H), 7.33 (s, 1H), 7.41-7.46 (m, 5H), 7.47-7.53 (m, 3H) |
| (clxxxii) | 6-[2-(difluoromethyl)-6-methylpyridin-4-yl]-5-(4-fluorophenyl)-1,2,4-triazin-3-amine (32 mg, 26%) | 6-bromo-5-(4-fluorophenyl)-1,2,4-triazin-3-amine (100 mg, 0.37 mmol) and (2-(difluoromethyl-4- | Mass spectroscopy: m/z 332.0 (M + H)⁺ (ES⁺), at 1.42 min, 100% (method A). | (400 MHz, DMSO) δ: 2.49(s, 3H), 6.82 (t, J 55.0 Hz, 1H), 7.19-7.31 (m, 1H), 7.36 (s, 1H), 7.44 (s, |

| No. | Product (yield) | Prepared From | LCMS | NMR |
|---|---|---|---|---|
| | | (4,4,5,5-tetramethyl-1,3,2-dioxaborolan-2-yl)-6-methylpyridine (110 mg, 0.41 mmol) | | 1H), 7.46-7.52 (m, 2H), 7.54-7.58 (, 2H) |
| (clxxxiii) | 6-[2,6-bis(fluoromethyl)pyridine-4-yl]-5-phenyl-1,2,4-triazin-3-amine (10 mg, 8%) | 6-bromo-5-phenyl-1,2,4-triazin-3-amine (100 mg, 0.40 mmol) and 2,6-bis-(fluoromethyl-4-(4,4,5,5-tetramethyl-1,3,2-dioxaborolan-2-yl)-6-methylpyridine (140 mg, 0.52 mmol) | Mass spectroscopy: m/z 314.0 (M + H)$^+$ (ES$^+$), at 1.33 min, 95% (method A). | (400 MHz, DMSO) δ: 5.43 (d, J 46.9 Hz, 4H), 7.38-7.45 (m, 6H), 7.47-7.51 (m, 1H), 7.65-7.75(bs, 2H). |
| (clxxxiv) | 6-[2-(fluoromethyl)-6-methylpyridin-4-yl]-5-phenyl-1,2,4-triazin-3-amine (10 mg, 8%) | 6-bromo-5-phenyl-1,2,4-triazin-3-amine (100 mg, 0.40 mmol) and (2-(fluoromethyl-4-(4,4,5,5-tetramethyl-1,3,2-dioxaborolan-2-yl)-6-methylpyridine (151 mg, 0.60 mmol) | Mass spectroscopy: m/z 296.0 (M + H)$^+$ (ES$^+$), at 2.58 min, 100% (method C). | (400 MHz, DMSO) δ: 2.40(s, 3H), 5.37 (d, J 46.9 Hz, 2H), 7.20 (s, 2H), 7.38-7.45 (m, 4H), 7.46-7.51 (m, 1H), 7.60-7.72 (bs, 2H) |
| (clxxxv) | 6-(2-chloro-6-methylpyridin-4-yl)-5-(2,5-difluorophenyl)-1,2,4-triazin-3-amine (24 mg, 18%) | 6-bromo-5-(2,5-difluorophenyl)-1,2,4-triazin-3-amine (115 mg, 0.40 mmol) and 2-chloro-4-(4,4,5,5-tetramethyl-1,3,2-dioxaborolan-2-yl)-6-methylpyridine(129 mg, 0.42 mmol) | Mass spectroscopy: m/z 334.0 (M + H)$^+$ (ES+); at 2.87 min, 95% (method C). | (400 MHz, DMSO) δ: 2.40 (s, 3H), 7.12 (s, 1H), 7.25-7.32 (m, 2H), 7.42-7.49 (m, 1H), 7.51-7.56 (m, 1H), 7.89 (br s, 2H). |
| (clxxxvi) | 6-[2-chloro-6-(trifluoromethyl)pyridin-4-yl]-5-(2-fluorophenyl)-1,2,4-triazin-3-amine (18 mg, 12%) | 6-bromo-5-(2-fluorophenyl)-1,2,4-triazin-3-amine (108 mg, 0.40 mmol) and 2-chloro-4-(4,4,5,5-tetramethyl-1,3,2-dioxaborolan-2-yl)-6-(trifluoromethyl)pyridine (129 mg, 0.42 mmol) | Mass spectroscopy: m/z 368.1(M + H)$^+$ (ES+), 370 (M − H)$^-$ (ES−); at 3.85 min, 95% (method C). | (400 MHz, DMSO) δ: 7.20-7.26 (m, 1H), 7.38-7.45 (m, 1H), 7.56-7.74 (m, 3H), 7.78 (s, 1H). |
| (clxxxvii) | 6-[2-chloro-6-(trifluoromethyl)pyridin-4-yl]-5-(2,5-difluorophenyl)-1,2,4-triazin-3-amine (17 mg, 11%) | 6-bromo-5-(2,5-difluorophenyl)-1,2,4-triazin-3-amine (115 mg, 0.40 mmol) and 2-chloro-4-(4,4,5,5-tetramethyl-1,3,2-dioxaborolan-2-yl)-6-(trifluoromethyl)pyridine (129 mg, 0.42 mmol) | Mass spectroscopy: m/z 386.1(M − H)$^-$ (ES−); at 3.93 min, 95% (method C). | (400 MHz, DMSO) δ: 7.27-7.35 (m, 1H), 7.45-7.52 (m, 1H), 7.52-7.58 (m, 1H), 7.79 (s, 1H), 7.82 (s, 1H), 8.08 (bs, 2H). |
| (clxxxviii) | 6-[2-cyclopropyl-6-(trifluoromethyl)pyridin-4-yl]-5-phenyl-1,2,4-triazin-3-amine (20 mg, 26%) | 6-bromo-5-phenyl-1,2,4-triazin-3-amine (50 mg, 0.20 mmol) and 2-cyclopropyl-4-(4,4,5,5-tetramethyl-1,3,2-dioxaborolan-2-yl)-6-(trifluoromethyl)pyridine (66 mg, 0.21 mmol) | Mass spectroscopy: m/z 358 (M + H)$^+$ (ES+); at 4.43 min, 100% (method C). | (400 MHz, DMSO) δ: 0.79-0.84 (m, 2H), 0.97-1.03 (m, 2H), 2.10-2.17 (m, 1H), 7.39-7.46 (m, 6H), 7.47-7.53 (m, 1H), 7.61 (bs, 2H). |
| (clxxxix) | 6-[2-ethyl-6-(trifluoromethyl)pyridin-4-yl]-5-phenyl-1,2,4-triazin-3-amine (37 mg, 55%) | 6-bromo-5-phenyl-1,2,4-triazin-3-amine (50 mg, 0.20 mmol) and 2-ethyl-4-(4,4,5,5-tetramethyl-1,3,2-dioxaborolan-2-yl)-6-(trifluoromethyl)pyridine (63 mg, 0.21 mmol) | Mass spectroscopy: m/z 346.0 (M + H)$^+$ (ES+), 344.2 (M − H)$^-$ (ES−) at 4.08 min, 100% (method C). | (400 MHz, DMSO) δ: 1.10 (t, 3H, J8.0 Hz), 2.75 (q, 2H, J 8.0), 7.40-7.44 (m, 4H), 7.47-7.53 (m, 2H), 7.57 (s, H), 7.76 (bs, 2H). |
| (cxc) | 6-(2-cyclopropyl-6-methylpyridin-4-yl)-5-phenyl-1,2,4-triazin-3-amine (32 mg, 46%) | 6-(2-chloro-6-methylpyridin-4-yl)-5-phenyl-1,2,4-triazin-3-amine (70 mg, 0.23 mmol) and cyclopropyltrifluoro- | Mass spectroscopy: m/z 304.1 (M + H)$^+$ (ES+); at 3.22 min, 100% (method C). | (400 MHz, DMSO) δ: 0.70-0.76 (m, 2H), 0.82-0.89 (m, 2H), 1.88-1.97 (m, 1H), 2.32 (s, 3H), 6.88 (s, 1H), 6.97 (s, 1H), |

| No. | Product (yield) | Prepared From | LCMS | NMR |
|---|---|---|---|---|
| | | borate potassium salt (340 mg, 2.30 mmol) | | 7.38-7.43 (m, 4H), 7.45-7.52 (m, 1H), 7.54-7.62 (bs, 2H). |
| (cxci) | 5-(2-fluorophenyl)-6-[2-methyl-6-(trifluoromethyl)pyridin-4-yl]-1,2,4-triazin-3-amine (65.3 mg, 47%) | 6-bromo-5-(2-fluorophenyl)-1,2,4-triazin-3-amine (108 mg, 0.40 mmol) and 2-methyl-6-trifluoromethyl-4-(4,4,5,5-tetramethyl-1,3,2-dioxaborolan-2-yl)pyridine (121 mg, 0.42 mmol) | Mass spectroscopy: m/z 350.0 $(M + H)^+$ $(ES^+)$ at 3.30 min, ~98% (method C). | (400 MHz, DMSO) δ: 2.51 (s, 3H), 7.17-7.22 (m, 1H), 7.38-7.42 (m, 2H), 7.56-7.63 (m, 2H), 7.67-7.71 (m, 1H), 7.88 (bs, 2H). |
| (cxcii) | 5-(3-fluorophenyl)-6-[2-methyl-6-(trifluoromethyl)pyridin-4-yl]-1,2,4-triazin-3-amine (72.8 mg, 52%) | 6-bromo-5-(3-fluorophenyl)-1,2,4-triazin-3-amine (108 mg, 0.40 mmol) and 2-methyl-6-trifluoromethyl-4-(4,4,5,5-tetramethyl-1,3,2-dioxaborolan-2-yl)pyridine (121 mg, 0.42 mmol) | Mass spectroscopy: m/z 350.0 $(M + H)^+$ $(ES^+)$ at 3.24 min, ~98% (method C). | (400 MHz, CDCl$_3$) δ: 2.61 (s, 3H), 5.62 (bs, 2H), 7.10-7.20 (m, 1H), 7.18-7.23 (m, 1H), 7.28-7.35 (m, 2H), 7.48-7.50 (m, 2H). |
| (cxciii) | 5-(4-fluorophenyl)-6-[2-methyl-6-(trifluoromethyl)pyridin-4-yl]-1,2,4-triazin-3-amine (78.9 mg, 56%) | 6-bromo-5-(4-fluorophenyl)-1,2,4-triazin-3-amine (108 mg, 0.40 mmol) and 2-methyl-6-trifluoromethyl-4-(4,4,5,5-tetramethyl-1,3,2-dioxaborolan-2-yl)pyridine (121 mg, 0.42 mmol) | Mass spectroscopy: m/z 350.0 $(M + H)^+$ $(ES^+)$ at 3.26 min, 98% (method C). | (400 MHz, CDCl$_3$) δ: 2.61 (s, 3H), 5.58 (bs, 2H), 7.07-7.11 (m, 2H), 7.46-7.52 (m, 4H). |
| (cxciv) | 5-(2,5-difluorophenyl)-6-[2-methyl-6-(trifluoromethyl)pyridin-4-yl]-1,2,4-triazin-3-amine (61.7 mg, 42%) | 6-bromo-5-(2,5-difluorophenyl)-1,2,4-triazin-3-amine (115 mg, 0.40 mmol) and 2-methyl-6-trifluoromethyl-4-(4,4,5,5-tetramethyl-1,3,2-dioxaborolan-2-yl)pyridine (121 mg, 0.42 mmol) | Mass spectroscopy: m/z 368.0 $(M + H)^+$ $(ES^+)$ at 3.38 min, 98% (method C). | (400 MHz, DMSO) δ: 2.53 (s, 3H), 7.25-7.30 (m, 1H), 7.44-7.50 (m, 2H), 7.55-7.59 (m, 1H), 7.65 (s, 1H), 7.95 (bs, 2H). |
| (cxcv) | 5-(3,4-difluorophenyl)-6-[2-methyl-6-(trifluoromethyl)pyridin-4-yl]-1,2,4-triazin-3-amine (40.0 mg, 27%) | 6-bromo-5-(3,4-difluorophenyl)-1,2,4-triazin-3-amine (115 mg, 0.40 mmol) and 2-methyl-6-trifluoromethyl-4-(4,4,5,5-tetramethyl-1,3,2-dioxaborolan-2-yl)pyridine (121 mg, 0.42 mmol) | Mass spectroscopy: m/z 368.0 $(M + H)^+$ $(ES^+)$ at 4.34 min, 100% (method B). | (400 MHz, DMSO) δ: 2.54 (s, 3H), 7.22-7.24 (m, 1H), 7.46-7.57 (m, 3H), 7.62 (s, 1H), 7.81 (bs, 2H). |
| (cxcvi) | 5-(3,5-difluorophenyl)-6-[2-methyl-6-(trifluoromethyl)pyridin-4-yl]-1,2,4-triazin-3-amine (73.3 mg, 49%) | 6-bromo-5-(3,5-difluorophenyl)-1,2,4-triazin-3-amine (115 mg, 0.40 mmol) and 2-methyl-6-trifluoromethyl-4-(4,4,5,5-tetramethyl-1,3,2-dioxaborolan-2-yl)pyridine (121 mg, 0.42 mmol) | Mass spectroscopy: m/z 368.0 $(M + H)^+$ $(ES^+)$ at 3.53 min, ~98% (254 nm). | (400 MHz, DMSO) δ: 2.54 (s, 3H), 7.16-7.19 (m, 2H), 7.42-7.49 (m, 2H), 7.64 (s, 1H), 7.81 (bs, 2H). |
| (cxcvii) | 6-[2-(azetidin-1-yl)-6-(trifluoromethyl)pyridin-4-yl]-5-(4-fluorophenyl)-1,2,4-triazin-3-amine (40.2 mg, 18%) | 6-bromo-5-(4-fluorophenyl)-1,2,4-triazin-3-amine (150 mg, 0.56 mmol) and 2-(azetid-1-yl)-6-trifluoromethyl-4-(4,4,5,5-tetramethyl-1,3,2-dioxaborolan-2-yl)pyridine (192 mg, 0.59 mmol) | Mass spectroscopy: m/z 391.0 $(M + H)^+$ $(ES^+)$ at 3.89 min, ~98% (method C). | (400 MHz, CDCl$_3$) δ: 2.27-2.35 (quint., J 7.4, 2H), 3.89 (t, J 7.4, 4H), 5.52 (bs, 2H), 6.54 (s, 1H), 6.83 (s, 1H), 7.06-7.10 (m, 2H), 7.49-7.53 (m, 2H). |
| (cxcviii) | 6-[2-methyl-6-(morpholin-4-yl)pyridin-4-yl]-5-phenyl-1,2,4-triazin- | 6-bromo-5-phenyl-1,2,4-triazin-3-amine (251 mg, 1.0 mmol) and 2-methyl-6- | Mass spectroscopy: m/z 349.1 $(M + H)^+$ $(ES^+)$ at 1.16 min, | (400 MHz, CDCl$_3$) δ: 2.33 (s, 3H), 3.39-3.42 (m, 2H), 3.76-3.78 (m, 2H), 5.49 |

| No. | Product (yield) | Prepared From | LCMS | NMR |
|---|---|---|---|---|
| | 3-amine (43.0 mg, 12%) | (morpholin-4-yl)-4-(4,4,5,5-tetramethyl-1,3,2-dioxaborolan-2-yl)pyridine (320 mg, 1.05 mmol) | ~95% (method B). | (bs, 2H), 6.52 (s, 1H), 6.55 (s, 1H), 7.34-7.38 (m, 2H), 7.43-7.45 (m, 1H), 7.50-7.52 (m, 2H). |
| (cxcix) | 6-(2-chloro-6-methylpyridin-4-yl)-5-(4-ethylphenyl)-1,2,4-triazin-3-amine (6 mg, 6%) | 6-bromo-5-(4-methylphenyl)-1,2,4-triazin-3-amine (94 mg, crude - assume 0.17 mmol) and 2-chloro-4-(4,4,5,5-tetramethyl-1,3,2-dioxaborolan-2-yl)-6-methylpyridine (128 mg, 0.506 mmol) | Mass spectroscopy: m/z 324.2 (M − H)⁻ (ES−) at 2.16 min, 97% (method B) | (400 MHz, DMSO) δ: 1.18 (t, 3H), 2.40 (s, 3H), 2.64 (q, 2H), 7.22 (s, 1H), 7.55 (m, 3H), 7.38 (m, 2H) (NH₂ not observed) |
| (cc) | 5-(2,5-difluorophenyl)-6-(2,6-dimethylpyridin-4-yl)-1,2,4-triazin-3-amine (12 mg, 12%) | 6-bromo-5-(2,5-difluorophenyl)-1,2,4-triazin-3-amine (90 mg, 0.314 mmol) and 2,6-dimethyl-4-(4,4,5,5-tetramethyl-1,3,2-dioxaborolan-2-yl)pyridine (110 mg, 0.47 mmol) | Mass spectroscopy: m/z 314.3 (M + H)⁺ (ES+) at 0.97 min, 100% (method B) | (400 MHz, DMSO) δ: 2.34 (s, 6H), 6.98 (s, 2H), 7.26 (m, 1H), 7.44 (m, 1H), 7.54 (m, 1H), 1.78 (bs, 2H) |
| (cci) | 6-(2,6-dimethylpyridin-4-yl)-5-(4-methylphenyl)-1,2,4-triazin-3-amine (16 mg, 17%) | 6-bromo-5-(4-methylphenyl)-1,2,4-triazin-3-amine (85 mg, 0.32 mmol) and 2,6-dimethyl-4-(4,4,5,5-tetramethyl-1,3,2-dioxaborolan-2-yl)pyridine (112 mg, 0.48 mmol) | Mass spectroscopy: m/z 293.3 (M + H)⁺ (ES+) at 1.06 min, 99% (method B) | (400 MHz, DMSO) δ: 2.31 (s, 3H), 2.36 (s, 6H), 6.99 (s, 2H), 7.20 (m, 2H), 7.33 (m, 2H), 7.53 (bs, 2H). |
| (ccii) | 6-[2-(difluoromethyl)-6-methylpyridin-4-yl]-5-(3-fluorophenyl)-1,2,4-triazin-3-amine (17 mg, 20%) | 6-bromo-5-(3-fluorophenyl)-1,2,4-triazin-3-amine (70 mg, 0.26 mmol) and (2-(difluoromethyl-4-(4,4,5,5-tetramethyl-1,3,2-dioxaborolan-2-yl)-6-methylpyridine (70 mg, 0.26 mmol) | Mass spectroscopy: m/z 332.3, M⁺ (ESI+) at 1.84 min, 96% (method B). | (400 MHz, CDCl₃) δ: 2.51 (s, 3H), 5.51 (bs, 2H), 6.55 (t, 1H), 7.13 (m, 1H), 7.29 (m, 1H), 7.32 (m, 1H), 7.40 (s, 1H), 7.44 (s, 1H) |
| (cciii) | 6-[2-(difluoromethyl)-6-methylpyridin-4-yl]-5-(2-fluorophenyl)-1,2,4-triazin-3-amine (20 mg, 23%) | 6-bromo-5-(3-fluorophenyl)-1,2,4-triazin-3-amine (70 mg, 0.26 mmol) and (2-(difluoromethyl-4-(4,4,5,5-tetramethyl-1,3,2-dioxaborolan-2-yl)-6-methylpyridine (70 mg, 0.26 mmol) | Mass spectroscopy: m/z 332.3, M⁺ (ESI+) at 1.80 min, 96% (method B). | (400 MHz, CDCl₃) δ: 2.55 (s, 3H), 5.54 (bs, 2H), 6.51 (t, 1H), 7.00 (m, 1H), 7.30 (s, 1H) 7.32 (m, 1H), 7.43 (s, 1H), 7.50 (m, 1H), 7.58 (m, 1H). |
| (cciv) | 6-(3,5-dichlorophenyl)-5-(pyridin-2-yl)-1,2,4-triazin-3-amine (23 mg, 7%) | 6-bromo-5-(pyridin-2-yl)-1,2,4-triazin-3-amine (0.25 g, 0.99 mmol) and 3,5-dichlorophenylboronic acid (0.20 g, 1.09 mmol) | HPLC purity: 98.56%; (268 nm). Mass spectroscopy: (ESI +ve) 318.0 [M + H]⁺, 316.1 [M + H]⁻. | (400 MHz, DMSO) δ: 7.26 (m, 2H), 7.49 (m, 1H), 7.54 (m, 1H), 7.68 (bs, 2H), 7.91 (m, 1H), 8.00 (t, 1H), 8.43 (d, 1H). |
| (ccv) | 6-(3-chloro-5-methylphenyl)-5-(pyridin-2-yl)-1,2,4-triazin-3-amine (12 mg, 5%) | 6-bromo-5-(pyridin-2-yl)-1,2,4-triazin-3-amine (0.20 g, 0.79 mmol) and 3-chloro-5-methylphenyl-boronic acid (0.175 g, 1.03 mmol) | HPLC purity: 99.60%; (266 nm). Mass spectroscopy: (ESI +ve) 298.2 [M + H]⁺. | (400 MHz, DMSO) δ: 2.22 (s, 3H), 6.99 (s, 1H), 7.07 (s, 1H), 7.18 (s, 1H), 7.45-7.48 (m, 1H), 7.56 (bs, 2H), 7.79 (d, 1H), 7.94-7.98 (m, 1H), 8.44 (d, 1H). |
| (ccvi) | 6-[2-chloro-6-(trifluoromethyl)pyridin-4-yl]-5-phenyl-1,2,4-triazin-3-amine (50 mg, 5%) | 6-bromo-5-phenyl-1,2,4-triazin-3-amine (0.70 g, 2.8 mmol) and 2-chloro-4-(4,4,5,5-tetramethyl-1,3,2-dioxaborolan-2-yl)-6-(trifluoromethyl)pyridine (1.02 g, 3.34 mmol) | HPLC purity: 96.75% (272 nm) Mass spectroscopy: (ESI +ve) 352.1 [M + H]⁺. | ¹H NMR: (400 MHz, DMSO) δ: 7.44 (m, 5H), 7.69 (s, 1H), 7.88 (s, 1H), 7.84 (bs, 2H). |

| No. | Product (yield) | Prepared From | LCMS | NMR |
|---|---|---|---|---|
| (ccvii) | 6-[2,6-bis(trifluoromethyl)pyridin-4-yl]-5-phenyl-1,2,4-triazin-3-amine (0.10 g, 13%) | 6-bromo-5-phenyl-1,2,4-triazin-3-amine (0.52 g, 2.07 mmol) and 2,6-bis(trifluoromethyl)-4-(4,4,5,5-tetramethyl-1,3,2-dioxaborolan-2-yl)pyridine (1.0 g, 3.1 mmol) | HPLC purity: 98.90% (232 nm) Mass spectroscopy: (ESI +ve) 386.1[M + H]$^+$, (ESI −ve) 384.2[M − H]$^−$. | $^1$H NMR: (400 MHz, DMSO) δ: 7.48 (m, 5H), 7.93 (bs, 2H), 8.03 (s, 2H). |
| (ccviii) | 6-[3-chloro-5-(trifluoromethyl)phenyl]-5-(pyridin-2-yl)-1,2,4-triazin-3-amine (30 mg, 10%) | 6-bromo-5-(pyridin-2-yl)-1,2,4-triazin-3-amine (0.225 g, 0.89 mmol) and 3-chloro-5-(trifluoromethyl)-phenylboronic acid (0.260 g, 1.16 mmol) | HPLC purity: 99.87%; (268 nm). Mass spectroscopy: (ESI +ve) 352.1 [M + H]$^+$. | (400 MHz, DMSO) δ: 7.45-7.48 (m, 2H), 7.65 (s, 1H), 7.70 (bs, 2H), 7.77 (s, 1H), 7.91 (m, 1H), 8.0 (m, 1H), 8.36 (d, 1H). |
| (ccix) | 6-[2-methyl-6-(trifluoromethyl)pyridin-4-yl]-5-phenyl-1,2,4-triazin-3-amine (0.32 g, 35%) | 6-bromo-5-phenyl-1,2,4-triazin-3-amine (0.70 g, 2.78 mmol) and 2-methyl-4-(4,4,5,5-tetramethyl-1,3,2-dioxaborolan-2-yl)-6-trifluoromethyl-pyridine (1.2 g, 4.1 mmol) | HPLC purity: 98.81% (269 nm) Mass spectroscopy: (ESI +ve) 332.0 [M + H]$^+$, (ESI −ve) 330.2 [M − H]$^−$. | (400 MHz, DMSO) δ: 2.48 (s, 3H), 7.38 (m, 5H), 7.47 (s, 1H), 7.58 (s, 1H), 7.73 (bs, 2H). |
| (ccx) | 6-(3,5-dimethylphenyl)-5-(pyridin-2-yl)-1,2,4-triazin-3-amine (16 mg, 7%) | 6-bromo-5-(pyridin-2-yl)-1,2,4-triazin-3-amine (0.20 g, 0.79 mmol) and 3,5-dimethylphenylboronic acid (0.15 g, 1.02 mmol) | HPLC purity: 98.96%; (268 nm). Mass spectroscopy: (ESI +ve) 277.9 [M + H]$^+$. | (400 MHz, DMSO) δ: 2.12 (s, 6H), 6.81 (s, 2H), 6.88 (s, 1H), 7.40-7.43 (m, 3H), 7.64-7.66 (m, 1H), 7.89 (m, 1H), 8.43 (m, 1H). |
| (ccxi) | 6-[2-(dimethylamino)pyridin-4-yl]-5-phenyl-1,2,4-triazin-3-amine (83 mg, 33%) | 6-bromo-5-phenyl-1,2,4-triazin-3-amine (0.5 g, 1.99 mmol) and 2-dimethylamino-(4,4,5,5-tetramethyl-1,3,2-dioxaborolan-2-yl)pyridine (0.98 g, 3.9 mmol) | HPLC purity: 99.18% (272 nm) Mass spectroscopy: (ESI +ve) 292.8 [M + H]$^+$. | (400 MHz, DMSO) δ: 2.97 (s, 6H), 6.46 (m, 1H), 6.56 (m, 1H), 7.37-7.47 (m, 5H), 7.54 (bs, 2H), 7.99 (m, 1H). |
| (ccxii) | 6-(2-bromo-6-methylpyridin-4-yl)-5-phenyl-1,2,4-triazin-3-amine (76 mg, 22%) | 6-bromo-5-phenyl-1,2,4-triazin-3-amine (0.25 g, 0.90 mmol) and 2-bromo-4-(4,4,5,5-tetramethyl-1,3,2-dioxaborolan-2-yl)-6-methylpyridine (0.44 g, 1.4 mmol) | HPLC purity: 98.71% (272 nm) Mass spectroscopy: (ESI +ve) 341.9 [M]$^+$, 343.9 [M]$^+$. | (400 MHz, DMSO) δ: 2.38 (s, 3H), 7.25 (s, 1H), 7.30 (s, 1H), 7.47 (m, 5H), 7.72 (bs, 2H). |
| (ccxiii) | 6-(2,6-dimethyl-1-oxidopyridin-4-yl)-5-phenyl-1,2,4-triazin-3-amine (87 mg, 15%) | 6-bromo-5-phenyl-1,2,4-triazin-3-amine (0.50 g, 1.99 mmol) and 2,6-dimethyl-4-(4,4,5,5-tetramethyl-1,3,2-dioxaborolan-2-yl)pyridine-N-oxide (0.74 g, 2.98 mmol) | HPLC purity: 98.85% (294 nm) Mass spectroscopy: (ESI +ve) 293.7 [M + H]$^+$, (ESI −ve) 292.0 [M − H]$^−$. | (400 MHz, CDCl$_3$) δ: 2.48 (s, 6H), 5.66 (bs, 2H), 7.24 (s, 1H), 7.28 (s, 1H), 7.49 (m, 2H), 7.52 (m, 3H). |
| (ccxiv) | 4-(3-amino-5-phenyl-1,2,4-triazin-6-yl)-6-methylpyridine-2-carbonitrile (140 mg, 49%) | 6-bromo-5-phenyl-1,2,4-triazin-3-amine (0.25 g, 0.99 mmol) and 2-cyano-4-(4,4,5,5-tetramethyl-1,3,2-dioxaborolan-2-yl)-6-methylpyridine (0.36 g, 1.4 mmol) | HPLC purity: 99.18% (272 nm) Mass spectroscopy: (ESI +ve) 288.9 [M + H]$^+$. | (400 MHz, DMSO) δ: 2.48 (s, 3H), 7.45-7.52 (m, 5H), 7.61 (s, 1H), 7.63 (s, 1H), 7.79 (bs, 2H). |
| (ccxv) | 6-(3,5-dichlorophenyl)-5-(pyridin-3-yl)-1,2,4-triazin-3-amine (3 mg, 1%) | 6-bromo-5-(pyridin-3-yl)-1,2,4-triazin-3-amine (0.3 g, 1.19 mmol) and 3,5-dichlorophenylboronic acid (0.22 g, 1.19 mmol) | HPLC purity: 98.66% (266 nm) Mass spectroscopy: (ESI +ve) 317.9 [M + H]$^+$. 315.9 [M + H]$^−$ | (400 MHz, DMSO) δ: 7.39 (m, 2H), 7.42-7.46 (m, 1H), 7.62 (m, 1H), 7.69 (bs, 2H), 7.82 (m, 1H), 8.59 (m, 1H), 8.63 (m, 1H). |
| (ccxvi) | 6-(3-chloro-5-methylphenyl)-5-(pyridin-3-yl)-1,2,4-triazin-3-amine (11 mg, 5%) | 6-bromo-5-(pyridin-3-yl)-1,2,4-triazin-3-amine (0.19 g, 0.75 mmol) and 3-chloro-5- | HPLC purity: 92.24% (218 nm) Mass spectroscopy: (ESI +ve) 297.9.0 | (400 MHz, DMSO) δ: 2.25 (s, 3H), 6.82 (s, 1H), 7.15-7.17 (m, 1H), 7.27 (s, 1H), 7.40 (m, 1H), 7.59 |

| No. | Product (yield) | Prepared From | LCMS | NMR |
|---|---|---|---|---|
| | | methylphenylboronic acid (0.166 g, 0.98 mmol) | [M + H]⁺, 295.9 [M + H]⁻ | (bs, 2H), 7.77 (m, 1H), 8.56 (m, 1H), 8.61 (m, 1H). |
| (ccxvii) | 6-(3,5-dichlorophenyl)-5-(pyrimidin-2-yl)-1,2,4-triazin-3-amine (40 mg, 6%) | 6-bromo-5-(pyrimidin-2-yl)-1,2,4-triazin-3-amine (0.5 g, 1.98 mmol) and 3,5-dichlorophenylboronic acid (0.414 g, 2.18 mmol) | HPLC purity: 97.14% (210 nm) Mass spectroscopy: (ESI +ve) 318.9 [M + H]⁺, 316.9 [M + H]⁻. | (400 MHz, DMSO) δ: 7.21 (s, 2H), 7.58 (s, 1H), 7.65 (t, 1H), 7.84 (bs, 2H), 8.93 (d, 2H). |
| (ccxviii) | 6-[3-chloro-5-(trifluoromethyl)phenyl]-5-(pyrimidin-2-yl)-1,2,4-triazin-3-amine (0.130 g, 19%) | 6-bromo-5-(pyrimidin-2-yl)-1,2,4-triazin-3-amine (0.50 g, 1.98 mmol) and 3-chloro-5-(trifluoromethyl)phenylboronic acid (0.488 g, 2.18 mmol) | HPLC purity: 93.30% (202 nm) Mass spectroscopy: (ESI +ve) 353.0 [M + H]⁺, 351.0 [M + H]⁻. | (400 MHz, DMSO) δ: 7.38 (s, 1H), 7.64 (m, 2H), 7.86 (m, 3H), 8.91 (d, 2H). |
| (ccxix) | 6-[2-bromo-6-(trifluoromethyl)pyridin-4-yl]-5-phenyl-1,2,4-triazin-3-amine (30 mg, 8%) | 6-bromo-5-phenyl-1,2,4-triazin-3-amine (0.25 g, 0.9 mmol) and 2-bromo-4-(4,4,5,5-tetramethyl-1,3,2-dioxaborolan-2-yl)-6-(trifluoromethyl)pyridine (0.52 g, 1.48 mmol) | HPLC purity: 94.90% (272 nm) Mass spectroscopy: (ESI +ve) 396.1 [M + H]⁺, 397.9 [M + H]⁺. | (400 MHz, DMSO) δ: 7.47 (m, 5H), 7.74 (s, 1H), 7.84 (s, 1H), 7.88 (bs, 2H). |
| (ccxx) | 6-[3-chloro-5-(trifluoromethyl)phenyl]-5-(pyridin-3-yl)-1,2,4-triazin-3-amine (8 mg, 3%) | 6-bromo-5-(pyridin-3-yl)-1,2,4-triazin-3-amine (0.20 g, 0.79 mmol) and 3-chloro-5-(trifluoromethyl)phenylboronic acid (0.21 g, 0.95 mmol) | HPLC purity: 91.22% (266 nm) Mass spectroscopy: (ESI +ve) 351.8 [M + H]⁺, 349.9 [M + H]⁻ | (400 MHz, DMSO) δ: 7.41 (m, 1H), 7.62 (s, 1H), 7.72 (bs, 2H), 7.76-7.80 (m, 2H), 7.87 (s, 1H), 8.58 (m, 1H), 8.62-8.64 (m, 1H). |
| (ccxxi) | 6-(3-chloro-5-methylphenyl)-5-(pyrimidin-2-yl)-1,2,4-triazin-3-amine (130 mg, 22%) | 6-bromo-5-(pyrimidin-2-yl)-1,2,4-triazin-3-amine (0.5 g, 1.98 mmol) and 3-chloro-5-methylphenylboronic acid (0.650 g, 2.18 mmol) | HPLC purity: 95.27% (266 nm) Mass spectroscopy: (ESI +ve) 299.0 [M + H]⁺, | (400 MHz, DMSO) δ: 2.21 (3H, s), 6.98 (m, 2H), 7.21 (s, 1H), 7.62 (t, 1H), 7.74 (s, 2H), 8.90 (d, 2H) |

The following compounds were prepared according to a modified version of the general procedure described for Example 1. In these cases, the reactions were run using palladium acetate (1.5 mol %), dppf (3.0 mol %), copper bromide (1.5 eq.), caesium carbonate (2.0 eq.) and DMF (0.8 mL).

| No. | Product (yield) | Prepared From | LCMS | NMR |
|---|---|---|---|---|
| (ccxxii) | 6-(6-chloropyridin-2-yl)-5-phenyl-1,2,4-triazin-3-amine (7 mg, 6%) | 6-bromo-5-phenyl-1,2,4-triazin-3-amine (100 mg, 0.398 mmol), 6-chloropyridin-2-ylboronic acid (141 mg, 0.896 mmol) | Mass spectroscopy: m/z 284.7 (M + H)⁺ (ES⁺), at 3.75 min, 99.2% purity (method B). | (400 MHz, DMSO) δ: 7.31-7.39 (m, 4H), 7.39-7.46 (m, 1H), 7.47 (dd, J = 8.0, 0.8 Hz, 1H), 7.66 (s, 2H), 7.77 (dd, J = 7.6, 0.8 Hz, 1H), 7.95 (t, J = 7.8 Hz, 1H). |
| (ccxxiii) | 6-(4-cyclopropylpyridin-2-yl)-5-phenyl-1,2,4-triazin-3-amine (3 mg, 5% | 6-bromo-5-phenyl-1,2,4-triazin-3-amine (50 mg, 0.199 mmol), and 4-cyclopropyl-2-(4,4,5,5-tetramethyl-1,3,2-dioxaborolan-2-yl)pyridine (110 mg, 0.448 mmol), | Mass spectroscopy: m/z 290.6 (M + H)⁺ (ES⁺); 288.9 (M − H)⁻ (ES⁻), at 3.93 min, 99.4% purity (method B). | (400 MHz, CDCl₃) δ: 0.89-1.01 (m, 4H), 1.97-2.06 (m, 1H), 5.50 (s, 2H), 6.98 (dd, J = 5.2, 1.7 Hz, 1H), 7.26-7.29 (m, 1H), 7.33-7.41 (m, 2H), 7.43-7.50 (m, 3H), 8.35 (d, J = 4.8 Hz, 1H). |

-continued

| No. | Product (yield) | Prepared From | LCMS | NMR |
|---|---|---|---|---|
| (ccxxiv) | 5-phenyl-6-(6-(trifluoromethyl)pyridin-2-yl)-1,2,4-triazin-3-amine (27 mg, 29%) | 6-bromo-5-phenyl-1,2,4-triazin-3-amine (100 mg, 0.398 mmol), 2-(4,4,5,5-tetramethyl-1,3,2-dioxaborolan-2-yl)-6-(trifluoromethyl)pyridine (245 mg, 0.896 mmol) | Mass spectroscopy: m/z 318.6 (M + H)$^+$ (ES$^+$); 316.9 (M − H)$^-$ (ES$^-$), at 4.09 min, 98.9% purity (method B). | (400 MHz, DMSO) δ: 7.27-7.35 (m, 4H), 7.36-7.44 (m, 1H), 7.69 (s, 2H), 7.84 (dd, J 7.4, 1.3 Hz, 1H), 8.11-8.23 (m, 2H). |
| (ccxxv) | 5-phenyl-6-(4-(trifluoromethyl)pyridin-2-yl)-1,2,4-triazin-3-amine (10 mg, 8%) | 6-bromo-5-phenyl-1,2,4-triazin-3-amine (100 mg, 0.398 mmol), 2-(4,4,5,5-tetramethyl-1,3,2-dioxaborolan-2-yl)-4-(trifluoromethyl)pyridine (245 mg, 0.896 mmol) | Mass spectroscopy: m/z 318.7 (M + H)$^+$ (ES$^+$); 316.9 (M − H)$^-$ (ES$^-$), at 4.12 min, 98.5% purity (method B). | (400 MHz, DMSO) δ: 7.26-7.38 (m, 4H), 7.38-7.45 (m, 1H), 7.69 (s, 2H), 7.74 (dd, J 5.1, 1.1 Hz, 1H), 8.18 (s, 1H), 8.63 (d, J 5.1 Hz, 1H). |
| (ccxxvi) | 6-(6-cyclopropylpyridin-2-yl)-5-phenyl-1,2,4-triazin-3-amine (2 mg, 3%) | 6-bromo-5-phenyl-1,2,4-triazin-3-amine (50 mg, 0.199 mmol), 2-cyclopropyl-6-(4,4,5,5-tetramethyl-1,3,2-dioxaborolan-2-yl)pyridine (110 mg, 0.448 mmol) | Mass spectroscopy: m/z 290.3 (M + H)$^+$ (ES$^+$), at 1.85 min, 98.4% purity (method B). | (400 MHz, CDCl$_3$) δ: 0.21-0.32 (m, 2H), 0.55-0.64 (m, 2H), 1.77 (tt, J 8.1, 4.7 Hz, 1H), 5.41 (s, 2H), 7.11 (dd, J 7.7, 1.0 Hz, 1H), 7.28-7.42 (m, 5H), 7.61-7.68 (m, 1H), 7.75 (dd, J 7.7, 1.0 Hz, 1H). |
| (ccxxvii) | 5-(3-amino-5-phenyl-1,2,4-triazin-6-yl)pyrazin-2-ol (2 mg, 2%) | 6-bromo-5-phenyl-1,2,4-triazin-3-amine (80 mg, 0.319 mmol), 5-(4,4,5,5-tetramethyl-1,3,2-dioxaborolan-2-yl)pyrazin-2-ol (159 mg, 0.717 mmol), | Mass spectroscopy: m/z 267.2 (M + H)$^+$ (ES$^+$), at 1.52 min, 96.4% purity (method B). | (400 MHz, CDCl$_3$) δ: 5.34 (s, 2H), 7.42-7.52 (m, 3H), 8.03-8.09 (m, 3H), 8.31 (d, J 2.6 Hz, 1H), 8.57 (d, J 7.5 Hz, 1H). |

Alternative Procedure for the Preparation of 5,6-Biaryl-3-amino-1,2,4-triazines

The Suzuki reaction to form 5,6-biaryl-3-amino-1,2,4-triazines may alternatively be performed with palladium-containing catalysts such as dichlorobis[di-tert-butyl(4-dimethylaminophenyl)phosphino]palladium(II) or dichloro[1,1'-bis(di-tert-butylphosphino)]fenocene palladium(II). Residual palladium species may then be removed from a solution of the triazine by treatment with a suitable scavenging agent, such as mercaptopropyl-functionalised silica (Quadrasil-MP; available from Johnson Matthey) or macroporous polystyrene-bound 2,4,6-trimercaptotriazine (MP-TMT; available from Biotage).

Typical Alternative to the General Procedure, as Exemplified with Example (xcv):

6-bromo-5-(4-fluorophenyl)-1,2,4-triazin-3-amine (1 molar eq.), 2-chloro-4-(4,4,5,5-tetramethyl-1,3,2-dioxaborolan-2-yl)-6-methylpyridine (1 molar eq.) and K$_2$CO$_3$ (1.5 molar eq.) are suspended in a mixture of 1,4-dioxane and water (2:1; 10 mL of solvent per gram of bromotriazine). The resulting mixture is degassed, treated with dichlorobis[di-tert-butyl(4-dimethylaminophenyl)phosphino]palladium(II) (2 mol %) and refluxed until full consumption of bromotriazine is observed by LCMS. The cooled reaction mixture is then diluted with water, extracted with DCM and passed through a phase separator. The organic phase is concentrated under reduced pressure and purified by gradient flash chromatography, eluting with mixtures of ethyl acetate and hexanes to afford 6-(2-chloro-6-methylpyridin-4-yl)-5-(4-fluorophenyl)-1,2,4-triazin-3-amine (61%).

Typical Alternative to General Procedure, as Exemplified with Example 1(ccix):

6-bromo-5-phenyl-1,2,4-triazin-3-amine (1 molar eq.), 2-methyl-4-(4,4,5,5-tetramethyl-1,3,2-dioxaborolan-2-yl)-6-(trifluoromethyl)pyridine (1 molar eq.) and K$_2$CO$_3$ (1.5 molar eq.) are suspended in a mixture of 1,4-dioxane and water (2:1; 10 mL of solvent per gram of bromotriazine). The resulting mixture is degassed, treated with dichlorobis[di-tert-butyl(4-dimethylaminophenyl)phosphino]palladium(II) (2 mol %) and refluxed until full consumption of bromotriazine is observed by LCMS. The cooled reaction mixture is then diluted with water, extracted with DCM and passed through a phase separator. The organic phase is concentrated under reduced pressure and purified by gradient flash chromatography, eluting with mixtures of ethyl acetate and hexanes to afford 6-[2-methyl-6-(trifluoromethyl)pyridin-4-yl]-5-phenyl-1,2,4-triazin-3-amine (90%).

General Procedure for the Removal of Palladium Contaminants from 5,6-Biaryl-3-amino-1,2,4-triazines A solution of a 5,6-biaryl-3-amino-1,2,4-triazine derivative (100 mg) in DCM (1.5 mL) is treated with Quadrasil-MP (42 mg) or MP-TMT (35 mg). The resulting mixture is heated to 50° C. for up to 24 hours then filtered. The filtrate is then concentrated under reduced pressure and the procedure repeated, if necessary.

Quadrasil-MP is available from Johnson Matthey, MP-TMT is available from Biotage.

Example 2

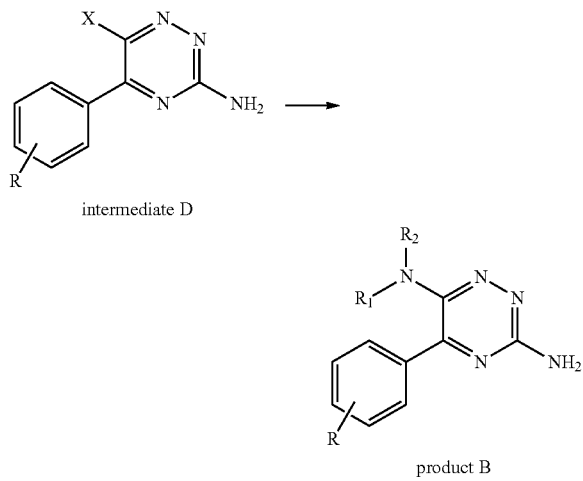

General procedure for the Preparation of 5-Aryl-3,6-diamino-1,2,4-triazines

Intermediate D, a 6-halo-5-aryl-1,2,4-triazin-3-amine derivative (0.80 mmol) is dissolved in dioxane or N-methyl-2-pyrolidone (5 mL) and treated with an amine (1.60 mmol) and an aqueous solution of $K_2CO_3$ (0.22 g, 1.60 mmol in 0.5 mL water). The mixture is heated in a microwave for two hrs at 140° C. with TLC monitoring (hexane/ethyl acetate, 1:1). After completion of the reaction the mixture is poured into water (50 mL) and extracted with ethyl acetate (2×100 mL). The organic layers are combined, dried over $Na_2SO_4$ and concentrated in vacuo. The crude compound, product B, is purified by gradient flash chromatography or preparative HPLC.

(i) 5-Phenyl-6-(piperidin-1-yl)-1,2,4-triazin-3-amine

5-Phenyl-6-(piperidin-1-yl)-1,2,4-triazin-3-amine (18 mg, 18%) was prepared from 6-bromo-5-phenyl-1,2,4-triazin-3-amine (0.21 g, 0.80 mmol) and piperidine (0.14 g, 1.60 mmol) according to the general procedure of Example 2.

HPLC purity: 96.95% (264 nm)
Mass spectroscopy: (ESI+ve) 256.0 [M+H]$^+$
$^1$H NMR: (400 MHz, CDCl$_3$) δ: 1.56-1.62 (m, 6H), 3.03 (m, 4H), 4.89 (s, 2H), 7.44-7.55 (m, 3H), 8.12 (m, 2H).

(ii) 6-(Morpholin-4-yl)-5-phenyl-1,2,4-triazin-3-amine 6-(Morpholin-4-yl)-5-phenyl-1,2,4-triazin-3-amine (50 mg, 20%) was prepared from 6-bromo-5-phenyl-1,2,4-triazin-3-amine (0.21 g, 0.80 mmol) and morpholine (0.126 g, 1.44 mmol) according to the general procedure of Example 2.

HPLC purity: 94.87% (265 nm)
Mass spectroscopy: (ESI+ve) 257.9 [M+H]$^+$
$^1$H NMR: (400 MHz, CDCl$_3$) δ: 2.88 (t, 4H), 3.59 (t, 4H), 6.75 (s, 2H), 7.54 (m, 3H), 8.06 (m, 2H).

(iii) 6-(3-Methylpiperidin-1-yl)-5-phenyl-1,2,4-triazin-3-amine 6-(3-Methylpiperidin-1-yl)-5-phenyl-1,2,4-triazin-3-amine (30 mg, 14%) was prepared from 6-bromo-5-phenyl-1,2,4-triazin-3-amine (0.21 g, 0.80 mmol) and 3-methylpiperidine (0.21 g, 1.92 mmol) according to the general procedure of Example 2.

HPLC purity: 98.87% (215 nm)
Mass spectroscopy: (ESI+ve) 270.0 [M+H]$^+$
$^1$H NMR: (400 MHz, CDCl$_3$) δ: 0.75 (d, 3H), 0.97 (m, 1H), 1.45 (m, 2H), 1.65 (m, 2H), 2.20 (m, 2H), 3.14 (m, 2H), 6.65 (s, 2H), 7.49 (m, 3H), 8.04 (m, 2H).

(iv) 6-(2,6-Dimethylmorpholin-4-yl)-5-phenyl-1,2,4-triazin-3-amine 6-(2,6-Dimethylmorpholin-4-yl)-5-phenyl-1,2,4-triazin-3-amine (35 mg, 10%) was prepared from 6-bromo-5-phenyl-1,2,4-triazin-3-amine (0.30 g, 1.19 mmol) and 2,6-dimethylmorpholine (0.27 g, 2.39 mmol) according to the general procedure of Example 2.

HPLC purity: 90% (271 nm)
Mass spectroscopy: (ESI+ve) 286.0 [M+H]$^+$
$^1$H NMR: (400 MHz, CDCl$_3$) δ: 1.10 (s, 6H), 2.52 (t, 2H), 3.23 (d, 2H), 3.71 (m, 2H), 5.06 (b, 2H), 8.07 (m, 3H), 8.07 (d, 2H).

(v) 6-(4,4-Difluoropiperidin-1-yl)-5-phenyl-1,2,4-triazin-3-amine 6-(4,4-Difluoropiperidin-1-yl)-5-phenyl-1,2,4-triazin-3-amine (39 mg, 14%) was prepared from 6-chloro-5-phenyl-1,2,4-triazin-3-amine (0.20 g, 0.96 mmol), $K_2CO_3$ (0.23 g, 1.67 mmol) and 4,4-difluoropiperidine hydrochloride (0.22 g, 1.45 mmol) according to the general procedure of Example 2.

HPLC purity: 98.48% (262 nm)
Mass spectroscopy: (ESI+ve) 292.0 [M+H]$^+$
$^1$H NMR: (400 MHz, CDCl$_3$) δ: 1.97 (m, 4H), 3.04 (m, 4H), 6.76 (s, 2H), 7.51 (m, 3H), 8.06 (m, 2H).

(vi) 6-(3,3-Dimethylpiperidin-1-yl)-5-phenyl-1,2,4-triazin-3-amine 6-(3,3-Dimethylpiperidin-1-yl)-5-phenyl-1,2,4-triazin-3-amine (54 mg, 10%) was prepared from 6-bromo-5-phenyl-1,2,4-triazin-3-amine (0.50 g, 1.99 mmol) and 3,3-dimethylpiperidine (0.27 g, 2.39 mmol) according to the general procedure of Example 2.

HPLC purity: 88% (274 nm)
Mass spectroscopy: (ESI+ve) 284.1 [M+H]$^+$
$^1$H NMR: (400 MHz. DMSO) δ: 0.89 (s, 6H), 1.24 (m, 2H), 1.40 (m, 2H), 2.65 (m, 2H), 2.70 (m, 2H), 6.67 (s, 2H), 7.49 (m, 3H), 7.94 (m, 2H).

(vii) 5-Phenyl-6-[3-(trifluoromethyl)piperidin-1-yl]-1,2,4-triazin-3-amine

5-Phenyl-6-[3-(trifluoromethyl)piperidin-1-yl]-1,2,4-triazin-3-amine (50 mg, 8%) was prepared from 6-bromo-5-phenyl-1,2,4-triazin-3-amine (0.50 g, 1.99 mmol) and 3-(trifluoromethyl)piperidine (0.40 g, 2.58 mmol) according to the general procedure of Example 2.

HPLC purity: 97.6% (263 nm)
Mass spectroscopy: (ESI+ve) 324.1 [M+H]$^+$
$^1$H NMR: (400 MHz, DMSO) δ: 1.35 (m, 1H), 1.48 (m, 1H), 1.57 (m, 1H), 1.90 (m, 1H), 2.48 (m, 2H), 2.73 (m, 1H), 3.05 (m, 1H), 3.50 (m, 1H), 6.74 (s, 2H), 7.50 (s, 3H), 8.02 (m, 2H).

(viii) 6-(Octahydroquinolin-1(2H)-yl)-5-phenyl-1,2,4-triazin-3-amine 6-(Octahydroquinolin-1(2H)-yl)-5-phenyl-1,2,4-triazin-3-amine (39 mg, 7%) was prepared from 6-bromo-5-phenyl-1,2,4-triazin-3-amine (1.00 g, 3.96 mmol) and decahydroquinoline (0.60 g, 4.36 mmol) according to the general procedure of Example 2.

HPLC purity: 98.75% (282 nm)
Mass spectroscopy: (ESI+ve) 310.1 [M+H]$^+$
$^1$H NMR: (400 MHz, DMSO) δ: 0.83 (m, 1H), 1.41 (m, 6H), 1.54 (m, 6H), 2.62 (m, 1H), 2.80 (m, 2H), 6.93 (bs, 2H), 7.47 (m, 3H), 8.15 (m, 2H).

(ix) 6-(3-Methoxypiperidin-1-yl)-5-phenyl-1,2,4-triazin-3-amine 6-(3-Methoxypiperidin-1-yl)-5-phenyl-1,2,4-triazin-3-amine (33 mg, 4%) was prepared from 6-bromo-5-phenyl-1,2,4-triazin-3-amine (0.70 g, 2.78 mmol), K$_2$CO$_3$ (0.80 g, 5.85 mmol) and 3-methoxy piperidine HCl (0.52 g, 3.34 mmol) according to the general procedure of Example 2.

HPLC purity: 99.32% (266 nm)
Mass spectroscopy: (ESI+ve) 286.0 [M+H]$^+$
$^1$H NMR: (400 MHz, DMSO) δ: 1.36 (m, 1H), 1.45 (m, 1H), 1.59 (m, 1H), 1.84 (m, 1H), 2.48 (m, 1H), 2.60 (m, 1H), 3.03 (m, 4H), 3.25 (m, 2H), 7.57 (m, 3H), 7.26 (bs, 2H), 7.99 (m, 2H).

(x) 6-(3-Ethynylpiperidin-1-yl)-5-phenyl-1,2,4-triazin-3-amine 6-(3-Ethynylpiperidin-1-yl)-5-phenyl-1,2,4-triazin-3-amine (10 mg, 2%) was prepared from 6-bromo-5-phenyl-1,2,4-triazin-3-amine (0.60 g, 2.40 mmol) and 3-ethynyl piperidine HCl (0.42 g, 2.87 mmol) according to the general procedure of Example 2.

HPLC purity: 95.99% (266 nm)
Mass spectroscopy: (ESI+ve) 280.0 [M+H]$^+$
$^1$H NMR: (400 MHz, DMSO) δ: 1.08-1.80 (m, 5H), 2.64 (m, 2H), 2.86 (m, 2H), 3.23 (t, 1H), 6.7 (bs, 2H), 7.48 (m, 3H), 8.06 (d, 2H).

(xi) 6-(2,6-Dimethylmorpholin-4-yl)-5-(4-fluorophenyl)-1,2,4-triazin-3-amine 6-(2,6-Dimethylmorpholin-4-yl)-5-(4-fluorophenyl)-1,2,4-triazin-3-amine (110 mg, 20%) was prepared from 6-bromo-5-(4-fluorophenyl)-1,2,4-triazin-3-amine (0.50 g, 1.87 mmol) and 2,6-dimethylmorpholine (1.06 g, 9.36 mmol) according to the general procedure of Example 2.

HPLC purity: 93.61% (264 nm)
Mass spectroscopy: (ESI+ve) 304 [M+H]$^+$
$^1$H NMR: (400 MHz, DMSO) δ: 1.12 (d, 6H), 2.54 (m, 2H), 3.19 (d, 2H), 3.30 (m, 2H), 5.13 (bs, 2H), 7.16 (m, 2H), 8.16 (m, 2H).

The following compounds were prepared by reacting the indicated starting materials with potassium carbonate (83 mg, 0.60 mmol) in 1,4-dioxane (0.8 mL) and water (0.2 mL) at 140° C. for 18 hours, unless a shorter time is specified:

| No. | Product (yield) | Prepared From | LCMS | NMR |
| --- | --- | --- | --- | --- |
| (xii) | 6-(2-ethylmorpholino)-5-phenyl-1,2,4-triazin-3-amine (60 mg, 35%) | 6-bromo-5-phenyl-1,2,4-triazin-3-amine (150 mg, 0.597 mmol), 2-ethylmorpholine (344 mg, 2.99 mmol) | Mass spectroscopy: m/z 286 (M + H)$^+$ (ES$^+$), at 4.03 min, 100% (method B). | (400 MHz, DMSO) δ: 0.73 (t, J 7.5, 3H), 1.22-1.44 (m, 2H), 2.38-2.47 (m, 1H), 2.65-2.77 (m, 1H), 3.02 (d, J 12.2, 1H), 3.12 (d, J 12.2, 1H), 3.33 (s, 1H), 3.48-3.58 (m, 1H), 3.77 (d, J 11.1, 1H), 6.74 (s, 2H), 7.48-7.57 (m, 3H), 8.01-8.08 (m, 2H). |
| (xiii) | 5-phenyl-6-(6-oxa-9-azaspiro[4.5]decan-9-yl)-1,2,4-triazin-3-amine (48 mg, 25%) | 6-bromo-5-phenyl-1,2,4-triazin-3-amine (150 mg, 0.597 mmol), 6-oxa-9-azaspiro[4.5]decane hydrochloride (425 mg, 2.390 mmol) | Mass spectroscopy: m/z 312 (M + H)$^+$ (ES$^+$), at 4.24 min, 97% purity (method B). | (400 MHz, DMSO) δ: 1.27-1.44 (m, 2H), 1.47-1.76 (m, 6H), 2.71-2.81 (m, 2H), 2.84 (s, 2H), 3.47-3.63 (m, 2H), 6.77 (s, 2H), 7.48-7.57 (m, 3H), 7.94-8.01 (m, 2H). |
| (xiv) | 6-(2,2-diethylmorpholino)-5-phenyl-1,2,4-triazin-3-amine (47 mg, 25%) | 6-bromo-5-phenyl-1,2,4-triazin-3-amine (150 mg, 0.597 mmol), 2,2-diethylmorpholine (428 mg, 2.99 mmol) | Mass spectroscopy: m/z 314 (M + H)$^+$ (ES$^+$), at 4.64 min, 100% (method B). | (400 MHz, DMSO) δ: 0.67 (t, J 7.5, 6H), 1.33 (dq, J 14.8, 7.5, 2H), 1.65 (dq, J 14.9, 7.5, 2H), 2.71-2.82 (m, 4H), 3.47-3.58 (m, 2H), 6.78 (s, 2H), 7.45-7.57 (m, 3H), 7.85-7.95 (m, 2H). |
| (xv) | 6-(2,2-dimethylmorpholino)-5-phenyl-1,2,4-triazin-3-amine (41 mg, 24%); prepared in 6 hours | 6-bromo-5-phenyl-1,2,4-triazin-3-amine (150 mg, 0.597 mmol), 2,2-dimethylmorpholine (344 mg, 2.99 mmol) | Mass spectroscopy: m/z 286 (M + H)$^+$ (ES$^+$), at 4.03 min, 98% (method B). | (400 MHz, DMSO) δ: 1.14 (s, 6H), 2.69-2.77 (m, 2H), 2.79 (s, 2H), 3.49-3.62 (m, 2H), 6.77 (s, 2H), 7.48-7.56 (m, 3H), 7.92-8.00 (m, 2H). |

-continued

| No. | Product (yield) | Prepared From | LCMS | NMR |
|---|---|---|---|---|
| (xvi) | (1-(3-amino-5-phenyl-1,2,4-triazin-6-yl)-3-methylpiperidin-3-yl)methanol (35 mg, 19%); prepared in 6 hours | 6-bromo-5-phenyl-1,2,4-triazin-3-amine (150 mg, 0.597 mmol), (3-methylpiperidin-3-yl)methanol (386 mg, 2.99 mmol) | Mass spectroscopy: m/z 300 (M + H)$^+$ (ES$^+$), at 4.10 min, 99% (method B). | (400 MHz, DMSO) δ: 0.88 (s, 3H), 1.10-1.20 (m, 1H), 1.31-1.45 (m, 3H), 2.54-2.63 (m, 1H), 2.63-2.72 (m, 1H), 2.75-2.93 (m, 2H), 3.23 (d, J 5.6, 2H), 4.51 (t, J 5.5, 1H), 6.68 (s, 2H), 7.47-7.55 (m, 3H), 7.92-8.00 (m, 2H). |
| (xvii) | 6-(3-(methoxymethyl)piperidin-1-yl)-5-phenyl-1,2,4-triazin-3-amine (75 mg, 42%) | 6-bromo-5-phenyl-1,2,4-triazin-3-amine (150 mg, 0.597 mmol), cis-3-(methoxymethyl)piperidine (386 mg, 2.99 mmol) | Mass spectroscopy: m/z 300 (M + H)$^+$ (ES$^+$), at 4.4 min, 100% (method B). | (400 MHz, DMSO) δ: 0.95-1.12 (m, 1H), 1.37-1.60 (m, 2H), 1.61-1.73 (m, 1H), 1.80-1.94 (m, 1H), 2.37-2.47 (m, 1H), 2.50-2.58 (m, 1H), 3.03-3.21 (m, 6H), 3.28-3.34 (m, 1H), 6.68 (s, 2H), 7.47-7.56 (m, 3H), 7.99-8.09 (m, 2H). |
| (xviii) | 1-(1-(3-amino-5-phenyl-1,2,4-triazin-6-yl)piperidin-3-yl)ethanol (80 mg, 43%) | 6-bromo-5-phenyl-1,2,4-triazin-3-amine (150 mg, 0.597 mmol) and 1-(piperidin-3-yl)ethanol (77 mg, 0.597 mmol) | Mass spectroscopy: m/z m/z 300 (M + H)$^+$ (ES$^+$), at 3.98 min, 96% (method B). | (400 MHz, DMSO) δ: 0.91-1.03 (m, 1H), 1.22-1.32 (m, 2H), 1.38-1.59 (m, 2H), 1.59-1.69 (m, 1H), 1.69-1.80 (m, 1H), 2.28-2.38 (m, 1H), 2.47-2.56 (m, 1H), 3.07-3.16 (m, 1H), 3.18-3.30 (m, 3H), 4.25-4.38 (m, 1H), 6.68 (s, 2H), 7.46-7.57 (m, 3H), 7.99-8.09 (m, 2H). |
| (xix) | (1-(3-amino-5-phenyl-1,2,4-triazin-6-yl)piperidin-3-yl)methanol (18 mg, 10%) | piperidin-3-ylmethanol (344 mg, 2.99 mmol) 6-bromo-5-phenyl-1,2,4-triazin-3-amine (150 mg, 0.597 mmol) | Mass spectroscopy: m/z 286 (M + H)$^+$ (ES$^+$), at 3.78 min, 94% (method B). | (400 MHz, DMSO) δ: 0.94-1.08 (m, 1H), 1.34-1.57 (m, 2H), 1.61-1.74 (m, 2H), 2.38-2.61 (m, 2H), 3.04 (s, 1H), 3.13-3.46 (m, 3H), 4.44 (t, J = 5.3 Hz, 1H), 6.67 (s, 2H), 7.45-7.57 (m, 3H), 7.98-8.11 (m, 2H). |
| (xx) | 1-(1-(3-amino-5-phenyl-1,2,4-triazin-6-yl)piperidin-3-yl)ethanone (13 mg, 7%) | 1-(piperidin-3-yl)ethanone (380 mg, 2.99 mmol), 6-bromo-5-phenyl-1,2,4-triazin-3-amine (150 mg, 0.597 mmol) | Mass spectroscopy: m/z 298 (M + H)$^+$ (ES$^+$); at 3.92 min, 95.06% (method B). | (400 MHz, DMSO) δ: 1.30-1.51 (m, 2H), 1.52-1.63 (m, 1H), 1.85-1.96 (m, 1H), 2.01 (s, 3H), 2.62-2.71 (m, 1H), 2.71-2.83 (m, 1H), 2.95-3.12 (m, 1H), 3.31-3.46 (m, 2H), 6.72 (s, 2H), 7.46-7.56 (m, 3H), 7.97-8.08 (m, 3H). |
| (xxi) | 6-(octahydroisoquinolin-2(1H)-yl)-5-phenyl-1,2,4-triazin-3-amine (54.2 mg, 2.1%); prepared in 8 hours | 6-bromo-5-phenyl-1,2,4-triazin-3-amine (2.00 g, 7.96 mmol) and perhydroisoquinoline (2.21 g, 15.9 mmol) | HPLC purity: 97.40% (277 nm); mass spectroscopy: (ESI +ve) m/z 310.1 [M + H]$^+$ | (400 MHz, DMSO) δ: 0.85 (m, 3H), 1.14 (m, 4H), 1.36 (m, 2H), 1.54 (m, 3H), 2.26 (m, 1H), 2.51 (m, 1H), 3.10 (m, 2H), 6.61 (bs, 2H), 7.48 (m, 3H), 8.04 (dd, 2H). |
| (xxii) | N$^6$-(4-methyl-1,3-thiazol-2-yl)-5-phenyl-1,2,4-triazine-3,6-diamine (10 mg, 1%) | 6-bromo-5-phenyl-1,2,4-triazin-3-amine (1.00 g, 3.98 mmol) and 2-amino-4-methyl thiazole (1.36 g, 11.95 mmol) | HPLC purity: 99.03% (298 nm); mass spectroscopy: (ESI +ve) m/z 284.9 [M + H]$^+$ | (400 MHz, DMSO) δ: 2.10 (s, 3H), 6.18 (s, 1H), 6.53 (bs, 2H), 7.48 (m, 3H), 8.15 (m, 2H), 11.61 (b, 1H). |
| (xxiii) | 5-phenyl-6-[4-(trifluoromethyl)piperidin-1-yl]-1,2,4-triazin- | 6-bromo-5-phenyl-1,2,4-triazin-3-amine (1.0 g, 3.9 mmol) and | HPLC purity: 99.9% (218 nm); mass | (400 MHz, DMSO) δ: 1.46 (m, 2H), 1.75 (m, 2H), 2.34 (m, 1H) |

| No. | Product (yield) | Prepared From | LCMS | NMR |
|---|---|---|---|---|
| | 3-amine (20 mg, 2%) | 4-trifluoromethyl piperidine hydrochloride (0.9 g, 4.8 mmol) | spectroscopy: (ESI +ve) m/z 323.9 [M]$^+$ | 2.66 (m, 2H), 3.23 (m, 2H), 6.72 (s, 2H), 7.51 (m, 3H), 8.02 (m, 2H). |
| (xxiv) | 5-phenyl-6-(3-phenylpiperidin-1-yl)-1,2,4-triazin-3-amine (62 mg, 31%) | 6-bromo-5-phenyl-1,2,4-triazin-3-amine (150 mg, 0.597 mmol), 3-phenylpiperidine (482 mg, 2.99 mmol) | Mass spectroscopy: m/z 332 (M + H)$^+$ (ES$^+$), at 4.92 min, 100% (method B). | (400 MHz, DMSO) δ: 1.51-1.77 (m, 3H), 1.83-1.92 (m, 1H), 2.58-2.72 (m, 2H), 2.74-2.84 (m, 1H), 3.24 (d, J 11.7, 1H) 3.34 (d, J 11.7, 1H), 6.67 (s, 2H), 7.04-7.12 (m, 2H), 7.13-7.20 (m, 1H), 7.20-7.28 (m, 2H), 7.52-7.58 (m, 3H), 8.03-8.13 (m, 2H). |
| (xxv) | (4-(3-amino-5-phenyl-1,2,4-triazin-6-yl)morpholin-2-yl)methanol (40 mg, 23%) | 6-bromo-5-phenyl-1,2,4-triazin-3-amine (150 mg, 0.597 mmol), morpholin-2-ylmethanol (350 mg, 2.99 mmol) | Mass spectroscopy: m/z 288 (M + H)$^+$ (ES$^+$), at 2.95 min, 100% (method B). | (400 MHz, DMSO) δ: 2.51-2.58 (m, 1H), 2.63-2.74 (m, 1H), 2.91-3.02 (m, 1H), 3.33 (s, 3H), 3.47-3.58 (m, 2H), 3.70-3.79 (m, 1H), 4.67 (t, J 5.8, 1H), 6.76 (s, 2H), 7.47-7.56 (m, 3H), 8.03-8.11 (m, 2H). |
| (xxvi) | 5-phenyl-6-(3-(propoxymethyl)pyrrolidin-1-yl)-1,2,4-triazin-3-amine (39 mg, 20%) | 6-bromo-5-phenyl-1,2,4-triazin-3-amine (150 mg, 0.597 mmol), 3-(propoxymethyl)pyrrolidine (428 mg, 2.99 mmol) | Mass spectroscopy: m/z 314 (M + H)$^+$ (ES$^+$), at 4.64 min, 95% (method B). | (400 MHz, DMSO) δ: 0.80 (t, J 7.4, 3H), 1.37-1.58 (m, 3H), 1.81-1.94 (m, 1H), 2.29-2.40 (m, 1H), 2.85 (dd, J 10.3, 6.4, 1H), 3.00-3.13 (m, 3H), 3.18-3.30 (m, 3H), 6.38 (s, 2H), 7.45-7.53 (m, 3H), 7.69-7.79 (m, 2H). |
| (xxvii) | 2-(1-(3-amino-5-phenyl-1,2,4-triazin-6-yl)piperidin-3-yl)propan-2-ol (56 mg, 31%) | 6-bromo-5-phenyl-1,2,4-triazin-3-amine (150 mg, 0.597 mmol), 2-(piperidin-3-yl)propan-2-ol (257 mg, 1.792 mmol) | Mass spectroscopy: m/z 314 (M + H)$^+$ (ES$^+$), 4.22 min, 100% (method B). | (400 MHz, DMSO) δ: 0.86 (s, 6H), 1.00-1.13 (m, 1H), 1.38-1.52 (m, 2H), 1.58-1.69 (m, 1H), 1.78-1.88 (m, 1H), 2.30 (app t, J 11.6, 1H), 2.42-2.50 (m, 1H), 3.20-3.28 (m, 1H), 3.31-3.38 (m, 1H), 4.07 (s, 1H), 6.65 (s, 2H), 7.45-7.56 (m, 3H), 7.97-8.09 (m, 2H), |
| (xxviii) | 6-(hexahydropyrrolo[1,2-a]pyrazin-2(1H)-yl)-5-phenyl-1,2,4-triazin-3-amine (16 mg, 9%) | 6-bromo-5-phenyl-1,2,4-triazin-3-amine (150 mg, 0.597 mmol), octahydropyrrolo[1,2-a]pyrazine (377 mg, 2.99 mmol) | Mass spectroscopy: m/z 297 (M + H)$^+$ (ES$^+$), at 4.17 min, 100% (method B). | (400 MHz, DMSO) δ: 1.21-1.35 (m, 2H), 1.55-1.73 (m, 2H), 1.96-2.20 (m, 3H), 2.69-2.81 (m, 1H), 2.81-3.03 (m, 2H), 3.06-3.19 (m, 1H), 3.29-3.36 (m, 2H), 6.71 (s, 2H), 7.46-7.56 (m, 3H), 8.00-8.09 (m, 2H). |
| (xxix) | 1-(3-amino-5-phenyl-1,2,4-triazin-6-yl)-3-ethylpiperidin-3-ol (42 mg, 23%) | 6-bromo-5-phenyl-1,2,4-triazin-3-amine (150 mg, 0.597 mmol), 3-ethylpiperidin-3-ol (386 mg, 2.99 mmol) | Mass spectroscopy: m/z 300 (M + H)$^+$ (ES$^+$), at 4.14 min, 97% (method B). | (400 MHz, DMSO) δ: 0.79 (t, J 7.4, 3H), 1.23 (s, 1H), 1.32-1.52 (m, 4H), 1.54-1.68 (m, 1H), 2.59-2.69 (m, 1H), 2.69-2.80 (m, 1H), 2.86-2.98 (m, 2H), 4.21 (s, 1H), 6.73 (s, 2H), 7.46-7.55 (m, 3H), 8.01-8.10 (m, 2H). |

-continued

| No. | Product (yield) | Prepared From | LCMS | NMR |
|---|---|---|---|---|
| (xxx) | 2-(4-(3-amino-5-phenyl-1,2,4-triazin-6-yl)morpholin-2-yl)ethanol (42 mg, 22%); prepared in 3 hours | 6-bromo-5-phenyl-1,2,4-triazin-3-amine (150 mg, 0.597 mmol), 2-(morpholin-2-yl)ethanol (392 mg, 2.99 mmol) | Mass spectroscopy: m/z 302 (M + H)$^+$ (ES$^+$), at 3.22 min, 96% (method B). | (400 MHz, DMSO) δ: 1.34-1.61 (m, 2H), 2.48-2.58 (m, 1H), 2.62-2.74 (m, 1H), 2.91-3.02 (m, 1H), 3.09-3.20 (m, 1H), 3.27-3.42 (m, 2H), 3.46-3.56 (m, 1H), 3.56-3.67 (m, 1H), 3.68-3.78 (m, 1H), 4.39 (t, J 5.1, 1H), 6.74 (s, 2H), 7.47-7.58 (m, 3H), 7.99-8.12 (m, 2H). |

Example 3

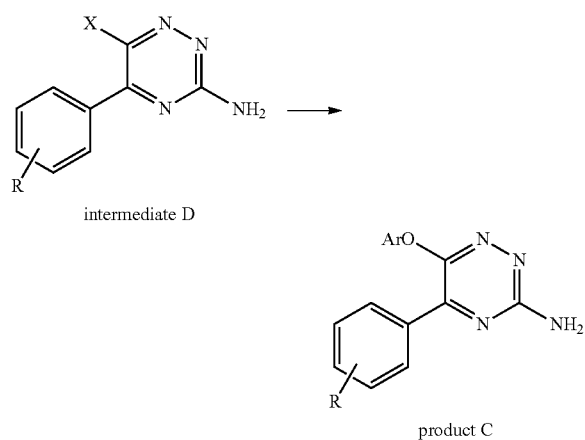

intermediate D product C

General Procedure for the Preparation of 3-amino-5-aryl-1-aryloxy-1,2,4-triazines A solution of intermediate D, a 6-halo-5-aryl-1,2,4-triazin-3-amine, (1.99 mmol) in DMSO (5 mL) is treated sequentially with a phenol derivative (7.90 mmol), NaOH (0.31 g, 7.9 mmol) and cesium carbonate (0.64 g, 1.99 mmol). The resulting mixture is stirred at 90° C. overnight with TLC monitoring (hexane/ethyl acetate, 7:3). Upon completion of the reaction, the mixture is diluted with water (15 mL) and extracted with ethyl acetate (3×15 mL). The combined organic extracts are dried over sodium sulfate and concentrated in vacuo. The crude product, product C, is purified by gradient flash chromatography, eluting with mixtures of ethyl acetate in hexane (e.g. 15%) or by preparative HPLC.

(i) 6-Phenoxy-5-phenyl-1,2,4-triazin-3-amine

6-Phenoxy-5-phenyl-1,2,4-triazin-3-amine (78 mg, 14%) was prepared from 6-bromo-5-phenyl-1,2,4-triazin-3-amine (0.5 g, 1.99 mmol) and phenol (0.74 g, 7.90 mmol) according to the general procedure of Example 3.

HPLC purity: 99.67% (210 nm)

Mass spectroscopy: (ESI+ve) 265.0 [M+H]$^+$.

$^1$H NMR: (400 MHz, CDCl$_3$) δ: 7.08 (s, 2H), 7.13 (m, 3H), 7.36 (m, 2H), 7.52 (m, 3H), 8.07 (m, 2H).

(ii) 6-(3-Aminophenoxy)-5-phenyl-1,2,4-triazin-3-amine 6-(3-Aminophenoxy)-5-phenyl-1,2,4-triazin-3-amine (25 mg, 8%) was prepared from 6-bromo-5-phenyl-1,2,4-triazin-3-amine (0.30 g, 1.19 mmol) and 3-amino phenol (0.19 g, 1.78 mmol) according to the general procedure of Example 3.

HPLC purity: 89.7% (238 nm)

Mass spectroscopy: (ESI+ve) 338.0 [M+H]$^+$ $^1$H NMR: (400 MHz, DMSO) δ: 5.19 (s, 2H), 6.15 (m, 2H), 6.27 (m, 1H), 6.93 (m, 1H), 7.10 (s, 2H), 7.48-7.56 (m, 3H), 8.04 (d, 2H).

(iii) 6-(3-Fluorophenoxy)-5-phenyl-1,2,4-triazin-3-amine 6-(3-Fluorophenoxy)-5-phenyl-1,2,4-triazin-3-amine (78 mg, 23%) was prepared from 6-bromo-5-phenyl-1,2,4-triazin-3-amine (0.30 g, 1.19 mmol) and 3-fluoro phenol (0.27 g, 2.39 mmol) according to the general procedure of Example 3.

HPLC purity: 99.67% (244 nm)

Mass spectroscopy: (ESI+ve) 283.1 [M+H]$^+$ $^1$H NMR: (400 MHz, CDCl$_3$) δ: 5.29 (s, 2H), 6.87-6.95 (m, 3H), 7.33 (m, 1H), 7.48-7.58 (m, 3H), 8.23 (m, 2H).

(iv) 5-Phenyl-6-[2-(propan-2-yl)phenoxy]-1,2,4-triazin-3-amine

5-Phenyl-6-[2-(propan-2-yl)phenoxy]-1,2,4-triazin-3-amine (20 mg, 7%) was prepared from 6-bromo-5-phenyl-1,2,4-triazin-3-amine (0.40 g, 1.59 mmol) and 2-isopropyl phenol (0.43 g, 3.18 mmol) according to the general procedure of Example 3.

HPLC purity: 96.5% (245 nm)

Mass spectroscopy: (ESI+ve) 307.1 [M+H]$^+$ $^1$H NMR: (400 MHz, CDCl$_3$) δ: 1.25 (d, 6H), 3.16 (m, 1H), 5.19 (s, 2H), 7.00 (m, 1H), 7.20 (m, 2H), 7.36 (m, 1H), 7.38-7.59 (m, 3H), 8.31 (m, 2H).

(v) 5-Phenyl-6-[3-(trifluoromethyl)phenoxy]-1,2,4-triazin-3-amine

5-Phenyl-6-[3-(trifluoromethyl)phenoxy]-1,2,4-triazin-3-amine (21 mg, 4%) was prepared from 6-bromo-5-phenyl-1,2,4-triazin-3-amine (0.40 g, 1.59 mmol) and 3-(trifluoromethyl)phenol (0.52 g, 3.18 mmol) according to the general procedure of Example 3.

HPLC purity: 88.72% (245 nm)
Mass spectroscopy: (ESI+ve) 332.9 [M+H]$^+$
$^1$H NMR: (400 MHz, de-DMSO) δ: 7.10 (s, 2H), 7.49-7.63 (m, 5H), 7.61-7.63 (m, 2H), 8.07-8.09 (d, 2H).

(vi) 6-(4-Fluorophenoxy)-5-phenyl-1,2,4-triazin-3-amine 6-(4-Fluorophenoxy)-5-phenyl-1,2,4-triazin-3-amine (35 mg, 8%) was prepared from 6-bromo-5-phenyl-1,2,4-triazin-3-amine (0.40 g, 1.59 mmol) and 4-fluorophenol (0.36 g, 3.18 mmol) according to the general procedure of Example 3.
HPLC purity: 96.39% (244 nm)
Mass spectroscopy: (ESI+ve) 283.1 [M+H]$^+$
$^1$H NMR: (400 MHz, de-DMSO) δ: 7.03 (s, 2H), 7.20-7.22 (m, 4H), 7.50-7.56 (m, 3H), 8.08 (dd, 2H).

(vii) 6-(2-Fluorophenoxy)-5-phenyl-1,2,4-triazin-3-amine 6-(2-Fluorophenoxy)-5-phenyl-1,2,4-triazin-3-amine (44 mg, 10%) was prepared from 6-bromo-5-phenyl-1,2,4-triazin-3-amine (0.40 g, 1.59 mmol) and 2-fluorophenol (0.36 g, 3.18 mmol) according to the general procedure of Example 3.
HPLC purity: 90.06% (244 nm)
Mass spectroscopy: (ESI+ve) 283.1 [M+H]$^+$
$^1$H NMR: (400 MHz, DMSO) δ: 7.04 (s, 2H), 7.25 (m, 2H), 7.37 (m, 2H), 7.53-8.11 (m, 3H), 8.12 (m, 2H).

(viii) 6-(4-Methoxyphenoxy)-5-phenyl-1,2,4-triazin-3-amine 6-(4-Methoxyphenoxy)-5-phenyl-1,2,4-triazin-3-amine (45 mg, 13%) was prepared from 6-bromo-5-phenyl-1,2,4-triazin-3-amine (0.30 g, 1.19 mmol) and 4-methoxyphenol (0.30 g, 2.39 mmol) according to the general procedure of Example 3.
HPLC purity: 92.08% (218 nm)
Mass spectroscopy: (ESI+ve) 295.1 [M+H]$^+$
$^1$H NMR: (400 MHz, CDCl$_3$) δ: 3.81 (s, 3H), 5.29 (s, 2H), 6.92 (d, 2H), 7.08 (d, 2H), 7.50-7.59 (m, 3H), 8.29 (m, 2H).

(ix) 6-[4-Fluoro-3-(trifluoromethyl)phenoxy]-5-phenyl-1,2,4-triazin-3-amine

6-[4-Fluoro-3-(trifluoromethyl)phenoxy]-5-phenyl-1,2,4-triazin-3-amine (198 mg, 36%) was prepared from 6-bromo-5-phenyl-1,2,4-triazin-3-amine (0.40 g, 1.59 mmol) and 4-fluoro-3-(trifluoromethyl)phenol (0.57 g, 3.18 mmol) according to the general procedure of Example 3.
HPLC purity: 95% (235 nm)
Mass spectroscopy: (ESI+ve) 350.9 [M+H]J, (ESI–ve) 349.1[M–H]$^-$.
$^1$H NMR: (400 MHz, DMSO) δ: 7.05 (s, 2H), 7.50-7.62 (m, 5H), 7.75 (m, 1H), 8.10 (m, 2H).

(x) 5-Phenyl-6-[3-(trifluoromethoxy)phenoxy]-1,2,4-triazin-3-amine

5-Phenyl-6-[3-(trifluoromethoxy)phenoxy]-1,2,4-triazin-3-amine (22 mg, 3%) was prepared from 6-bromo-5-phenyl-1,2,4-triazin-3-amine (0.50 g, 1.99 mmol) and 3-(trifluoromethoxy)phenol (0.42 g, 2.39 mmol) according to the general procedure of Example 3.
HPLC purity: 95.6% (235 nm)
Mass spectroscopy: (ESI+ve) 348.9 [M+H]$^+$
$^1$H NMR: (400 MHz, CDCl$_3$) δ: 5.17 (s, 2H), 7.08 (m, 3H), 7.39 (t, 1H) 7.54 (m, 3H), 8.21 (d, 2H).

(xi) 6-(3-Chlorophenoxy)-5-phenyl-1,2,4-triazin-3-amine 6-(3-Chlorophenoxy)-5-phenyl-1,2,4-triazin-3-amine (147 mg, 31%) was prepared from 6-bromo-5-phenyl-1,2,4-triazin-3-amine (0.40 g, 1.58 mmol) 3-chloro phenol (0.40 g, 3.16 mmol) and K$_2$CO$_3$ (432 mg, 3.15 mmol), according to the general procedure of Example 3.
HPLC purity: 98% (245 nm)
Mass spectroscopy: (ESI+ve) 298.9 [M+H]$^+$
$^1$H NMR: (400 MHz, DMSO) δ: 7.12 (s, 2H), 7.14 (m, 1H), 7.21 (m, 1H), 7.35 (m, 1H), 7.40 (m, 1H), 7.55 (m, 3H), 8.06 (m, 2H).

(xii) 6-(3,5-Dichlorophenoxy)-5-phenyl-1,2,4-triazin-3-amine 6-(3,5-Dichlorophenoxy)-5-phenyl-1,2,4-triazin-3-amine (89 mg, 17%) was prepared from 6-bromo-5-phenyl-1,2,4-triazin-3-amine (0.40 g, 1.59 mmol) and 3-5-dichlorophenol (0.52 g, 3.18 mmol) according to the general procedure of Example 3.
HPLC purity: 99.03% (246 nm)
Mass spectroscopy: (ESI+ve) 332.9 [M+H]$^+$
$^1$H NMR: (400 MHz, DMSO) δ: 7.15 (s, 2H), 7.40 (m, 3H), 7.54 (m, 3H), 8.02 (d, 2H).

(xiii) 6-(3,5-Difluorophenoxy)-5-phenyl-1,2,4-triazin-3-amine 6-(3,5-Difluorophenoxy)-5-phenyl-1,2,4-triazin-3-amine (101 mg, 17%) was prepared from 6-bromo-5-phenyl-1,2,4-triazin-3-amine (0.50 g, 1.99 mmol) and 3,5-difluorophenol (0.31 g, 3.98 mmol) according to the general procedure of Example 3.
HPLC purity: 90.33% (244 nm)
Mass spectroscopy: (ESI+ve) 300.9 [M+H]$^+$
$^1$H NMR: (400 MHz, CDCl$_3$) δ: 5.46 (bs, 2H), 6.65 (m, 1H), 6.71 (m, 2H), 7.50 (m, 2H), 7.58 (m, 1H), 8.12 (m, 2H).

The following compounds were prepared by reacting the indicated starting materials according to the general procedure of Example 3.

| No. | Product (yield) | Prepared From | LCMS | NMR |
| --- | --- | --- | --- | --- |
| (xiv) | 6-(3,5-dimethylphenoxy)-5-phenyl-1,2,4-triazin-3-amine (26 mg, 5%) | 6-bromo-5-phenyl-1,2,4-triazin-3-amine (0.40 g, 1.59 mmol) and 3,5-(dimethyl) phenol (0.39 g, 2.07 mmol) | HPLC purity: 96.6% (246 nm); mass spectroscopy: (ESI +ve) m/z 293.0 [M + H]$^+$ | (400 MHz, DMSO) δ: 2.22 (s, 6H), 6.71 (s, 2H), 6.76 (s, 1H) 7.06 (s, 2H), 7.52 (m, 3H), 8.05 (d, 2H). |

-continued

| No. | Product (yield) | Prepared From | LCMS | NMR |
|---|---|---|---|---|
| (xv) | 6-(3-chloro-5-methoxyphenoxy)-5-phenyl-1,2,4-triazin-3-amine (120 mg, 23%) | 6-bromo-5-phenyl-1,2,4-triazin-3-amine (0.40 g, 1.59 mmol) and 3-chloro-5-methoxyphenol (0.50 g, 31.8 mmol) | HPLC purity: 98% (245 nm); mass spectroscopy: (ESI +ve) m/z 328.9 $[M + H]^+$ | (400 MHz, DMSO) δ: 3.74 (s, 3H), 6.75 (m, 1H), 6.82 (m, 1H), 6.85 (m, 1H), 7.12 (s, 2H), 7.53 (m, 3H), 8.03 (m, 2H). |

The following compounds were prepared by heating the neat mixture of a phenol derivative and bromotriazine derivative (as indicated) with DBU (270 μl, 1.792 mmol), at 110° C. overnight:

| No. | Product (yield) | Prepared From | LCMS | NMR |
|---|---|---|---|---|
| (xvi) | 1-(3-amino-5-phenyl-1,2,4-triazin-6-yl)pyridin-4(1H)-one (29 mg, 0.109 mmol, 27.5%) | 6-chloro-5-phenyl-1,2,4-triazin-3-amine (0.082 g, 0.393 mmol), DBU (0.298 μl, 1.990 mmol) and pyridin-4-ol (189 mg, 1.990 mmol) | Mass spectroscopy: m/z 266.2 $(M + H)^+$ $(ES^+)$; 264.4 $(M - H)^-$ $(ES^-)$, at 2.45 min, 100% (method B). | (400 MHz, DMSO) δ: 6.08-6.16 (m, 2H), 7.42-7.55 (m, 5H), 7.68-7.77 (m, 4H). |
| (xvii) | 6-(4-methylphenoxy)-5-phenyl-1,2,4-triazin-3-amine (51 mg, 51%) | 6-bromo-5-phenyl-1,2,4-triazin-3-amine (90 mg, 0.358 mmol), p-cresol (194 mg, 1.792 mmol), and DBU (270 μl, 1.792 mmol) | Mass spectroscopy: m/z 279.82 $(M + H)^+$ $(ES^+)$, at 4.75 min, 99% (method B). | (400 MHz, DMSO) δ: 2.28 (s, 3H), 7.00-7.04 (m, 2H), 7.05 (s, 2H), 7.12-7.22 (m, 2H), 7.49-7.60 (m, 3H), 8.04-8.13 (m, 2H). |
| (xviii) | 6-(4-chlorophenoxy)-5-phenyl-1,2,4-triazin-3-amine (38 mg, 35%) | 6-bromo-5-phenyl-1,2,4-triazin-3-amine (90 mg, 0.358 mmol), 4-chlorophenol (230 mg, 1.792 mmol), and DBU (270 μl, 1.792 mmol) | Mass spectroscopy: m/z 299.6 $(M + H)^+$ $(ES^+)$, at 4.77 min, 99% (method B). | (400 MHz, DMSO) δ: 7.12 (s, 2H), 7.18-7.25 (m, 2H), 7.40-7.46 (m, 2H), 7.49-7.60 (m, 3H), 8.03-8.11 (m, 2H). |
| (xix) | 6-(3,4-difluorophenoxy)-5-phenyl-1,2,4-triazin-3-amine | 6-bromo-5-phenyl-1,2,4-triazin-3-amine (90 mg, 0.358 mmol), 3,4-difluorophenol (233 mg, 1.792 mmol), and DBU (270 μl, 1.792 mmol) | Mass spectroscopy: m/z 301.64 $(M + H)^+$ $(ES^+)$; 299.94 $(M - H)^-$ $(ES^-)$, at 4.59 min, 97% (method B). | (400 MHz, DMSO) δ: 7.03-7.11 (m, 1H), 7.11 (s, 2H), 7.41-7.51 (m, 2H), 7.51-7.61 (m, 3H), 8.03-8.11 (m, 2H). |
| (xx) | 6-[(6-methoxypyridin-3-yl)oxy]-5-phenyl-1,2,4-triazin-3-amine | 6-bromo-5-phenyl-1,2,4-triazin-3-amine (90 mg, 0.358 mmol), 6-methoxypyridin-3-ol (224 mg, 1.792 mmol), and DBU (270 μl, 1.792 mmol) | Mass spectroscopy: m/z 296.0 $(M + H)^+$ $(ES^+)$: 4.59 min, 95% (method B). | (400 MHz, DMSO) δ: 3.85 (s, 3H), 6.88 (dd, J 8.9, 0.5, 1H), 7.00 (s, 2H), 7.52-7.63 (m, 3H), 7.68 (dd, J 8.9, 3.0, 1H), 8.11 (dd, J 2.9, 0.5, 1H), 8.12-8.16 (m, 2H). |
| (xxi) | 6-[(2-methylpyridin-3-yl)oxy]-5-phenyl-1,2,4-triazin-3-amine | 6-bromo-5-phenyl-1,2,4-triazin-3-amine (90 mg, 0.358 mmol), 2-methylpyridin-3-ol (196 mg, 1.792 mmol), and DBU (270 μl 1.792 mmol) | Mass spectroscopy: m/z 280.73 $(M + H)^+$ $(ES^+)$; 278.94 $(M - H)^-$ $(ES^-)$, at 3.90 min, 99% (method B). | (400 MHz, DMSO) δ: 2.38 (s, 3H), 7.05 (s, 2H), 7.28 (ddd, J 8.2, 4.7, 0.5, 1H), 7.52-7.63 (m, 4H), 8.11-8.18 (m, 2H), 8.31 (dd, J 4.7, 1.4, 1H). |
| (xxii) | 6-[(6-chloropyridin-3-yl)oxy]-5-phenyl-1,2,4-triazin-3-amine | 6-bromo-5-phenyl-1,2,4-triazin-3-amine (90 mg, 0.358 mmol), 6-chloropyridin-3-ol (232 mg, 1.792 mmol), and DBU (270 μl, 1.792 mmol) | Mass spectroscopy: m/z 300.70 $(M + H)^+$ $(ES^+)$, at 3.90 min, 97% (method B). | (400 MHz, DMSO) δ: 7.14 (s, 2H), 7.51-7.63 (m, 4H), 7.83 (dd, J 8.7, 3.0, 1H), 8.06-8.13 (m, 2H), 8.42 (dd, J 3.0, 0.5, 1H). |
| (xxiii) | 4-[(3-amino-5-phenyl-1,2,4-triazin-6-yl)oxy]benzonitrile | 6-bromo-5-phenyl-1,2,4-triazin-3-amine (90 mg, 0.358 mmol), 4-hydroxybenzonitrile | Mass spectroscopy: m/z 290.72 $(M + H)^+$ $(ES^+)$; 288.96 $(M - H)^-$ $(ES^-)$, at 4.09 | (400 MHz, DMSO) δ: 7.28 (s, 2H), 7.34-7.39 (m, 2H), 7.48-7.59 (m, 3H), 7.82-7.90 (m, 2H), 8.00- |

-continued

| No. | Product (yield) | Prepared From | LCMS | NMR |
|---|---|---|---|---|
| | | (213 mg, 1.792 mmol), and DBU (270 μl, 1.792 mmol) | min, 99% (method B). | 8.05 (m, 2H). |
| (xxiv) | 6-{[1-methyl-3-(trifluoromethyl)-1H-pyrazol-5-yl]oxy}-5-phenyl-1,2,4-triazin-3-amine | 6-bromo-5-phenyl-1,2,4-triazin-3-amine (90 mg, 0.358 mmol), 1-methyl-3-(trifluoromethyl)-1H-pyrazol-5-ol (298 mg, 1.792 mmol), and DBU (270 μl, 1.792 mmol) | Mass spectroscopy: m/z 337.60 (M + H)$^+$ (ES$^+$); 335.81 (M − H)$^-$ (ES$^-$), at 4.35 min, 97% (method B). | (400 MHz, DMSO) δ: 3.79 (s, 3H), 6.58 (s, 1H), 7.27 (s, 2H), 7.52-7.66 (m, 3H), 8.04-8.12 (m, 2H). |
| (xxv) | 6-[(1-methyl-1H-benzimidazol-5-yl)oxy]-5-phenyl-1,2,4-triazin-3-amine | 6-bromo-5-phenyl-1,2,4-triazin-3-amine (90 mg, 0.358 mmol), 1-methyl-1H-benzo[d]imidazol-5-ol (266 mg, 1.792 mmol) and DBU (270 μl, 1.792 mmol) | Mass spectroscopy: m/z 319.69 (M + H)$^+$ (ES$^+$), at 4.05 min, 99% (method B). | (400 MHz, DMSO) δ: 3.85 (s, 3H), 7.01 (s, 2H), 7.14 (dd, J 8.7, 2.2, 1H), 7.42 (d, J 2.1, 1H), 7.51-7.63 (m, 4H), 8.12-8.19 (m, 2H), 8.26 (s, 1H). |
| (xxvi) | 1-(3-amino-5-phenyl-1,2,4-triazin-6-yl)pyridazin-4(1H)-one | 6-bromo-5-phenyl-1,2,4-triazin-3-amine (90 mg, 0.358 mmol), pyridazin-4-ol (172 mg, 1.792 mmol), and DBU (270 μl, 1.792 mmol) | Mass spectroscopy: m/z 267.80$^+$ (ES$^+$); 266.01 (M − H)$^-$ (ES$^-$), at 2.80 min, 96% (method B). | (400 MHz, DMSO) δ: 6.54 (dd, J 8.0, 3.1, 1H), 7.41-7.56 (m, 5H), 7.74 (dd, J 3.1, 0.6, 1H), 7.90 (s, 2H), 8.60 (dd, J 8.0, 0.6, 1H). |
| (xxvii) | 1-(3-amino-5-phenyl-1,2,4-triazin-6-yl)-3,5-dichloropyridin-4(1H)-one (10 mg, 5%) | 6-bromo-5-phenyl-1,2,4-triazin-3-amine (150 mg, 0.597 mmol), 3,5-dichloropyridin-4-ol (490 mg, 2.99 mmol), | Mass spectroscopy: m/z 334.55 (M + H)$^+$ (ES$^+$), at 3.05 min, 96% (method B). | (400 MHz, DMSO) δ: 7.44-7.60 (m, 5H), 7.94 (s, 2H), 8.42 (s, 2H). |
| (xxviii) | 6-(2,4-dichlorophenoxy)-5-phenyl-1,2,4-triazin-3-amine (16 mg, 13%) | 6-bromo-5-phenyl-1,2,4-triazin-3-amine (90 mg, 0.358 mmol), 2,4-dichlorophenol (292 mg, 1.792 mmol), and DBU (270 μl, 1.792 mmol) | Mass spectroscopy: m/z 333.5 (M + H)+ (ES+), at 5.03 min, 98% purity (method B). | (400 MHz, DMSO) δ: 7.10 (s, 2H), 7.42-7.51 (m, 2H), 7.54-7.64 (m, 3H), 7.80 (d, J 2.4, 1H), 8.11-8.18 (m, 2H). |
| (xxix) | 6-(2,4-difluorophenoxy)-5-phenyl-1,2,4-triazin-3-amine (12 mg, 11%) | 6-bromo-5-phenyl-1,2,4-triazin-3-amine (90 mg, 0.358 mmol), 2,4-difluorophenol (233 mg, 1.792 mmol) and DBU (270 μl, 1.792 mmol) | Mass spectroscopy: m/z 301.67 (M + H)$^+$ (ES$^+$), 99% (method B). | (400 MHz, DMSO) δ: 7.06 (s, 2H), 7.12-7.21 (m, 1H), 7.44-7.65 (m, 5H), 8.09-8.18 (m, 2H). |
| (xxx) | 5-phenyl-6-(pyridin-3-yloxy)-1,2,4-triazin-3-amine | 6-bromo-5-phenyl-1,2,4-triazin-3-amine (90 mg, 0.358 mmol), pyridin-3-ol (170 mg, 1.792 mmol) | Mass spectroscopy: m/z 266.76 (M + H)$^+$ (ES$^+$); 264.96 (M − H)$^-$ (ES$^-$), at 3.70 min, 99% (method B). | (400 MHz, DMSO) δ: 7.11 (s, 2H), 7.45 (ddd, J 8.4, 4.7, 0.6, 1H), 7.50-7.63 (m, 3H), 7.69 (ddd, J 8.4, 2.8, 1.4, 1H), 8.05-8.15 (m, 2H), 8.41 (dd, J 4.7, 1.3, 1H), 8.53 (d, J 2.5, 1H). |
| (xxxi) | 6-[(4-methylpyridin-3-yl)oxy]-5-phenyl-1,2,4-triazin-3-amine | 6-bromo-5-phenyl-1,2,4-triazin-3-amine (90 mg, 0.358 mmol), 4-methylpyridin-3-ol (196 mg, 1.792 mmol | Mass spectroscopy: m/z 280.79 (M + H)$^+$ (ES$^+$), at 3.97 min, 99% (method B). | (400 MHz, DMSO) δ: 2.19 (s, 3H), 7.02 (s, 2H), 7.39 (d, J 4.9, 1H), 7.54-7.64 (m, 3H), 8.13-8.21 (m, 2H), 8.32 (d, J 4.8, 1H), 8.39 (s, 1H). |
| (xxxii) | 5-phenyl-6-(p-tolylthio)-1,2,4-triazin-3-amine (407 mg, 1.383 mmol, 69.4%) | 6-bromo-5-phenyl-1,2,4-triazin-3-amine (0.50 g, 1.991 mmol) and 4-methylbenzenethiol (1.24 g, 9.96 mmol) | Mass spectroscopy: m/z 295.2 (M + H)$^+$ (ES$^+$), at 4.77 min, 100% (method B). | (400 MHz, DMSO) δ: 2.26 (s, 3H), 7.09-7.15 (m, 4H), 7.44 (s, 2H), 7.46-7.55 (m, 3H), 7.67-7.72 (m, 2H). |

Example 4

Preparation of (i) 3-(3-Amino-5-phenyl-1,2,4-triazin-6-yl)-5-chlorophenol; and (ii) 3-(3-Amino-5-phenyl-1,2,4-triazin-6-yl)-5-chlorophenyltrifluoromethanesulfonate

Step 1: 3-(3-Amino-5-phenyl-1,2,4-triazin-6-yl)-5-chlorophenol 3-(3-Amino-5-phenyl-1,2,4-triazin-6-yl)-5-chlorophenol (890 mg, 85%) was prepared by demethylation of 6-(3-chloro-5-methoxyphenyl)-5-phenyl-1,2,4-triazin-3-amine (1.2 g, 3.84 mmol; vide supra) with $BBr_3$ (5 mL) at −70° C. for 2 hours and then for a further 16 hours at RT. The resulting mixture was then poured into water (25 mL) and extracted with DCM (3×30 mL). The combined organic extracts were then dried over $Na_2SO_4$ and concentrated under vacuum. The crude compound was purified by gradient flash chromatography, eluting with 30% ethyl acetate in hexane to afford the target compound.

HPLC purity: 96.94% (262 nm)
Mass spectroscopy: (ESI+ve) 298.9 $[M+H]^+$.
$^1$H NMR: (400 MHz, DMSO) δ: 6.68 (m, 1H), 6.75 (m, 2H), 7.35-7.45 (m, 7H), 9.98 (s, 1H).

Step 2: 3-(3-Amino-5-phenyl-1,2,4-triazin-6-yl)-5-chlorophenyl trifluoromethanesulfonate 3-(3-Amino-5-phenyl-1,2,4-triazin-6-yl)-5-chlorophenyl trifluoromethanesulfonate (2.5 g, 90%) was prepared from 3-(3-amino-5-phenyl-1,2,4-triazin-6-yl)-5-chlorophenol (1.5 g, 5.03 mmol). The alcohol was dissolved in DCM (15 mL), cooled to 0° C. and treated with triethylamine (0.66 g) for 10 minutes. Trifluoromethane sulphonyl chloride was then added at 0° C. and the mixture was warmed to RT and maintained at this temperature for 1.5 hours. The mixture then was poured into water (25 mL) and extracted with DCM (3×30 mL); the combined organic extracts were then dried over $Na_2SO_4$ and concentrated in vacuo. The crude compound was used as such in the next step.

Mass spectroscopy: (ESI+ve) 431.0 [M+H]J, (ESI−ve) 429.0 $[M-H]^+$.

General Procedure for Pd-Mediated Cross-Couplings of 3-(3-amino-5-phenyl-1,2,4-triazin-6-yl)-5-chlorophenyltrifluoromethanesulfonate 3-(3-Amino-5-phenyl-1,2,4-triazin-6-yl)-5-chlorophenyl trifluoromethanesulfonate (0.65 g, 1.51 mmol) was dissolved in DMF (10 mL) and the resulting solution was treated sequentially with LiCl (0.21 g) and a suitable organostannane or -boronic acid coupling partner (1.81 mmol). The resulting mixture was stirred at room temperature for 5-10 minutes then treated with palladium(0) tetrakis triphenylphosphine (0.087 g, 0.075 mmol) at reflux (90° C.) for 4-5 hours. After this time, the mixture was poured into water (25 mL) and extracted with an organic solvent such as DCM or ethyl acetate (3×30 mL). The combined organic extracts were then dried over $Na_2SO_4$, concentrated in vacuo and the isolated target compound was purified by gradient flash chromatography, eluting with ethyl acetate/hexane mixtures.

(i) 6-(3-Chloro-5-ethenylphenyl)-5-phenyl-1,2,4-triazin-3-amine 6-(3-Chloro-5-ethenylphenyl)-5-phenyl-1,2,4-triazin-3-amine (54 mg, 11%) was prepared from 3-(3-amino-5-phenyl-1,2,4-triazin-6-yl)-5-chlorophenyl trifluoromethanesulfonate (0.65 g, 1.51 mmol and tri-n-butyl(vinyl) tin (0.57 g, 1.81 mmol) according to the general procedure for Example 4.

HPLC purity: 98.35% (248 nm)
Mass spectroscopy: (ESI+ve) 309.0 $[M+H]^+$.
$^1$H NMR: (400 MHz, DMSO) δ: 5.27 (d, 1H), 5.72 (d, 1H), 6.62 (dd, 1H), 7.23 (m, 1H), 7.44 (m, 6H), 7.51 (m, 1H), 7.57 (bs, 2H).

(ii) 6-(3-Chloro-5-cyclopropylphenyl)-5-phenyl-1,2,4-triazin-3-amine 6-(3-Chloro-5-cyclopropylphenyl)-5-phenyl-1,2,4-triazin-3-amine (20 mg, 7%) was prepared from 3-(3-amino-5-phenyl-1,2,4-triazin-6-yl)-5-chlorophenyl trifluoromethane-sulfonate (0.40 g, 0.93 mmol) and tri-n-butyl (cyclopropyl) tin (0.37 g, 1.11 mmol) according to the general procedure for Example 4.

HPLC purity: 95.98% (227 nm)
Mass spectroscopy: (ESI+ve) 322.9 $[M+H]^+$.
$^1$H NMR: (400 MHz, CDCl3) δ: 0.47 (m, 2H), 0.87 (m, 2H), 1.36 (m, 1H), 5.58 (bs, 2H), 6.84 (s, 1H), 7.06 (s, 1H), 7.26 (s, 1H), 7.37 (m, 2H), 7.45 (m, 3H).

Example 5: Other Synthetic Methods

(i) 6-(3,5-Dichlorophenyl)-5-(3-methylpiperidin-1-yl)-1,2,4-triazin-3-amine

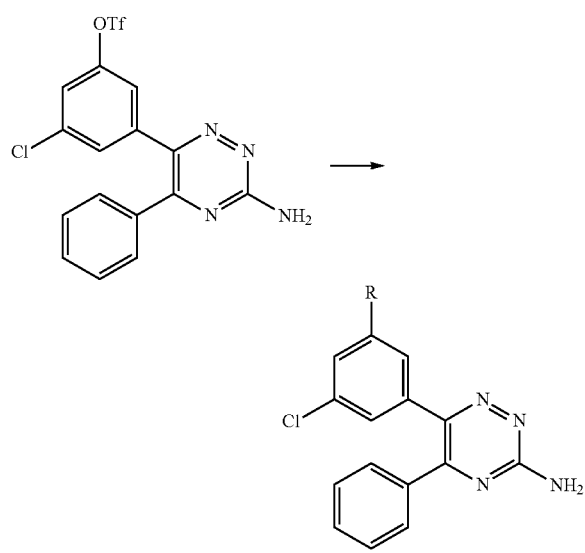

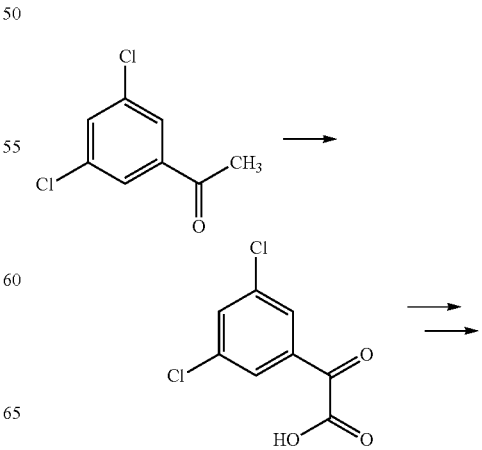

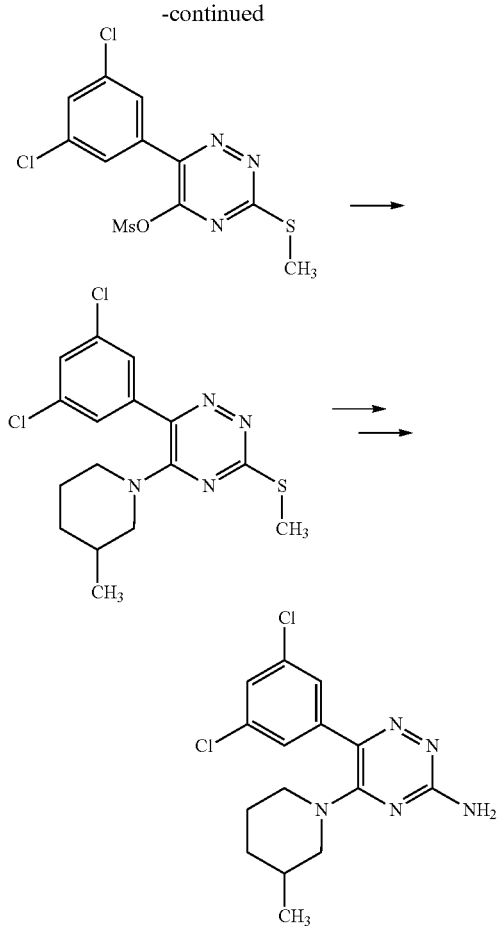

Step 1: Selenium dioxide (30.0 g 270 mmol) was dissolved in dioxane (450 mL) and warmed to 50° C. 3,5-Dichloroacetophenone (30.0 g, 158 mmol) was added at this temperature and the resulting mixture was refluxed for 4 h. After completion of the reaction, the mixture was filtered through celite and concentrated in vacuo. (3,5-Dichlorophenyl)(oxo)acetic acid was isolated and purified by column chromatography, eluting with ethyl acetate/hexane mixtures (28 g, 80%).

Mass spectroscopy: (ESI−ve) 217 [M−H]−

Step 2: (3,5-Dichlorophenyl)(oxo)acetic acid (28.0 g 129.0 mmol) was dissolved in ethanol (280 mL) and treated successively with a catalytic quantity of sulfuric acid and methyl hydrazinecarbimidothioate (20.5 g, 193.5 mmol). The resulting mixture was stirred for 1 hr at 78° C. After completion of the reaction (TLC), the mixture was concentrated in vacuo, poured into water (150 mL), and extracted with DCM (3×250 ml). The combined organic extracts were then dried over $Na_2SO_4$, concentrated in vacuo, and purified by gradient flash chromatography, affording 6-(3,5-dichlorophenyl)-3-(methylthio)-1,2,4-triazin-5-ol (19 g, 46%).

Mass spectroscopy: (ESI+ve) 287.9 [M−H]+, (ESI−ve) 286.0 [M−H]+

$^1$H NMR: (400 MHz, DMSO) δ: 2.49 (s, 3H), 7.73 (m, 1H), 8.05 (d, 2H), 14.32 (s, 1H).

Step 3: 6-(3,5-Dichlorophenyl)-3-(methylthio)-1,2,4-triazin-5-ol (2.0 g, 6.96 mmol) was dissolved in 1,4-dioxane (20 mL) and cooled to 15° C. TEA (1.76 g, 17.4 mmol) was added drop wise to the solution, followed 5 minutes later, by methanesulfonyl chloride (1.99 g, 17.42 mmol). After stirring at room temperature for 3 hours, 6-(3,5-dichlorophenyl)-3-(methylsulfanyl)-1,2,4-triazin-5-yl methanesulfonate was detected by LCMS and the crude mixture was used directly in the next step.

Mass spectroscopy: (ESI+ve) 366.9 [M−H]+

Step 4: A crude solution of 6-(3,5-dichlorophenyl)-3-(methylsulfanyl)-1,2,4-triazin-5-yl methanesulfonate (5.43 mmol) in dioxane (3 mL), was treated with $K_2CO_3$ (1.0 g, 7.2 mmol) and 3-methyl piperidine (1.68 g, 16.9 mmol), and the resulting mixture was stirred at room temperature overnight. After completion of the reaction (TLC, ethyl acetate/hexane, 1:1), the mixture was poured into water (25 mL) and extracted with DCM or ethyl acetate (3×25 ml). The combined organic extracts were then dried over $Na_2SO_4$, concentrated in vacuo and purified by flash chromatography, eluting with 15% ethyl acetate in hexane to afford 6-(3,5-dichlorophenyl)-5-(3-methylpiperidin-1-yl)-3-(methylsulfanyl)-1,2,4-triazine (0.8 g, 40%).

Mass spectroscopy: (ESI+ve) 369.0 [M+H]+

$^1$H NMR: (400 MHz, DMSO) δ: 0.67 (m, 3H), 1.07 (m, 2H), 1.35 (m, 1H), 1.53 (m, 2H), 1.67 (m, 1H), 2.45 (s, 3H), 2.74 (m, 1H), 3.64 (m, 1H), 3.76 (s, 1H), 7.60 (d, 2H), 7.64 (m, 1H).

Step 5: m-CPBA (0.654 g, 3.78 mmol) was added to a solution of a 6-(3,5-dichlorophenyl)-5-(3-methylpiperidin-1-yl)-3-(methylsulfanyl)-1,2,4-triazine (0.4 g, 1.08 mmol) in DCM (5 mL) at −15° C. and the resulting mixture was stirred at this temperature until the reaction was judged to be complete by TLC (8 hrs). The reaction was then quenched with saturated aqueous $NaHCO_3$ solution (15 ml) and extracted with ethyl acetate (3×15 ml). The combined organic extracts were dried over $Na_2SO_4$ and evaporated under reduced pressure to afford crude 6-(3,5-dichlorophenyl)-5-(3-methylpiperidin-1-yl)-3-(methylsulfonyl)-1,2,4-triazine (1.0 g, 91%) which was used without further purification.

Step 6: A 6-(3,5-Dichlorophenyl)-5-(3-methylpiperidin-1-yl)-3-(methylsulfonyl)-1,2,4-triazine (0.25 g, 0.625 mmol) was dissolved in THF (5 mL) and the solution was purged with anhydrous $NH_3$ gas for 1 hour. After completion of the reaction (TLC), the mixture was poured into water (15 mL) and extracted with DCM or ethyl acetate (3×15 ml). The combined organic extracts were dried over $Na_2SO_4$, concentrated in vacuo and then treated with 1N HCl solution for 10 min and extracted with ethyl acetate. The separated aqueous layer was neutralized with $K_2CO_3$ and extracted with ethyl acetate (3×150 ml); the organic phases were then dried over $Na_2SO_4$ and purified by gradient flash chromatography, affording 6-(3,5-dichlorophenyl)-5-(3-methylpiperidin-1-yl)-1,2,4-triazin-3-amine (0.01 g, 1%).

HPLC purity: 88.07% (218 nm)

Mass spectroscopy: (ESI+ve) 338.9 [M+H]+

$^1$H NMR: (400 MHz, DMSO) δ: 0.90 (m, 1H), 1.16 (m, 2H), 1.42 (m, 2H), 1.58 (s, 1H), 1.72 (m, 1H), 2.52 (m, 3H), 2.61 (m, 1H), 2.79 (m, 1H), 7.64 (s, 2H), 7.76 (s, 1H), 7.64 (bs, 2H).

(ii) 6-(6-(Methylamino)pyridin-3-yl)-5-phenyl-1,2,4-triazin-3-amine 6-(6-(Methylamino)pyridin-3-yl)-5-phenyl-1,2,4-triazin-3-amine (49.5 mg, 0.177 mmol, 71.4%) was prepared from 5-(3-amino-5-phenyl-1,2,4-triazin-6-yl)pyridin-2-yl (methyl)carbamate (vide supra), by BOC deprotection with trifluoroacetic acid (0.4 mL) in dichloromethane (1.6 mL) for 1 hour at room temperature.

HPLC purity: 99.7% (254 nm) at 3.45 min
Mass spectroscopy: (ESI+ve) 279.8 [M+H]⁺
¹H NMR: (400 MHz, DMSO) δ: 2.74 (d, J 4.8, 3H), 6.36 (dd, J 8.7, 0.7, 1H), 6.62-6.75 (m, 1H), 7.27 (s, 2H), 7.30 (dd, J 8.7, 2.4, 1H), 7.36-7.47 (m, 5H), 7.90 (dd, J 2.4, 0.6, 1H).

(iii) 4-(3-amino-5-phenyl-1,2,4-triazin-6-yl)-2,6-diiodophenol 4-(3-Amino-5-phenyl-1,2,4-triazin-6-yl)-phenol (vide supra; 140 mg, 0.530 mmol) was reacted with AcOH (2 mL) and 1-iodopyrrolidine-2,5-dione (119 mg, 0.530 mmol). The mixture was stirred at room temperature for 1 hour then concentrated in vacuo and purified by column chromatography (88 mg, 64%).
HPLC purity: 99% (254 nm) at 3.1 min
Mass spectroscopy: (ESI+ve) 517 [M+H]⁺; (ESI−ve) 515 [M−H]⁻
¹H NMR: (400 MHz, DMSO) δ: 7.35-7.50 (m, 7H), 7.64 (s, 2H), 9.69 (s, 1H).

(iv) 4-(3-amino-5-phenyl-1,2,4-triazin-6-yl)-2-iodophenol 4-(3-Amino-5-phenyl-1,2,4-triazin-6-yl)-phenol (vide supra; 140 mg, 0.530 mmol) was reacted with AcOH (2 mL) and 1-iodopyrrolidine-2,5-dione (119 mg, 0.530 mmol). The mixture was stirred at room temperature for 1 hour then concentrated in vacuo and purified by column chromatography (35 mg, 32%).
HPLC purity: 99% (254 nm) at 2.7 min
Mass spectroscopy: (ESI+ve) 391 [M+H]⁺; (ESI−ve) 389 [M−H]⁻
¹H NMR: (400 MHz, DMSO) δ: 6.77 (d. J 8.4 Hz, 1H), 7.06 (dd, J 8.4, 2.2 Hz, 1H), 7.28-7.47 (m, 7H), 7.68 (d, J 2.2 Hz, 1H), 10.51 (s, 1H).

(v) 6-(3-Methoxy-5-(trifluoromethoxy)phenyl)-5-phenyl-1,2,4-triazin-3-amine 6-(3-Methoxy-5-(trifluoromethoxy)phenyl)-5-phenyl-1,2,4-triazin-3-amine was prepared from 3-(3-amino-5-phenyl-1,2,4-triazin-6-yl)-5-(trifluoromethoxy)phenol (100 mg, 0.287 mmol). The phenol was dissolved in THF (2 mL) and treated with iodomethane (17.87 μL, 0.287 mmol) at 0° C. After ~15 minutes, the mixture was then allowed to warm to r.t. slowly.
Solvent was removed in vacuo; water (2 ml) and DCM (2 ml) were added and the layers were separated through a phase separator cartridge. The organic was concentrated to dryness in vacuo and purified by column chromatography (33 mg, 32%).
HPLC purity: 100% (254 nm) at 4.82 min
Mass spectroscopy: (ESI+ve) 363 [M+H]⁺; (ESI−ve) 361 [M−H]⁻
¹H NMR: (400 MHz, DMSO) δ: 3.71 (s, 3H), 6.75-6.76 (m, 1H), 6.89-6.90 (m, 1H), 7.00-7.01 (m, 1H), 7.32-7.48 (m, 5H), 7.53 (s, 2H)

(vi) N-[5-(3-amino-5-phenyl-1,2,4-triazin-6-yl)-2-methoxyphenyl]acetamide

Step 1: Preparation of N-(5-bromo-2-hydroxyphenyl)acetamide

2-Amino-4-bromophenol (1 g, 5.32 mmol) was dissolved in DCM (10 mL) and cooled to 10° C. Triethylamine (0.65 g, 6.38 mmol) was then added drop-wise and stirring continued for 5 minutes before acetyl chloride (0.54 g, 6.91 mmol) was added. The reaction mixture was monitored to completion by TLC (hexane/ethyl acetate, 7:3) then quenched by saturated sodium bicarbonate solution (30 mL). The aqueous layer was extracted with ethyl acetate (3×30 mL) and the combined organic phases were dried over Na₂SO₄ and concentrated in vacuo. The crude residue (0.57 g, 47%) was used in the next step without further purification.
TLC R_f: 0.6 (hexane/ethyl acetate, 7:3)
Mass spectroscopy: (ESI+ve) 230.9 [M+H]⁺, (ESI−ve) 229.0 [M+H]⁺.
¹H NMR: (400 MHz, DMSO) δ: 2.07 (s, 3H), 6.78 (d, 1H), 7.04 (d, 1H), 8.04 (d, 1H), 9.26 (s, 1H), 10.15 (s, 1H).

Step 2: Preparation of N-(5-bromo-2-methoxyphenyl)acetamide

N-(5-Bromo-2-hydroxyphenyl)acetamide (0.56 g, 2.43 mmol) was dissolved in anhydrous DMF (7.0 mL) and treated with K₂CO₃ (0.85 g, 6.09 mmol). The resulting mixture was heated at 70° C. for 30 minutes then treated with methyl iodide (0.69 g, 4.87 mmol). After stirring for a further 16 hours at 60° C., the reaction mixture was quenched with water (25 mL) and the aqueous layer was extracted with ethyl acetate (3×30 mL). The combined organic layers were dried over Na₂SO₄ and concentrated in vacuo. The resulting residue (0.54 g, 92%) was used in the next step without further purification.
Mass spectroscopy: (ESI+ve) 244.9 [M+H]J.
TLC R_f: 0.8 (hexane/ethyl acetate, 7:3)

Step 3: Preparation of N-[2-methoxy-5-(4,4,5,5-tetramethyl-1,3,2-dioxaborolan-2-yl)phenyl]acetamide N-(5-Bromo-2-methoxyphenyl) acetamide (0.52 g, 2.13 mmol) was dissolved in DME (10 mL) and treated with palladium(II) dibenzylidene acetone (65 mg, 0.11 mmol), triphenyl phosphine (40 mg, 0.15 mmol), bis(pinacolato)diboron (0.65 g, 2.56 mmol) and potassium acetate (0.63 g, 6.4 mmol). The resulting mixture was heated at 150° C. overnight then quenched with water (30 mL). The aqueous layer was extracted with ethyl acetate (3×30 mL) and the combined organic phases were dried over Na₂SO₄ and concentrated in vacuo. The crude residue (1.08 g, 91%) was used in the next step without further purification.
Mass spectroscopy: (ESI+ve) 292.1 [M+H]⁺.
TLC R_f: 0.5 (hexane/ethyl acetate, 7:3)

Step 4: Preparation of N-[5-(3-amino-5-phenyl-1,2,4-triazin-6-yl)-2-methoxyphenyl]acetamide N-[5-(3-Amino-5-phenyl-1,2,4-triazin-6-yl)-2-methoxyphenyl]acetamide (0.170 g, 25%) was prepared from 6-bromo-5-phenyl-1,2,4-triazin-3-amine (0.5 g, 1.99 mmol) and N-[2-methoxy-5-(4,4,5,5-tetramethyl-1,3,2-dioxaborolan-2-yl)phenyl]acetamide according to the general procedure of Example 1.
HPLC purity: 97.62% (283 nm)
Mass spectroscopy: (ESI+ve) 336.1 [M+H]⁺.
NMR: (400 MHz. DMSO) δ: 2.04 (s, 3H), 3.79 (s, 3H), 6.82 (d, 1H), 6.90 (d, 1H), 7.33 (m, 4H), 7.39 (m, 3H), 8.13 (s, 1H), 9.13 (s, 1H).

(vii) N-[5-(3-Amino-5-phenyl-1,2,4-triazin-6-yl)-2-hydroxyphenyl]acetamide

N-[5-(3-amino-5-phenyl-1,2,4-triazin-6-yl)-2-hydroxyphenyl]acetamide was prepared by O-demethylation of N-[5-(3-amino-5-phenyl-1,2,4-triazin-6-yl)-2-methoxyphenyl]acetamide (0.05 g, 0.15 mmol: vide supra). The methyl ether was dissolved in DCM (5 mL), cooled to −78° C. and treated with borontribromide (5.25 mmol, 1.32 g). The resulting mixture was gradually warmed to RT then stirred at this temperature for a further 16 hours. The mixture was poured into water (15 mL) and extracted with DCM (3×15 mL). The combined organic extracts were dried over $Na_2SO_4$, concentrated in vacuum and purified by gradient flash chromatography, eluting with 30% ethyl acetate in hexane to afford the target compound (0.30 g, 85%).

HPLC purity: 96.15% (219 nm)
Mass spectroscopy: (ESI+ve) 322.0 $[M+H]^+$.
$^1$H NMR: (400 MHz, DMSO) δ: 2.05 (s, 3H), 6.71 (m, 2H), 7.43 (m, 5H), 8.00 (m, 1H), 8.49 (bs, 2H), 9.26 (s, 1H), 10.26 (bs, 1H).

(viii) 6-(2-Methyl-6-$d_3$-methylpyridin-4-yl)-5-phenyl-1,2,4-triazin-3-amine

Step 1: Preparation of 2,4,6-tri($d_3$-methyl)cyclotriboroxane-pyridine complex A solution of trimethyl borate (10.0 mL) in THF (100 mL) was cooled under $N_2$ to −78° C. and a solution of methyl-$d_3$-magnesium iodide (50.0 mL, 1 M in diethyl ether, 50.0 mmol) was added drop-wise over 1 hour. After stirring at −78° C. for a further 1.5 hours 1 M aqueous HCl (25 mL) was added drop-wise over approximately 5 min and the mixture was allowed to warm to room temperature. Brine (20 mL) was added and the mixture was filtered through a short pad of celite, rinsing the celite pad with diethyl ether (50 mL). The phases were separated and the aqueous phase was extracted with diethyl ether (3×50 mL). The combined organic phases were washed with water (50 mL) and brine (50 mL) and then concentrated in vacuo to approximately 25 mL volume. Pyridine (10 mL) was added and the light yellow solution was stirred at ambient temperature for 19.5 hours before concentration in vacuo to yield the title compound (1.39 g, crude) as a light-yellow semi-solid which was used without purification.

LCMS: m/z 214.1 $[M+H]^+$ (ESI+ve), 0.3 min (method A).

Step 2: Synthesis of 6-(2-methyl-6-$d_s$-methylpyridin-4-yl)-5-phenyl-1,2,4-triazin-3-amine A mixture of 6-(2-chloro-6-methylpyridin-4-yl)-5-phenyl-1,2,4-triazin-3-amine (70.4 mg, 0.236 mmol), crude 2,4,6-tri($d_3$)methylcyclotriboroxane-pyridine complex (504 mg, approximately 2.36 mmol), 1 M aqueous sodium carbonate solution (0.59 mL, 0.59 mmol) and tetrakis(triphenylphosphine)palladium(0) (27.2 mg, 0.024 mmol) in 1,4-dioxane (3 mL) and water (2 mL) in a sealed vial was heated in a microwave reactor at 150° C. for 20 mins. After concentration in vacuo, DCM (10 mL) and water (10 mL) were added and the phases were separated. The aqueous phase was extracted with DCM (2×5 mL) and the combined organic phases concentrated in vacuo. Purification by gradient flash chromatography ($SiO_2$, 5 to 40% solvent A in B. Solvent A: $CH_2Cl_2$, solvent B: 7N $NH_3$ in MeOH/MeOH/$CH_2Cl_2$ 5:5:90) yielded the title compound as a yellow solid (30.5 mg, 46%).

LCMS m/z 281.1 $(M+H)^+$ $(ES^+)$ at 2.26 min, 100% (method C).
NMR (400 MHz, $CDCl_3$) δ: 2.47 (s, 3H), 5.44 (s, 2H), 7.02 (s, 2H), 7.33-7.39 (m, 2H), 7.43-7.49 (m, 3H).

(ix) 1-(3-Amino-5-phenyl-1,2,4-triazin-6-yl)-3,5-dimethylpyridin-4(1H)-one

Step 1: Preparation of 1-(3,5-dimethylpyridin-4-yl)-3,5-dimethylpyridinium chloride 3,5-lutidine (1.0 g, 9.3 mmol) was added to $SOCl_2$ (2.0 mL, 27.9 mmol) at −10° C. The resulting mixture was heated to 120'C and was stirred for a further two to three hours. The reaction was monitored to completion by TLC (ethyl acetate/hexane, 1:1) then precipitated with ethyl acetate. The desired product was collected by filtration and used in the next step without further purification (1.79 g, 90%).

Mass: (ESI+ve) 214.1 [M+H]r
TLC $R_f$: 0.05 (methanol/chloroform, 3:7).

Step 2: Preparation of 3,5-dimethylpyridin-4-ol 1-(3,5-dimethylpyridin-4-yl)-3,5-dimethylpyridinium chloride (1.0 g, 4.7 mmol) and anhydrous $H_3PO_3$ (0.97 g, 11.7 mmol) were heated, as a neat mixture, to 150-160° C. in a sealed tube for 8 hours with TLC monitoring (methanol/chloroform 5:5). Upon completion of the reaction, the mixture was diluted with ethanol and acetone (1:1, 50 mL), filtered and concentrated under vacuum. The product was purified employing Dowex 50 resin.

Mass: (ESI+ve) 124.0 $[M+H]^+$
TLC $R_f$: 0.38 (methanol/chloroform, 2:8).

Step 3: Preparation of 1-(3-amino-5-phenyl-1,2,4-triazin-6-yl)-3,5-dimethylpyridin-4(1H)-one 1-(3-Amino-5-phenyl-1,2,4-triazin-6-yl)-3,5-dimethyl-pyridin-4(1H)-one (40 mg, 5%) was prepared from 6-bromo-5-phenyl-1,2,4-triazin-3-amine (0.70 g, 2.7 mmol), 3,5-dimethylpyridin-4-ol (0.45 g, 3.7 mmol) and $K_2CO_3$ (0.93 g, 6.7 mmol) according to the general procedure of Example 3.

HPLC purity: 92.33% (286 nm)
Mass spectroscopy: (ESI+ve) 294.1 $[M+H]^+$
$^1$H NMR: (400 MHz, CDCl3) δ: 1.77 (s, 6H), 7.44 (m, 5H), 7.66 (s, 2H), 7.74 (bs, 2H).

(x) 6-[2-(Azetidin-1-yl)-6-methylpyridin-4-yl]-5-phenyl-1,2,4-triazin-3-amine 6-[2-(Azetidin-1-yl)-6-methylpyridin-4-yl]-5-phenyl-1,2,4-triazin-3-amine was prepared from 5-phenyl-6-(2-chloro-6-methyl-pyridin-4-yl)-1,2,4-triazin-3-amine (100 mg, 0.34 mmol) and azetidine (96 mg, 0.11 ml, 1.69 mmol) according to the general procedure for Preparation 4a.

LCMS: $(ES^+)$ 319.1 $(M+H)^+$ at 4.02 min, 99% (method C).
$^1$H NMR: (400 MHz, DMSO) δ: 2.22 (s, 3H), 2.22-2.28 (m, 2H), 3.76 (t, J 7.3, 4H), 5.99 (s, 1H), 6.47 (s, 1H), 7.39-7.50 (m, 5H), 7.52 (bs, 2H).

(xi) 6-[2-(azetidin-1-yl)-6-methylpyridin-4-yl]-5-(4-fluorophenyl)-1,2,4-triazin-3-amine 6-[2-(azetidin-1-yl)-6-methylpyridin-4-yl]-5-(4-fluorophenyl)-1,2,4-triazin-3-amine (6.0 mg, 4%) was prepared from 5-(4-fluorophenyl)-6-(2-chloro-6-methyl-pyridin-4-yl)-1,2,4-triazin-3-amine (150 mg, 0.48 mmol) and azetidine (136 mg, 0.16 ml, 2.38 mmol) according to the general procedure for Preparation 4a.

LCMS: (ES$^+$) 337.1 (M+H)$^+$ at 4.18 min, 97% (method C).

$^1$H NMR: (400 MHz, DMSO) δ: 2.23 (s, 3H), 2.24-2.30 (m, 2H), 3.79 (t, J 7.6, 4H), 6.52 (s, 1H), 6.86 (s, 1H), 7.24-7.29 (m, 2H), 7.48-7.50 (m, 2H), 7.55 (bs, 2H).

(xii) 6-[2-(Azetidin-1-yl)-6-(trifluoromethyl)pyridin-4-yl]-5-phenyl-1,2,4-triazin-3-amine 6-[2-(Azetidin-1-yl)-6-(trifluoromethyl)pyridin-4-yl]-5-phenyl-1,2,4-triazin-3-amine (20.0 mg, 19%) was prepared from 5-phenyl-6-(2-chloro-6-trifluoromethyl-pyridin-4-yl)-1,2,4-triazin-3-amine (100 mg, 0.28 mmol) and azetidine according to the general procedure for Preparation 4a.

LCMS: (ES$^+$) 373.0 (M+H)$^+$ at 4.52 min, 99% (method C).

$^1$H NMR: (400 MHz, DMSO) δ: 2.27-2.35 (m, 2H), 3.89 (t, J 7.5, 4H), 6.03 (s, 1H), 6.46 (s, 1H), 7.41-7.53 (m, 5H), 7.69 (br. s, 2H).

Example 6

The compounds of Examples 1 to 5 were found to possess activity in biological tests described above. Biological activity determined by Test A includes IC$_{50}$ and pKi values for human A$_{2a}$ and A$_1$ receptors, and the compounds of Examples 1 to 5 were found to possess pKi values in excess of 5 (or 6) vs. at least one of these receptors (for example as illustrated for certain compounds in the table below).

| Example no. | pKi A2a | pKi A1 |
|---|---|---|
| 1(vi) | 7.29 | 7.25 |
| 1(ix) | 7.70 | 7.81 |
| 1(xiii) | 8.40 | 7.36 |
| 1(xv) | 7.11 | 8.45 |
| 1(xviii) | 6.75 | 6.91 |
| 1(xxiv) | 6.97 | 8.03 |
| 1(xxx) | 6.30 | ND |
| 1(xxxv) | 7.19 | 8.20 |
| 1(xli) | 8.68 | 7.83 |
| 1(xlii) | 8.86 | 9.84 |
| 1(xliii) | 7.74 | 8.54 |
| 1(li) | 8.66 | 6.87 |
| 1(lvi) | 8.22 | 7.33 |
| 1(lxxii) | 6.99 | 8.52 |
| 1(lxxvii) | 8.11 | 7.29 |
| 1(lxxix) | 7.45 | 9.35 |
| 1(lxxx) | 6.61 | 6.01 |
| 1(xc) | 8.07 | 7.26 |
| 1(xcv) | 7.86 | 6.67 |
| 1(cxxxiv) | 5.62 | 7.62 |
| 1(cxlvi) | 6.31 | 7.40 |
| 1(cliv) | 7.56 | 6.77 |
| 1(clviii) | 7.98 | 6.96 |
| 1(clix) | 7.81 | 7.07 |
| 1(clxix) | 8.40 | 6.99 |
| 1(clxxiv) | 8.07 | 6.89 |
| 1(clxxvi) | 8.03 | 6.93 |
| 1(clxxix) | 8.62 | 7.52 |
| 1(clxxx) | 8.90 | 7.76 |
| 1(clxxxi) | 8.71 | 7.17 |
| 1(cxci) | 8.26 | 7.36 |
| 1(cxciii) | 8.34 | 6.93 |
| 1(cciv) | 7.21 | 5.97 |
| 1(ccix) | 8.59 | 7.60 |
| 1(ccxi) | 7.71 | 8.74 |
| 1(ccxii) | 8.66 | 7.68 |
| 1(ccxiii) | 7.51 | 7.12 |
| 1(ccxviii) | 6.58 | 5.25 |
| 2(iii) | 7.31 | 5.37 |
| 2(iv) | 7.79 | <5 |
| 2(vi) | 7.39 | <5 |
| 2(xxii) | 5.07 | 6.71 |
| 2(xxv) | 5.53 | 7.49 |
| 3(i) | 7.17 | <5 |
| 3(v) | 5.96 | ND |
| 3(xvi) | 7.41 | 7.15 |
| 3(xxi) | 6.22 | 8.07 |
| 3(xxiv) | 7.39 | 8.46 |
| 3(xxxii) | 5.82 | 7.00 |
| 4(ii) | 7.89 | 7.43 |
| 5(vii) | 6.73 | 8.69 |
| 5(viii) | 7.91 | 7.26 |
| 5(ix) | 7.77 | 7.62 |
| 5(x) | 8.52 | 8.05 |
| 5(xi) | 7.76 | 6.90 |

Example 7

The compounds of Example 1(vi) and Example 1 (xliii) (dose of 2-10 mg/kg or 0.3-3 mg/kg, p.o., respectively; 120 min pre-test time) were found to reverse cataleptic behaviour in rats pre-treated with haloperidol in a dose-dependent manner with an ED$_{50}$ of 9.8 and 0.27 mg/kg (p.o.), respectively, using the procedure described in Test B above. In a similar manner, the compounds of Examples 1(xiii), 1(li), 1(lvi), 1(lxxvii), 1(xc), 1(xcv), 1(cliv), 1(clviii), 1(clix), 1(ccix), 1(cxci), 1(cxciii), 1(clxix), 1(clxxix), 1(clxxxiv), 1(ccxii) and 5(x) were found to reverse cataleptic behavior in rats pre-treated with haloperidol in a statistically significant manner at a dose of 1 mg/kg (p.o.) (with a 120 min pre-test time, according to Test B above.

Abbreviations m-CPBA=m-chloroperoxybenzoic acid
bmim=1-butyl-3-methylimidazolium
DCM=dichloromethane
DME=dimethoxyethane
DMF=dimethylformamide
DMSO=dimethylsulfoxide
ESI=electro spray ionisation
EtOAc=Ethyl acetate
FT=fourier transform
HPLC=high performance liquid chromatography
IR=infra-red
LC=liquid chromatography
MS=mass spectrometry
NMP=N-methyl pyrrolidinone
NMR=nuclear magnetic resonance
rt=room temperature
THF=tetrahydrofuran
TLC=thin layer chromatography Prefixes n-, s-, i-, t- and tert- have their usual meanings: normal, secondary, iso, and tertiary.

The invention claimed is:
1. A method of treatment of cancer, comprising administering an effective amount of 6-(2-chloro-6-methylpyridin-4-yl)-5-(4-fluorophenyl)-1,2,4-triazin-3-amine, or a pharmaceutically acceptable salt or solvate, to a patient in need of such treatment, wherein the cancer is selected from the group consisting of prostate cancer, rectal cancer, renal cancer, ovarian cancer, endometrial cancer, thyroid cancer, pancreatic cancer, breast cancer, colon cancer, bladder cancer, brain cancer, glia cancer, melanoma cancer, pineal gland cancer, and lung cancer.

2. The method as claimed in claim 1, wherein the cancer is selected from the group consisting of rectal cancer, pancreatic cancer, colon cancer, brain cancer, glia cancer, and lung cancer.

3. A compound, wherein the compound is 6-(2-chloro-6-methylpyridin-4-yl)-5-(4-fluorophenyl)-1,2,4-triazin-3-amine, or a pharmaceutically acceptable salt or solvate.

* * * * *

UNITED STATES PATENT AND TRADEMARK OFFICE
CERTIFICATE OF CORRECTION

PATENT NO.         : 10,112,923 B2
APPLICATION NO.    : 15/344048
DATED              : October 30, 2018
INVENTOR(S)        : Miles Stuart Congreve et al.

Page 1 of 1

It is certified that error appears in the above-identified patent and that said Letters Patent is hereby corrected as shown below:

In the Claims

At Column 172, Claim number 1, Line number 64, after "solvate" insert --thereof--.

At Column 173, Claim number 3, Line 10, after "solvate" insert --thereof--.

Signed and Sealed this
Eighteenth Day of February, 2020

Andrei Iancu
*Director of the United States Patent and Trademark Office*